(12) United States Patent
Nielson et al.

(10) Patent No.: US 11,453,720 B2
(45) Date of Patent: *Sep. 27, 2022

(54) ANTI-TIGIT ANTIGEN-BINDING PROTEINS AND METHODS OF USE THEREOF

(71) Applicant: Potenza Therapeutics, Inc., Cambridge, MA (US)

(72) Inventors: Nels P. Nielson, Cambridge, MA (US); Daniel Hicklin, Cambridge, MA (US); Cynthia Seidel-Dugan, Cambridge, MA (US); William Winston, Cambridge, MA (US); Heather Brodkin, Cambridge, MA (US); Jose-Andres Salmeron-Garcia, Cambridge, MA (US); Christopher James Nirschl, Cambridge, MA (US); Philipp Steiner, Cambridge, MA (US)

(73) Assignee: Potenza Therapeutics, Inc., Cambridge, MA (US)

( * ) Notice: Subject to any disclaimer, the term of this patent is extended or adjusted under 35 U.S.C. 154(b) by 70 days.

This patent is subject to a terminal disclaimer.

(21) Appl. No.: 16/498,520

(22) PCT Filed: Mar. 30, 2018

(86) PCT No.: PCT/US2018/025460
§ 371 (c)(1),
(2) Date: Sep. 27, 2019

(87) PCT Pub. No.: WO2018/183889
PCT Pub. Date: Oct. 4, 2018

(65) Prior Publication Data
US 2020/0095324 A1   Mar. 26, 2020

Related U.S. Application Data

(60) Provisional application No. 62/479,042, filed on Mar. 30, 2017.

(51) Int. Cl.
*C07K 16/28* (2006.01)
*C07K 16/22* (2006.01)

(52) U.S. Cl.
CPC ..........  *C07K 16/2818* (2013.01); *C07K 16/22* (2013.01); *C07K 16/2875* (2013.01); *C07K 16/2878* (2013.01); *C07K 2317/34* (2013.01); *C07K 2317/73* (2013.01); *C07K 2317/75* (2013.01); *C07K 2317/76* (2013.01)

(58) Field of Classification Search
CPC ........ C07K 16/00–468; C07K 16/2803; A61K 39/395–39558
See application file for complete search history.

(56) References Cited

U.S. PATENT DOCUMENTS

| | | | |
|---|---|---|---|
| 8,354,509 B2 | 1/2013 | Carven et al. | |
| 8,431,350 B2 | 4/2013 | Baldwin et al. | |
| 8,716,254 B2 | 5/2014 | Xiang et al. | |
| 8,822,642 B2 | 9/2014 | Levin et al. | |
| 9,499,596 B2 | 11/2016 | Clark et al. | |
| 9,713,641 B2 | 7/2017 | Hicklin et al. | |
| 10,507,244 B2 | 12/2019 | Hicklin et al. | |
| 2004/0005560 A1 | 1/2004 | Isogai et al. | |
| 2006/0105376 A1 | 5/2006 | Isogai et al. | |
| 2007/0041982 A1 | 2/2007 | Ponath et al. | |
| 2007/0054360 A1 | 3/2007 | Gao et al. | |
| 2008/0038264 A1 | 2/2008 | Bodary et al. | |
| 2008/0050809 A1 | 2/2008 | Abuin et al. | |
| 2009/0156495 A1 | 6/2009 | Gao et al. | |
| 2009/0181024 A1 | 7/2009 | Baldwin et al. | |
| 2009/0258013 A1 | 10/2009 | Clark et al. | |
| 2010/0316646 A1 | 12/2010 | Gao et al. | |
| 2011/0104170 A1 | 5/2011 | Baldwin et al. | |
| 2011/0172114 A1 | 7/2011 | Bodary et al. | |
| 2012/0219540 A1 | 8/2012 | Gao et al. | |
| 2013/0065791 A1 | 3/2013 | Rosenthal et al. | |
| 2013/0095102 A1 | 4/2013 | Levin et al. | |
| 2014/0010861 A1 | 1/2014 | Bancel et al. | |
| 2014/0056890 A1 | 2/2014 | Gurney et al. | |
| 2014/0128277 A1 | 5/2014 | Moller et al. | |
| 2016/0176963 A1* | 6/2016 | Maurer .............. | C07K 16/2803 424/139.1 |
| 2016/0355589 A1 | 12/2016 | Williams et al. | |
| 2017/0165366 A1* | 6/2017 | Hicklin .............. | C07K 16/2803 |
| 2020/0101158 A1 | 4/2020 | Hicklin et al. | |

FOREIGN PATENT DOCUMENTS

| | | |
|---|---|---|
| JP | 2011-523034 A | 8/2011 |
| JP | 2016-525117 A | 8/2016 |
| JP | 2018-536698 A | 12/2018 |
| RU | 2015123032 A | 1/2017 |

(Continued)

OTHER PUBLICATIONS

Ge et al. Front. Immunol. (2021) 12:699895; doi: 10.3389/fimmu. 2021.699895 (Year: 2021).*

(Continued)

*Primary Examiner* — Jessica H Roark

(74) *Attorney, Agent, or Firm* — McCarter & English, LLP; Maria Laccotripe Zacharakis

(57) ABSTRACT

Provided herein are antigen-binding proteins (ABPs) that selectively bind to TIGIT and its isoforms and homologs, and compositions comprising the ABPs. Also provided are methods of using the ABPs, such as therapeutic and diagnostic methods.

21 Claims, 18 Drawing Sheets

Specification includes a Sequence Listing.

(56) References Cited

FOREIGN PATENT DOCUMENTS

| | | |
|---|---|---|
| WO | WO-2006/124667 A2 | 11/2006 |
| WO | WO-2007/073478 A2 | 6/2007 |
| WO | WO-2009/036379 A2 | 3/2009 |
| WO | WO-2009/126688 A2 | 10/2009 |
| WO | WO-2010/105256 A1 | 9/2010 |
| WO | WO-2011/144718 A2 | 11/2011 |
| WO | WO-2011/156356 A1 | 12/2011 |
| WO | WO-2011/161699 A2 | 12/2011 |
| WO | WO-2012/009568 A2 | 1/2012 |
| WO | 2012/058065 A1 | 5/2012 |
| WO | WO-2013/151665 A2 | 10/2013 |
| WO | 2014/089169 A2 | 6/2014 |
| WO | WO-2014/089113 A1 | 6/2014 |
| WO | WO-2014/179363 A1 | 11/2014 |
| WO | WO-2015/009856 A2 | 1/2015 |
| WO | WO-2016/028656 A1 | 2/2016 |
| WO | WO-2016/073282 A1 | 5/2016 |
| WO | WO-2016/106302 A1 | 6/2016 |
| WO | WO-2016/191643 A2 | 12/2016 |
| WO | WO-2017/037707 A1 | 3/2017 |
| WO | WO-2017/059095 A1 | 4/2017 |

OTHER PUBLICATIONS

Anderson et al., Lag-3, Tim-3, and TIGIT: Co-inhibitory Receptors with Specialized Functions in Immune Regulation. Immunity. May 17, 2016;44(5):989-1004.

Anderson et al., Preclinical characterization of AB154, a fully humanized anti-TIGIT antibody, for use in combination therapies. Cancer Immunology Research. Abstract A124, retrieved online at: http://cancerimmunolres.aacrjournals.org/content/7/2_Supplement/A124. 2 page, Feb. 2019.

Aspeslagh et al., Rationale for anti-OX40 cancer immunotherapy. Eur J Cancer. Jan. 2016;52:50-66.

Ayano et al., Increased CD226 Expression on CD8+ T Cells Is Associated with Upregulated Cytokine Production and Endothelial Cell Injury in Patients with Systemic Sclerosis. J Immunol. Aug. 1, 2015;195(3):892-900.

Bashir et al., Fusobacterium nucleatum, inflammation, and immunity: the fire within human gut. Tumour Biol. Mar. 2016;37(3):2805-10.

Bi et al., T-cell Ig and ITIM domain regulates natural killer cell activation in murine acute viral hepatitis. Hepatology. May 2014;59(5):1715-25.

Bi et al., TIGIT safeguards liver regeneration through regulating natural killer cell-hepatocyte crosstalk. Hepatology. Oct. 2014;60(4):1389-98.

Bin Dhuban et al., Coexpression of TIGIT and FCRL3 identifies Helios+ human memory regulatory T cells. J Immunol. Apr. 15, 2015;194(8):3687-96.

Blake et al., Molecular Pathways: Targeting CD96 and TIGIT for Cancer Immunotherapy. Clin Cancer Res. Nov. 1, 2016;22(21):5183-5188.

Blake et al., Suppression of Metastases Using a New Lymphocyte Checkpoint Target for Cancer Immunotherapy. Cancer Discov. Apr. 2016;6(4):446-59.

Boerman et al., Role of NKG2D, DNAM-1 and natural cytotoxicity receptors in cytotoxicity toward rhabdomyosarcoma cell lines mediated by resting and IL-15-activated human natural killer cells. Cancer Immunol Immunother. May 2015;64(5):573-83.

Boles et al., A novel molecular interaction for the adhesion of follicular CD4 T cells to follicular DC. Eur J Immunol. Mar. 2009;39(3):695-703.

Bottino et al., Identification of PVR (CD155) and Nectin-2 (CD112) as cell surface ligands for the human DNAM-1 (CD226) activating molecule. J Exp Med. Aug. 18, 2003;198(4):557-67.

Braun et al., Blockade of death receptor-mediated pathways early in the signaling cascade coincides with distinct apoptosis resistance in cutaneous T-cell lymphoma cells. J Invest Dermatol. Oct. 2007;127(10):2425-37.

Burchill et al., Memory re-differentiation and reduced lymphocyte activation in chronic HCV-infected patients receiving direct-acting antivirals. J Viral Hepat. Dec. 2015;22(12):983-91.

Burton et al., Sequential transcriptional changes dictate safe and effective antigen-specific immunotherapy. Nat Commun. Sep. 3, 2014;5:4741. 13 pages.

Butcher et al., Atherosclerosis-Driven Treg Plasticity Results in Formation of a Dysfunctional Subset of Plastic IFN?+ Th1/Tregs. Circ Res. Nov. 11, 2016;119(11):1190-1203.

Chan et al., Receptors that interact with nectin and nectin-like proteins in the immunosurveillance and immunotherapy of cancer. Curr Opin Immunol. Apr. 2012;24(2):246-51.

Chan et al., The receptors CD96 and CD226 oppose each other in the regulation of natural killer cell functions. Nat Immunol. May 2014;15(5):431-8.

Chan et al., Therapeutic antibodies for autoimmunity and inflammation. Nat Rev Immunol. May 2010;10(5):301-16.

Chauvin et al., TIGIT and PD-1 impair tumor antigen-specific CD8? T cells in melanoma patients. J Clin Invest. May 2015;125(5):2046-58.

Chen et al., TIGIT negatively regulates inflammation by altering macrophage phenotype. Immunobiology. Jan. 2016;221(1):48-55.

Chew et al., TIGIT Marks Exhausted T Cells, Correlates with Disease Progression, and Serves as a Target for Immune Restoration in HIV and SIV Infection. PLoS Pathog. Jan. 7, 2016;12(1):e1005349. 28 pages.

Chruscinski et al., Role of Regulatory T Cells (Treg) and the Treg Effector Molecule Fibrinogen-like Protein 2 in Alloimmunity and Autoimmunity. Rambam Maimonides Med J. Jul. 30, 2015;6(3):e0024. 17 pages.

De Andrade et al., DNAM-1 control of natural killer cells functions through nectin and nectin-like proteins. Immunol Cell Biol. Mar. 2014;92(3):237-44.

El-Sherbiny et al., The requirement for DNAM-1, NKG2D, and NKp46 in the natural killer cell-mediated killing of myeloma cells. Cancer Res. Sep. 15, 2007;67(18):8444-9.

Elahi et al., Atorvastatin restricts HIV replication in CD4+ T cells by upregulation of p21. AIDS. Jan. 2016;30(2):171-83.

Elhai et al., Targeting CD226/DNAX accessory molecule-1 (DNAM-1) in collagen-induced arthritis mouse models. J Inflamm (Lond). Feb. 8, 2015;12:9. 12 pages.

Fionda et al., Nitric oxide donors increase PVR/CD155 DNAM-1 ligand expression in multiple myeloma cells: role of DNA damage response activation. BMC Cancer. 2015;15(17):1-14.

Foks et al., Agonistic anti-TIGIT treatment inhibits T cell responses in LDLr deficient mice without affecting atherosclerotic lesion development. PLoS One. Dec. 20, 2013;8(12):e83134. 7 pages.

Fromentin et al., CD4+ T Cells Expressing PD-1, TIGIT and LAG-3 Contribute to HIV Persistence during ART. PLoS Pathog. Jul. 14, 2016;12(7):e1005761. 19 pages.

Fuhrman et al., Divergent Phenotypes of Human Regulatory T Cells Expressing the Receptors TIGIT and CD226. J Immunol. Jul. 1, 2015;195(1):145-55.

Gao et al., Generation and characterization of polyclonal antibodies against mouse T-cell immunoglobulin and immunoreceptor tyrosine-based inhibitory domain by DNA-based immunization. Transplant Proc. Jan.-Feb. 2014;46(1):260-5.

GenBank Accession No. NM_173799.3, Homo sapiens T cell immunoreceptor with Ig and ITIM domains (TIGIT), mRNA. Aug. 28, 2016, 5 pages.

Georgiev et al., CD155/CD226-interaction impacts on the generation of innate CD8(+) thymocytes by regulating iNKT-cell differentiation. Eur J Immunol. Apr. 2016;46(4):993-1003.

Georgiev et al., To the editor: TIGIT versus CD226: hegemony or coexistence? Eur J Immunol. Jan. 2014;44(1):307-8.

Godefroy et al., TIGIT-positive circulating follicular helper T cells display robust B-cell help functions: potential role in sickle cell alloimmunization. Haematologica. Nov. 2015;100(11):1415-25.

Goding et al., Restoring immune function of tumor-specific CD4+ T cells during recurrence of melanoma. J Immunol. May 1, 2013;190(9):4899-909.

(56) References Cited

OTHER PUBLICATIONS

Grauwet et al., Modulation of CD112 by the alphaherpesvirus gD protein suppresses DNAM-1-dependent NK cell-mediated lysis of infected cells. Proc Natl Acad Sci U S A. Nov. 11, 2014;111(45):16118-23.

Grogan et al., TIGIT inhibits CD8+ T cell effector function during chronic viral infection and cancer (TUM7P.933). J Immunol. May 1, 2014;192(Suppl 1):203.15.

Guillerey et al., Immunosurveillance and therapy of multiple myeloma are CD226 dependent. J Clin Invest. May 2015;125(5):2077-89.

Gur et al., Binding of the Fap2 protein of Fusobacterium nucleatum to human inhibitory receptor TIGIT protectstumors from immune cell attack. Immunity. Feb. 17, 2015;42(2):344-355.

Hosken et al., The effect of antigen dose on CD4+ T helper cell phenotype development in a T cell receptor-alpha beta-transgenic model. J Exp Med. Nov. 1, 1995;182(5):1579-84.

Hou et al., Recombinant soluble CD226 protein directly inhibits cancer cell proliferation in vitro. Int Immunopharmacol. Mar. 2014;19(1):119-26.

Huntington et al., DNAM-1: would the real natural killer cell please stand up! Oncotarget. Oct. 6, 2015;6(30):28537-8.

Iguchi-Manaka et al., Increased Soluble CD155 in the Serum of Cancer Patients. PLoS One. Apr. 6, 2016;11 (4):e0152982. 12 pages.

Inozume et al., Melanoma Cells Control Anti-Melanoma CTL Responses via Interaction between TIGIT and CD155 in the Effector Phase. J Invest Dermatol. Jan. 2016;136(1):255-263.

Jariwala et al., TIGIT and Helios Are Highly Expressed on CD4(+) T Cells in Sezary Syndrome Patients. J Invest Dermatol. Jan. 2017;137(1):257-260.

Jian et al., Identification and characterization of the CD226 gene promoter. J Biol Chem. Sep. 29, 2006;281(39):28731-6.

Johnston et al., The checkpoint inhibitor TIGIT limits antitumor and antiviral CD8(+) T cell responses. Oncoimmunology. May 27, 2015;4(9):e1036214. 2 pages.

Johnston et al., The immunoreceptor TIGIT regulates antitumor and antiviral CD8(+) T cell effector function. Cancer Cell. Dec. 8, 2014;26(6):923-937.

Joller et al., Cutting edge: TIGIT has T cell-intrinsic inhibitory functions. J Immunol. Feb. 1, 2011;186(3):1338-42.

Joller et al., Immune checkpoints in central nervous system autoimmunity. Immunol Rev. Jul. 2012;248(1):122-39.

Joller et al., Treg cells expressing the coinhibitory molecule TIGIT selectively inhibit proinflammatory Th1 and Th 17 cell responses. Immunity. Apr. 17, 2014;40(4):569-81.

Kamran et al., Toll-like receptor ligands induce expression of the costimulatory molecule CD155 on antigen-presenting cells. PLoS One. 2013;8(1):e54406. 13 pages.

Kinosada et al., HTLV-1 bZIP Factor Enhances T-Cell Proliferation by Impeding the Suppressive Signaling of Co-inhibitory Receptors. PLoS Pathog. Jan. 3, 2017;13(1):e1006120. With Correction: HTLV-1 bZIP Factor Enhances T-cell Proliferation by Impeding the Suppressive Signaling of Co-inhibitory Receptors. PLoS Pathog. Feb. 23, 2017;13(2):e1006228.

Klemke et al., Lack of T-cell receptor-induced signaling is crucial for CD95 ligand up-regulation and protects cutaneous T-cell lymphoma cells from activation-induced cell death. Cancer Res. May 15, 2009;69(10):4175-83. .

Kong et al., T-Cell Immunoglobulin and ITIM Domain (TIGIT) Associates with CD8+ T-Cell Exhaustion and Poor Clinical Outcome in AML Patients. Clin Cancer Res. Jun. 15, 2016;22(12):3057-66.

Kourepini et al., TIGIT Enhances Antigen-Specific Th2 Recall Responses and Allergic Disease. J Immunol. May 1, 2016;196(9):3570-80.

Kurtulus et al., TIGIT predominantly regulates the immune response via regulatory T cells. J Clin Invest. Nov. 2, 2015;125(11):4053-62.

Le Mercier et al., Beyond CTLA-4 and PD-1, the Generation Z of Negative Checkpoint Regulators. Front Immunol. Aug. 21, 2015;6:418. 15 pages.

Lenac Rovis et al., Inflammatory monocytes and NK cells play a crucial role in DNAM-1-dependent control of cytomegalovirus infection. J Exp Med. Aug. 22, 2016;213(9):1835-50.

Levin et al., Vstm3 is a member of the CD28 family and an important modulator of T-cell function. Eur J Immunol. Apr. 2011;41(4):902-15.

Li et al., CD226 as a genetic adjuvant to enhance immune efficacy induced by Ag85A DNA vaccination. Int Immunopharmacol. Mar. 2015;25(1):10-8.

Li et al., Expression of glucocorticoid induced TNF receptor family related protein (GITR) on peripheral T cells from normal human donors and patients with non-infectious uveitis. J Autoimmun. Aug. 2003;21(1):83-92.

Li et al., T-cell immunoglobulin and ITIM domain (TIGIT) receptor/ poliovirus receptor (PVR) ligand engagement suppresses interferon-? production of natural killer cells via β-arrestin 2-mediated negative signaling. J Biol Chem. Jun. 20, 2014;289(25):17647-57.

Liu et al., Crystal structure of cell adhesion molecule nectin-2/ CD112 and its binding to immune receptor DNAM-1/CD226. J Immunol. Jun. 1, 2012;188(11):5511-20.

Liu et al., Recruitment of Grb2 and SHIP1 by the ITT-like motif of TIGIT suppresses granule polarization and cytotoxicity of NK cells. Cell Death Differ. Mar. 2013;20(3):456-64.

Lozano et al., The TIGIT/CD226 axis regulates human T cell function. J Immunol. Apr. 15, 2012;188(8):3869-75.

Mahnke et al., TIGIT-CD155 Interactions in Melanoma: A Novel Co-Inhibitory Pathway with Potential for Clinical Intervention. J Invest Dermatol. Jan. 2016;136(1):9-11.

Manieri et al., TIGIT: A Key Inhibitor of the Cancer Immunity Cycle. Trends Immunol. Jan. 2017;38(1):20-28.

Martinet et al., Balancing natural killer cell activation through paired receptors. Nat Rev Immunol. Apr. 2015;15(4):243-54.

Martinet et al., DNAM-1 expression marks an alternative program of NK cell maturation. Cell Rep. Apr. 7, 2015;11(1):85-97.

Mirjacic Martinovic et al., Decreased expression of NKG2D, NKp46, DNAM-1 receptors, and intracellular perforin and STAT-1 effector molecules in NK cells and their dim and bright subsets in metastatic melanoma patients. Melanoma Res. Aug. 2014;24(4):295-304.

Moorman et al., Tim-3 pathway controls regulatory and effector T cell balance during hepatitis C virus infection. J Immunol. Jul. 15, 2012;189(2):755-66.

Nagumo et al., Increased CD112 expression in methylcholanthrene-induced tumors in CD155-deficient mice. PLoS One. Nov. 10, 2014;9(11):e112415. 7 pages.

Ni et al., Resistance to activation-induced cell death and bystander cytotoxicity via the Fas/Fas ligand pathway are implicated in the pathogenesis of cutaneous T cell lymphomas. J Invest Dermatol. Apr. 2005;124(4):741-50.

Nishiwada et al., Clinical significance of CD155 expression in human pancreatic cancer. Anticancer Res. Apr. 2015;35(4):2287-97.

Oshima et al., Nectin-2 is a potential target for antibody therapy of breast and ovarian cancers. Mol Cancer. Jun. 12, 2013;12:60. 13 pages.

Panka et al., Variable region framework differences result in decreased or increased affinity of variant anti-digoxin antibodies. Proc Natl Acad Sci U S A. May 1988;85(9):3080-4.

Pearson, Tragic drug trial spotlights potent molecule. Nature. Retrieved online at: https://www.nature.com/news/2006/060313/full/060313-17.html. Mar. 17, 2006.

Peng et al., Altered expression of CD226 and CD96 on natural killer cells in patients with pancreatic cancer. Oncotarget. Oct. 11, 2016;7(41):66586-66594.

Piedavent-Salomon et al., Multiple sclerosis associated genetic variants of CD226 impair regulatory T cell function. Brain. Nov. 2015;138(Pt 11):3263-74.

Pirenne, TIGIT-positive circulating follicular helper T cells and sickle cell alloimmunization. Haematologica. Nov. 2015;100(11):1371-3.

Qu et al., Loss of CD155 expression predicts poor prognosis in hepatocellular carcinoma. Histopathology. Apr. 2015;66(5):706-14.

Rudikoff et al., Single amino acid substitution altering antigen-binding specificity. Proc Natl Acad Sci U S A. Mar. 1982;79(6):1979-83.

(56) References Cited

OTHER PUBLICATIONS

Rueda et al., Effect of chorioamnionitis on regulatory T cells in moderate/late preterm neonates. Hum Immunol. Jan. 2015;76(1):65-73.
Ruggeri et al., Animal models of disease: pre-clinical animal models of cancer and their applications and utility in drug discovery. Biochem Pharmacol. Jan. 1, 2014;87(1):150-61.
Samanta et al., Nectin family of cell-adhesion molecules: structural and molecular aspects of function and specificity. Cell Mol Life Sci. Feb. 2015;72(4):645-58.
Samanta et al., Structural, mutational and biophysical studies reveal a canonical mode of molecular recognition between immune receptor TIGIT and nectin-2. Mol Immunol. Jan. 2017;81:151-159.
Sanmamed et al., Agonists of Co-stimulation in Cancer Immunotherapy Directed Against CD137, OX40, GITR, CD27, CD28, and ICOS. Seminars in Oncology. Aug. 2015;42(4):640-655.
Serr et al., Type 1 diabetes vaccine candidates promote human Foxp3(+)Treg induction in humanized mice. Nat Commun. Mar. 15, 2016;7:10991. 18 pages.
Seth et al., Abundance of follicular helper T cells in Peyer's patches is modulated by CD155. Eur J Immunol. Nov. 2009;39(11):3160-70.
Sheiko et al., CD4+ and CD8+ T Cell Activation in Children with Hepatitis C. J Pediatr. Mar. 2016;170:142-8.e1.
Shibuya et al., CD226 (DNAM-1) is involved in lymphocyte function-associated antigen 1 costimulatory signal for naive T cell differentiation and proliferation. J Exp Med. Dec. 15, 2003;198(12):1829-39.
Shibuya et al., DNAM-1, a novel adhesion molecule involved in the cytolytic function of T lymphocytes. Immunity. Jun. 1996;4(6):573-81.
Shon et al., Survivin reduces activation-induced T cell death in G1 phase. Mol Cells. Oct. 31, 2003;16(2):147-53.
Siegel et al., High efficiency recovery and epitope-specific sorting of an scFv yeast display library. J Immunol Methods. Mar. 2004;286(1-2):141-53.
Siew et al., Oxaliplatin regulates expression of stress ligands in ovarian cancer cells and modulates their susceptibility to natural killer cell-mediated cytotoxicity. Int Immunol. Dec. 2015;27(12):621-32.
Smith et al., Sensitivity of dendritic cells to NK-mediated lysis depends on the inflammatory environment and is modulated by CD54/CD226-driven interactions. J Leukoc Biol. Oct. 2016;100(4):781-789.
Solomon et al., TIGIT: a novel immunotherapy target moving from bench to bedside. Cancer Immunol Immunother. Nov. 2018;67(11):1659-1667.
Son et al., Nectin-2 (CD112) Is Expressed on Outgrowth Endothelial Cells and Regulates Cell Proliferation and Angiogenic Function. PLoS One. Sep. 27, 2016;11(9):e0163301. 16 pages.
Stanietsky et al., Mouse TIGIT inhibits NK-cell cytotoxicity upon interaction with PVR. Eur J Immunol. Aug. 2013;43(8):2138-50.
Stanietsky et al., Paired NK cell receptors controlling NK cytotoxicity. FEBS Lett. Dec. 15, 2010;584(24):4895-900.
Stanietsky et al., The interaction of TIGIT with PVR and PVRL2 inhibits human NK cell cytotoxicity. Proc Natl Acad Sci U S A. Oct. 20, 2009;106(42):17858-63.
Stein et al., The paired receptors TIGIT and DNAM-1 as targets for therapeutic antibodies. Hum Antibodies. 2017;25(3-4):111-119.
Stengel et al., Structure of TIGIT immunoreceptor bound to poliovirus receptor reveals a cell-cell adhesion and signaling mechanism that requires cis-trans receptor clustering. Proc Natl Acad Sci U S A. Apr. 3, 2012;109(14):5399-404.
Sun et al., Expression regulation of co-inhibitory molecules on human natural killer cells in response to cytokine stimulations. Cytokine. Jan. 2014;65(1):33-41.
Tahara-Hanaoka et al., Functional characterization of DNAM-1 (CD226) interaction with its ligands PVR (CD155) and nectin-2 (PRR-2/CD112). Int Immunol. Apr. 2004;16(4):533-8.

Tassi et al., Early Effector T Lymphocytes Coexpress Multiple Inhibitory Receptors in Primary Non-Small Cell Lung Cancer. Cancer Res. Feb. 15, 2017;77(4):851-861.
Tauriainen et al., Perturbed CD8+ T cell TIGIT/CD226/PVR axis despite early initiation of antiretroviral treatment in HIV infected individuals. Scientific Reports. Jan. 13, 2017;7(40354):1-14.
Vitetta et al., Immunology. Considering therapeutic antibodies. Science. Jul. 21, 2006;313(5785):308-9.
Wang et al., NK cells play a significant role in immunosurveillance at the early stage of MLL-AF9 acute myeloid leukemia via CD226/CD155 interactions. Sci China Life Sci. Dec. 2015;58(12):1288-98.
Wang et al., TIGIT expression levels on human NK cells correlate with functional heterogeneity among healthy individuals. Eur J Immunol. Oct. 2015;45(10):2886-97.
Weinmann, Cancer Immunotherapy: Selected Targets and Small-Molecule Modulators. ChemMedChem. Mar. 4, 2016;11(5):450-66. doi: 10.1002/cmdc.201500566. Epub Feb. 2, 2016. Review. Erratum in: ChemMedChem. Jul. 19, 2016;11(14 ):1576.
White et al., Tr1-Like T Cells—An Enigmatic Regulatory T Cell Lineage. Front Immunol. Sep. 14, 2016;7:355. 7 pages.
Wu et al., DNAM-1-based chimeric antigen receptors enhance T cell effector function and exhibit in vivo efficacy against melanoma. Cancer Immunol Immunother. Apr. 2015;64(4):409-18.
Xie et al., Expression of immune checkpoints in T cells of esophageal cancer patients. Oncotarget. Sep. 27, 2016;7(39):63669-63678.
Xu et al., Addressing polyspecificity of antibodies selected from an in vitro yeast presentation system: a FACS-based, high-throughput selection and analytical tool. Protein Eng Des Sel. Oct. 2013;26(10):663-70.
Yamamoto et al., Comprehensive analysis of FOXP3 mRNA expression in leukemia and transformed cell lines. Leuk Res. Apr. 2008;32(4):651-8.
Yamashita-Kanemaru et al., CD155 (PVR/Necl5) mediates a costimulatory signal in CD4+ T cells and regulates allergic inflammation. J Immunol. Jun. 15, 2015;194(12):5644-53.
Yang et al., DNA methylation and childhood asthma in the inner city. J Allergy Clin Immunol. Jul. 2015;136(1):69-80.
Yano et al., Defucosylated anti CC chemokine receptor 4 monoclonal antibody combined with immunomodulatory cytokines: a novel immunotherapy for aggressive/refractory Mycosis fungoides and Sezary syndrome. Clin Cancer Res. Nov. 1, 2007;13(21):6494-500.
Yasuma et al., HTLV-1 bZIP Factor Impairs Anti-viral Immunity by Inducing Co-inhibitory Molecule, T Cell Immunoglobulin and ITIM Domain (TIGIT). PLoS Pathog. Jan. 6, 2016;12(1):e1005372. 22 pages.
Yu et al., The surface protein TIGIT suppresses T cell activation by promoting the generation of mature immunoregulatory dendritic cells. Nat Immunol. Jan. 2009;10(1):48-57.
Zhang et al., CD226 ligation protects against EAE by promoting IL-10 expression via regulation of CD4+ T cell differentiation. Oncotarget. Apr. 12, 2016;7(15):19251-64.
Zhang et al., DNAM-1 controls NK cell activation via an ITT-like motif. J Exp Med. Nov. 16, 2015;212(12):2165-82.
Zhang et al., Genome-wide DNA methylation analysis identifies hypomethylated genes regulated by FOXP3 in human regulatory T cells. Blood. Oct. 17, 2013;122(16):2823-36.
Zhang et al., Immunoreceptor TIGIT inhibits the cytotoxicity of human cytokine-induced killer cells by interacting with CD155. Cancer Immunol Immunother. Mar. 2016;65(3):305-14.
Zhang et al., Increased expression of TIGIT on CD4+ T cells ameliorates immune-mediated bone marrow failure of aplastic anemia. J Cell Biochem. Nov. 2014;115(11):1918-27.
Zhang et al., MicroRNAs in CD4(+) T cell subsets are markers of disease risk and T cell dysfunction in individuals at risk for type 1 diabetes. J Autoimmun. Apr. 2016;68:52-61.
Zhang et al., Profiling the dynamic expression of checkpoint molecules on cytokine-induced killer cells from non-small-cell lung cancer patients. Oncotarget. Jul. 12, 2016;7(28):43604-43615.
Zhao et al., TIGIT overexpression diminishes the function of CD4 T cells and ameliorates the severity of rheumatoid arthritis in mouse models. Exp Cell Res. Jan. 1, 2016;340(1):132-8.

(56) References Cited

OTHER PUBLICATIONS

Zhu et al., Identification of CD112R as a novel checkpoint for human T cells. J Exp Med. Feb. 8, 2016;213(2):167-76.
International Search Report and Written Opinion for Application No. PCT/US2018/025460, dated Aug. 21, 2018, 12 pages.
International Search Report for Application No. PCT/US2016/054484, dated Jan. 25, 2017, 22 pages.
Invitation to Pay Additional Fees for Application No. PCT/US2016/054484, dated Dec. 2, 2016, 11 pages.
U.S. Appl. No. 14/221,160, filed Mar. 20, 2014, 102 pages.
U.S. Appl. No. 14/228,172, filed Mar. 27, 2014, 101 pages.
U.S. Appl. No. 14/228,173, filed Mar. 27, 2014, 102 pages.
U.S. Appl. No. 14/699,845, filed Apr. 29, 2015, 100 pages.
U.S. Office Action for U.S. Appl. No. 15/430,998, dated Mar. 20, 2017, 7 pages.

\* cited by examiner

SEQUENCE LISTING

<160> NUMBER OF SEQ ID NOS: 144

<210> SEQ ID NO 1
<211> LENGTH: 244
<212> TYPE: PRT
<213> ORGANISM: Homo sapiens
<220> FEATURE:
<221> NAME/KEY: MISC_FEATURE
<222> LOCATION: (1)..(244)
<223> OTHER INFORMATION: /note="hTIGIT"

<400> SEQUENCE: 1

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu

```
            115                 120                 125
Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 2
<211> LENGTH: 245
<212> TYPE: PRT
<213> ORGANISM: Macaca fascicularis
<220> FEATURE:
<221> NAME/KEY: MISC_FEATURE
<222> LOCATION: (1)..(245)
<223> OTHER INFORMATION: /note="cTIGIT"

<400> SEQUENCE: 2

Met Arg Trp Cys Leu Phe Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Lys Lys Gly Gly Ser Val Ile Leu Gln Cys His Leu Ser
        35                  40                  45

Ser Thr Met Ala Gln Val Thr Gln Val Asn Trp Glu Gln His Asp His
    50                  55                  60

Ser Leu Leu Ala Ile Arg Asn Ala Glu Leu Gly Trp His Ile Tyr Pro
65                  70                  75                  80

Ala Phe Lys Asp Arg Val Ala Pro Gly Pro Gly Leu Gly Leu Thr Leu
                85                  90                  95

Gln Ser Leu Thr Met Asn Asp Thr Gly Glu Tyr Phe Cys Thr Tyr His
            100                 105                 110

Thr Tyr Pro Asp Gly Thr Tyr Arg Gly Arg Ile Phe Leu Glu Val Leu
        115                 120                 125

Glu Ser Ser Val Ala Glu His Ser Ala Arg Phe Gln Ile Pro Leu Leu
    130                 135                 140

Gly Ala Met Ala Met Met Leu Val Val Ile Cys Ile Ala Val Ile Val
145                 150                 155                 160

Val Val Val Leu Ala Arg Lys Lys Lys Ser Leu Arg Ile His Ser Val
                165                 170                 175

Glu Ser Gly Leu Gln Arg Lys Ser Thr Gly Gln Glu Glu Gln Ile Pro
            180                 185                 190

Ser Ala Pro Ser Pro Pro Gly Ser Cys Val Gln Ala Glu Ala Ala Pro
        195                 200                 205

Ala Gly Leu Cys Gly Glu Gln Gln Gly Asp Asp Cys Ala Glu Leu His
    210                 215                 220
```

```
Asp Tyr Phe Asn Val Leu Ser Tyr Arg Ser Leu Gly Ser Cys Ser Phe
225                 230                 235                 240

Phe Thr Glu Thr Gly
                245
```

<210> SEQ ID NO 3
<211> LENGTH: 241
<212> TYPE: PRT
<213> ORGANISM: Mus musculus
<220> FEATURE:
<221> NAME/KEY: MISC_FEATURE
<222> LOCATION: (1)..(241)
<223> OTHER INFORMATION: /note="mTIGIT"

<400> SEQUENCE: 3

```
Met His Gly Trp Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
                20                  25                  30

Asn Ile Ser Ala Glu Glu Gly Gly Ser Val Ile Leu Gln Cys His Phe
            35                  40                  45

Ser Ser Asp Thr Ala Glu Val Thr Gln Val Asp Trp Lys Gln Gln Asp
50                  55                  60

Gln Leu Leu Ala Ile Tyr Ser Val Asp Leu Gly Trp His Val Ala Ser
65                  70                  75                  80

Val Phe Ser Asp Arg Val Val Pro Gly Pro Ser Leu Gly Leu Thr Phe
                85                  90                  95

Gln Ser Leu Thr Met Asn Asp Thr Gly Glu Tyr Phe Cys Thr Tyr His
            100                 105                 110

Thr Tyr Pro Gly Gly Ile Tyr Lys Gly Arg Ile Phe Leu Lys Val Gln
        115                 120                 125

Glu Ser Ser Val Ala Gln Phe Gln Thr Ala Pro Leu Gly Gly Thr Met
130                 135                 140

Ala Ala Val Leu Gly Leu Ile Cys Leu Met Val Thr Gly Val Thr Val
145                 150                 155                 160

Leu Ala Arg Lys Lys Ser Ile Arg Met His Ser Ile Glu Ser Gly Leu
                165                 170                 175

Gly Arg Thr Glu Ala Glu Pro Gln Glu Trp Asn Leu Arg Ser Leu Ser
            180                 185                 190

Ser Pro Gly Ser Pro Val Gln Thr Gln Thr Ala Pro Ala Gly Pro Cys
        195                 200                 205

Gly Glu Gln Ala Glu Asp Asp Tyr Ala Asp Pro Gln Glu Tyr Phe Asn
    210                 215                 220

Val Leu Ser Tyr Arg Ser Leu Glu Ser Phe Ile Ala Val Ser Lys Thr
225                 230                 235                 240

Gly
```

<210> SEQ ID NO 4
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB1-IgG4; VH"

<400> SEQUENCE: 4

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ala Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser
        115                 120

<210> SEQ ID NO 5
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB2-IgG4; VH"

<400> SEQUENCE: 5

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Lys Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser
        115                 120

<210> SEQ ID NO 6
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB3-IgG4; VH"

<400> SEQUENCE: 6

-continued

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser
        115                 120

<210> SEQ ID NO 7
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB4-IgG4; VH"

<400> SEQUENCE: 7

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Ala Asn Tyr Tyr Gly Gly Ala Trp Ala Phe Asp Pro
            100                 105                 110

Trp Gly Gln Gly Thr Leu Val Thr Val Ser Ser
        115                 120

<210> SEQ ID NO 8
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB5-IgG4; VH"

<400> SEQUENCE: 8

Gln Leu Gln Leu Gln Glu Ser Gly Pro Gly Leu Val Lys Pro Ser Glu
```

```
1               5                   10                  15
Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
                100                 105                 110

Trp Gly Gln Gly Thr Leu Val Thr Val Ser Ser
            115                 120
```

<210> SEQ ID NO 9
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB6-IgG4; VH"

<400> SEQUENCE: 9

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Glu Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Gly Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
                100                 105                 110

Trp Gly Gln Gly Thr Met Val Thr Val Ser Ser
            115                 120
```

<210> SEQ ID NO 10
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB7-IgG4; VH"

<400> SEQUENCE: 10

```
Gln Val Gln Leu Gln Glu Ser Gly Pro Gly Leu Val Lys Pro Ser Gln
1               5                   10                  15
```

-continued

```
Thr Leu Ser Leu Thr Cys Thr Val Ser Gly Gly Ser Ile Glu Ser Gly
            20                  25                  30

Val Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser
        115                 120
```

<210> SEQ ID NO 11
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB8-IgG4; VH"

<400> SEQUENCE: 11

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ala Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Gln Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser
        115                 120
```

<210> SEQ ID NO 12
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB9-IgG4; VH"

<400> SEQUENCE: 12

```
Gln Val Gln Leu Gln Glu Ser Gly Pro Gly Leu Val Lys Pro Ser Gln
1               5                   10                  15
```

```
Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser
        115                 120

<210> SEQ ID NO 13
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB10-IgG4; VH"

<400> SEQUENCE: 13

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser
        115                 120

<210> SEQ ID NO 14
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB11-IgG4; VH"

<400> SEQUENCE: 14

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
```

```
                  20                  25                  30

Leu Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser
        115                 120

<210> SEQ ID NO 15
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB12-IgG4; VH"

<400> SEQUENCE: 15

Gln Val Gln Leu Gln Glu Ser Gly Pro Gly Leu Val Lys Pro Ser Gln
1               5                   10                  15

Thr Leu Ser Leu Thr Cys Thr Ala Ser Gly Gly Ser Ile Glu Ser Gly
                20                  25                  30

Leu Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser
        115                 120

<210> SEQ ID NO 16
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB13-IgG4; VH"

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
                20                  25                  30
```

-continued

Tyr Met His Trp Val Arg Gln Ala Pro Gly Gln Gly Leu Glu Trp Met
            35                  40                  45

Gly Ile Ile Asn Pro Ser Leu Gly Leu Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser
            115                 120

<210> SEQ ID NO 17
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB14-IgG4; VH"

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Met His Trp Val Arg Gln Ala Pro Gly Gln Gly Leu Glu Trp Met
            35                  40                  45

Gly Ile Ile Asn Pro Ser Leu Gly Leu Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser
            115                 120

<210> SEQ ID NO 18
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB15-IgG4; VH"

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Glu Tyr
            20                  25                  30

```
            Tyr Met His Trp Val Arg Gln Ala Pro Gly Gln Gly Leu Glu Trp Met
                         35                   40                  45

Gly Ile Ile Asn Pro Ser Ile Gly Leu Thr Ser Tyr Ala Arg Lys Phe
             50                      55                  60

Gln Gly Arg Val Thr Met Thr Arg Asp Thr Ser Thr Ser Thr Val Tyr
             65                  70                  75                  80

Met Glu Leu Ser Ser Leu Arg Ser Glu Asp Thr Ala Val Tyr Tyr Cys
                             85                  90                  95

Ala Arg Gly Gly Arg Thr Thr Trp Ile Gly Ala Phe Asp Ile Trp Gly
                        100                 105                 110

Gln Gly Thr Met Val Thr Val Ser Ser
                        115                 120
```

<210> SEQ ID NO 19
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB16-IgG4; VH"

<400> SEQUENCE: 19

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Arg Glu Tyr
            20                  25                  30

Tyr Met His Trp Val Arg Gln Ala Pro Gly Gln Gly Leu Glu Trp Met
             35                  40                  45

Gly Ile Ile Asn Pro Ser Ile Gly Leu Thr Ser Tyr Ala Arg Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Arg Thr Thr Trp Ile Gly Ala Leu Asp Ile Trp Gly
            100                 105                 110

Gln Gly Thr Met Val Thr Val Ser Ser
            115                 120
```

<210> SEQ ID NO 20
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB17-IgG4; VH"

<400> SEQUENCE: 20

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Pro Ala Tyr
            20                  25                  30

Tyr Ile His Trp Val Arg Gln Ala Pro Gly Gln Gly Leu Glu Trp Met
```

```
                35                  40                  45

Gly Ile Ile Asn Pro Ser Leu Gly Leu Thr Ser Tyr Ala Arg Lys Phe
            50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Leu Asp Ile Trp Gly
            100                 105                 110

Gln Gly Thr Met Val Thr Val Ser Ser
            115                 120

<210> SEQ ID NO 21
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB18-IgG4; VH"

<400> SEQUENCE: 21

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Pro Ala Tyr
                20                  25                  30

Tyr Met His Trp Val Arg Gln Ala Pro Gly Gln Gly Leu Glu Trp Met
            35                  40                  45

Gly Ile Ile Asn Pro Ser Leu Gly Leu Thr Ser Tyr Ala Arg Lys Phe
            50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser
            115                 120

<210> SEQ ID NO 22
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB19-IgG4; VH"

<400> SEQUENCE: 22

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser His
                20                  25                  30

Tyr Met Gly Trp Val Arg Gln Ala Pro Gly Gln Gly Leu Glu Trp Met
            35                  40                  45
```

```
Gly Val Ile Asn Pro Ser Met Gly Ala Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
                100                 105                 110

Trp Gly Gln Gly Thr Met Val Thr Val Ser Ser
            115                 120
```

<210> SEQ ID NO 23
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB20-IgG4; VH"

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Tyr Met Gly Trp Val Arg Gln Ala Pro Gly Gln Gly Leu Glu Trp Val
            35                  40                  45

Gly Ile Ile Asn Pro Ser Met Gly Ala Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
                100                 105                 110

Trp Gly Gln Gly Thr Met Val Thr Val Ser Ser
            115                 120
```

<210> SEQ ID NO 24
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB21-IgG4; VH"

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Tyr Met Gly Trp Val Arg Gln Ala Pro Gly Gln Gly Leu Glu Trp Met
            35                  40                  45
```

```
Gly Ile Ile Asn Pro Ser Met Gly Ala Thr Ser Tyr Thr Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
                100                 105                 110

Trp Gly Gln Gly Thr Met Val Thr Val Ser Ser
            115                 120
```

<210> SEQ ID NO 25
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB1-IgG4, MAB2-IgG4,
      MAB3-IgG4, MAB4-IgG4, MAB5-IgG4; VL"

<400> SEQUENCE: 25

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Phe Asn Leu Pro Thr
                85                  90                  95

Phe Gly Gly Gly Thr Lys Val Glu Ile Lys
            100                 105
```

<210> SEQ ID NO 26
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB6-IgG4, MAB7-IgG4,
      MAB8-IgG4, MAB9-IgG4, MAB10-IgG4, MAB11-IgG4, MAB12-IgG4; VL"

<400> SEQUENCE: 26

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Thr Val Arg Pro
                85                  90                  95

Pro Leu Thr Phe Gly Gly Gly Thr Lys Val Glu Ile Lys
            100                 105

<210> SEQ ID NO 27
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB13-IgG4, MAB14-IgG4,
      MAB15-IgG4, MAB16-IgG4, MAB17-IgG4, MAB18-IgG4; VL"

<400> SEQUENCE: 27

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Val Val Trp Pro Pro
                85                  90                  95

Leu Thr Phe Gly Gly Gly Thr Lys Val Glu Ile Lys
            100                 105

<210> SEQ ID NO 28
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB19-IgG4, MAB20-IgG4,
      MAB21-IgG4; VL"

<400> SEQUENCE: 28

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg His Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ile Val Phe Pro Trp

Thr Phe Gly Gly Gly Thr Lys Val Glu Ile Lys
            100                 105

<210> SEQ ID NO 29
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB1-IgG4, MAB2-IgG4,
      MAB3-IgG4, MAB5-IgG4; H3-IMGT"

<400> SEQUENCE: 29

Ala Arg Asp Ala Asn Tyr Tyr Gly Ser Ala Trp Ala Phe Asp Pro
1               5                   10                  15

<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB4-IgG4; H3-IMGT"

<400> SEQUENCE: 30

Ala Arg Asp Ala Asn Tyr Tyr Gly Gly Ala Trp Ala Phe Asp Pro
1               5                   10                  15

<210> SEQ ID NO 31
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB6-IgG4, MAB7-IgG4,
      MAB8-IgG4, MAB9-IgG4; H3-IMGT"

<400> SEQUENCE: 31

Ala Arg Asp Gly Val Leu Thr Leu Asn Lys Arg Ser Phe Asp Ile
1               5                   10                  15

<210> SEQ ID NO 32
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB10-IgG4, MAB11-IgG4,
      MAB12-IgG4; H3-IMGT"

<400> SEQUENCE: 32

Ala Arg Asp Gly Val Leu Ala Leu Asn Lys Arg Ser Phe Asp Ile
1               5                   10                  15

<210> SEQ ID NO 33
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB13-IgG4, MAB14-IgG4,
      MAB15-IgG4, MAB18-IgG4; H3-IMGT"

<400> SEQUENCE: 33

Ala Arg Gly Gly Arg Thr Thr Trp Ile Gly Ala Phe Asp Ile
1               5                   10

<210> SEQ ID NO 34
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB16-IgG4, MAB17-IgG4;
      H3-IMGT"

<400> SEQUENCE: 34

Ala Arg Gly Gly Arg Thr Thr Trp Ile Gly Ala Leu Asp Ile
1               5                   10

<210> SEQ ID NO 35
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB19-IgG4, MAB20-IgG4,
      MAB21-IgG4; H3-IMGT"

<400> SEQUENCE: 35

Ala Arg Leu His Val Ser Gly Ser Tyr Tyr Pro Ala Tyr Leu Asp Tyr
1               5                   10                  15

<210> SEQ ID NO 36
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB1-IgG4; H2-Kabat"

<400> SEQUENCE: 36

Ser Ile Tyr Tyr Ser Gly Ala Thr Phe Tyr Asn Pro Ser Leu Lys Ser
1               5                   10                  15

<210> SEQ ID NO 37
<211> LENGTH: 16

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB2-IgG4, MAB3-IgG4,
      MAB4-IgG4; H2-Kabat"

<400> SEQUENCE: 37

Ser Ile Tyr Tyr Ser Gly Ser Thr Phe Tyr Asn Pro Ser Leu Lys Ser
1               5                   10                  15

<210> SEQ ID NO 38
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB5-IgG4; H2-Kabat"

<400> SEQUENCE: 38

Ser Ile Tyr Tyr Ser Gly Ser Thr Phe Tyr Asn Pro Ser Leu Lys Gly
1               5                   10                  15

<210> SEQ ID NO 39
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB6-IgG4; H2-Kabat"

<400> SEQUENCE: 39

Ser Ile Tyr Tyr Ser Gly Gly Thr Tyr Tyr Asn Pro Ser Leu Lys Ser
1               5                   10                  15

<210> SEQ ID NO 40
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB7-IgG4, MAB9-IgG4,
      MAB10-IgG4, MAB11-IgG4, MAB12-IgG4; H2-Kabat"

<400> SEQUENCE: 40

Ser Ile Tyr Tyr Ser Gly Ser Thr Tyr Tyr Asn Pro Ser Leu Lys Ser
1               5                   10                  15

<210> SEQ ID NO 41
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                           Synthetic peptide"
<220> FEATURE:
<221> NAME/KEY: source
<223> OTHER INFORMATION: /note="Synthetic - MAB8-IgG4; H2-Kabat"

<400> SEQUENCE: 41

Ser Ile Tyr Tyr Ser Gly Gln Thr Tyr Tyr Asn Pro Ser Leu Lys Ser
1               5                   10                  15

<210> SEQ ID NO 42
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB13-IgG4, MAB14-IgG4;
      H2-Kabat"

<400> SEQUENCE: 42

Ile Ile Asn Pro Ser Leu Gly Leu Thr Ser Tyr Ala Gln Lys Phe Gln
1               5                   10                  15

Gly

<210> SEQ ID NO 43
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB15-IgG4, MAB16-IgG4;
      H2-Kabat"

<400> SEQUENCE: 43

Ile Ile Asn Pro Ser Ile Gly Leu Thr Ser Tyr Ala Arg Lys Phe Gln
1               5                   10                  15

Gly

<210> SEQ ID NO 44
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB17-IgG4, MAB18-IgG4;
      H2-Kabat"

<400> SEQUENCE: 44

Ile Ile Asn Pro Ser Leu Gly Leu Thr Ser Tyr Ala Arg Lys Phe Gln
1               5                   10                  15

Gly

<210> SEQ ID NO 45
<211> LENGTH: 17
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB19-IgG4; H2-Kabat"

<400> SEQUENCE: 45

Val Ile Asn Pro Ser Met Gly Ala Thr Ser Tyr Ala Gln Lys Phe Gln
1               5                   10                  15
Gly

<210> SEQ ID NO 46
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB20-IgG4; H2-Kabat"

<400> SEQUENCE: 46

Ile Ile Asn Pro Ser Met Gly Ala Thr Ser Tyr Ala Gln Lys Phe Gln
1               5                   10                  15
Gly

<210> SEQ ID NO 47
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB21-IgG4; H2-Kabat"

<400> SEQUENCE: 47

Ile Ile Asn Pro Ser Met Gly Ala Thr Ser Tyr Thr Gln Lys Phe Arg
1               5                   10                  15
Gly

<210> SEQ ID NO 48
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB1-IgG4; H1-Chothia +
      Kabat"

<400> SEQUENCE: 48

Gly Ser Ile Thr Ser Ser Ser Tyr Tyr Trp Gly
1               5                   10

<210> SEQ ID NO 49
<211> LENGTH: 11
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB2-IgG4; H1-Chothia +
      Kabat"

<400> SEQUENCE: 49

Gly Ser Ile Ser Ser Ser Lys Tyr Tyr Trp Gly
1               5                   10

<210> SEQ ID NO 50
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB3-IgG4, MAB4-IgG4,
      MAB5-IgG4; H1-Chothia + Kabat"

<400> SEQUENCE: 50

Gly Ser Ile Ser Ser Thr Ser His Tyr Trp Gly
1               5                   10

<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB6-IgG4; H1-Chothia +
      Kabat"

<400> SEQUENCE: 51

Gly Ser Ile Glu Ser Gly Ser Tyr Tyr Trp Gly
1               5                   10

<210> SEQ ID NO 52
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB7-IgG4; H1-Chothia +
      Kabat"

<400> SEQUENCE: 52

Gly Ser Ile Glu Ser Gly Val Tyr Tyr Trp Gly
1               5                   10

<210> SEQ ID NO 53
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: source
<223> OTHER INFORMATION: /note="Synthetic - MAB8-IgG4; H1-Chothia +
      Kabat"

<400> SEQUENCE: 53

Gly Ser Ile Ala Ser Gly Ser Tyr Tyr Trp Gly
1               5                   10

<210> SEQ ID NO 54
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB9-IgG4, MAB10-IgG4,
      MAB11-IgG4, MAB12-IgG4; H1-Chothia + Kabat"

<400> SEQUENCE: 54

Gly Ser Ile Glu Ser Gly Leu Tyr Tyr Trp Gly
1               5                   10

<210> SEQ ID NO 55
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - IgG4; Constant, S228P hinge
      stabilizing"

<400> SEQUENCE: 55

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
```

```
              180                 185                 190
Trp Leu Asn Gly Lys Glu Tyr Lys Cys Lys Val Ser Asn Lys Gly Leu
            195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 56
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - IgG4; Constant S228P, N297A,
      C terminal Lys deleted"

<400> SEQUENCE: 56

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Ala Ser Thr Tyr Arg Val Val Ser Val Leu Thr Val Leu His Gln Asp
```

```
                    180                 185                 190
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
            325

<210> SEQ ID NO 57
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - IgG1; Constant (G1m(3)
      allotype)"

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

```
                180               185               190
His Gln Asp Trp Leu Asn Gly Lys Glu Tyr Lys Cys Lys Val Ser Asn
                195               200               205
Lys Ala Leu Pro Ala Pro Ile Glu Lys Thr Ile Ser Lys Ala Lys Gly
        210               215               220
Gln Pro Arg Glu Pro Gln Val Tyr Thr Leu Pro Pro Ser Arg Glu Glu
225               230               235               240
Met Thr Lys Asn Gln Val Ser Leu Thr Cys Leu Val Lys Gly Phe Tyr
                245               250               255
Pro Ser Asp Ile Ala Val Glu Trp Glu Ser Asn Gly Gln Pro Glu Asn
            260               265               270
Asn Tyr Lys Thr Thr Pro Pro Val Leu Asp Ser Asp Gly Ser Phe Phe
                275               280               285
Leu Tyr Ser Lys Leu Thr Val Asp Lys Ser Arg Trp Gln Gln Gly Asn
            290               295               300
Val Phe Ser Cys Ser Val Met His Glu Ala Leu His Asn His Tyr Thr
305               310               315               320
Gln Lys Ser Leu Ser Leu Ser Pro Gly Lys
                325               330

<210> SEQ ID NO 58
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB13-IgG4; H1-Chothia +
      Kabat"

<400> SEQUENCE: 58

Tyr Thr Phe Gly Asn Tyr Tyr Met His
1               5

<210> SEQ ID NO 59
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB14-IgG4, MAB18-IgG4;
      H1-Chothia + Kabat"

<400> SEQUENCE: 59

Tyr Thr Phe Pro Ala Tyr Tyr Met His
1               5

<210> SEQ ID NO 60
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB15-IgG4, MAB16-IgG4;
```

H1-Chothia + Kabat"

<400> SEQUENCE: 60

Tyr Thr Phe Arg Glu Tyr Tyr Met His
1               5

<210> SEQ ID NO 61
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB17-IgG4; H1-Chothia +
      Kabat"

<400> SEQUENCE: 61

Tyr Thr Phe Pro Ala Tyr Tyr Ile His
1               5

<210> SEQ ID NO 62
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB19-IgG4, MAB20-IgG4,
      MAB21-IgG4; H1-Chothia + Kabat"

<400> SEQUENCE: 62

Tyr Thr Phe Thr Ser His Tyr Met Gly
1               5

<210> SEQ ID NO 63
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB1-IgG4, MAB2-IgG4,
      MAB3-IgG4, MAB4-IgG4, MAB5-IgG4; L3 - Chothia/Kabat/IMGT"

<400> SEQUENCE: 63

Gln Gln His Phe Asn Leu Pro Thr
1               5

<210> SEQ ID NO 64
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB6-IgG4, MAB7-IgG4,
      MAB8-IgG4, MAB9-IgG4, MAB10-IgG4, MAB11-IgG4, MAB12-IgG4; L3 -
      Chothia/Kabat/IMGT"

```
<400> SEQUENCE: 64

Gln Gln His Thr Val Arg Pro Pro Leu Thr
1               5                   10

<210> SEQ ID NO 65
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB13-IgG4, MAB14-IgG4,
      MAB15-IgG4, MAB16-IgG4, MAB17-IgG4, MAB18-IgG4; L3 - Chothia/
      Kabat/IMGT"

<400> SEQUENCE: 65

Gln Gln Tyr Val Val Trp Pro Pro Leu Thr
1               5                   10

<210> SEQ ID NO 66
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB19-IgG4, MAB20-IgG4,
      MAB21-IgG4; L3 - Chothia/Kabat/IMGT"

<400> SEQUENCE: 66

Gln Gln Tyr Ile Val Phe Pro Trp Thr
1               5

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB1-IgG4, MAB2-IgG4,
      MAB3-IgG4, MAB4-IgG4, MAB5-IgG4; L2 - Chothia/Kabat"

<400> SEQUENCE: 67

Asp Ala Ser Asn Arg Ala Thr
1               5

<210> SEQ ID NO 68
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB6-IgG4, MAB7-IgG4,
      MAB8-IgG4, MAB9-IgG4, MAB10-IgG4, MAB11-IgG4, MAB12-IgG4;
      L2 - Chothia/Kabat"

<400> SEQUENCE: 68
```

```
Gly Ala Ser Ser Arg Ala Thr
1               5

<210> SEQ ID NO 69
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB13-IgG4, MAB14-IgG4,
      MAB15-IgG4, MAB16-IgG4, MAB17-IgG4, MAB18-IgG4, MAB19-IgG4,
      MAB20-IgG4, MAB21-IgG4; L2 - Chothia/Kabat"

<400> SEQUENCE: 69

Gly Ala Ser Thr Arg Ala Thr
1               5

<210> SEQ ID NO 70
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB1-IgG4, MAB2-IgG4,
      MAB3-IgG4, MAB4-IgG4; L1 - Chothia/Kabat"

<400> SEQUENCE: 70

Arg Ala Ser Gln Ser Val Ser Ser Tyr Leu Ala
1               5                   10

<210> SEQ ID NO 71
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB6-IgG4, MAB7-IgG4,
      MAB8-IgG4, MAB9-IgG4, MAB10-IgG4, MAB11-IgG4, MAB12-IgG4;
      L1 - Chothia/Kabat"

<400> SEQUENCE: 71

Arg Ala Ser Gln Ser Val Ser Ser Ser Tyr Leu Ala
1               5                   10

<210> SEQ ID NO 72
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - MAB13-IgG4, MAB14-IgG4,
      MAB15-IgG4, MAB16-IgG4, MAB17-IgG4, MAB18-IgG4, MAB19-IgG4,
      MAB20-IgG4, MAB21-IgG4; L1 - Chothia/Kabat"

<400> SEQUENCE: 72
```

-continued

```
Arg Ala Ser Gln Ser Val Ser Ser Asn Leu Ala
1               5                   10

<210> SEQ ID NO 73
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - SEC1; Human IgG4 S228P Heavy
      Chain"

<400> SEQUENCE: 73

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
                20                  25                  30

Thr Met His Trp Val Arg Gln Ser Pro Gly Lys Gly Leu Glu Trp Val
            35                  40                  45

Ala Phe Ile Arg Ser Gly Ser Gly Ile Val Phe Tyr Ala Asp Ala Val
        50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 74
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: /note="SEC1; Heavy Chain Variable Region"

<400> SEQUENCE: 74

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
            35                  40                  45

Ala Phe Ile Arg Ser Gly Ser Gly Ile Val Phe Tyr Ala Asp Ala Val
        50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
            85                  90                  95

Ala Arg Arg Pro Leu Gly His Asn Thr Phe Asp Ser Trp Gly Gln Gly
            100                 105                 110

Thr Leu Val Thr Val Ser Ser
            115

<210> SEQ ID NO 75
<211> LENGTH: 220
<212> TYPE: PRT
<213> ORGANISM: Homo sapiens
<220> FEATURE:
<221> NAME/KEY: MISC_FEATURE
<222> LOCATION: (1)..(220)
<223> OTHER INFORMATION: /note="SEC1 Human Kappa Chain"

<400> SEQUENCE: 75

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30
```

```
Gly Val Lys Glu Asn Leu Leu Ala Trp Tyr Gln Gln Lys Pro Gly Gln
            35                  40                  45

Ser Pro Lys Leu Leu Ile Tyr Tyr Ala Ser Ile Arg Phe Thr Gly Val
 50                  55                  60

Pro Asp Arg Phe Thr Gly Ser Gly Ser Gly Thr Asp Tyr Thr Leu Thr
 65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
               100                 105                 110

Lys Arg Thr Val Ala Ala Pro Ser Val Phe Ile Phe Pro Pro Ser Asp
               115                 120                 125

Glu Gln Leu Lys Ser Gly Thr Ala Ser Val Val Cys Leu Leu Asn Asn
       130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
               165                 170                 175

Ser Thr Tyr Ser Leu Ser Ser Thr Leu Thr Leu Ser Lys Ala Asp Tyr
               180                 185                 190

Glu Lys His Lys Val Tyr Ala Cys Glu Val Thr His Gln Gly Leu Ser
               195                 200                 205

Ser Pro Val Thr Lys Ser Phe Asn Arg Gly Glu Cys
               210                 215                 220

<210> SEQ ID NO 76
<211> LENGTH: 113
<212> TYPE: PRT
<213> ORGANISM: Homo sapiens
<220> FEATURE:
<221> NAME/KEY: MISC_FEATURE
<222> LOCATION: (1)..(113)
<223> OTHER INFORMATION: /note="SEC1; Light Chain Variable Region"

<400> SEQUENCE: 76

Asp Ile Val Met Thr Gln Ser Pro Ser Ser Leu Ala Val Ser Pro Gly
 1               5                  10                  15

Glu Lys Val Thr Met Thr Cys Lys Ser Ser Gln Ser Leu Tyr Tyr Ser
                20                  25                  30

Gly Val Lys Glu Asn Leu Leu Ala Trp Tyr Gln Gln Lys Pro Gly Gln
            35                  40                  45

Ser Pro Lys Leu Leu Ile Tyr Tyr Ala Ser Ile Arg Phe Thr Gly Val
 50                  55                  60

Pro Asp Arg Phe Thr Gly Ser Gly Ser Gly Thr Asp Tyr Thr Leu Thr
 65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
               100                 105                 110

Lys

<210> SEQ ID NO 77
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
```

```
      Synthetic polypeptide"
<220> FEATURE:
<221> NAME/KEY: source
<223> OTHER INFORMATION: /note="Synthetic - SEC1; Mouse IgG2a N297A
      Heavy Chain"

<400> SEQUENCE: 77

Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
        35                  40                  45

Ala Phe Ile Arg Ser Gly Ser Gly Ile Val Phe Tyr Ala Asp Ala Val
    50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Ala Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380
```

```
Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
            405                 410                 415

Lys Asn Trp Val Glu Arg Asn Ser Tyr Ser Cys Ser Val His Glu
    420                 425                 430

Gly Leu His Asn His Thr Thr Lys Ser Phe Ser Arg Thr Pro Gly
        435                 440                 445

Lys

<210> SEQ ID NO 78
<211> LENGTH: 220
<212> TYPE: PRT
<213> ORGANISM: Mus musculus
<220> FEATURE:
<221> NAME/KEY: MISC_FEATURE
<222> LOCATION: (1)..(220)
<223> OTHER INFORMATION: /note="SEC1; Mouse Kappa Chain"

<400> SEQUENCE: 78

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220

<210> SEQ ID NO 79
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
```

<221> NAME/KEY: source
<223> OTHER INFORMATION: /note="Synthetic - MAB1; Full length IgG4 S228P"

<400> SEQUENCE: 79

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ala Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
```

-continued

```
                385                 390                 395                 400
Leu Asp Ser Asp Gly Ser Phe Phe Leu Tyr Ser Arg Leu Thr Val Asp
                    405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 80
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB1; Full length IgG1"

<400> SEQUENCE: 80

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ala Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 81
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB1, MAB2, MAB3, MAB4,
      MAB5; Full length Kappa"

<400> SEQUENCE: 81

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Phe Asn Leu Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 82
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB2; Full length IgG4
      S228P"

<400> SEQUENCE: 82

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Lys Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 83
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB2; Full length IgG1"

<400> SEQUENCE: 83

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Lys Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
        115                 120                 125
```

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 84
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB3; Full length IgG4
      S228P"

<400> SEQUENCE: 84

-continued

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Thr
            20                  25                  30

Ser His Tyr Trp Gly Trp Ile Arg Gln Pro Pro Gly Lys Gly Leu Glu
            35                  40                  45

Trp Ile Gly Ser Ile Tyr Tyr Ser Gly Ser Thr Phe Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
            210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
```

```
                    420             425             430
Glu Ala Leu His Asn His Tyr Thr Gln Lys Ser Leu Ser Leu Ser Leu
            435                 440                 445

Gly Lys
    450

<210> SEQ ID NO 85
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB3; Full length IgG1"

<400> SEQUENCE: 85

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 86
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB4; Full length IgG4
      S228P"

<400> SEQUENCE: 86

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
            35                  40                  45

Trp Ile Gly Ser Ile Tyr Tyr Ser Gly Ser Thr Phe Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Ala Asn Tyr Tyr Gly Gly Ala Trp Ala Phe Asp Pro
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175
```

```
Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 87
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB4; Full length IgG1"

<400> SEQUENCE: 87

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45
```

```
Trp Ile Gly Ser Ile Tyr Tyr Ser Gly Ser Thr Phe Tyr Asn Pro Ser
         50                  55                  60
Leu Lys Ser Arg Val Thr Ile Ser Val Asp Thr Ser Lys Asn Gln Phe
 65                  70                  75                  80
Ser Leu Lys Leu Ser Ser Val Thr Ala Ala Asp Thr Ala Val Tyr Tyr
                 85                  90                  95
Cys Ala Arg Asp Ala Asn Tyr Tyr Gly Gly Ala Trp Ala Phe Asp Pro
            100                 105                 110
Trp Gly Gln Gly Thr Leu Val Thr Val Ser Ser Ala Ser Thr Lys Gly
            115                 120                 125
Pro Ser Val Phe Pro Leu Ala Pro Ser Ser Lys Ser Thr Ser Gly Gly
130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
            195                 200                 205
Asn His Lys Pro Ser Asn Thr Lys Val Asp Lys Arg Val Glu Pro Lys
        210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
            275                 280                 285
Glu Val His Asn Ala Lys Thr Lys Pro Arg Glu Glu Gln Tyr Asn Ser
        290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
            355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
            435                 440                 445
Leu Ser Pro Gly Lys
450
```

```
<210> SEQ ID NO 88
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB5; Full length IgG4
      S228P"

<400> SEQUENCE: 88
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr

```
                340                 345                 350
Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
        435                 440                 445

Gly Lys
    450

<210> SEQ ID NO 89
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB5; Full length IgG1"

<400> SEQUENCE: 89

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Phe Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ala Asn Tyr Tyr Gly Ser Ala Trp Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220
```

```
Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 90
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB6; Full length IgG4
      S228P"

<400> SEQUENCE: 90

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Glu Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Gly Thr Tyr Tyr Asn Pro Ser
    50                  55                  60

Leu Lys Ser Arg Val Thr Ile Ser Val Asp Ser Lys Asn Gln Phe
65                  70                  75                  80

Ser Leu Lys Leu Ser Ser Val Thr Ala Ala Asp Thr Ala Val Tyr Tyr
            85                  90                  95
```

```
Cys Ala Arg Asp Gly Val Leu Thr Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 91
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<220> FEATURE:
<221> NAME/KEY: source
<223> OTHER INFORMATION: /note="Synthetic - MAB6; Full length IgG1"

<400> SEQUENCE: 91

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Glu Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Gly Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
```

```
                385                 390                 395                 400
Pro Pro Val Leu Asp Ser Asp Gly Ser Phe Phe Leu Tyr Ser Lys Leu
                405                         410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 92
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB6, MAB7, MAB8, MAB9,
      MAB10, MAB11, MAB12; Full length Kappa"

<400> SEQUENCE: 92

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Thr Val Arg Pro
                85                  90                  95

Pro Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 93
<211> LENGTH: 450
<212> TYPE: PRT
<213> ORGANISM: Artificial Sequence
<220> FEATURE:
<221> NAME/KEY: source
```

-continued

<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB7; Full length IgG4
      S228P"

<400> SEQUENCE: 93

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Val Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
```

```
              370                 375                 380
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
    450

<210> SEQ ID NO 94
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB7; Full length IgG1"

<400> SEQUENCE: 94

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
                20                  25                  30

Val Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255
```

```
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 95
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB8; Full length IgG4
      S228P"

<400> SEQUENCE: 95

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ala Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Gln Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser Ala Ser Thr Lys Gly
        115                 120                 125
```

```
Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
    435                 440                 445

Gly Lys
    450

<210> SEQ ID NO 96
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB8; Full length IgG1"

<400> SEQUENCE: 96
```

-continued

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ala Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Gln Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser

```
                    420                425                430
Val Met His Glu Ala Leu His Asn His Tyr Thr Gln Lys Ser Leu Ser
            435                440                445

Leu Ser Pro Gly Lys
        450

<210> SEQ ID NO 97
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB9; Full length IgG4
      S228P"

<400> SEQUENCE: 97

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
```

```
                            290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 98
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB9; Full length IgG1"

<400> SEQUENCE: 98

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Thr Leu Asn Lys Arg Ser Phe Asp Ile
                100                 105                 110

Trp Gly Gln Gly Thr Met Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 99
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB10; Full length IgG4
      S228P"

<400> SEQUENCE: 99

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45
```

-continued

```
Trp Ile Gly Ser Ile Tyr Tyr Ser Gly Ser Thr Tyr Tyr Asn Pro Ser
         50                  55                  60

Leu Lys Ser Arg Ala Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                     85                  90                  95

Cys Ala Arg Asp Gly Val Leu Ala Leu Asn Lys Arg Ser Phe Asp Ile
                100                 105                 110

Trp Gly Gln Gly Thr Met Val Thr Val Ser Ser Ala Ser Thr Lys Gly
                115                 120                 125

Pro Ser Val Phe Pro Leu Ala Pro Cys Ser Arg Ser Thr Ser Glu Ser
                130                 135                 140

Thr Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
                195                 200                 205

Asp His Lys Pro Ser Asn Thr Lys Val Asp Lys Arg Val Glu Ser Lys
                210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
450
```

<210> SEQ ID NO 100
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Synthetic - MAB10; Full length IgG1"

<400> SEQUENCE: 100

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Ala Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
```

-continued

```
                340                 345                 350
Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 101
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB11; Full length IgG4
      S228P"

<400> SEQUENCE: 101

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
```

```
                210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
    450

<210> SEQ ID NO 102
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB11; Full length IgG1"

<400> SEQUENCE: 102

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Glu Ser Gly
                20                  25                  30

Leu Tyr Tyr Trp Gly Trp Ile Arg Gln Pro Pro Gly Lys Gly Leu Glu
                35                  40                  45

Trp Ile Gly Ser Ile Tyr Tyr Ser Gly Ser Thr Tyr Tyr Asn Pro Ser
            50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

Cys Ala Arg Asp Gly Val Leu Ala Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 103
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<220> FEATURE:
<221> NAME/KEY: source
<223> OTHER INFORMATION: /note="Synthetic - MAB12; Full length IgG4
      S228P"

<400> SEQUENCE: 103
```

| | | | | | | | | | | | | | | |
|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Gln |
| 1 | | | | 5 | | | | | 10 | | | | | 15 | |

| Thr | Leu | Ser | Leu | Thr | Cys | Thr | Ala | Ser | Gly | Gly | Ser | Ile | Glu | Ser | Gly |
|---|---|---|---|---|---|---|---|---|---|---|---|---|---|---|---|
| | | | 20 | | | | | 25 | | | | | 30 | | |

| Leu | Tyr | Tyr | Trp | Gly | Trp | Ile | Arg | Gln | Pro | Pro | Gly | Lys | Gly | Leu | Glu |
|---|---|---|---|---|---|---|---|---|---|---|---|---|---|---|---|
| | | | 35 | | | | | 40 | | | | | 45 | | |

| Trp | Ile | Gly | Ser | Ile | Tyr | Tyr | Ser | Gly | Ser | Thr | Tyr | Tyr | Asn | Pro | Ser |
|---|---|---|---|---|---|---|---|---|---|---|---|---|---|---|---|
| 50 | | | | | 55 | | | | | 60 | | | | | |

| Leu | Lys | Ser | Arg | Val | Thr | Ile | Ser | Val | Asp | Thr | Ser | Lys | Asn | Gln | Phe |
|---|---|---|---|---|---|---|---|---|---|---|---|---|---|---|---|
| 65 | | | | | 70 | | | | | 75 | | | | | 80 |

| Ser | Leu | Lys | Leu | Ser | Ser | Val | Thr | Ala | Ala | Asp | Thr | Ala | Val | Tyr | Tyr |
|---|---|---|---|---|---|---|---|---|---|---|---|---|---|---|---|
| | | | | 85 | | | | | 90 | | | | | 95 | |

| Cys | Ala | Arg | Asp | Gly | Val | Leu | Ala | Leu | Asn | Lys | Arg | Ser | Phe | Asp | Ile |
|---|---|---|---|---|---|---|---|---|---|---|---|---|---|---|---|
| | | | 100 | | | | | 105 | | | | | 110 | | |

| Trp | Gly | Gln | Gly | Thr | Met | Val | Thr | Val | Ser | Ser | Ala | Ser | Thr | Lys | Gly |
|---|---|---|---|---|---|---|---|---|---|---|---|---|---|---|---|
| | | | 115 | | | | | 120 | | | | | 125 | | |

| Pro | Ser | Val | Phe | Pro | Leu | Ala | Pro | Cys | Ser | Arg | Ser | Thr | Ser | Glu | Ser |
|---|---|---|---|---|---|---|---|---|---|---|---|---|---|---|---|
| 130 | | | | | 135 | | | | | 140 | | | | | |

| Thr | Ala | Ala | Leu | Gly | Cys | Leu | Val | Lys | Asp | Tyr | Phe | Pro | Glu | Pro | Val |
|---|---|---|---|---|---|---|---|---|---|---|---|---|---|---|---|
| 145 | | | | | 150 | | | | | 155 | | | | | 160 |

| Thr | Val | Ser | Trp | Asn | Ser | Gly | Ala | Leu | Thr | Ser | Gly | Val | His | Thr | Phe |
|---|---|---|---|---|---|---|---|---|---|---|---|---|---|---|---|
| | | | | 165 | | | | | 170 | | | | | 175 | |

| Pro | Ala | Val | Leu | Gln | Ser | Ser | Gly | Leu | Tyr | Ser | Leu | Ser | Ser | Val | Val |
|---|---|---|---|---|---|---|---|---|---|---|---|---|---|---|---|
| | | | 180 | | | | | 185 | | | | | 190 | | |

| Thr | Val | Pro | Ser | Ser | Ser | Leu | Gly | Thr | Lys | Thr | Tyr | Thr | Cys | Asn | Val |
|---|---|---|---|---|---|---|---|---|---|---|---|---|---|---|---|
| | | | 195 | | | | | 200 | | | | | 205 | | |

| Asp | His | Lys | Pro | Ser | Asn | Thr | Lys | Val | Asp | Lys | Arg | Val | Glu | Ser | Lys |
|---|---|---|---|---|---|---|---|---|---|---|---|---|---|---|---|
| 210 | | | | | 215 | | | | | 220 | | | | | |

| Tyr | Gly | Pro | Pro | Cys | Pro | Pro | Cys | Pro | Ala | Pro | Glu | Phe | Leu | Gly | Gly |
|---|---|---|---|---|---|---|---|---|---|---|---|---|---|---|---|
| 225 | | | | | 230 | | | | | 235 | | | | | 240 |

| Pro | Ser | Val | Phe | Leu | Phe | Pro | Pro | Lys | Pro | Lys | Asp | Thr | Leu | Met | Ile |
|---|---|---|---|---|---|---|---|---|---|---|---|---|---|---|---|
| | | | | 245 | | | | | 250 | | | | | 255 | |

| Ser | Arg | Thr | Pro | Glu | Val | Thr | Cys | Val | Val | Val | Asp | Val | Ser | Gln | Glu |
|---|---|---|---|---|---|---|---|---|---|---|---|---|---|---|---|
| | | | 260 | | | | | 265 | | | | | 270 | | |

| Asp | Pro | Glu | Val | Gln | Phe | Asn | Trp | Tyr | Val | Asp | Gly | Val | Glu | Val | His |
|---|---|---|---|---|---|---|---|---|---|---|---|---|---|---|---|
| | | | 275 | | | | | 280 | | | | | 285 | | |

| Asn | Ala | Lys | Thr | Lys | Pro | Arg | Glu | Glu | Gln | Phe | Asn | Ser | Thr | Tyr | Arg |
|---|---|---|---|---|---|---|---|---|---|---|---|---|---|---|---|
| 290 | | | | | 295 | | | | | 300 | | | | | |

| Val | Val | Ser | Val | Leu | Thr | Val | Leu | His | Gln | Asp | Trp | Leu | Asn | Gly | Lys |
|---|---|---|---|---|---|---|---|---|---|---|---|---|---|---|---|
| 305 | | | | | 310 | | | | | 315 | | | | | 320 |

| Glu | Tyr | Lys | Cys | Lys | Val | Ser | Asn | Lys | Gly | Leu | Pro | Ser | Ser | Ile | Glu |
|---|---|---|---|---|---|---|---|---|---|---|---|---|---|---|---|
| | | | | 325 | | | | | 330 | | | | | 335 | |

| Lys | Thr | Ile | Ser | Lys | Ala | Lys | Gly | Gln | Pro | Arg | Glu | Pro | Gln | Val | Tyr |
|---|---|---|---|---|---|---|---|---|---|---|---|---|---|---|---|
| | | | 340 | | | | | 345 | | | | | 350 | | |

| Thr | Leu | Pro | Pro | Ser | Gln | Glu | Glu | Met | Thr | Lys | Asn | Gln | Val | Ser | Leu |
|---|---|---|---|---|---|---|---|---|---|---|---|---|---|---|---|
| | | | 355 | | | | | 360 | | | | | 365 | | |

| Thr | Cys | Leu | Val | Lys | Gly | Phe | Tyr | Pro | Ser | Asp | Ile | Ala | Val | Glu | Trp |
|---|---|---|---|---|---|---|---|---|---|---|---|---|---|---|---|
| 370 | | | | | 375 | | | | | 380 | | | | | |

-continued

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
        435                 440                 445

Gly Lys
    450

<210> SEQ ID NO 104
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB12; Full length IgG1"

<400> SEQUENCE: 104

Gln Val Gln Leu Gln Glu Ser Gly Pro Gly Leu Val Lys Pro Ser Gln
1               5                   10                  15

Thr Leu Ser Leu Thr Cys Thr Ala Ser Gly Gly Ser Ile Glu Ser Gly
            20                  25                  30

Leu Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Val Leu Ala Leu Asn Lys Arg Ser Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
```

```
                  260                 265                 270
Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 105
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB13; Full length IgG4
      S228P"

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Leu Gly Leu Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
```

```
            130                 135                 140
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 106
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB13; Full length IgG1"

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
                20                  25                  30
```

-continued

```
Tyr Met His Trp Val Arg Gln Ala Pro Gly Gln Gly Leu Glu Trp Met
         35                  40                  45
Gly Ile Ile Asn Pro Ser Leu Gly Leu Thr Ser Tyr Ala Gln Lys Phe
 50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Gly Gly Arg Thr Thr Trp Ile Gly Ala Phe Asp Ile Trp Gly
                100                 105                 110
Gln Gly Thr Met Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Arg Val Glu Pro Lys Ser Cys
        210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
        420                 425                 430
His Glu Ala Leu His Asn His Tyr Thr Gln Lys Ser Leu Ser Leu Ser
        435                 440                 445
```

Pro Gly Lys
    450

<210> SEQ ID NO 107
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB13, MAB14, MAB15, MAB16,
      MAB17, MAB18; Full length Kappa"

<400> SEQUENCE: 107

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Val Trp Pro Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 108
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB14; Full length IgG4
      S228P"

<400> SEQUENCE: 108

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Pro Ala Tyr
            20                  25                  30

Tyr Met His Trp Val Arg Gln Ala Pro Gly Gln Gly Leu Glu Trp Met
        35                  40                  45

Gly Ile Ile Asn Pro Ser Leu Gly Leu Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
            85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430
```

```
Leu His Asn His Tyr Thr Gln Lys Ser Leu Ser Leu Ser Leu Gly Lys
            435                 440                 445
```

<210> SEQ ID NO 109
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB14; Full length IgG1"

<400> SEQUENCE: 109

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
                20                  25                  30

Tyr Met His Trp Val Arg Gln Ala Pro Gly Gln Gly Leu Glu Trp Met
            35                  40                  45

Gly Ile Ile Asn Pro Ser Leu Gly Leu Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                        325                 330                 335
Glu Lys Thr Ile Ser Lys Ala Lys Gly Gln Pro Arg Glu Pro Gln Val
                    340                 345                 350
Tyr Thr Leu Pro Pro Ser Arg Glu Glu Met Thr Lys Asn Gln Val Ser
                355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys
    450

<210> SEQ ID NO 110
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB15; Full length IgG4
      S228P"

<400> SEQUENCE: 110

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Arg Glu Tyr
            20                  25                  30
Tyr Met His Trp Val Arg Gln Ala Pro Gly Gln Gly Leu Glu Trp Met
        35                  40                  45
Gly Ile Ile Asn Pro Ser Ile Gly Leu Thr Ser Tyr Ala Arg Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Gly Arg Thr Thr Trp Ile Gly Ala Phe Asp Ile Trp Gly
            100                 105                 110
Gln Gly Thr Met Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
```

-continued

```
            195                 200                 205
Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 111
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB15; Full length IgG1"

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Glu Tyr
            20                  25                  30

Tyr Met His Trp Val Arg Gln Ala Pro Gly Gln Gly Leu Glu Trp Met
        35                  40                  45

Gly Ile Ile Asn Pro Ser Ile Gly Leu Thr Ser Tyr Ala Arg Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Gly Gly Arg Thr Thr Trp Ile Gly Ala Phe Asp Ile Trp Gly
            100                 105                 110

Gln Gly Thr Met Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 112
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

```
<220> FEATURE:
<221> NAME/KEY: source
<223> OTHER INFORMATION: /note="Synthetic - MAB16; Full length IgG4
      S228P"

<400> SEQUENCE: 112
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 |

| Ser | Val | Lys | Val | Ser | Cys | Lys | Ala | Ser | Gly | Tyr | Thr | Phe | Arg | Glu | Tyr |
| | | | 20 | | | | | 25 | | | | | 30 | | |

| Tyr | Met | His | Trp | Val | Arg | Gln | Ala | Pro | Gly | Gln | Gly | Leu | Glu | Trp | Met |
| | | 35 | | | | | 40 | | | | | 45 | | | |

| Gly | Ile | Ile | Asn | Pro | Ser | Ile | Gly | Leu | Thr | Ser | Tyr | Ala | Arg | Lys | Phe |
| 50 | | | | | 55 | | | | | 60 | | | | | |

| Gln | Gly | Arg | Val | Thr | Met | Thr | Arg | Asp | Thr | Ser | Thr | Ser | Thr | Val | Tyr |
| 65 | | | | | 70 | | | | | 75 | | | | | 80 |

| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |

| Ala | Arg | Gly | Gly | Arg | Thr | Thr | Trp | Ile | Gly | Ala | Leu | Asp | Ile | Trp | Gly |
| | | | 100 | | | | | 105 | | | | | 110 | | |

| Gln | Gly | Thr | Met | Val | Thr | Val | Ser | Ser | Ala | Ser | Thr | Lys | Gly | Pro | Ser |
| | | 115 | | | | | 120 | | | | | 125 | | | |

| Val | Phe | Pro | Leu | Ala | Pro | Cys | Ser | Arg | Ser | Thr | Ser | Glu | Ser | Thr | Ala |
| 130 | | | | | 135 | | | | | 140 | | | | | |

| Ala | Leu | Gly | Cys | Leu | Val | Lys | Asp | Tyr | Phe | Pro | Glu | Pro | Val | Thr | Val |
| 145 | | | | | 150 | | | | | 155 | | | | | 160 |

| Ser | Trp | Asn | Ser | Gly | Ala | Leu | Thr | Ser | Gly | Val | His | Thr | Phe | Pro | Ala |
| | | | | 165 | | | | | 170 | | | | | 175 | |

| Val | Leu | Gln | Ser | Ser | Gly | Leu | Tyr | Ser | Leu | Ser | Ser | Val | Val | Thr | Val |
| | | | 180 | | | | | 185 | | | | | 190 | | |

| Pro | Ser | Ser | Ser | Leu | Gly | Thr | Lys | Thr | Tyr | Thr | Cys | Asn | Val | Asp | His |
| | | 195 | | | | | 200 | | | | | 205 | | | |

| Lys | Pro | Ser | Asn | Thr | Lys | Val | Asp | Lys | Arg | Val | Glu | Ser | Lys | Tyr | Gly |
| 210 | | | | | 215 | | | | | 220 | | | | | |

| Pro | Pro | Cys | Pro | Pro | Cys | Pro | Ala | Pro | Glu | Phe | Leu | Gly | Gly | Pro | Ser |
| 225 | | | | | 230 | | | | | 235 | | | | | 240 |

| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |

| Thr | Pro | Glu | Val | Thr | Cys | Val | Val | Val | Asp | Val | Ser | Gln | Glu | Asp | Pro |
| | | | 260 | | | | | 265 | | | | | 270 | | |

| Glu | Val | Gln | Phe | Asn | Trp | Tyr | Val | Asp | Gly | Val | Glu | Val | His | Asn | Ala |
| | | 275 | | | | | 280 | | | | | 285 | | | |

| Lys | Thr | Lys | Pro | Arg | Glu | Glu | Gln | Phe | Asn | Ser | Thr | Tyr | Arg | Val | Val |
| 290 | | | | | 295 | | | | | 300 | | | | | |

| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |

| Lys | Cys | Lys | Val | Ser | Asn | Lys | Gly | Leu | Pro | Ser | Ser | Ile | Glu | Lys | Thr |
| | | | | 325 | | | | | 330 | | | | | 335 | |

| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |

| Pro | Pro | Ser | Gln | Glu | Glu | Met | Thr | Lys | Asn | Gln | Val | Ser | Leu | Thr | Cys |
| | | 355 | | | | | 360 | | | | | 365 | | | |

| Leu | Val | Lys | Gly | Phe | Tyr | Pro | Ser | Asp | Ile | Ala | Val | Glu | Trp | Glu | Ser |
| 370 | | | | | 375 | | | | | 380 | | | | | |

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
        435                 440                 445

<210> SEQ ID NO 113
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB16; Full length IgG1"

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Glu Tyr
            20                  25                  30

Tyr Met His Trp Val Arg Gln Ala Pro Gly Gln Gly Leu Glu Trp Met
        35                  40                  45

Gly Ile Ile Asn Pro Ser Ile Gly Leu Thr Ser Tyr Ala Arg Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Leu Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val

```
                275                 280                 285
His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 114
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB17; Full length IgG4
      S228P"

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
                20                  25                  30

Tyr Ile His Trp Val Arg Gln Ala Pro Gly Gln Gly Leu Glu Trp Met
            35                  40                  45

Gly Ile Ile Asn Pro Ser Leu Gly Leu Thr Ser Tyr Ala Arg Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Leu Asp Ile Trp Gly
                100                 105                 110

Gln Gly Thr Met Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
```

Ser Trp Asn Ser Gly Ala Leu Thr Ser Gly Val His Thr Phe Pro Ala
145                 150                 155                 160

Val Leu Gln Ser Ser Gly Leu Tyr Ser Leu Ser Ser Val Val Thr Val
            165                 170                 175

Pro Ser Ser Ser Leu Gly Thr Lys Thr Tyr Thr Cys Asn Val Asp His
        180                 185                 190

Lys Pro Ser Asn Thr Lys Val Asp Lys Arg Val Glu Ser Lys Tyr Gly
    195                 200                 205

Pro Pro Cys Pro Pro Cys Pro Ala Pro Glu Phe Leu Gly Gly Pro Ser
210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser Gln Glu Asp Pro
            245                 250                 255

Glu Val Gln Phe Asn Trp Tyr Val Asp Gly Val Glu Val His Asn Ala
        260                 265                 270

Lys Thr Lys Pro Arg Glu Glu Gln Phe Asn Ser Thr Tyr Arg Val Val
    275                 280                 285

Ser Val Leu Thr Val Leu His Gln Asp Trp Leu Asn Gly Lys Glu Tyr
290                 295                 300

Lys Cys Lys Val Ser Asn Lys Gly Leu Pro Ser Ser Ile Glu Lys Thr
305                 310                 315                 320

Ile Ser Lys Ala Lys Gly Gln Pro Arg Glu Pro Gln Val Tyr Thr Leu
            325                 330                 335

Pro Pro Ser Gln Glu Glu Met Thr Lys Asn Gln Val Ser Leu Thr Cys
        340                 345                 350

Leu Val Lys Gly Phe Tyr Pro Ser Asp Ile Ala Val Glu Trp Glu Ser
    355                 360                 365

Asn Gly Gln Pro Glu Asn Asn Tyr Lys Thr Thr Pro Pro Val Leu Asp
370                 375                 380

Ser Asp Gly Ser Phe Phe Leu Tyr Ser Arg Leu Thr Val Asp Lys Ser
385                 390                 395                 400

Arg Trp Gln Glu Gly Asn Val Phe Ser Cys Ser Val Met His Glu Ala
            405                 410                 415

Leu His Asn His Tyr Thr Gln Lys Ser Leu Ser Leu Ser Leu Gly Lys
        420                 425                 430

435                 440                 445

<210> SEQ ID NO 115
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB17; Full length IgG1"

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Ile His Trp Val Arg Gln Ala Pro Gly Gln Gly Leu Glu Trp Met
        35                  40                  45

```
Gly Ile Ile Asn Pro Ser Leu Gly Leu Thr Ser Tyr Ala Arg Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Arg Thr Thr Trp Ile Gly Ala Leu Asp Ile Trp Gly
            100                 105                 110

Gln Gly Thr Met Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450
```

<210> SEQ ID NO 116
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Synthetic - MAB18; Full length IgG4 S228P"

<400> SEQUENCE: 116

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Met His Trp Val Arg Gln Ala Pro Gly Gln Gly Leu Glu Trp Met
        35                  40                  45

Gly Ile Ile Asn Pro Ser Leu Gly Leu Thr Ser Tyr Ala Arg Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335
```

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 117
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB18; Full length IgG1"

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ala Tyr
            20                  25                  30

Tyr Met His Trp Val Arg Gln Ala Pro Gly Gln Gly Leu Glu Trp Met
            35                  40                  45

Gly Ile Ile Asn Pro Ser Leu Gly Leu Thr Ser Tyr Ala Arg Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Thr Thr Trp Ile Gly Ala Phe Asp Ile Trp Gly
            100                 105                 110

Gln Gly Thr Met Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Leu Leu Gly

```
                225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 118
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB19; Full length IgG4
      S228P"

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Tyr Met Gly Trp Val Arg Gln Ala Pro Gly Gln Gly Leu Glu Trp Met
                35                  40                  45

Gly Val Ile Asn Pro Ser Met Gly Ala Thr Ser Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
```

```
            100                 105                 110
Trp Gly Gln Gly Thr Met Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
    450

<210> SEQ ID NO 119
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
```

<223> OTHER INFORMATION: /note="Synthetic - MAB19; Full length IgG1"

<400> SEQUENCE: 119

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met Gly Trp Val Arg Gln Ala Pro Gly Gln Gly Leu Glu Trp Met
        35                  40                  45

Gly Val Ile Asn Pro Ser Met Gly Ala Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 120
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB19, MAB20, MAB21; Full
      length Kappa"

<400> SEQUENCE: 120

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg His Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ile Val Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 121
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<220> FEATURE:
<221> NAME/KEY: source
<223> OTHER INFORMATION: /note="Synthetic - MAB20; Full length IgG4 S228P"

<400> SEQUENCE: 121

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met Gly Trp Val Arg Gln Ala Pro Gly Gln Gly Leu Glu Trp Val
        35                  40                  45

Gly Ile Ile Asn Pro Ser Met Gly Ala Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly Lys
    450

<210> SEQ ID NO 122
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"
<220> FEATURE:
<221> NAME/KEY: source
<223> OTHER INFORMATION: /note="Synthetic - MAB20; Full length IgG1"

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met Gly Trp Val Arg Gln Ala Pro Gly Gln Gly Leu Glu Trp Val
        35                  40                  45

Gly Ile Ile Asn Pro Ser Met Gly Ala Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val

```
                260                 265                 270
Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 123
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB21; Full length IgG4
      S228P"

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met Gly Trp Val Arg Gln Ala Pro Gly Gln Gly Leu Glu Trp Met
        35                  40                  45

Gly Ile Ile Asn Pro Ser Met Gly Ala Thr Ser Tyr Thr Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Cys Ser Arg Ser Thr Ser Glu Ser
```

```
              130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
                195                 200                 205

Asp His Lys Pro Ser Asn Thr Lys Val Asp Lys Arg Val Glu Ser Lys
            210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 124
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - MAB21; Full length IgG1"

<400> SEQUENCE: 124

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser His
            20                  25                  30

Tyr Met Gly Trp Val Arg Gln Ala Pro Gly Gln Gly Leu Glu Trp Met
        35                  40                  45

Gly Ile Ile Asn Pro Ser Met Gly Ala Thr Ser Tyr Thr Gln Lys Phe
 50                  55                  60

Arg Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Leu His Val Ser Gly Ser Tyr Tyr Pro Ala Tyr Leu Asp Tyr
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

Val Met His Glu Ala Leu His Asn His Tyr Thr Gln Lys Ser Leu Ser
    435                 440                 445

Leu Ser Pro Gly Lys
    450

<210> SEQ ID NO 125
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - IgG1; Constant (G1m(17,1)
      allotype, N297A"

<400> SEQUENCE: 125

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 126
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Synthetic - Kappa; Constant"

<400> SEQUENCE: 126

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 127
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - Linker"

<400> SEQUENCE: 127

Gly Gly Gly Gly Ser
1               5

<210> SEQ ID NO 128
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - CDR-H3"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: MISC_FEATURE
<222> LOCATION: (1)..(15)

```
<223> OTHER INFORMATION: /note="Variant residues given in the sequence
      have no preference with respect to those in the annotations
      for variant positions"

<400> SEQUENCE: 128

Ala Arg Asp Gly Val Leu Ala Leu Asn Lys Arg Ser Phe Asp Ile
1               5                   10                  15

<210> SEQ ID NO 129
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - CDR-H2"
<220> FEATURE:
<221> NAME/KEY: VARIANT
<222> LOCATION: (7)..(7)
<223> OTHER INFORMATION: /replace="Gln" or "Gly"
<220> FEATURE:
<221> NAME/KEY: MISC_FEATURE
<222> LOCATION: (1)..(16)
<223> OTHER INFORMATION: /note="Variant residues given in the sequence
      have no preference with respect to those in the annotations
      for variant positions"

<400> SEQUENCE: 129

Ser Ile Tyr Tyr Ser Gly Ser Thr Tyr Tyr Asn Pro Ser Leu Lys Ser
1               5                   10                  15

<210> SEQ ID NO 130
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - CDR-H1"
<220> FEATURE:
<221> NAME/KEY: VARIANT
<222> LOCATION: (4)..(4)
<223> OTHER INFORMATION: /replace="Ala"
<220> FEATURE:
<221> NAME/KEY: VARIANT
<222> LOCATION: (7)..(7)
<223> OTHER INFORMATION: /replace="Val" or "Ser"
<220> FEATURE:
<221> NAME/KEY: MISC_FEATURE
<222> LOCATION: (1)..(11)
<223> OTHER INFORMATION: /note="Variant residues given in the sequence
      have no preference with respect to those in the annotations
      for variant positions"

<400> SEQUENCE: 130

Gly Ser Ile Glu Ser Gly Leu Tyr Tyr Trp Gly
1               5                   10

<210> SEQ ID NO 131
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: source
<223> OTHER INFORMATION: /note="Synthetic - CDR-H3"
<220> FEATURE:
<221> NAME/KEY: VARIANT
<222> LOCATION: (9)..(9)
<223> OTHER INFORMATION: /replace="Gly"
<220> FEATURE:
<221> NAME/KEY: MISC_FEATURE
<222> LOCATION: (1)..(15)
<223> OTHER INFORMATION: /note="Variant residues given in the sequence
      have no preference with respect to those in the annotations
      for variant positions"

<400> SEQUENCE: 131

Ala Arg Asp Ala Asn Tyr Tyr Gly Ser Ala Trp Ala Phe Asp Pro
1               5                   10                  15

<210> SEQ ID NO 132
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - CDR-H2"
<220> FEATURE:
<221> NAME/KEY: VARIANT
<222> LOCATION: (7)..(7)
<223> OTHER INFORMATION: /replace="Ala"
<220> FEATURE:
<221> NAME/KEY: VARIANT
<222> LOCATION: (16)..(16)
<223> OTHER INFORMATION: /replace="Gly"
<220> FEATURE:
<221> NAME/KEY: MISC_FEATURE
<222> LOCATION: (1)..(16)
<223> OTHER INFORMATION: /note="Variant residues given in the sequence
      have no preference with respect to those in the annotations
      for variant positions"

<400> SEQUENCE: 132

Ser Ile Tyr Tyr Ser Gly Ser Thr Phe Tyr Asn Pro Ser Leu Lys Ser
1               5                   10                  15

<210> SEQ ID NO 133
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - CDR-H1"
<220> FEATURE:
<221> NAME/KEY: VARIANT
<222> LOCATION: (4)..(4)
<223> OTHER INFORMATION: /replace="Thr"
<220> FEATURE:
<221> NAME/KEY: VARIANT
<222> LOCATION: (6)..(6)
<223> OTHER INFORMATION: /replace="Thr"
<220> FEATURE:
<221> NAME/KEY: VARIANT
<222> LOCATION: (7)..(7)
<223> OTHER INFORMATION: /replace="Lys"
<220> FEATURE:
<221> NAME/KEY: VARIANT
<222> LOCATION: (8)..(8)
<223> OTHER INFORMATION: /replace="Tyr"
<220> FEATURE:
```

```
<221> NAME/KEY: MISC_FEATURE
<222> LOCATION: (1)..(11)
<223> OTHER INFORMATION: /note="Variant residues given in the sequence
      have no preference with respect to those in the annotations
      for variant positions"

<400> SEQUENCE: 133

Gly Ser Ile Ser Ser Ser Ser His Tyr Trp Gly
1               5                   10

<210> SEQ ID NO 134
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - CDR-H3"
<220> FEATURE:
<221> NAME/KEY: VARIANT
<222> LOCATION: (12)..(12)
<223> OTHER INFORMATION: /replace="Leu"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"

<400> SEQUENCE: 134

Ala Arg Gly Gly Arg Thr Thr Trp Ile Gly Ala Phe Asp Ile
1               5                   10

<210> SEQ ID NO 135
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - CDR-H2"
<220> FEATURE:
<221> NAME/KEY: VARIANT
<222> LOCATION: (6)..(6)
<223> OTHER INFORMATION: /replace="Ile"
<220> FEATURE:
<221> NAME/KEY: VARIANT
<222> LOCATION: (13)..(13)
<223> OTHER INFORMATION: /replace="Arg"
<220> FEATURE:
<221> NAME/KEY: MISC_FEATURE
<222> LOCATION: (1)..(17)
<223> OTHER INFORMATION: /note="Variant residues given in the sequence
      have no preference with respect to those in the annotations
      for variant positions"

<400> SEQUENCE: 135

Ile Ile Asn Pro Ser Leu Gly Leu Thr Ser Tyr Ala Gln Lys Phe Gln
1               5                   10                  15

Gly

<210> SEQ ID NO 136
<211> LENGTH: 9
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - CDR-H1"
<220> FEATURE:
<221> NAME/KEY: VARIANT
<222> LOCATION: (4)..(4)
<223> OTHER INFORMATION: /replace="Pro" or "Arg"
<220> FEATURE:
<221> NAME/KEY: VARIANT
<222> LOCATION: (5)..(5)
<223> OTHER INFORMATION: /replace="Ala" or "Glu"
<220> FEATURE:
<221> NAME/KEY: VARIANT
<222> LOCATION: (8)..(8)
<223> OTHER INFORMATION: /replace="Ile"
<220> FEATURE:
<221> NAME/KEY: MISC_FEATURE
<222> LOCATION: (1)..(9)
<223> OTHER INFORMATION: /note="Variant residues given in the sequence
      have no preference with respect to those in the annotations
      for variant positions"

<400> SEQUENCE: 136

Tyr Thr Phe Gly Asn Tyr Tyr Met His
1               5

<210> SEQ ID NO 137
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Synthetic - CDR-H2"
<220> FEATURE:
<221> NAME/KEY: VARIANT
<222> LOCATION: (1)..(1)
<223> OTHER INFORMATION: /replace="Ile"
<220> FEATURE:
<221> NAME/KEY: VARIANT
<222> LOCATION: (12)..(12)
<223> OTHER INFORMATION: /replace="Thr"
<220> FEATURE:
<221> NAME/KEY: VARIANT
<222> LOCATION: (16)..(16)
<223> OTHER INFORMATION: /replace="Arg"
<220> FEATURE:
<221> NAME/KEY: MISC_FEATURE
<222> LOCATION: (1)..(17)
<223> OTHER INFORMATION: /note="Variant residues given in the sequence
      have no preference with respect to those in the annotations
      for variant positions"

<400> SEQUENCE: 137

Val Ile Asn Pro Ser Met Gly Ala Thr Ser Tyr Ala Gln Lys Phe Gln
1               5                   10                  15

Gly

<210> SEQ ID NO 138
<211> LENGTH: 249
<212> TYPE: PRT
<213> ORGANISM: Mus musculus
<220> FEATURE:
<221> NAME/KEY: source
<223> OTHER INFORMATION: /note="mTIGIT2"

<400> SEQUENCE: 138
```

Met His Gly Trp Leu Leu Val Trp Val Gln Gly Leu Ile Gln Ala
1               5                   10                  15

Ala Phe Leu Ala Thr Ala Ile Gly Ala Thr Ala Gly Thr Ile Asp Thr
            20                  25                  30

Lys Arg Asn Ile Ser Ala Glu Glu Gly Gly Ser Val Ile Leu Gln Cys
            35                  40                  45

His Phe Ser Ser Asp Thr Ala Glu Val Thr Gln Val Asp Trp Lys Gln
50                  55                  60

Gln Asp Gln Leu Leu Ala Ile Tyr Ser Val Asp Leu Gly Trp His Val
65                  70                  75                  80

Ala Ser Val Phe Ser Asp Arg Val Val Pro Gly Pro Ser Leu Gly Leu
                85                  90                  95

Thr Phe Gln Ser Leu Thr Met Asn Asp Thr Gly Glu Tyr Phe Cys Thr
                100                 105                 110

Tyr His Thr Tyr Pro Gly Gly Ile Tyr Lys Gly Arg Ile Phe Leu Lys
                115                 120                 125

Val Gln Glu Ser Ser Asp Asp Arg Asn Gly Leu Ala Gln Phe Gln Thr
            130                 135                 140

Ala Pro Leu Gly Gly Thr Met Ala Ala Val Leu Gly Leu Ile Cys Leu
145                 150                 155                 160

Met Val Thr Gly Val Thr Val Leu Ala Arg Lys Asp Lys Ser Ile Arg
                165                 170                 175

Met His Ser Ile Glu Ser Gly Leu Gly Arg Thr Glu Ala Glu Pro Gln
                180                 185                 190

Glu Trp Asn Leu Arg Ser Leu Ser Ser Pro Gly Ser Pro Val Gln Thr
            195                 200                 205

Gln Thr Ala Pro Ala Gly Pro Cys Gly Glu Gln Ala Glu Asp Asp Tyr
210                 215                 220

Ala Asp Pro Gln Glu Tyr Phe Asn Val Leu Ser Tyr Arg Ser Leu Glu
225                 230                 235                 240

Ser Phe Ile Ala Val Ser Lys Thr Gly
                245

<210> SEQ ID NO 139
<211> LENGTH: 687
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Leu Gly Trp Gly Trp Ile Arg Gln Pro Pro Gly Lys Gly Leu Glu Trp
            35                  40                  45

Ile Gly Gly Ile Tyr Glu Ser Gly Ser Thr Tyr Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala His Glu Arg Val Arg Gly Tyr Gly Asp Tyr Gly Gly His His Ala

-continued

```
            100                 105                 110
Phe Asp Ile Trp Gly Gln Gly Thr Met Val Thr Val Ser Ser Ala Ser
            115                 120                 125
Thr Lys Gly Pro Ser Val Phe Pro Leu Ala Pro Ser Ser Lys Ser Thr
130                 135                 140
Ser Gly Gly Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
            165                 170                 175
His Thr Phe Pro Ala Val Leu Gln Ser Ser Gly Leu Tyr Ser Leu Ser
            180                 185                 190
Ser Val Val Thr Val Pro Ser Ser Ser Leu Gly Thr Gln Thr Tyr Ile
            195                 200                 205
Cys Asn Val Asn His Lys Pro Ser Asn Thr Lys Val Asp Lys Arg Val
            210                 215                 220
Glu Pro Lys Ser Cys Gly Gly Gly Ser Gln Val Gln Leu Gln Glu
225                 230                 235                 240
Ser Gly Pro Gly Leu Val Lys Pro Ser Glu Thr Leu Ser Leu Thr Cys
            245                 250                 255
Ala Val Ser Gly Tyr Ser Ile Ser Ser Gly Leu Gly Trp Gly Trp Ile
            260                 265                 270
Arg Gln Pro Pro Gly Lys Gly Leu Glu Trp Ile Gly Ile Tyr Glu
            275                 280                 285
Ser Gly Ser Thr Tyr Tyr Asn Pro Ser Leu Lys Ser Arg Val Thr Ile
            290                 295                 300
Ser Val Asp Thr Ser Lys Asn Gln Phe Ser Leu Lys Leu Ser Ser Val
305                 310                 315                 320
Thr Ala Ala Asp Thr Ala Val Tyr Tyr Cys Ala His Glu Arg Val Arg
            325                 330                 335
Gly Tyr Gly Asp Tyr Gly Gly His His Ala Phe Asp Ile Trp Gly Gln
            340                 345                 350
Gly Thr Met Val Thr Val Ser Ser Ala Ser Thr Lys Gly Pro Ser Val
            355                 360                 365
Phe Pro Leu Ala Pro Cys Ser Arg Ser Thr Ser Glu Ser Thr Ala Ala
            370                 375                 380
Leu Gly Cys Leu Val Lys Asp Tyr Phe Pro Glu Pro Val Thr Val Ser
385                 390                 395                 400
Trp Asn Ser Gly Ala Leu Thr Ser Gly Val His Thr Phe Pro Ala Val
            405                 410                 415
Leu Gln Ser Ser Gly Leu Tyr Ser Leu Ser Ser Val Val Thr Val Pro
            420                 425                 430
Ser Ser Ser Leu Gly Thr Lys Thr Tyr Thr Cys Asn Val Asp His Lys
            435                 440                 445
Pro Ser Asn Thr Lys Val Asp Lys Arg Val Glu Ser Lys Tyr Gly Pro
            450                 455                 460
Pro Cys Pro Pro Cys Pro Ala Pro Glu Phe Leu Gly Gly Pro Ser Val
465                 470                 475                 480
Phe Leu Phe Pro Pro Lys Pro Lys Asp Thr Leu Met Ile Ser Arg Thr
            485                 490                 495
Pro Glu Val Thr Cys Val Val Val Asp Val Ser Gln Glu Asp Pro Glu
            500                 505                 510
Val Gln Phe Asn Trp Tyr Val Asp Gly Val Glu Val His Asn Ala Lys
            515                 520                 525
```

```
Thr Lys Pro Arg Glu Glu Gln Phe Asn Ser Thr Tyr Arg Val Val Ser
    530                 535                 540

Val Leu Thr Val Leu His Gln Asp Trp Leu Asn Gly Lys Glu Tyr Lys
545                 550                 555                 560

Cys Lys Val Ser Asn Lys Gly Leu Pro Ser Ser Ile Glu Lys Thr Ile
                565                 570                 575

Ser Lys Ala Lys Gly Gln Pro Arg Glu Pro Gln Val Tyr Thr Leu Pro
            580                 585                 590

Pro Ser Gln Glu Glu Met Thr Lys Asn Gln Val Ser Leu Thr Cys Leu
        595                 600                 605

Val Lys Gly Phe Tyr Pro Ser Asp Ile Ala Val Glu Trp Glu Ser Asn
    610                 615                 620

Gly Gln Pro Glu Asn Asn Tyr Lys Thr Thr Pro Pro Val Leu Asp Ser
625                 630                 635                 640

Asp Gly Ser Phe Phe Leu Tyr Ser Arg Leu Thr Val Asp Lys Ser Arg
                645                 650                 655

Trp Gln Glu Gly Asn Val Phe Ser Cys Ser Val Met His Glu Ala Leu
            660                 665                 670

His Asn His Tyr Thr Gln Lys Ser Leu Ser Leu Ser Leu Gly Lys
        675                 680                 685

<210> SEQ ID NO 140
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Tyr Ala Thr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 141
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Val
            20                  25                  30

Ala Met Val Trp Val Arg Gln Ala Pro Gly Lys Gly Leu Glu Trp Val
            35                  40                  45

Ser Ala Ile Ser Gly Ser Gly Gly Ala Thr Tyr Tyr Ala Asp Ser Val
50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Pro Gly Tyr Asp Ser Ser Arg Tyr Tyr Tyr Ser Asn Tyr
            100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
            195                 200                 205

Thr Cys Asn Val Asp His Lys Pro Ser Asn Thr Lys Val Asp Lys Arg
210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
            275                 280                 285

Val Glu Val His Asn Ala Lys Thr Lys Pro Arg Glu Glu Gln Phe Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
```

```
                325                 330                 335
Ser Ser Ile Glu Lys Thr Ile Ser Lys Ala Lys Gly Gln Pro Arg Glu
            340                 345                 350
Pro Gln Val Tyr Thr Leu Pro Pro Ser Gln Glu Glu Met Thr Lys Asn
            355                 360                 365
Gln Val Ser Leu Thr Cys Leu Val Lys Gly Phe Tyr Pro Ser Asp Ile
            370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Arg
                405                 410                 415
Leu Thr Val Asp Lys Ser Arg Trp Gln Glu Gly Asn Val Phe Ser Cys
                420                 425                 430
Ser Val Met His Glu Ala Leu His Asn His Tyr Thr Gln Lys Ser Leu
                435                 440                 445
Ser Leu Ser Leu Gly Lys
            450

<210> SEQ ID NO 142
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
                20                  25                  30
Leu Asn Trp Tyr Gln Gln Lys Pro Gly Lys Ala Pro Lys Leu Leu Ile
            35                  40                  45
Tyr Gly Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Thr Tyr Ser Leu Tyr Thr
                85                  90                  95
Phe Gly Gly Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 143
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Val
            20                  25                  30

Ala Met Val Trp Val Arg Gln Ala Pro Gly Lys Gly Leu Glu Trp Val
        35                  40                  45

Ser Ala Ile Ser Gly Ser Gly Gly Ala Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Tyr Asp Ser Ser Arg Tyr Tyr Tyr Ser Asn Tyr
            100                 105                 110

Gly Met Asp Val Trp Gly Gln Gly Thr Thr Val Thr Val Ser Ser Ala
        115                 120                 125

Lys Thr Thr Ala Pro Ser Val Tyr Pro Leu Ala Pro Val Cys Gly Asp
130                 135                 140

Thr Thr Gly Ser Ser Val Thr Leu Gly Cys Leu Val Lys Gly Tyr Phe
145                 150                 155                 160

Pro Glu Pro Val Thr Leu Thr Trp Asn Ser Gly Ser Leu Ser Ser Gly
                165                 170                 175

Val His Thr Phe Pro Ala Val Leu Gln Ser Asp Leu Tyr Thr Leu Ser
            180                 185                 190

Ser Ser Val Thr Val Thr Ser Ser Thr Trp Pro Ser Gln Ser Ile Thr
        195                 200                 205

Cys Asn Val Ala His Pro Ala Ser Ser Thr Lys Val Asp Lys Lys Ile
    210                 215                 220

Glu Pro Arg Gly Pro Thr Ile Lys Pro Cys Pro Pro Cys Lys Cys Pro
225                 230                 235                 240

Ala Pro Asn Leu Leu Gly Gly Pro Ser Val Phe Ile Phe Pro Pro Lys
                245                 250                 255

Ile Lys Asp Val Leu Met Ile Ser Leu Ser Pro Ile Val Thr Cys Val
            260                 265                 270

Val Val Asp Val Ser Glu Asp Asp Pro Asp Val Gln Ile Ser Trp Phe
        275                 280                 285

Val Asn Asn Val Glu Val His Thr Ala Gln Thr Gln Thr His Arg Glu
    290                 295                 300

Asp Tyr Ala Ser Thr Leu Arg Val Val Ser Ala Leu Pro Ile Gln His
305                 310                 315                 320

Gln Asp Trp Met Ser Gly Lys Glu Phe Lys Cys Lys Val Asn Asn Lys
                325                 330                 335

Asp Leu Pro Ala Pro Ile Glu Arg Thr Ile Ser Lys Pro Lys Gly Ser
            340                 345                 350

```
Val Arg Ala Pro Gln Val Tyr Val Leu Pro Pro Glu Glu Met
            355                 360                 365

Thr Lys Lys Gln Val Thr Leu Thr Cys Met Val Thr Asp Phe Met Pro
370                 375                 380

Glu Asp Ile Tyr Val Glu Trp Thr Asn Asn Gly Lys Thr Glu Leu Asn
385                 390                 395                 400

Tyr Lys Asn Thr Glu Pro Val Leu Asp Ser Asp Gly Ser Tyr Phe Met
            405                 410                 415

Tyr Ser Lys Leu Arg Val Glu Lys Lys Asn Trp Val Glu Arg Asn Ser
            420                 425                 430

Tyr Ser Cys Ser Val Val His Glu Gly Leu His Asn His His Thr Thr
            435                 440                 445

Lys Ser Phe Ser Arg Thr Pro Gly Lys
            450                 455
```

<210> SEQ ID NO 144
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Leu Tyr Thr
                85                  90                  95

Phe Gly Gly Gly Thr Lys Val Glu Ile Lys Arg Ala Asp Ala Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
210
```

ANTI-TIGIT ANTIGEN-BINDING PROTEINS AND METHODS OF USE THEREOF

This application is a 35 U.S.C. § 371 national stage filing of International Application No. PCT/US2018/025460 filed on Mar. 30, 2018, which in turn claims the benefit of priority to U.S. Provisional Application No. 62/479,042, filed on Mar. 30, 2017. The entire contents of each of the foregoing applications are hereby incorporated herein by reference.

SEQUENCE LISTING

The Sequence Listing associated with this application is filed in electronic format via EFS-Web and hereby incorporated by reference into the specification in its entirety. The name of the text file containing the Sequence Listing is 127206_03720_SL.txt. The size of the text file is 292,091 bytes, and the text file was created on Feb. 7, 2019.

FIELD

Provided herein are antigen-binding proteins (ABPs) with binding specificity for T cell immunoreceptor with Ig and ITIM domains (TIGIT) and compositions comprising such ABPs, including pharmaceutical compositions, diagnostic compositions, and kits. Also provided are methods of making TIGIT ABPs, and methods of using TIGIT ABPs, for example, for therapeutic purposes, diagnostic purposes, and research purposes.

BACKGROUND

TIGIT has been identified as a co-inhibitory receptor that limits the response of T cells to cancer and chronic infection. See Grogan et al., *J. Immunol.*, 2014, 192: (1 Supplement) 203.15, incorporated by reference in its entirety. Blockade of TIGIT has been shown to contribute to the enhancement CD8+ T cell effector function, and improvement of viral clearance and tumor rejection. See id.

Thus, there is a need for therapeutics that can antagonize TIGIT. Provided herein are ABPs that fulfill this need.

This application is related to U.S. Provisional Application No. 62/235,990, filed Oct. 1, 2015, International Publication No. WO/2017/059095, and U.S. Pat. No. 9,713,641; each of which is hereby incorporated by reference in its entirety for all purposes.

SUMMARY

Provided herein are ABPs that specifically bind TIGIT and methods of using such ABPs. In some embodiments, the TIGIT is selected from human TIGIT ("hTIGIT", SEQ ID NO:1), cynomolgus monkey TIGIT ("cTIGIT", SEQ ID NO:2), and murine TIGIT ("mTIGIT", SEQ ID NO:3 or 138).

In one aspect is provided an isolated antigen binding protein (ABP) that specifically binds an epitope of human TIGIT (hTIGIT; SEQ ID NO: 1) and is capable of at least one of the following: a) blocking MAB7, MAB9, MAB10, MAB11 and MAB12 binding to human TIGIT; b) blocking binding of human TIGIT to CD155; and c) specifically binding to hTIGIT residues H76, I77, S78, and P79.

In another embodiment, the ABP specifically binds one or more additional hTIGIT residues from the group consisting of T55, Q56, N58, L65, I68, N70, D72, L73, H111, T117, S129, and S130.

In another embodiment, the ABP does not specifically bind hTIGIT residues Q61, Q62, D63, Q64, Y113, or P114.

In one embodiment, the ABP is MAB7, MAB9, MAB10, MAB11, or MAB12. In another embodiment, the ABP is capable of at least one of the following: a) blocking MAB1, MAB2, MAB3, MAB4 and MAB5 binding to human TIGIT; blocking binding of human TIGIT to CD155; and specifically binding to hTIGIT residues Q56 and I77. In another embodiment, the ABP does not specifically bind hTIGIT residues I68, L73, H76, S78, and P79.

In one embodiment, the ABP is capable of at least one of the following: a) blocking MAB13, MAB14, MAB15, MAB16, MAB 17, and MAB18 binding to human TIGIT; b) blocking binding of human TIGIT to CD155; and c) specifically binding to hTIGIT residues Q56, I68, L73, H76, and I77. In one embodiment, the ABP does not specifically bind hTIGIT residue S78.

In one embodiment, the ABP is capable of at least one of the following: a) blocking MAB19, MAB20, and MAB21 binding to human TIGIT; b) blocking binding of human TIGIT to CD155; and c) specifically binding to hTIGIT residues Q56, I68, L73, and I77.

In one embodiment, the ABP is capable of at least one of the following: a) inhibits binding of hTIGIT to CD112; b) increases a T effector cell function; c) increases a natural killer (NK) cell function; d) decreases the number of regulatory T cells in tissues or in circulation; e) suppresses a regulatory T cell or a regulatory T cell activity; 0 inhibits association of TIGIT and CD226; and g) does not bind specifically to Nectin-4 (also known as poliovirus-receptor-like 4, PVRL4).

In another embodiment, the ABP is MAB1, MAB2, MAB3, MAB4, MAB5, MAB6, MAB8, MAB13, MAB14, MAB15, MAB16, MAB17, MAB18, MAB19, MAB20, or MAB21.

In another aspect is provided a method of treating or preventing a disease or condition in a subject in need thereof, comprising administering to the subject an effective amount of: (i) an ABP that specifically binds hTIGIT, chosen from the group consisting of MAB1, MAB2, MAB3, MAB4, MAB5, MAB6, MAB7, MAB8, MAB9, MAB10, MB11, MAB12, MAB13, MAB14, MAB15, MAB16, MAB17, MAB18, MAB19, MAB20, and MAB21; and one or more of (ii) an additional immunotherapeutic agent that blocks signaling of an inhibitory receptor of an immune cell or a ligand thereof; and (iii) additional immunotherapeutic agent that modulates signaling of co-stimulatory receptor; or a nucleic acid encoding such agent.

In one embodiment, the inhibitory receptor or ligand thereof is selected from CTLA-4, PD-1, PD-L1, PD-L2, Tim-3, neuritin, BTLA, CECAM-1, CECAM-5, VISTA, LAIR1, CD160, 2B4, KIR, and combinations thereof.

In one embodiment, the co-stimulatory receptor is CD3, GITR, OX40, ICOS, LAG-2, CD27, CD28, CD40, or 4-1BB.

In one embodiment, the additional therapeutic is MAB22. In another embodiment, the additional immunotherapeutic is MAB23. In various embodiments, the ABP is MAB10, MAB2, MAB15, or MAB21.

In one embodiment, the additional immunotherapeutic agent is an antibody against Tim-3, 4-1BB, GITR, PD-1 or PD-L1, or is OX40. In some embodiments, the combination therapy produces an additive or synergistic effect on the immune response of the subject receiving such therapy.

In one embodiment, the disease or condition is a cancer, and the cancer is selected from a solid tumor and a hematological tumor. In some embodiments, the cancer is a solid tumor.

In some embodiments, the additional therapeutic agent is formulated in the same pharmaceutical composition as the ABP and the ABP and the additional therapeutic agent are co-administered. In another embodiment, the additional therapeutic agent is formulated in a different pharmaceutical composition from the ABP and the ABP and the additional therapeutic agent are administered separately. Such separate administration may occur on the same day or on different days. In some embodiments, the ABP is administered before the additional therapeutic agent; in other embodiments, the additional therapeutic agent is administered prior to administering the ABP.

BRIEF DESCRIPTION OF THE DRAWINGS

FIGS. 1A-1L are a series of graphs showing a lymphoproliferation assay to test for T cell responses in cytomegalovirus positive (CMV+) T cells, using PBMCs from individual donors. Cells were stimulated with 1 μg/ml, 0.1 μg/ml, or 0.01 μg/ml CMV lysate and treated with MAB10 and pembrolizumab each individually or in combination (FIGS. 1A-1C, respectively); cells stimulated with 1 μg/ml, 0.1 μg/ml, or 0.01 μg/ml CMV lysate and treated with MAB10 and anti-TIM-3 antibody each individually or in combination (FIGS. 1D-1F); cells stimulated with 1 μg/ml, 0.1 μg/ml, or 0.01 μg/ml CMV lysate and treated with MAB10 and an anti-41BB antibody, each individually or in combination (FIGS. 1G-1I); and cells stimulated with 1 μg/ml, 0.1 μg/ml, or 0.01 μg/ml CMV lysate and treated with MAB10 and rhOX40L, each individually or in combination (FIGS. 1J-1L). Statistical differences were calculated both between the two individual treatment groups and their matched controls, as well as between the two individual treatments groups and their combination using an unpaired Student's T test (*=p<0.05, =p<0.01, *=p<0.005, ****=p<0.001).

FIG. 2A shows activation of DTCs from a 50-year-old male with stage IV melanoma, as evidenced by production of IFNγ. Cells were cultured and stimulated with a control OVA peptide (3 μg/ml) or a melanoma peptide mix consistent of 1 μg/mL NY-ESO-1+1 μg/mL MelanA/MART-1+1 μg/mL gp100. Anti-GITR antibody MAB22, pembrolizumab, and anti-TIGIT antibody MAB10 were added to the peptide stimulated samples, either alone or in pairwise combinations. As a control, equal amounts of isotype control antibodies were used. For single antibody stimulation, the total amount of antibody was kept constant by supplementing with the isotype control antibody. MAB10 and pembrolizumab were used at a final concentration of 10 μg/ml, and MAB22 was used at a final concentration of 1 μg/ml. To assess activation, cells were in culture for 7 days, the supernatants were collected, and the level of IFNγ produced was quantified using AlphaLISA® (PerkinElmer). Statistical significance was calculated using One-Way ANOVA with multiple comparisons. FIG. 2B shows activation of DTCs from an 80-year-old female with stage IIa non-small cell lung cancer (NSCLC). Cells were cultured and left unstimulated (control) or were stimulated with soluble anti-CD3+anti-CD28 antibodies for two days. As a control, an equal amount of an isotype control antibody (IgG4) was used. For single antibody stimulation, the total amount of antibody was kept constant by supplementing the samples with the isotype control antibody. MAB10 and pembrolizumab were used at a final concentration of 10 μg/ml. To assess activation, Brefeldin A was added to the cells during the last 5 hours of culture and FACS analysis and quantification of IFNγ-producing CD4+ and CD8+ T cells was performed using ICS. Statistical significance was calculated using One-Way ANOVA with multiple comparisons.

In FIGS. 3A-3B, $1 \times 10^5$ mouse EMT6 cells were implanted subcutaneously into female BALB/c mice. Once the tumors reached an average size of 80-120 mm$^3$, the mice were randomized into treatment groups and the indicated antibodies were administered intraperitoneally at 1000 μg/animal (control IgG2b and 1B4), 500 μg/animal (mMAB23 and 1B4), 250 μg/animal (mMAB23 and 1B4), or 200 μg/animal (αPD-1). The black arrows indicate treatment days. The average (mean)+/−standard error of the mean (SEM) tumor volume from 8 mice per group is shown for each treatment group. Statistical significance (differences of least squares means with Tukey-Kramer adjustment) of the treated mice compared to control mice was calculated on day 14. The control, rat anti-mouse αPD-1 (clone RMP1-14), single agent (250 μg), and combination (250 μg each) curves were evaluated over time using a mixed models analysis. In FIGS. 3C-3D the individual EMT6 tumor volumes for each of the 8 mice per group are shown for all treatment groups (indicated at the top of each graph). The EMT6 mouse tumor cells were injected into female BALB/c mice and randomized at an average size of 80-120 mm$^3$. Treatment began at randomization and the indicated antibodies were administered intraperitoneally at 1000 μg/animal (control IgG2b and 1B4), 500 μg/animal (mMAB23 and 1B4), 250 μg/animal (mMAB23 and 1B4), or 200 μg/animal (αPD-1). The black arrows indicate treatment days. The y-axes indicate tumor volume, and the x-axes indicate the time after the start of treatment in days. The study endpoint was defined as Day 40 or mean tumor volume of 2,000 mm$^3$ dependent on the treatment group.

DETAILED DESCRIPTION

1. Definitions

Figure 1A:
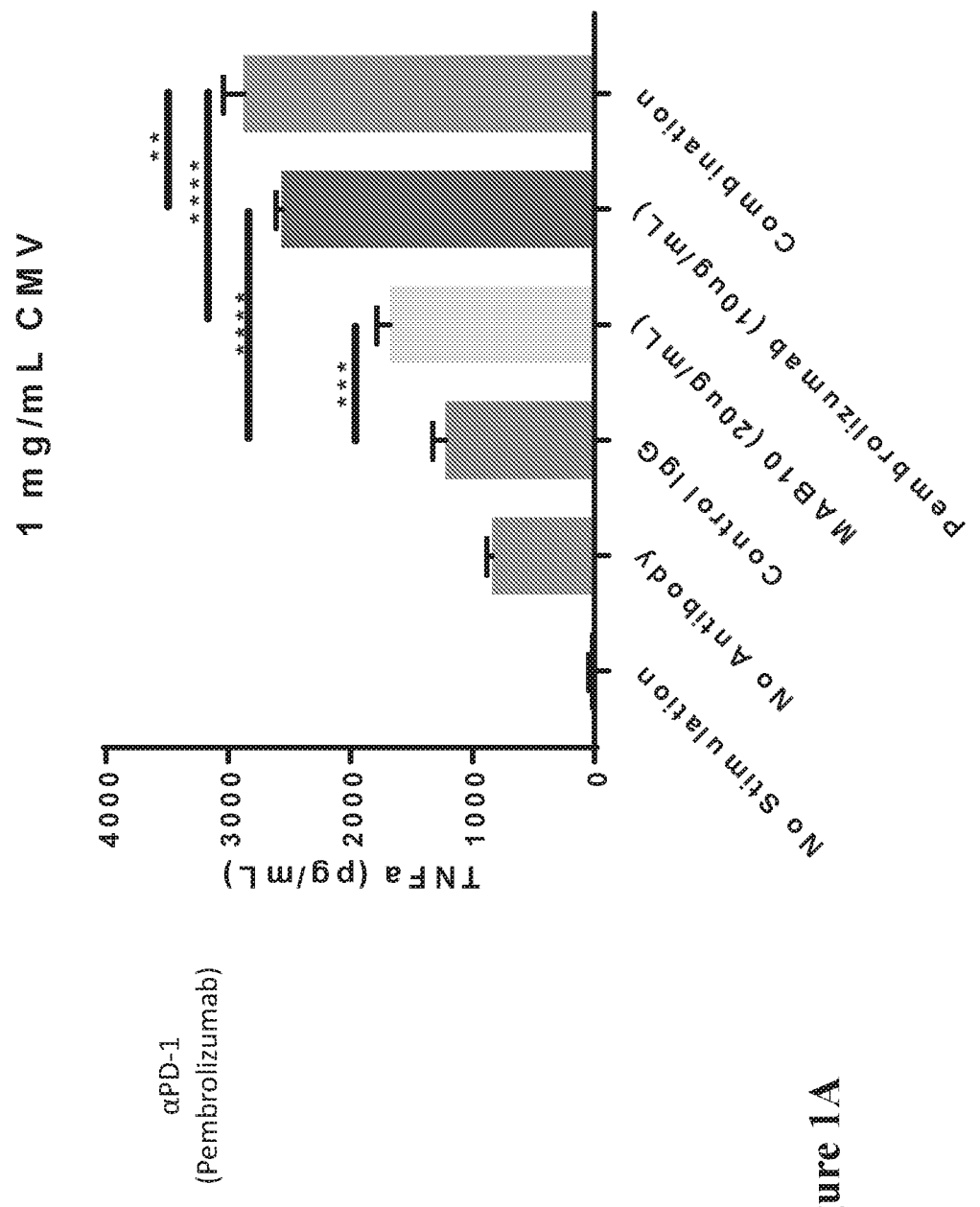
Figure 1B:
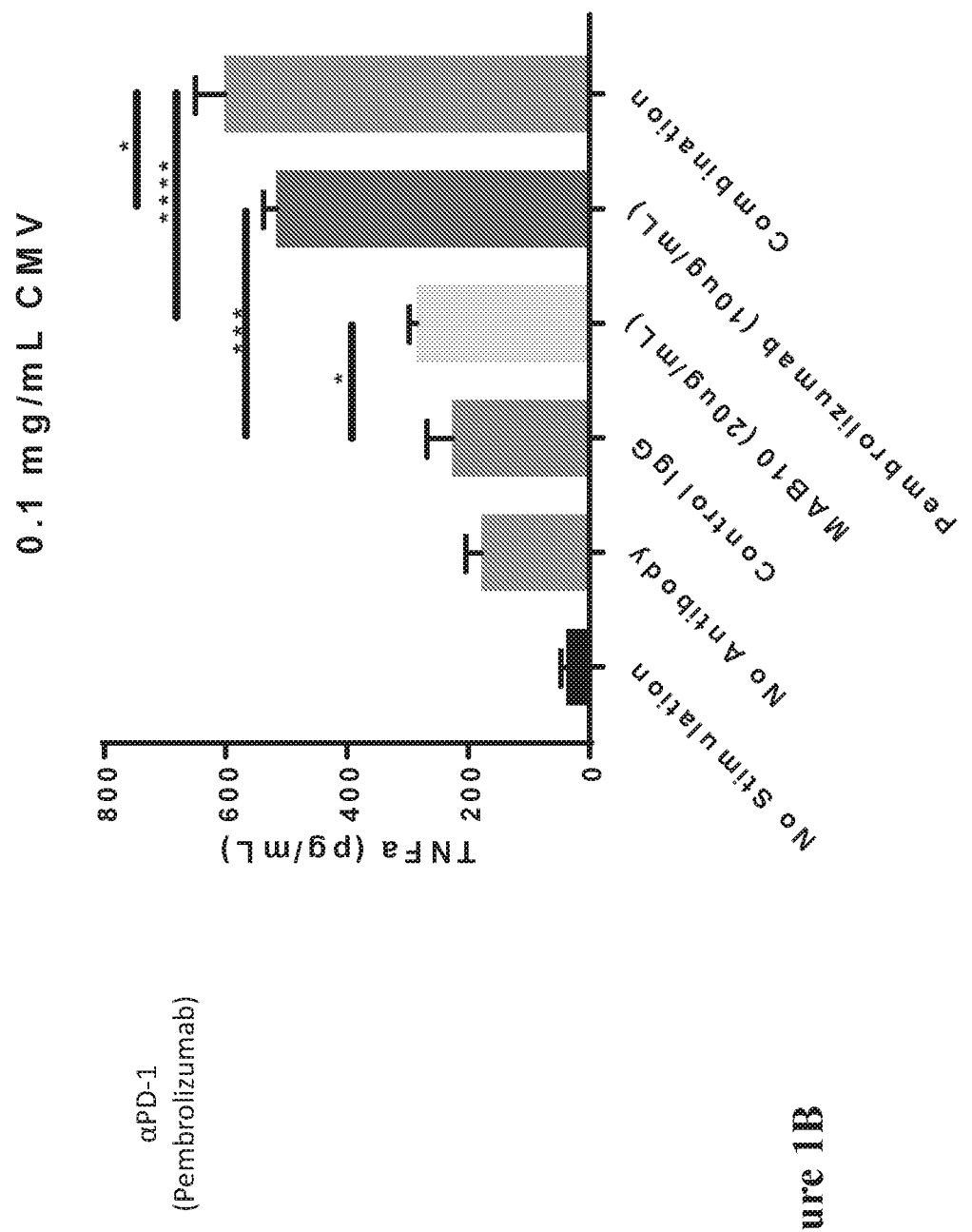
Figure 1C:
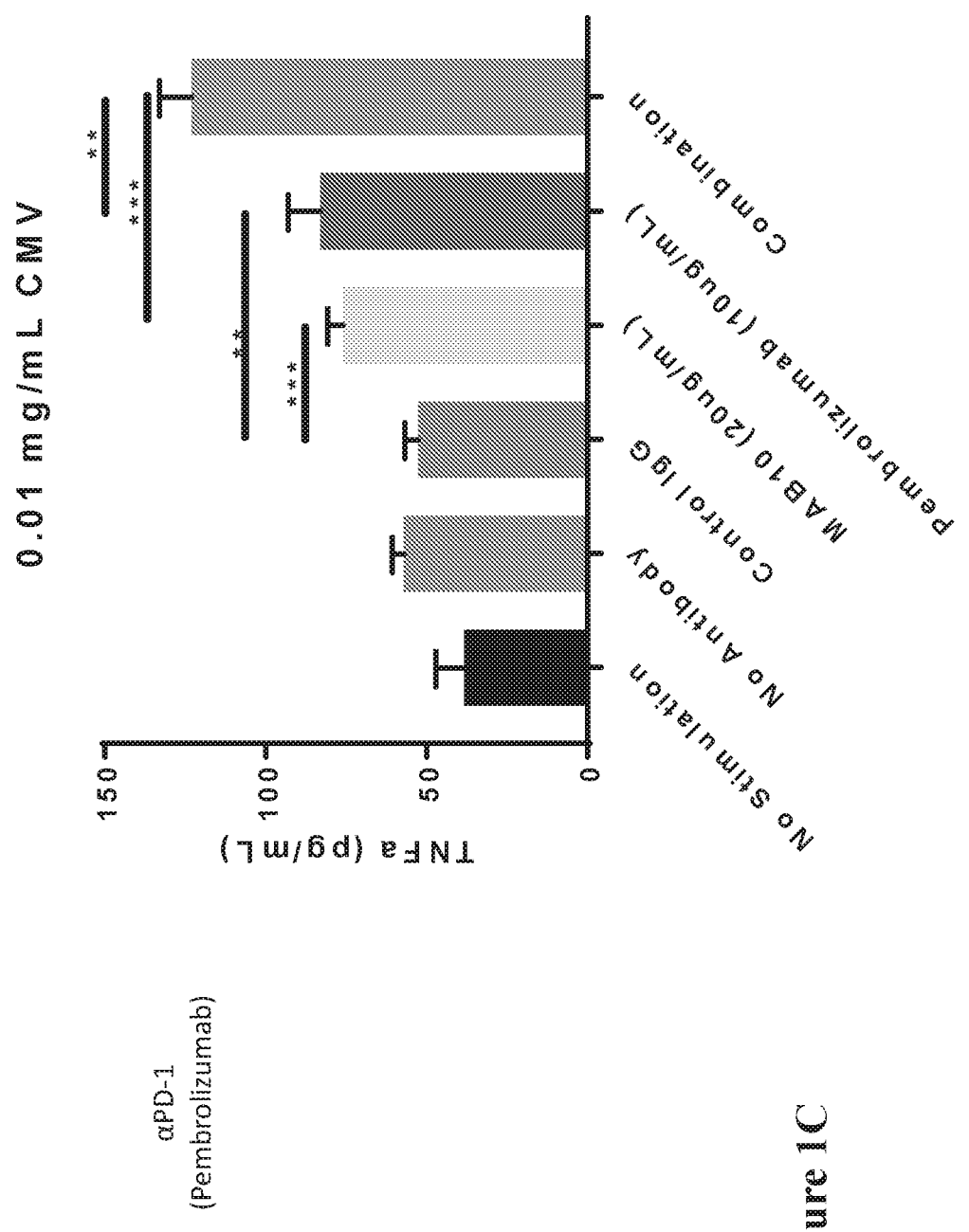
Figure 1D:
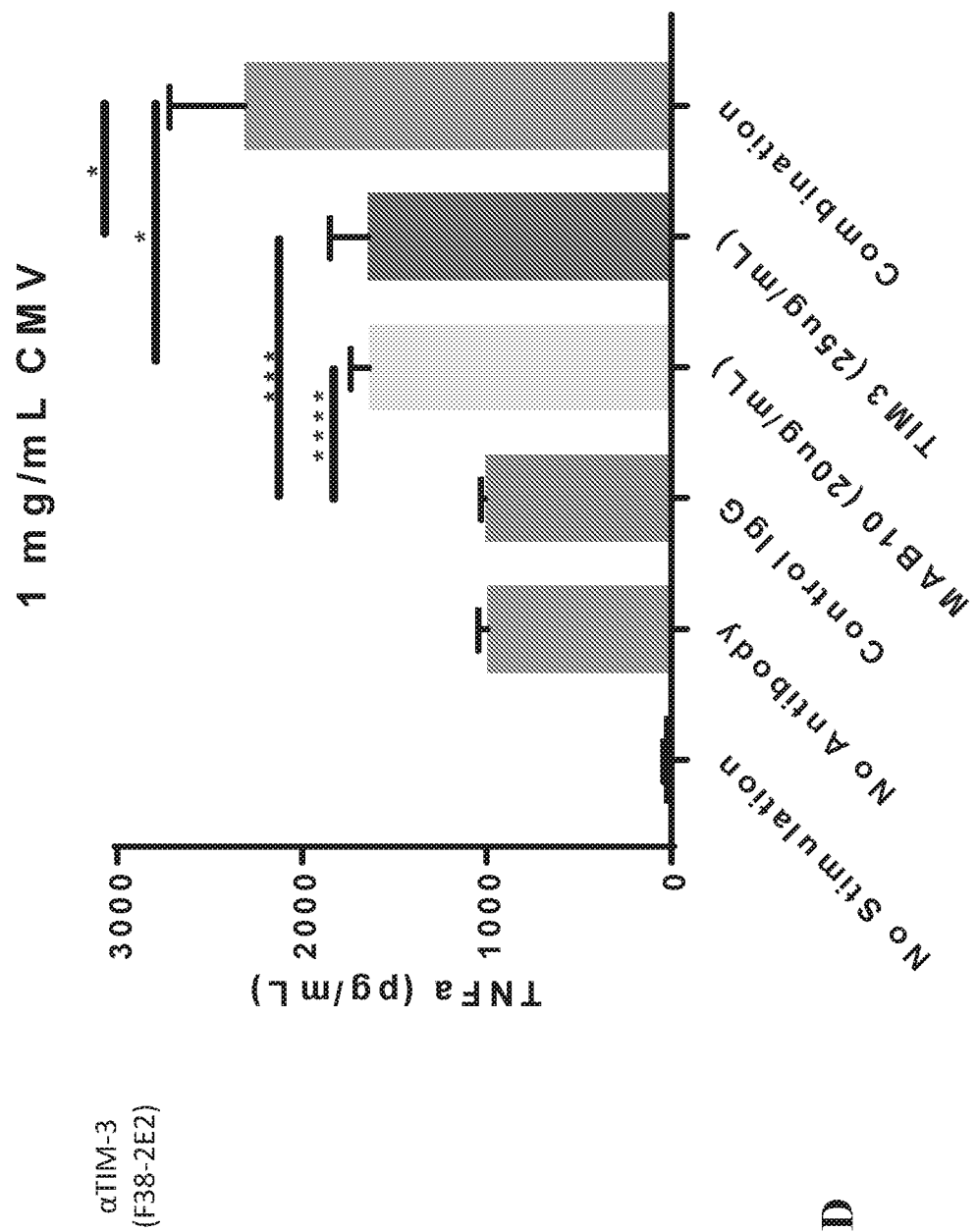
Figure 1E:
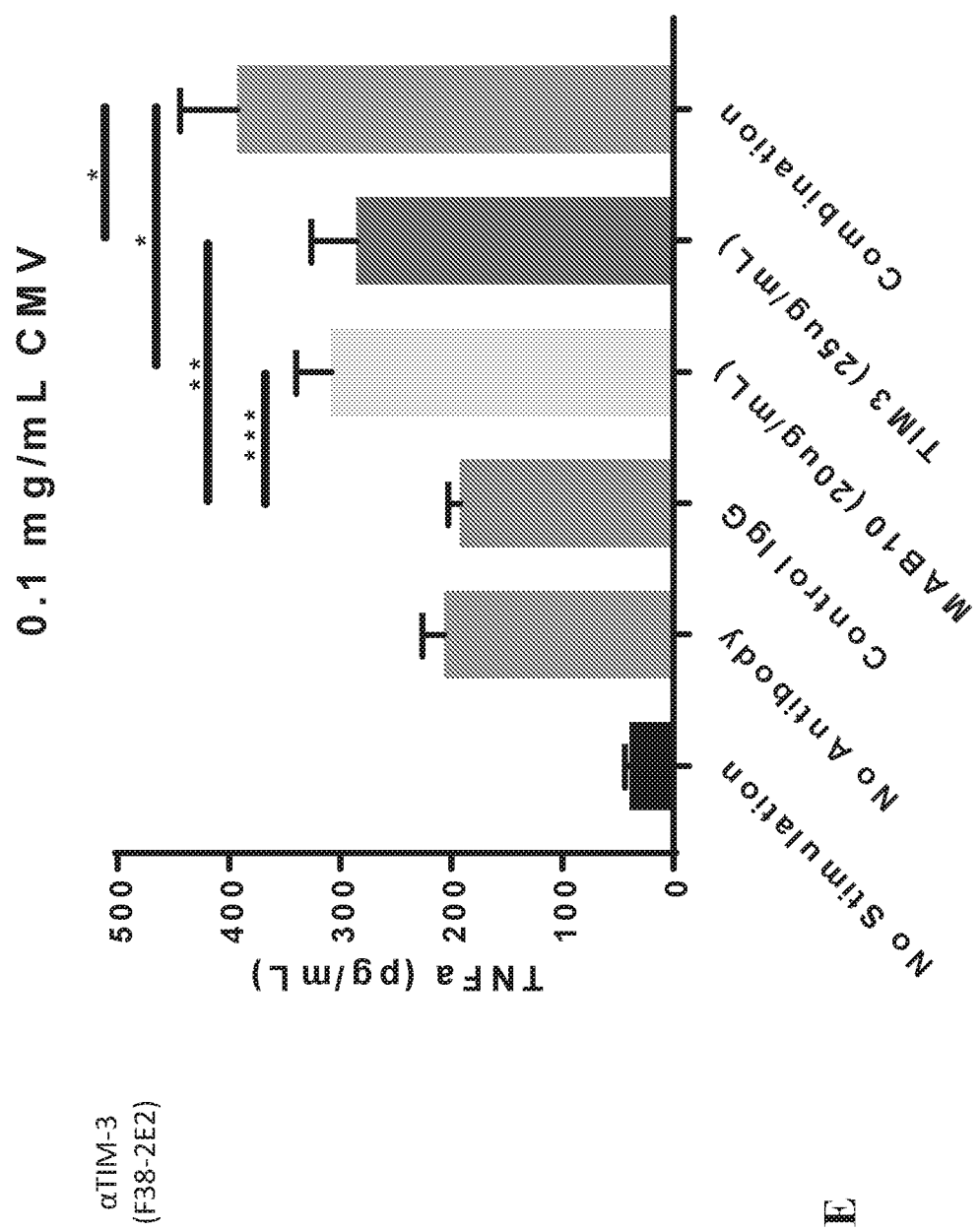
Figure 1F:
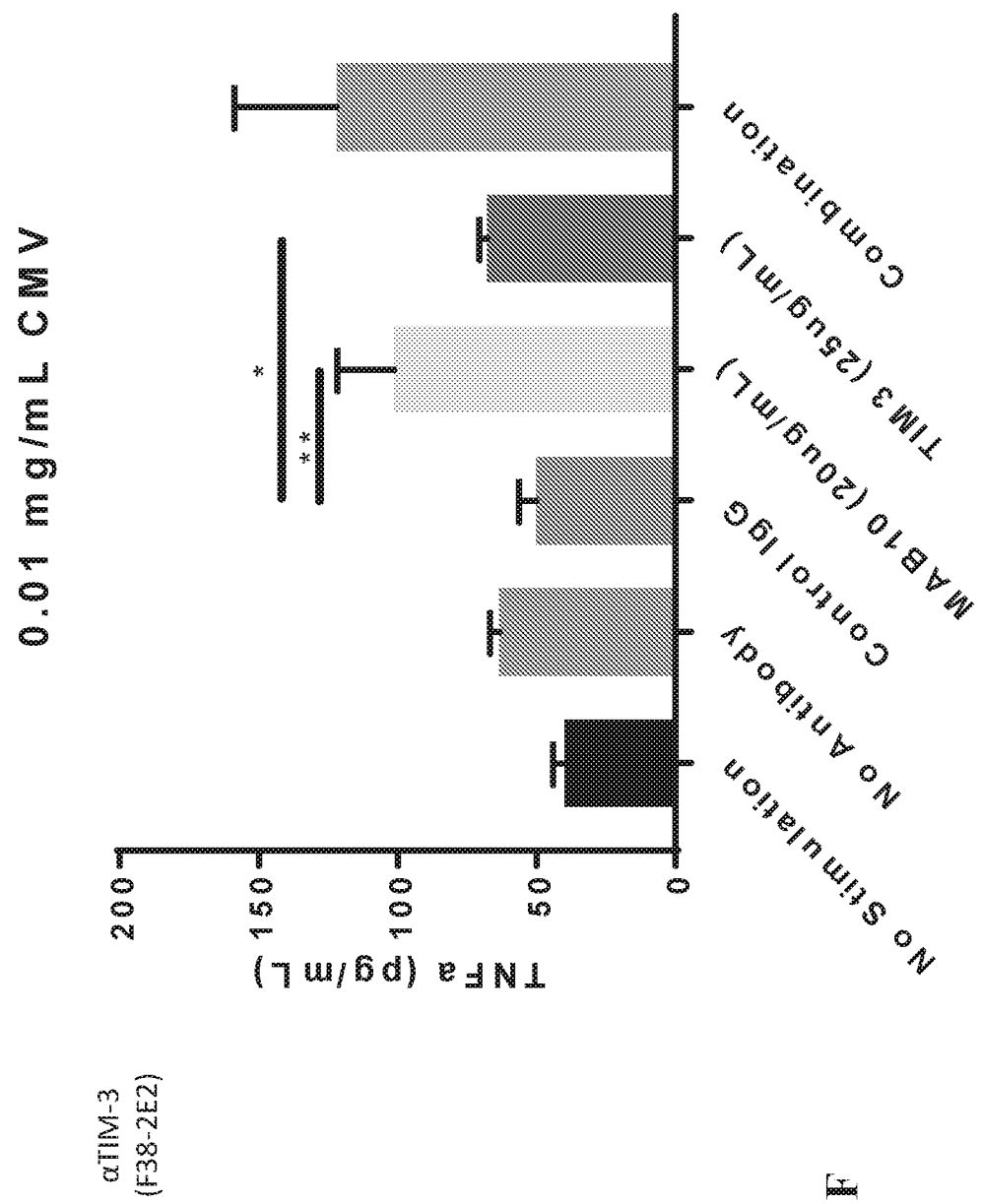
Figure 1G:
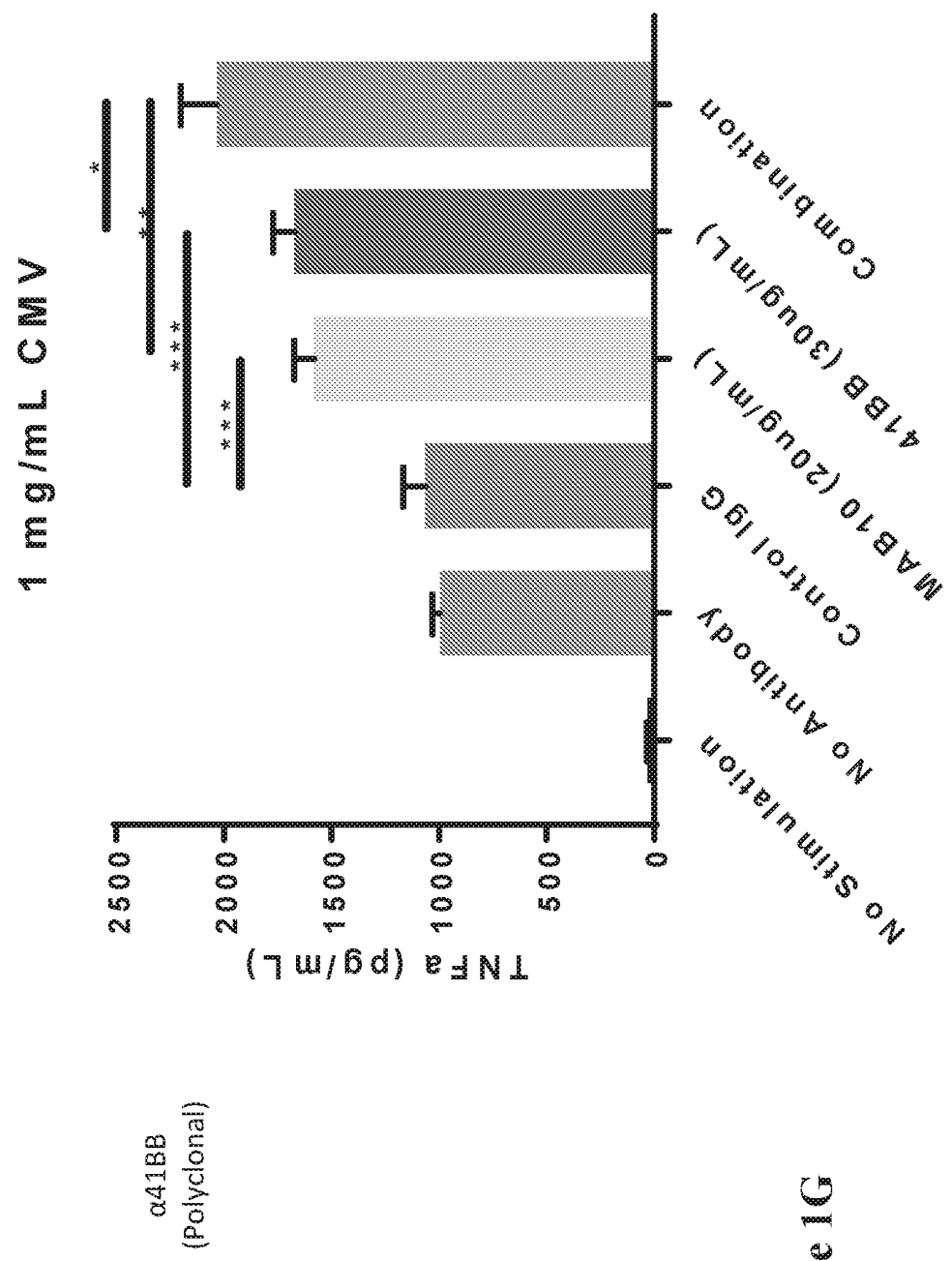
Figure 1H:
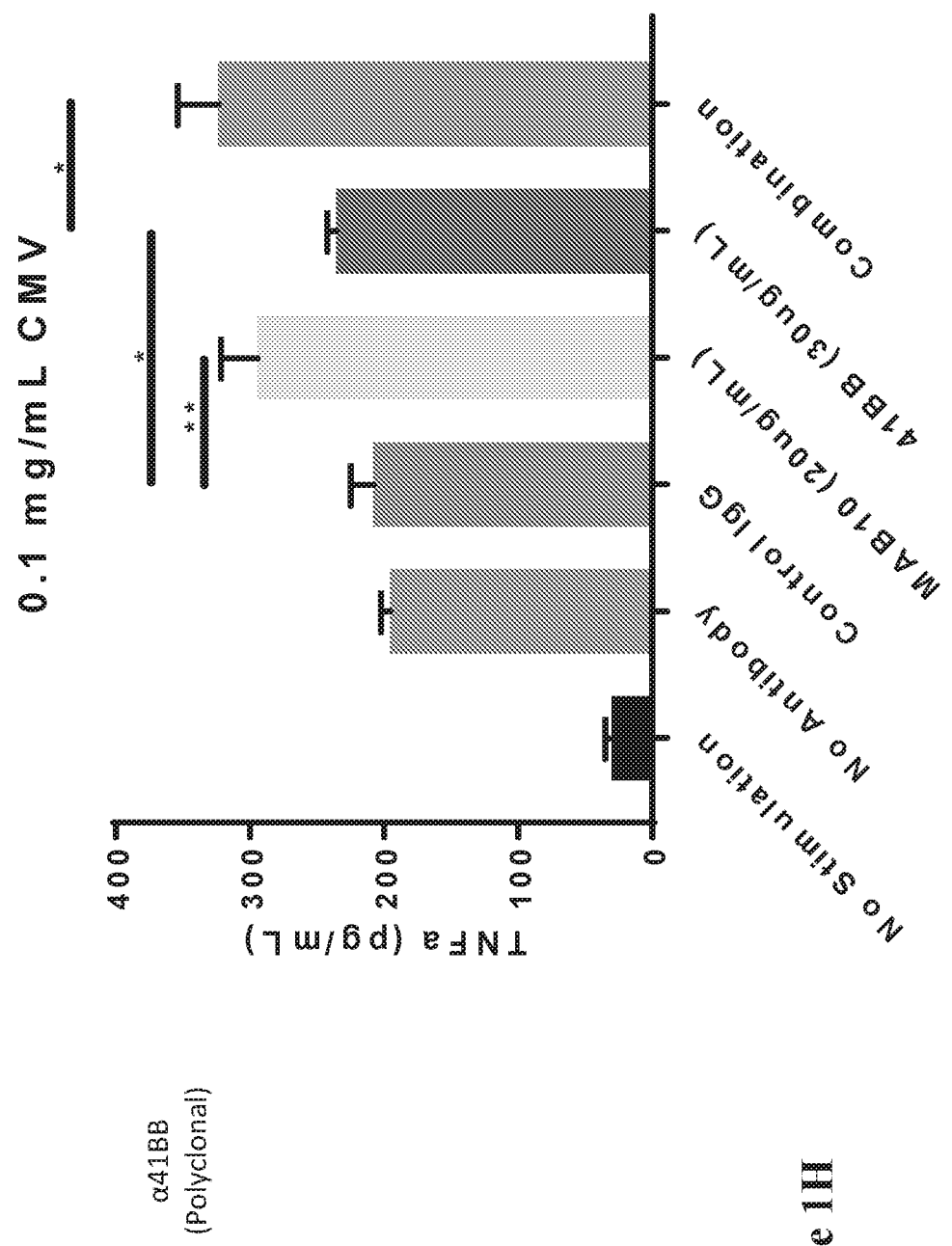
Figure 11:
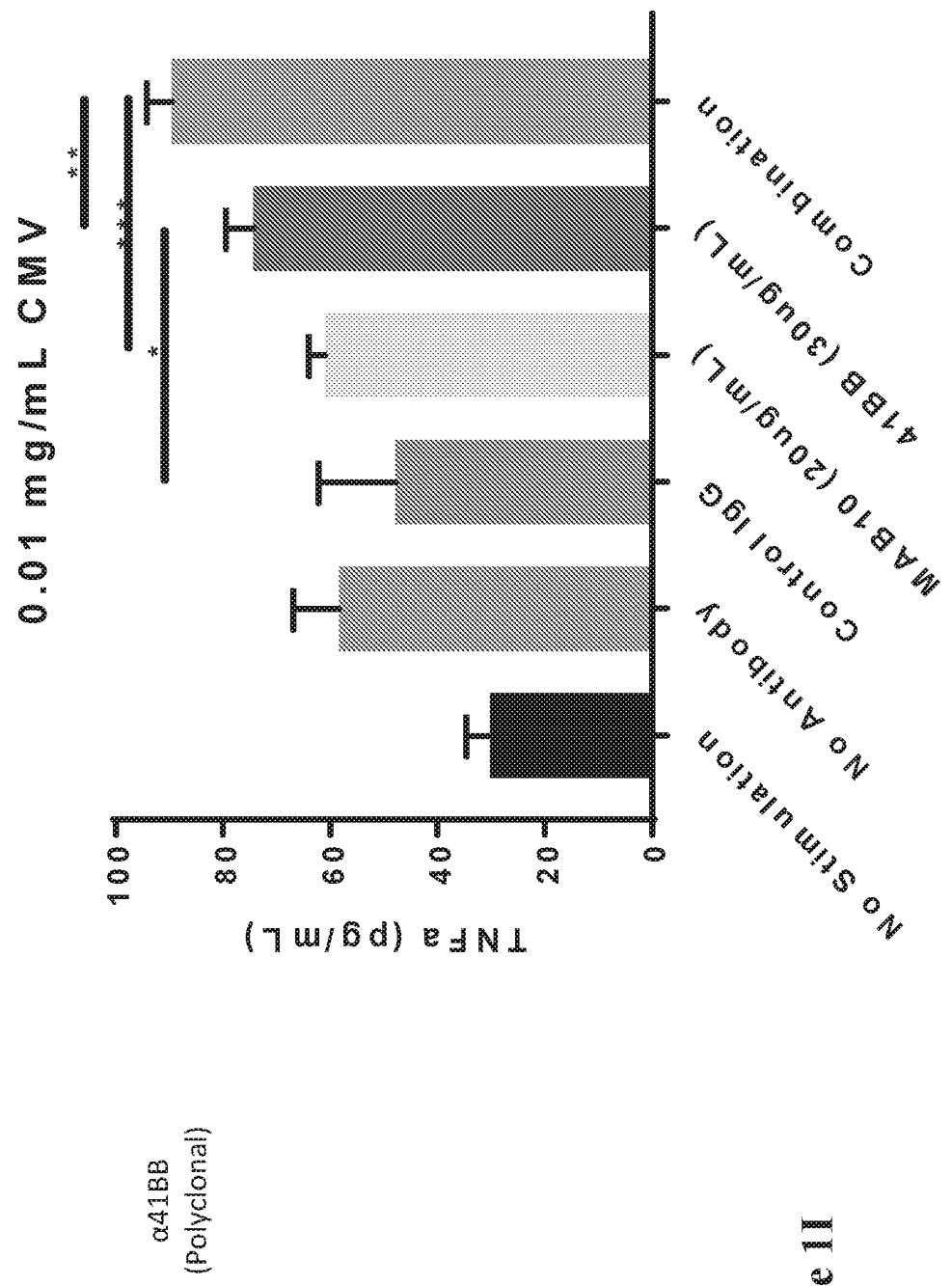

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, N.Y. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise. The terms "include," "such as," and the like are intended to convey inclusion without limitation, unless otherwise specifically indicated.

As used herein, the term "comprising" also specifically includes embodiments "consisting of" and "consisting essentially of" the recited elements, unless specifically indicated otherwise.

The term "about" indicates and encompasses an indicated value and a range above and below that value. In certain embodiments, the term "about" indicates the designated value ±10%, ±5%, or ±1%. In certain embodiments, where applicable, the term "about" indicates the designated value(s) ±one standard deviation of that value(s).

The terms "TIGIT," "TIGIT protein," and "TIGIT antigen" are used interchangeably herein to refer to human TIGIT, or any variants (e.g., splice variants and allelic variants), isoforms, and species homologs of human TIGIT that are naturally expressed by cells, or that are expressed by cells transfected with a tigit gene. In some aspects, the TIGIT protein is a TIGIT protein naturally expressed by a primate (e.g., a monkey or a human), a rodent (e.g., a mouse or a rat), a dog, a camel, a cat, a cow, a goat, a horse, or a sheep. In some aspects, the TIGIT protein is human TIGIT (hTIGIT; SEQ ID NO:1). Without being bound by theory, it is believed that positions 1-21 of SEQ ID NO:1 encode a signal peptide; positions 22-141 of SEQ ID NO:1 encode the extracellular domain of the mature TIGIT protein; positions 142-162 of SEQ ID NO:1 encode a transmembrane domain; and positions 163-244 of SEQ ID NO:1 encode a cytoplasmic domain. See UniProt KB-Q495A1 (TIGIT_HUMAN), at www.uniprot.org/uniprot/Q495A1, accessed Sep. 28, 2015. In some aspects, the TIGIT protein is a cynomolgus monkey TIGIT (cTIGIT; SEQ ID NO:2). In some aspects, the TIGIT protein is a murine TIGIT (mTIGIT) having the sequence provided in SEQ ID NO:3. In some aspects, the TIGIT protein is a murine TIGIT (mTIGIT) having the sequence provided in SEQ ID NO:138. As used herein, if a SEQ ID NO is not specified, the terms "mTIGIT," "murine TIGIT" and "mouse TIGIT mean SEQ ID NO: 3 and/or SEQ ID NO: 138. In some aspects, the TIGIT protein is a full-length or unprocessed TIGIT protein. In some aspects, the TIGIT protein is a truncated or processed TIGIT protein produced by post-translational modification. TIGIT is also known by a variety of synonyms, including WUCAM, VSIG9, and Vstm3.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated CL.

The term "antigen-binding protein" (ABP) refers to a protein comprising one or more antigen-binding domains that specifically bind to an antigen or epitope. In some embodiments, the antigen-binding domain binds the antigen or epitope with specificity and affinity similar to that of naturally occurring antibodies. In some embodiments, the ABP comprises an antibody. In some embodiments, the ABP consists of an antibody. In some embodiments, the ABP consists essentially of an antibody. In some embodiments, the ABP comprises an alternative scaffold. In some embodiments, the ABP consists of an alternative scaffold. In some embodiments, the ABP consists essentially of an alternative scaffold. In some embodiments, the ABP comprises an antibody fragment. In some embodiments, the ABP consists of an antibody fragment. In some embodiments, the ABP consists essentially of an antibody fragment. A "TIGIT ABP," "anti-TIGIT ABP," or "TIGIT-specific ABP" is an ABP, as provided herein, which specifically binds to the antigen TIGIT. In some embodiments, the ABP binds the extracellular domain of TIGIT. In certain embodiments, a TIGIT ABP provided herein binds to an epitope of TIGIT that is conserved between or among TIGIT proteins from different species.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies. An antibody is one type of ABP.

The term "antigen-binding domain" means the portion of an ABP that is capable of specifically binding to an antigen or epitope. One example of an antigen-binding domain is an antigen-binding domain formed by a $V_H$-$V_L$ dimer of an antibody. Another example of an antigen-binding domain is an antigen-binding domain formed by diversification of certain loops from the tenth fibronectin type III domain of an Adnectin.

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "Fc region" means the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini, *J. Allergy Clin. Immunol.*, 2010, 125:S41-52, incorporated by reference in its entirety. The Fc region may be a naturally occurring Fc region, or an Fc region modified as described in the art or elsewhere in this disclosure.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme); each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at www.bioinf.org.uk/abs/abnum/, and described in Abhinandan and Martin, *Immunology*, 2008, 45:3832-3839, incorporated by reference in its entirety.

TABLE 1

Residues in CDRs according to Kabat and Chothia numbering schemes.

| CDR | Kabat | Chothia |
| --- | --- | --- |
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen-binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain (CH1) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). Any suitable linker may be used. In some embodiments, the linker is a $(GGGGS)_n$ (SEQ ID NO: 127). In some embodiments, n=1, 2, 3, 4, 5, or 6. See Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$). Any suitable Fc domain known in the art or described herein may be used. In some cases, the Fc domain comprises an IgG4 Fc domain.

A "monospecific ABP" is an ABP that comprises one or more binding sites that specifically bind to a single epitope. An example of a monospecific ABP is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated ABP" or "isolated nucleic acid" is an ABP or nucleic acid that has been separated and/or recovered from a component of its natural environment. Components of the natural environment may include enzymes, hormones, and other proteinaceous or nonproteinaceous materials. In some embodiments, an isolated ABP is purified to a degree sufficient to obtain at least 15 residues of N-terminal or internal amino acid sequence, for example by use of a spinning cup sequenator. In some embodiments, an isolated ABP is purified to homogeneity by gel electrophoresis (e.g., SDS-PAGE) under reducing or nonreducing conditions, with detection by Coomassie blue or silver stain. In some embodiments, an isolated ABP may include an ABP in situ within recombinant cells, since at least one component of the ABP's natural environment is not present. In some aspects, an isolated ABP or isolated nucleic acid is prepared by at least one purification step. In some embodiments, an isolated ABP or isolated nucleic acid is purified to at least 80%, 85%, 90%, 95%, or 99% by weight. In some embodiments, an isolated ABP or isolated nucleic acid is purified to at least 80%, 85%, 90%, 95%, or 99% by volume. In some embodiments, an isolated ABP or isolated nucleic acid is provided as a solution comprising at least 85%, 90%, 95%, 98%, 99% to 100% ABP or nucleic acid by weight. In some embodiments, an isolated ABP or isolated nucleic acid is provided as a solution comprising at least 85%, 90%, 95%, 98%, 99% to 100% ABP or nucleic acid by volume.

"Affinity" refers to the strength of the sum total of non-covalent interactions between a single binding site of a molecule (e.g., an ABP) and its binding partner (e.g., an antigen or epitope). Unless indicated otherwise, as used herein, "affinity" refers to intrinsic binding affinity, which reflects a 1:1 interaction between members of a binding pair (e.g., ABP and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

With regard to the binding of an ABP to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the ABP to the target molecule is competitively inhibited by the control molecule. In some aspects, the affinity of a TIGIT ABP for a non-target molecule is less than about 50% of the affinity for TIGIT. In some aspects, the affinity of a TIGIT ABP for a non-target molecule is less than about 40% of the affinity for TIGIT. In some aspects, the affinity of a TIGIT ABP for a non-target molecule is less than about 30% of the affinity for TIGIT. In some aspects, the affinity of a TIGIT ABP for a non-target molecule is less than about 20% of the affinity for TIGIT. In some aspects, the affinity of a TIGIT ABP for a non-target molecule is less than about 10% of the affinity for TIGIT. In some aspects, the affinity of a TIGIT ABP for a non-target molecule is less than about 1% of the affinity for TIGIT. In some aspects, the affinity of a TIGIT ABP for a non-target molecule is less than about 0.1% of the affinity for TIGIT.

The term "$k_d$" ($sec^{-1}$), as used herein, refers to the dissociation rate constant of a particular ABP-antigen interaction. This value is also referred to as the $k_{off}$ value.

The term "$k_a$" ($M^{-1} \times sec^{-1}$), as used herein, refers to the association rate constant of a particular ABP-antigen interaction. This value is also referred to as the $k_{on}$ value.

The term "$K_D$" (M), as used herein, refers to the dissociation equilibrium constant of a particular ABP-antigen interaction. $K_D = k_d/k_a$. In some embodiments, the affinity of an ABP is described in terms of the $K_D$ for an interaction between such ABP and its antigen. For clarity, as known in the art, a smaller $K_D$ value indicates a higher affinity interaction, while a larger $K_D$ value indicates a lower affinity interaction.

The term "$K_A$" ($M^{-1}$), as used herein, refers to the association equilibrium constant of a particular ABP-antigen interaction. $K_A = k_a/k_d$.

An "affinity matured" ABP is an ABP with one or more alterations (e.g., in one or more CDRs or FRs) relative to a parent ABP (i.e., an ABP from which the altered ABP is derived or designed) that result in an improvement in the affinity of the ABP for its antigen, compared to the parent ABP which does not possess the alteration(s). In some embodiments, an affinity matured ABP has nanomolar or picomolar affinity for the target antigen Affinity matured ABPs may be produced using a variety of methods known in the art. For example, Marks et al. (*Bio/Technology*, 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. USA.*, 1994, 91:3809-3813); Schier et al., *Gene*, 1995, 169:147-155; Yelton et al., *J. Immunol.*, 1995, 155:1994-2004; Jackson et al., *J. Immunol.*, 1995, 154:3310-33199; and Hawkins et al, *J. Mol. Biol.*, 1992, 226:889-896; each of which is incorporated by reference in its entirety.

An "immunoconjugate" is an ABP conjugated to one or more heterologous molecule(s), such as a therapeutic or diagnostic agent.

"Effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP).

When used herein in the context of two or more ABPs, the term "competes with" or "cross-competes with" indicates that the two or more ABPs compete for binding to an antigen (e.g., TIGIT). In one exemplary assay, TIGIT is coated on a surface and contacted with a first TIGIT ABP, after which a second TIGIT ABP is added. In another exemplary assay, a first TIGIT ABP is coated on a surface and contacted with TIGIT, and then a second TIGIT ABP is added. If the presence of the first TIGIT ABP reduces binding of the second TIGIT ABP, in either assay, then the ABPs compete with each other. The term "competes with" also includes combinations of ABPs where one ABP reduces binding of another ABP, but where no competition is observed when the ABPs are added in the reverse order. However, in some embodiments, the first and second ABPs inhibit binding of each other, regardless of the order in which they are added. In some embodiments, one ABP reduces binding of another ABP to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the ABPs for TIGIT and the valency of the ABPs. The assays described in this definition are illustrative, and a skilled artisan can utilize any suitable assay to determine if antibodies compete with each other. Suitable assays are described, for example, in Cox et al., "Immunoassay Methods," in *Assay Guidance Manual [Internet], Updated Dec. 24, 2014* (www.ncbi.nlm.nih.gov/books/NBK92434/; accessed Sep. 29, 2015); Silman et al., *Cytometry*, 2001, 44:30-37; and Finco et al., *J. Pharm. Biomed. Anal.*, 2011, 54:351-358; each of which is incorporated by reference in its entirety.

The term "epitope" means a portion of an antigen that specifically binds to an ABP. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an ABP binds can be determined using known techniques for epitope determination such as, for example, testing for ABP binding to TIGIT variants with different point-mutations, or to chimeric TIGIT variants.

Similarly, the term "paratope" refers to the amino acid residues in an antibody that bind to the epitope of a target protein.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution an amino acid with a chemically or functionally similar amino acid. Conservative substitution tables providing similar amino acids are well known in the art. By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An ABP generated by making one or more conservative substitutions of amino acid residues in a parent ABP is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations.

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

As used herein, the term "therapeutically effective amount" or "effective amount" refers to an amount of an ABP or pharmaceutical composition provided herein that, when administered to a subject, is effective to treat a disease or disorder.

As used herein, the term "subject" means a mammalian subject. Exemplary subjects include humans, monkeys, dogs, cats, mice, rats, cows, horses, camels, goats, rabbits, and sheep. In certain embodiments, the subject is a human. In some embodiments the subject has a disease or condition that can be treated with an ABP provided herein. In some aspects, the disease or condition is a cancer. In some aspects, the disease or condition is a viral infection.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

The term "cytotoxic agent," as used herein, refers to a substance that inhibits or prevents a cellular function and/or causes cell death or destruction.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "cytostatic agent" refers to a compound or composition which arrests growth of a cell either in vitro or in vivo. In some embodiments, a cytostatic agent is an agent that reduces the percentage of cells in S phase. In some embodiments, a cytostatic agent reduces the percentage of cells in S phase by at least about 20%, at least about 40%, at least about 60%, or at least about 80%.

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein. The terms "cell proliferative disorder" and "proliferative disorder" refer to disorders that are associated with some degree of abnormal cell proliferation. In some embodiments, the cell proliferative disorder is a cancer. In some aspects, the tumor is a solid tumor. In some aspects, the tumor is a hematologic malignancy.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor.

The term "effector T cell" includes T helper (i.e., CD4+) cells and cytotoxic (i.e., CD8+) T cells. CD4+ effector T cells contribute to the development of several immunologic processes, including maturation of B cells into plasma cells and memory B cells, and activation of cytotoxic T cells and macrophages. CD8+ effector T cells destroy virus-infected cells and tumor cells. See Seder and Ahmed, *Nature Immunol.*, 2003, 4:835-842, incorporated by reference in its entirety, for additional information on effector T cells.

The term "regulatory T cell" includes cells that regulate immunological tolerance, for example, by suppressing effector T cells. In some aspects, the regulatory T cell has a CD4+CD25+Foxp3+ phenotype. In some aspects, the regulatory T cell has a CD8+CD25+ phenotype. See Nocentini et al., *Br. J. Pharmacol.*, 2012, 165:2089-2099, incorporated by reference in its entirety, for additional information on regulatory T cells expressing TIGIT.

The term "dendritic cell" refers to a professional antigen-presenting cell capable of activating a naïve T cell and stimulating growth and differentiation of a B cell.

2. TIGIT Antigen-Binding Proteins 2.1. TIGIT Binding and Target Cells

Provided herein are ABPs that specifically bind to TIGIT. In some aspects, the TIGIT is hTIGIT (SEQ ID NO:1). In some aspects, the TIGIT is cTIGIT (SEQ ID NO:2). In some aspects, the TIGIT is mTIGIT with the sequence provided in SEQ ID NO:3. In some aspects, the TIGIT is mTIGIT with the sequence provided in SEQ ID NO:138.

In some embodiments, the ABPs provided herein specifically bind to hTIGIT (SEQ ID NO:1), cTIGIT (SEQ ID NO:2), and mTIGIT of SEQ ID NO:3. In some embodiments, the ABPs provided herein specifically bind to hTIGIT (SEQ ID NO:1), cTIGIT (SEQ ID NO:2), and mTIGIT of SEQ ID NO:138. In some embodiments, the ABPs provided herein specifically bind to hTIGIT (SEQ ID NO:1), and cTIGIT (SEQ ID NO:2). In some embodiments, the ABPs provided herein specifically bind to hTIGIT (SEQ ID NO:1). In some embodiments, the ABPs provided herein do not bind mTIGIT of SEQ ID NO:3. In some embodiments, the ABPs provided herein do not bind mTIGIT of SEQ ID NO:138.

In some embodiments, the ABPs provided herein specifically bind to the extracellular domain of TIGIT.

In some embodiments, an ABP provided herein is an antibody. In some embodiments, an ABP provided herein is an antibody fragment. In some embodiments, an ABP provided herein is an alternative scaffold.

The TIGIT may be expressed on the surface of any suitable target cell. In some embodiments, the target cell is a T cell. In some embodiments, the target cell is an effector T cell. In some embodiments, the target cell is a regulatory T cell. In some embodiments, the target cell is a natural killer (NK) cell. In some embodiments, the target cell is a natural killer T (NKT) cell.

In some embodiments, the ABPs provided herein comprise an immunoglobulin molecule. In some embodiments, the ABPs provided herein consist of an immunoglobulin molecule. In some embodiments, the ABPs provided herein consist essentially of an immunoglobulin molecule. In some aspects, the immunoglobulin molecule comprises an antibody. In some aspects, the immunoglobulin molecule consists of an antibody. In some aspects, the immunoglobulin molecule consists essentially of an antibody.

In some embodiments, the ABPs provided herein comprise a light chain. In some aspects, the light chain is a kappa light chain. In some aspects, the light chain is a lambda light chain.

In some embodiments, the ABPs provided herein comprise a kappa light chain comprising SEQ ID NO: 126.

In some embodiments, the ABPs provided herein comprise a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the ABPs provided herein comprise an IgG4 heavy chain comprising a sequence selected from SEQ ID NO:55 and SEQ ID NO:56. In some embodiments, the ABPs provided herein comprise an IgG1 heavy chain comprising a sequence selected from SEQ ID NO:57 and SEQ ID NO: 125.

In some embodiments, the ABPs provided herein comprise an antibody fragment. In some embodiments, the ABPs provided herein consist of an antibody fragment. In some embodiments, the ABPs provided herein consist essentially of an antibody fragment. In some aspects, the antibody fragment is an Fv fragment. In some aspects, the antibody fragment is a Fab fragment. In some aspects, the antibody fragment is a F(ab')$_2$ fragment. In some aspects, the antibody fragment is a Fab' fragment. In some aspects, the antibody fragment is an scFv (sFv) fragment. In some aspects, the antibody fragment is an scFv-Fc fragment. In some aspects, the antibody fragment is a fragment of a single domain antibody.

In some embodiments, an antibody fragment provided herein is derived from an illustrative antibody provided herein. In some embodiments, an antibody fragments provided herein is not derived from an illustrative antibody provided herein and may, for example, be isolated de novo according to the methods provided herein for obtaining antibody fragments.

In some embodiments, an antibody fragment provided specifically binds hTIGIT. In some embodiments, an antibody fragment provided herein specifically binds cTIGIT. In some embodiments, an antibody fragment provided herein specifically binds mTIGIT. In some embodiments, an antibody fragment provided herein specifically binds hTIGIT and cTIGIT. In some embodiments, an antibody fragment provided herein specifically binds hTIGIT and mTIGIT. In some embodiments, an antibody fragment provided herein specifically binds cTIGIT and mTIGIT. In some embodiments, an antibody fragment provided herein specifically binds hTIGIT, cTIGIT and mTIGIT.

In some embodiments, an antibody fragment derived from an antibody provided herein retains affinity, as measured by $K_D$, for hTIGIT that is within about 1.5-fold, about 2-fold, about 3-fold, about 4-fold, about 5-fold, about 6-fold, about 7-fold, about 8-fold, about 9-fold or about 10-fold the affinity of such antibody. In some embodiments, an antibody fragment derived from an antibody provided herein retains affinity, as measured by $K_D$, for cTIGIT that is within about 1.5-fold, about 2-fold, about 3-fold, about 4-fold, about 5-fold, about 6-fold, about 7-fold, about 8-fold, about 9-fold or about 10-fold the affinity of such antibody. In some embodiments, an antibody fragment derived from an antibody provided herein retains affinity, as measured by $K_D$, for mTIGIT that is within about 1.5-fold, about 2-fold, about 3-fold, about 4-fold, about 5-fold, about 6-fold, about 7-fold, about 8-fold, about 9-fold or about 10-fold the affinity of such antibody. In some embodiments, an antibody fragment derived from an antibody provided herein retains affinity, as measured by $K_D$, for both hTIGIT and cTIGIT that is within about 1.5-fold, about 2-fold, about 3-fold, about 4-fold, about 5-fold, about 6-fold, about 7-fold, about 8-fold, about 9-fold or about 10-fold the affinity of such antibody. In some embodiments, an antibody fragment derived from an antibody provided herein retains affinity, as measured by $K_D$, for both hTIGIT and mTIGIT that is within about 1.5-fold, about 2-fold, about 3-fold, about 4-fold, about 5-fold, about 6-fold, about 7-fold, about 8-fold, about 9-fold or about 10-fold the affinity of such antibody. In some embodiments, an antibody fragment derived from an antibody provided herein retains affinity, as measured by $K_D$, for both cTIGIT and mTIGIT that is within about 1.5-fold, about 2-fold, about 3-fold, about 4-fold, about 5-fold, about 6-fold, about 7-fold, about 8-fold, about 9-fold or about 10-fold the affinity of such antibody. In some embodiments, an antibody fragment derived from an antibody provided herein retains affinity, as measured by $K_D$, for all three of hTIGIT, cTIGIT and mTIGIT that is within about 1.5-fold, about 2-fold, about 3-fold, about 4-fold, about 5-fold, about 6-fold, about 7-fold, about 8-fold, about 9-fold or about 10-fold the affinity of such antibody.

In some embodiments, an antibody fragment provided herein retains the ability to antagonize TIGIT, as measured by one or more assays or biological effects described herein. In some embodiments, an antibody fragment provided herein retains the ability to prevent TIGIT from interacting with one or more of its ligands, as described herein.

In some embodiments, an antibody fragment provided herein competes for binding to TIGIT with an antibody selected from MAB1, MAB2, MAB3, MAB4, MAB5, MAB6, MAB7, MAB8, MAB9, MAB10, MAB11, MAB12, MAB13, MAB14, MAB15, MAB16, MAB17, MAB18, MAB19, MAB20, or MAB21, each as provided in Table 5 of this disclosure.

In some embodiments, an antibody fragment provided herein inhibits binding of CD155 to TIGIT. In some embodiments, an antibody fragment provided herein inhibits binding of CD112 to TIGIT. In some embodiments, an antibody fragment provided herein inhibits association of CD226 with TIGIT.

In some embodiments, an antibody fragment provided herein activates an effector T cell or a natural killer (NK) cell. In some embodiments, an antibody fragment provided herein decreases the number of regulatory T cells in a tissue or in circulation. In some embodiments, an antibody fragment provided herein inhibits the suppression of an effector T cell by a regulatory T cell.

In some embodiments, an antibody fragment provided herein does not bind specifically to any of PVRL1, PVRL2, PVRL3, or PVRL4.

In some embodiments, an antibody fragment provided herein binds murine TIGIT (mTIGIT; SEQ ID NO: 3) with an affinity lower (as indicated by higher $K_D$) than the affinity of the antibody fragment for hTIGIT or does not bind mTIGIT.

In some embodiments, a fragment of an antibody provided herein binds the same epitope of TIGIT as such antibody.

In some embodiments, the ABPs provided herein are monoclonal antibodies. In some embodiments, the ABPs provided herein are polyclonal antibodies.

In some embodiments, the ABPs provided herein comprise a chimeric antibody. In some embodiments, the ABPs provided herein consist of a chimeric antibody. In some embodiments, the ABPs provided herein consist essentially of a chimeric antibody. In some embodiments, the ABPs provided herein comprise a humanized antibody. In some embodiments, the ABPs provided herein consist of a humanized antibody. In some embodiments, the ABPs provided herein consist essentially of a humanized antibody. In some embodiments, the ABPs provided herein comprise a human antibody. In some embodiments, the ABPs provided herein consist of a human antibody. In some embodiments, the ABPs provided herein consist essentially of a human antibody.

In some embodiments, the ABPs provided herein are affinity matured. In some aspects, the affinity matured ABPs are affinity matured ABPs derived from an illustrative ABP provided herein.

In some embodiments, the ABPs provided herein comprise an alternative scaffold. In some embodiments, the ABPs provided herein consist of an alternative scaffold. In some embodiments, the ABPs provided herein consist essentially of an alternative scaffold. Any suitable alternative scaffold may be used. In some aspects, the alternative scaffold is selected from an Adnectin™, an iMab, an Anticalin®, an EETI-II/AGRP, a Kunitz domain, a thioredoxin peptide aptamer, an Affibody®, a DARPin, an Affilin, a Tetranectin, a Fynomer, and an Avimer.

In some embodiments, an ABP provided herein inhibits binding of TIGIT to one or more ligands of TIGIT. In some aspects, the ligand of TIGIT is selected from one or more of poliovirus receptor (PVR; CD155) and nectin-2 (CD112, PVRL2). In some aspects, the ABP inhibits binding of TIGIT to one or more ligands of TIGIT by at least about 50%. In some aspects, the ABP inhibits binding of TIGIT to one or more ligands of TIGIT by at least about 75%. In some aspects, the ABP inhibits binding of TIGIT to one or more ligands of TIGIT by at least about 90%. In some aspects, the ABP inhibits binding of TIGIT to one or more ligands of TIGIT by at least about 95%.

In some embodiments, an ABP of the invention is an ABP that competes with an illustrative ABP provided herein. In some aspects, the ABP that competes with the illustrative ABP provided herein binds the same epitope as an illustrative ABP provided herein.

In some embodiments, an ABP provided herein does not bind PVRL4.

It is known that when an antibody is expressed in cells, the antibody is modified after translation. Examples of the posttranslational modification include cleavage of lysine at the C terminal of the heavy chain by a carboxypeptidase; modification of glutamine or glutamic acid at the N terminal of the heavy chain and the light chain to pyroglutamic acid by pyroglutamylation; glycosylation; oxidation; deamidation; and glycation, and it is known that such posttranslational modifications occur in various antibodies (See Journal of Pharmaceutical Sciences, 2008, Vol. 97, p. 2426-2447, incorporated by reference in its entirety). In some embodiments, an ABP of the invention is an antibody or antigen-binding fragment thereof which has undergone posttranslational modification. Examples of an antibody or antigen-binding fragment thereof which have undergone posttranslational modification include an antibody or antigen-binding fragments thereof which have undergone pyroglutamylation at the N terminal of the heavy chain variable region and/or deletion of lysine at the C terminal of the heavy chain. It is known in the art that such posttranslational modification due to pyroglutamylation at the N terminal and deletion of lysine at the C terminal does not have any influence on the activity of the antibody or fragment thereof (Analytical Biochemistry, 2006, Vol. 348, p. 24-39, incorporated by reference in its entirety).

2.2. Sequences of TIGIT Antigen-Binding Proteins 2.2.1. $V_H$ Domains

In some embodiments, an ABP provided herein comprises a $V_H$ sequence selected from SEQ ID NOs: 4-24. In some embodiments an ABP provided herein comprises a $V_H$ sequence of SEQ ID NO:4. In some embodiments an ABP provided herein comprises a $V_H$ sequence of SEQ ID NO:5. In some embodiments an ABP provided herein comprises a $V_H$ sequence of SEQ ID NO:6. In some embodiments an ABP provided herein comprises a $V_H$ sequence of SEQ ID NO:7. In some embodiments an ABP provided herein comprises a $V_H$ sequence of SEQ ID NO:8. In some embodiments an ABP provided herein comprises a $V_H$ sequence of SEQ ID NO:9. In some embodiments an ABP provided herein comprises a $V_H$ sequence of SEQ ID NO:10. In some embodiments an ABP provided herein comprises a $V_H$ sequence of SEQ ID NO:11. In some embodiments an ABP provided herein comprises a $V_H$ sequence of SEQ ID NO:12. In some embodiments an ABP provided herein comprises a $V_H$ sequence of SEQ ID NO:13. In some embodiments an ABP provided herein comprises a $V_H$ sequence of SEQ ID NO:14. In some embodiments an ABP provided herein comprises a $V_H$ sequence of SEQ ID NO:15. In some embodiments an ABP provided herein comprises a $V_H$ sequence of SEQ ID NO:16. In some embodiments an ABP provided herein comprises a $V_H$ sequence of SEQ ID NO:17. In some embodiments an ABP provided herein comprises a $V_H$ sequence of SEQ ID NO:18. In some embodiments an ABP provided herein comprises a $V_H$ sequence of SEQ ID NO:19. In some embodiments an ABP provided herein comprises a $V_H$ sequence of SEQ ID NO:20. In some embodiments an ABP provided herein comprises a $V_H$ sequence of SEQ ID NO:21. In some embodiments an ABP provided herein comprises a $V_H$ sequence of SEQ ID NO:22. In some embodiments an ABP provided herein comprises a $V_H$ sequence of SEQ ID NO:23. In some embodiments an ABP provided herein comprises a $V_H$ sequence of SEQ ID NO:24.

In some embodiments, an ABP provided herein comprises a $V_H$ sequence having at least about 50%, 60%, 70%, 80%, 90%, 95%, or 99% identity to an illustrative $V_H$ sequence provided in SEQ ID NOs: 4-24. In some embodiments, an ABP provided herein comprises a $V_H$ sequence provided in SEQ ID NOs: 4-24, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

2.2.2. $V_L$ Domains

In some embodiments, an ABP provided herein comprises a $V_L$ sequence selected from SEQ ID NOs: 25-28. In some embodiments an ABP provided herein comprises a $V_L$ sequence of SEQ ID NO:25. In some embodiments an ABP provided herein comprises a $V_L$ sequence of SEQ ID NO:26. In some embodiments an ABP provided herein comprises a $V_L$ sequence of SEQ ID NO:27. In some embodiments an ABP provided herein comprises a $V_L$ sequence of SEQ ID NO:28.

In some embodiments, an ABP provided herein comprises a $V_L$ sequence having at least about 50%, 60%, 70%, 80%, 90%, 95%, or 99% identity to an illustrative $V_L$ sequence provided in SEQ ID NOs: 25-28. In some embodiments, an ABP provided herein comprises a $V_L$ sequence provided in SEQ ID NOs: 25-28, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

2.2.3. $V_H$-$V_L$ Combinations

In some embodiments, an ABP provided herein comprises a $V_H$ sequence selected from SEQ ID NOs: 4-24 and a $V_L$ sequence selected from SEQ ID NOs: 25-28.

In some embodiments, an ABP provided herein comprises a $V_H$ sequence of SEQ ID NO:4 and a $V_L$ sequence of SEQ ID NO:25. In some embodiments, an ABP provided herein comprises a VH sequence of SEQ ID NO:5 and a $V_L$ sequence of SEQ ID NO:25. In some embodiments, an ABP provided herein comprises a $V_H$ sequence of SEQ ID NO:6 and a $V_L$ sequence of SEQ ID NO:25. In some embodiments, an ABP provided herein comprises a $V_H$ sequence of SEQ ID NO:7 and a $V_L$ sequence of SEQ ID NO:25. In some embodiments, an ABP provided herein comprises a $V_H$ sequence of SEQ ID NO:8 and a $V_L$ sequence of SEQ ID NO:25. In some embodiments, an ABP provided herein comprises a $V_H$ sequence of SEQ ID NO:9 and a $V_L$ sequence of SEQ ID NO:26. In some ABP provided herein comprises a $V_H$ sequence of SEQ ID NO:10 and a $V_L$ sequence of SEQ ID NO:26. In some embodiments, an ABP provided herein comprises a $V_H$ sequence of SEQ ID NO:11 and a $V_L$ sequence of SEQ ID NO:26. In some embodiments, an ABP provided herein comprises a $V_H$ sequence of SEQ ID NO:12 and a $V_L$ sequence of SEQ ID NO:26. In some embodiments, an ABP provided herein comprises a $V_H$ sequence of SEQ ID NO:13 and a $V_L$ sequence of SEQ ID NO:26. In some embodiments, an ABP provided herein comprises a $V_H$ sequence of SEQ ID NO:14 and a $V_L$ sequence of SEQ ID NO:26. In some embodiments, an ABP provided herein comprises a $V_H$ sequence of SEQ ID NO:15 and a $V_L$ sequence of SEQ ID NO:26. In some embodiments, an ABP provided herein comprises a $V_H$ sequence of SEQ ID NO:16 and a $V_L$ sequence of SEQ ID NO:27. In some embodiments, an ABP provided herein comprises a $V_H$ sequence of SEQ ID NO:17 and a $V_L$ sequence of SEQ ID NO:27. In some embodiments, an ABP provided herein comprises a $V_H$ sequence of SEQ ID NO:18 and a $V_L$ sequence of SEQ ID NO:27. In some embodiments, an ABP provided herein comprises a $V_H$ sequence of SEQ ID NO:19 and a $V_L$ sequence of SEQ ID NO:27. In some embodiments, an ABP provided herein comprises a $V_H$ sequence of SEQ ID NO:20 and a $V_L$ sequence of SEQ ID NO:27. In some embodiments, an ABP provided herein comprises a $V_H$ sequence of SEQ ID NO:21 and a $V_L$ sequence of SEQ ID NO:27. In some embodiments, an ABP provided herein comprises a $V_H$ sequence of SEQ ID NO:22 and a $V_L$ sequence of SEQ ID NO:28. In some embodiments, an ABP provided herein comprises a $V_H$ sequence of SEQ ID NO:23 and a $V_L$ sequence of SEQ ID NO:28. In some embodiments, an ABP provided herein comprises a $V_H$ sequence of SEQ ID NO:24 and a $V_L$ sequence of SEQ ID NO:28.

In some embodiments, an ABP provided herein comprises a $V_H$ sequence of SEQ ID NO:4 and a $V_L$ sequence of SEQ ID NO:26. In some embodiments, an ABP provided herein comprises a $V_H$ sequence of SEQ ID NO:4 and a $V_L$ sequence of SEQ ID NO:27. In some embodiments, an ABP provided herein comprises a $V_H$ sequence of SEQ ID NO:4 and a $V_L$ sequence of SEQ ID NO:28.

In some embodiments, an ABP provided herein comprises a $V_H$ sequence of SEQ ID NO:5 and a $V_L$ sequence of SEQ ID NO:26. In some embodiments, an ABP provided herein comprises a $V_H$ sequence of SEQ ID NO:5 and a $V_L$ sequence of SEQ ID NO:27. In some embodiments, an ABP provided herein comprises a $V_H$ sequence of SEQ ID NO:5 and a $V_L$ sequence of SEQ ID NO:28.

In some embodiments, an ABP provided herein comprises a $V_H$ sequence of SEQ ID NO:6 and a $V_L$ sequence of SEQ ID NO:26. In some embodiments, an ABP provided herein comprises a $V_H$ sequence of SEQ ID NO:6 and a $V_L$ sequence of SEQ ID NO:27. In some embodiments, an ABP provided herein comprises a $V_H$ sequence of SEQ ID NO:6 and a $V_L$ sequence of SEQ ID NO:28.

In some embodiments, an ABP provided herein comprises a $V_H$ sequence of SEQ ID NO:7 and a $V_L$ sequence of SEQ ID NO:26. In some embodiments, an ABP provided herein comprises a $V_H$ sequence of SEQ ID NO:7 and a $V_L$ sequence of SEQ ID NO:27. In some embodiments, an ABP provided herein comprises a $V_H$ sequence of SEQ ID NO:7 and a $V_L$ sequence of SEQ ID NO:28.

In some embodiments, an ABP provided herein comprises a $V_H$ sequence of SEQ ID NO:8 and a $V_L$ sequence of SEQ ID NO:26. In some embodiments, an ABP provided herein comprises a $V_H$ sequence of SEQ ID NO:8 and a $V_L$ sequence of SEQ ID NO:27. In some embodiments, an ABP provided herein comprises a $V_H$ sequence of SEQ ID NO:8 and a $V_L$ sequence of SEQ ID NO:28.

In some embodiments, an ABP provided herein comprises a $V_H$ sequence of SEQ ID NO:9 and a $V_L$ sequence of SEQ ID NO:25. In some embodiments, an ABP provided herein comprises a $V_H$ sequence of SEQ ID NO:9 and a $V_L$ sequence of SEQ ID NO:27. In some embodiments, an ABP provided herein comprises a $V_H$ sequence of SEQ ID NO:9 and a $V_L$ sequence of SEQ ID NO:28.

In some embodiments, an ABP provided herein comprises a $V_H$ sequence of SEQ ID NO:10 and a $V_L$ sequence of SEQ ID NO:25. In some embodiments, an ABP provided herein comprises a $V_H$ sequence of SEQ ID NO:10 and a $V_L$ sequence of SEQ ID NO:27. In some embodiments, an ABP provided herein comprises a $V_H$ sequence of SEQ ID NO:10 and a $V_L$ sequence of SEQ ID NO:28.

In some embodiments, an ABP provided herein comprises a $V_H$ sequence of SEQ ID NO:11 and a $V_L$ sequence of SEQ ID NO:25. In some embodiments, an ABP provided herein comprises a $V_H$ sequence of SEQ ID NO:11 and a $V_L$ sequence of SEQ ID NO:27. In some embodiments, an ABP provided herein comprises a $V_H$ sequence of SEQ ID NO:11 and a $V_L$ sequence of SEQ ID NO:28.

In some embodiments, an ABP provided herein comprises a $V_H$ sequence of SEQ ID NO:12 and a $V_L$ sequence of SEQ ID NO:25. In some embodiments, an ABP provided herein comprises a $V_H$ sequence of SEQ ID NO:12 and a $V_L$ sequence of SEQ ID NO:27. In some embodiments, an ABP provided herein comprises a $V_H$ sequence of SEQ ID NO:12 and a $V_L$ sequence of SEQ ID NO:28.

In some embodiments, an ABP provided herein comprises a $V_H$ sequence of SEQ ID NO:13 and a $V_L$ sequence of SEQ ID NO:25. In some embodiments, an ABP provided herein comprises a $V_H$ sequence of SEQ ID NO:13 and a $V_L$ sequence of SEQ ID NO:27. In some embodiments, an ABP provided herein comprises a $V_H$ sequence of SEQ ID NO:13 and a $V_L$ sequence of SEQ ID NO:28.

In some embodiments, an ABP provided herein comprises a $V_H$ sequence of SEQ ID NO:14 and a $V_L$ sequence of SEQ ID NO:25. In some embodiments, an ABP provided herein comprises a $V_H$ sequence of SEQ ID NO:14 and a $V_L$ sequence of SEQ ID NO:27. In some embodiments, an ABP provided herein comprises a $V_H$ sequence of SEQ ID NO:14 and a $V_L$ sequence of SEQ ID NO:28.

In some embodiments, an ABP provided herein comprises a $V_H$ sequence of SEQ ID NO:15 and a $V_L$ sequence of SEQ ID NO:25. In some embodiments, an ABP provided herein comprises a $V_H$ sequence of SEQ ID NO:15 and a $V_L$ sequence of SEQ ID NO:27. In some embodiments, an ABP provided herein comprises a $V_H$ sequence of SEQ ID NO:15 and a $V_L$ sequence of SEQ ID NO:28.

In some embodiments, an ABP provided herein comprises a $V_H$ sequence of SEQ ID NO:16 and a $V_L$ sequence of SEQ ID NO:25. In some embodiments, an ABP provided herein comprises a $V_H$ sequence of SEQ ID NO:16 and a $V_L$ sequence of SEQ ID NO:26. In some embodiments, an ABP provided herein comprises a $V_H$ sequence of SEQ ID NO:16 and a $V_L$ sequence of SEQ ID NO:28.

In some embodiments, an ABP provided herein comprises a $V_H$ sequence of SEQ ID NO:17 and a $V_L$ sequence of SEQ ID NO:25. In some embodiments, an ABP provided herein comprises a $V_H$ sequence of SEQ ID NO:17 and a $V_L$ sequence of SEQ ID NO:26. In some embodiments, an ABP provided herein comprises a $V_H$ sequence of SEQ ID NO:17 and a $V_L$ sequence of SEQ ID NO:28.

In some embodiments, an ABP provided herein comprises a $V_H$ sequence of SEQ ID NO:18 and a $V_L$ sequence of SEQ ID NO:25. In some embodiments, an ABP provided herein comprises a $V_H$ sequence of SEQ ID NO:18 and a $V_L$ sequence of SEQ ID NO:26. In some embodiments, an ABP provided herein comprises a $V_H$ sequence of SEQ ID NO:18 and a $V_L$ sequence of SEQ ID NO:28.

In some embodiments, an ABP provided herein comprises a $V_H$ sequence of SEQ ID NO:19 and a $V_L$ sequence of SEQ ID NO:25. In some embodiments, an ABP provided herein comprises a $V_H$ sequence of SEQ ID NO:19 and a $V_L$ sequence of SEQ ID NO:26. In some embodiments, an ABP provided herein comprises a $V_H$ sequence of SEQ ID NO:19 and a $V_L$ sequence of SEQ ID NO:28.

In some embodiments, an ABP provided herein comprises a $V_H$ sequence of SEQ ID NO:20 and a $V_L$ sequence of SEQ ID NO:25. In some embodiments, an ABP provided herein comprises a $V_H$ sequence of SEQ ID NO:20 and a $V_L$ sequence of SEQ ID NO:26. In some embodiments, an ABP provided herein comprises a $V_H$ sequence of SEQ ID NO:20 and a $V_L$ sequence of SEQ ID NO:28.

In some embodiments, an ABP provided herein comprises a $V_H$ sequence of SEQ ID NO:21 and a $V_L$ sequence of SEQ ID NO:25. In some embodiments, an ABP provided herein comprises a $V_H$ sequence of SEQ ID NO:21 and a $V_L$ sequence of SEQ ID NO:26. In some embodiments, an ABP provided herein comprises a $V_H$ sequence of SEQ ID NO:21 and a $V_L$ sequence of SEQ ID NO:28.

In some embodiments, an ABP provided herein comprises a $V_H$ sequence of SEQ ID NO:22 and a $V_L$ sequence of SEQ ID NO:25. In some embodiments, an ABP provided herein comprises a $V_H$ sequence of SEQ ID NO:22 and a $V_L$ sequence of SEQ ID NO:26. In some embodiments, an ABP provided herein comprises a $V_H$ sequence of SEQ ID NO:22 and a $V_L$ sequence of SEQ ID NO:27.

In some embodiments, an ABP provided herein comprises a $V_H$ sequence of SEQ ID NO:23 and a $V_L$ sequence of SEQ ID NO:25. In some embodiments, an ABP provided herein comprises a $V_H$ sequence of SEQ ID NO:23 and a $V_L$ sequence of SEQ ID NO:26. In some embodiments, an ABP provided herein comprises a $V_H$ sequence of SEQ ID NO:23 and a $V_L$ sequence of SEQ ID NO:27.

In some embodiments, an ABP provided herein comprises a $V_H$ sequence of SEQ ID NO:24 and a $V_L$ sequence of SEQ ID NO:25. In some embodiments, an ABP provided herein comprises a $V_H$ sequence of SEQ ID NO:24 and a $V_L$ sequence of SEQ ID NO:26. In some embodiments, an ABP provided herein comprises a $V_H$ sequence of SEQ ID NO:24 and a $V_L$ sequence of SEQ ID NO:27.

In some embodiments, an ABP provided herein comprises a $V_H$ sequence having at least about 50%, 60%, 70%, 80%, 90%, 95%, or 99% identity to an illustrative $V_H$ sequence provided in SEQ ID NOs: 4-24, and a $V_L$ sequence having at least about 50%, 60%, 70%, 80%, 90%, 95%, or 99% identity to an illustrative $V_L$ sequence provided in SEQ ID NOs: 25-28. In some embodiments, an ABP provided herein comprises a $V_H$ sequence provided in SEQ ID NOs: 4-24, with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a $V_L$ sequence provided in SEQ ID NOs: 25-28, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

2.2.4. CDRs

In some embodiments, an ABP provided herein comprises one to three CDRs of a $V_H$ domain selected from SEQ ID NOs: 4-24. In some embodiments, an ABP provided herein comprises two to three CDRs of a $V_H$ domain selected from SEQ ID NOs: 4-24. In some embodiments, an ABP provided herein comprises three CDRs of a $V_H$ domain selected from SEQ ID NOs: 4-24. In some aspects, the CDRs are Kabat CDRs. In some aspects, the CDRs are Chothia CDRs. In some aspects, the CDRs are IMGT CDRs.

In some embodiments, the CDRs are CDRs having at least about 50%, 75%, 80%, 85%, 90%, or 95% identity with a CDR-H1, CDR-H2, or CDR-H3 of SEQ ID NOs: 4-24. In some embodiments, the CDR-H1 is a CDR-H1 of a $V_H$ domain selected from SEQ ID NOs: 4-24, with up to 1, 2, 3, 4, or 5 amino acid substitutions. In some embodiments, the CDR-H2 is a CDR-H2 of a $V_H$ domain selected from SEQ ID NOs: 4-24, with up to 1, 2, 3, 4, 5, 6, 7, or 8 amino acid substitutions. In some embodiments, the CDR-H3 is a CDR-H3 of a $V_H$ domain selected from SEQ ID NOs: 4-24, with up to 1, 2, 3, 4, 5, 6, 7, or 8 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises one to three CDRs of a $V_L$ domain selected from SEQ ID NOs: 25-28. In some embodiments, an ABP provided herein comprises two to three CDRs of a $V_L$ domain selected from SEQ ID NOs: 25-28. In some embodiments, an ABP provided herein comprises three CDRs of a $V_L$ domain selected from SEQ ID NOs: 25-28. In some aspects, the CDRs are Kabat CDRs. In some aspects, the CDRs are Chothia CDRs. In some aspects, the CDRs are IMGT CDRs.

In some embodiments, the CDRs are CDRs having at least about 50%, 75%, 80%, 85%, 90%, or 95% identity with a CDR-L1, CDR-L2, or CDR-L3 of SEQ ID NOs: 25-28. In some embodiments, the CDR-L1 is a CDR-L1 of a $V_L$ domain selected from SEQ ID NOs: 25-28, with up to 1, 2, 3, 4, 5, or 6 amino acid substitutions. In some embodiments, the CDR-L2 is a CDR-L2 of a $V_L$ domain selected from SEQ ID NOs: 25-28, with up to 1, 2, 3, or 4 amino acid substitutions. In some embodiments, the CDR-L3 is a CDR-L3 of a $V_L$ domain selected from SEQ ID NOs: 25-28, with up to 1, 2, 3, 4, or 5 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises one to three CDRs of a $V_H$ domain selected from SEQ ID NOs: 4-24 and one to three CDRs of a $V_L$ domain selected from SEQ ID NOs: 25-28. In some embodiments, an ABP provided herein comprises two to three CDRs of a $V_H$ domain selected from SEQ ID NOs: 4-24 and two to three CDRs of a $V_L$ domain selected from SEQ ID NOs: 25-28. In some embodiments, an ABP provided herein comprises three CDRs of a $V_H$ domain selected from SEQ ID NOs: 4-24 and three CDRs of a $V_L$ domain selected from SEQ ID NOs: 25-28. In some aspects, the CDRs are Kabat CDRs. In some aspects, the CDRs are Chothia CDRs. In some aspects, the CDRs are IMGT CDRs.

In some embodiments, the CDRs are CDRs having at least about 50%, 75%, 80%, 85%, 90%, or 95% identity with a CDR-H1, CDR-H2, or CDR-H3 of SEQ ID NOs: 4-24 and at least about 50%, 75%, 80%, 85%, 90%, or 95% identity with a CDR-L1, CDR-L2, or CDR-L3 of SEQ ID NOs: 25-28. In some embodiments, the CDR-H1 is a CDR-H1 of a $V_H$ domain selected from SEQ ID NOs: 4-24, with up to 1, 2, 3, 4, or 5 amino acid substitutions; the CDR-H2 is a CDR-H2 of a $V_H$ domain selected from SEQ ID NOs: 4-24, with up to 1, 2, 3, 4, 5, 6, 7, or 8 amino acid substitutions; the CDR-H3 is a CDR-H3 of a $V_H$ domain selected from SEQ ID NOs: 4-24, with up to 1, 2, 3, 4, 5, 6, 7, or 8 amino acid substitutions; the CDR-L1 is a CDR-L1 of a $V_L$ domain selected from SEQ ID NOs: 25-28, with up to 1, 2, 3, 4, 5, or 6 amino acid substitutions; the CDR-L2 is a CDR-L2 of a $V_L$ domain selected from SEQ ID NOs: 25-28, with up to 1, 2, 3, or 4 amino acid substitutions; and the CDR-L3 is a CDR-L3 of a $V_L$ domain selected from SEQ ID NOs: 25-28, with up to 1, 2, 3, 4, or 5 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-H3 selected from SEQ ID NOs: 29-35. In some aspects, the CDR-H3 has at least about 50%, 75%, 80%, 85%, 90%, or 95% identity with a CDR-H3 of SEQ ID NOs: 29-35. In some aspects, the CDR-H3 is a CDR-H3 according to the IMGT numbering system. In some embodiments, the CDR-H3 is a CDR-H3 selected from SEQ ID NOs: 29-35, with up to 1, 2, 3, 4, 5, 6, 7, or 8 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-H2 selected from SEQ ID NOs: 36-47. In some aspects, the CDR-H2 has at least about 50%, 75%, 80%, 85%, 90%, or 95% identity with a CDR-H2 of SEQ ID NOs: 36-47. In some aspects, the CDR-H2 is a CDR-H2 according to the Kabat numbering system. In some embodiments, the CDR-H2 is a CDR-H2 selected from SEQ ID NOs: 36-47, with up to 1, 2, 3, 4, 5, 6, 7, or 8 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-H1 selected from SEQ ID NOs: 48-54 or 58-62. In some aspects, the CDR-H1 has at least about 50%, 75%, 80%, 85%, 90%, or 95% identity with a CDR-H1 of SEQ ID NOs: 48-54 or 58-62. In some aspects, the CDR-H1 is a CDR-H1 that spans the CDR-H1 as defined by both the Chothia and Kabat numbering systems. In some embodiments, the CDR-H1 is a CDR-H1 selected from SEQ ID NOs: 48-54 or 58-62, with up to 1, 2, 3, 4, or 5 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-H3 selected from SEQ ID NOs: 29-35 and a CDR-H2 selected from SEQ ID NOs: 36-47. In some embodiments, an ABP provided herein comprises a CDR-H3 selected from SEQ ID NOs: 29-35, a CDR-H2 selected from SEQ ID NOs: 36-47, and a CDR-H1 selected from SEQ ID NOs: 48-54 or 58-62. In some embodiments, the CDR-H3 has at least about 50%, 75%, 80%, 85%, 90%, or 95% identity with a CDR-H3 of SEQ ID NOs: 29-35, the CDR-H2 has at least about 50%, 75%, 80%, 85%, 90%, or 95% identity with a CDR-H2 of SEQ ID NOs: 36-47, and the CDR-H1 has at least about 50%, 75%, 80%, 85%, 90%, or 95% identity with a CDR-H1 of SEQ ID NOs: 48-54 or 58-62. In some embodiments, the CDR-H3 is a CDR-H3 selected from SEQ ID NOs: 29-35, with up to 1, 2, 3, 4, 5, 6, 7, or 8 amino acid substitutions; the CDR-H2 is a CDR-H2 selected from SEQ ID NOs: 36-47, with up to 1, 2, 3, 4, 5, 6, 7, or 8 amino acid substitutions; and the CDR-H1 is a CDR-H1 selected from SEQ ID NOs: 48-54 or 58-62, with up to 1, 2, 3, 4, or 5 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-L3 selected from SEQ ID NOs: 63-66. In some aspects, the CDR-L3 has at least about 50%, 75%, 80%, 85%, 90%, or 95% identity with a CDR-L3 of SEQ ID NOs: 63-66. In some aspects, the CDR-L3 is a CDR-L3 according to the Kabat, Chothia, and IMGT numbering systems. In some embodiments, the CDR-L3 is a CDR-L3 selected from SEQ ID NOs: 63-66, with up to 1, 2, 3, 4, or 5 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-L2 selected from SEQ ID NOs: 67-69. In some aspects, the CDR-L2 has at least about 50%, 75%, 80%, 85%, 90%, or 95% identity with a CDR-L2 of SEQ ID NOs: 67-69. In some aspects, the CDR-L2 is a CDR-L2 according to the Kabat and Chothia numbering systems. In some embodiments, the CDR-L2 is a CDR-L2 selected from SEQ ID NOs: 67-69, with up to 1, 2, 3, or 4 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-L1 selected from SEQ ID NOs: 70-72. In some aspects, the CDR-L1 has at least about 50%, 75%, 80%, 85%, 90%, or 95% identity with a CDR-L1 of SEQ ID NOs: 70-72. In some aspects, the CDR-L1 is a CDR-L1 according to the Kabat and Chothia numbering systems. In some embodiments, the CDR-L1 is a CDR-L1 selected from SEQ ID NOs: 70-72, with up to 1, 2, 3, 4, 5, or 6 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-L3 selected from SEQ ID NOs: 63-66 and a CDR-L2 selected from SEQ ID NOs: 67-69. In some embodiments, an ABP provided herein comprises a CDR-L3 selected from SEQ ID NOs: 63-66, a CDR-L2 selected from SEQ ID NOs: 67-69, and a CDR-L1 selected from SEQ ID NOs: 70-72. In some embodiments, the CDR-L3 has at least about 50%, 75%, 80%, 85%, 90%, or 95% identity with a CDR-L3 of SEQ ID NOs: 63-66, the CDR-L2 has at least about 50%, 75%, 80%, 85%, 90%, or 95% identity with a CDR-L2 of SEQ ID NOs: 67-69, and the CDR-L1 has at least about 50%, 75%, 80%, 85%, 90%, or 95% identity with a CDR-L1 of SEQ ID NOs: 70-72. In some embodiments, the CDR-L3 is a CDR-L3 selected from SEQ ID NOs: 63-66, with up to 1, 2, 3, 4, or 5 amino acid substitutions; the CDR-L2 is a CDR-L2 selected from SEQ ID NOs: 67-69, with up to 1, 2, 3, or 4 amino acid substitutions; and the CDR-L1 is a CDR-L1 selected from SEQ ID NOs: 70-72, with up to 1, 2, 3, 4, 5, or 6 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-H3 selected from SEQ ID NOs: 29-35, a CDR-H2 selected from SEQ ID NOs: 36-47, a CDR-H1 selected from SEQ ID NOs: 48-54 or 58-62, a CDR-L3 selected from SEQ ID NOs: 63-66, a CDR-L2 selected from SEQ ID NOs: 67-69, and a CDR-L1 selected from SEQ ID NOs: 70-72. In some embodiments, the CDR-H3 has at least about 50%, 75%, 80%, 85%, 90%, or 95% identity with a CDR-H3 of SEQ ID NOs: 29-35, the CDR-H2 has at least about 50%, 75%, 80%, 85%, 90%, or 95% identity with a CDR-H2 of SEQ ID NOs: 36-47, the CDR-H1 has at least about 50%, 75%, 80%, 85%, 90%, or 95% identity with a CDR-H1 of SEQ ID NOs: 48-54 or 58-62, the CDR-L3 has at least about 50%, 75%, 80%, 85%, 90%, or 95% identity with a CDR-L3 of SEQ ID NOs: 63-66, the CDR-L2 has at least about 50%, 75%, 80%, 85%, 90%, or 95% identity with a CDR-L2 of SEQ ID NOs: 67-69, and the CDR-L1 has at least about 50%, 75%, 80%, 85%, 90%, or 95% identity with a CDR-L1 of SEQ ID NOs: 70-72. In some embodiments, the CDR-H3 is a CDR-H3 selected from SEQ ID NOs: 29-35, with up to 1, 2, 3, 4, 5, 6, 7, or 8 amino acid substitutions; the CDR-H2 is a CDR-H2 selected from SEQ ID NOs: 36-47, with up to 1, 2, 3, 4, 5, 6, 7, or 8 amino acid substitutions; the CDR-H1 is a CDR-H1 selected from SEQ ID NOs: 48-54 or 58-62, with up to 1, 2, 3, 4, or 5 amino acid substitutions; the CDR-L3 is a CDR-L3 selected from SEQ ID NOs: 63-66, with up to 1, 2, 3, 4, or 5 amino acid substitutions; the CDR-L2 is a CDR-L2 selected from SEQ ID NOs: 67-69, with up to 1, 2, 3, or 4 amino acid substitutions; and the CDR-L1 is a CDR-L1 selected from SEQ ID NOs: 70-72, with up to 1, 2, 3, 4, 5, or 6 amino acid substitutions. In some aspects, the amino acid substitutions are conservative amino acid substitutions. In some embodiments, the ABPs described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining ABPs.

In some embodiments, an ABP provided herein comprises a CDR-H3 of SEQ ID NO:29, a CDR-H2 of SEQ ID NO:36, a CDR-H1 of SEQ ID NO:48, a CDR-L3 of SEQ ID NO:63, a CDR-L2 of SEQ ID NO:67, and a CDR-L1 of SEQ ID NO:70.

In some embodiments, an ABP provided herein comprises a CDR-H3 of SEQ ID NO:29, a CDR-H2 of SEQ ID NO:37, a CDR-H1 of SEQ ID NO:49, a CDR-L3 of SEQ ID NO:63, a CDR-L2 of SEQ ID NO:67, and a CDR-L1 of SEQ ID NO:70.

In some embodiments, an ABP provided herein comprises a CDR-H3 of SEQ ID NO:29, a CDR-H2 of SEQ ID NO:37, a CDR-H1 of SEQ ID NO:50, a CDR-L3 of SEQ ID NO:63, a CDR-L2 of SEQ ID NO:67, and a CDR-L1 of SEQ ID NO:70.

In some embodiments, an ABP provided herein comprises a CDR-H3 of SEQ ID NO:30, a CDR-H2 of SEQ ID NO:37, a CDR-H1 of SEQ ID NO:50, a CDR-L3 of SEQ ID NO:63, a CDR-L2 of SEQ ID NO:67, and a CDR-L1 of SEQ ID NO:70.

In some embodiments, an ABP provided herein comprises a CDR-H3 of SEQ ID NO:29, a CDR-H2 of SEQ ID NO:38, a CDR-H1 of SEQ ID NO:50, a CDR-L3 of SEQ ID NO:63, a CDR-L2 of SEQ ID NO:67, and a CDR-L1 of SEQ ID NO:70.

In some embodiments, an ABP provided herein comprises a CDR-H3 of SEQ ID NO:31, a CDR-H2 of SEQ ID NO:39, a CDR-H1 of SEQ ID NO:51, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:31, a CDR-H2 of SEQ ID NO:40, a CDR-H1 of SEQ ID NO:52, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:31, a CDR-H2 of SEQ ID NO:41, a CDR-H1 of SEQ ID NO:53, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:31, a CDR-H2 of SEQ ID NO:40, a CDR-H1 of SEQ ID NO:54, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:32, a CDR-H2 of SEQ ID NO:40, a CDR-H1 of SEQ ID NO:54, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:32, a CDR-H2 of SEQ ID NO:40, a CDR-H1 of SEQ ID NO:54, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:32, a CDR-H2 of SEQ ID NO:40, a CDR-H1 of SEQ ID NO:54, a CDR-L3 of SEQ ID NO:64, a CDR-L2 of SEQ ID NO:68, and a CDR-L1 of SEQ ID NO:71.

In some embodiments, an ABP provided herein comprises a CDR-H3 of SEQ ID NO:33, a CDR-H2 of SEQ ID NO:42, a CDR-H1 of SEQ ID NO:58, a CDR-L3 of SEQ ID NO:65, a CDR-L2 of SEQ ID NO:69, and a CDR-L1 of SEQ ID NO:72.

In some embodiments, an ABP provided herein comprises a CDR-H3 of SEQ ID NO:33, a CDR-H2 of SEQ ID NO:42, a CDR-H1 of SEQ ID NO:59, a CDR-L3 of SEQ ID NO:65, a CDR-L2 of SEQ ID NO:69, and a CDR-L1 of SEQ ID NO:72.

In some embodiments, an ABP provided herein comprises a CDR-H3 of SEQ ID NO:33, a CDR-H2 of SEQ ID NO:43, a CDR-H1 of SEQ ID NO:60, a CDR-L3 of SEQ ID NO:65, a CDR-L2 of SEQ ID NO:69, and a CDR-L1 of SEQ ID NO:72.

In some embodiments, an ABP provided herein comprises a CDR-H3 of SEQ ID NO:34, a CDR-H2 of SEQ ID NO:43, a CDR-H1 of SEQ ID NO:60, a CDR-L3 of SEQ ID NO:65, a CDR-L2 of SEQ ID NO:69, and a CDR-L1 of SEQ ID NO:72.

In some embodiments, an ABP provided herein comprises a CDR-H3 of SEQ ID NO:34, a CDR-H2 of SEQ ID NO:44, a CDR-H1 of SEQ ID NO:61, a CDR-L3 of SEQ ID NO:65, a CDR-L2 of SEQ ID NO:69, and a CDR-L1 of SEQ ID NO:72.

In some embodiments, an ABP provided herein comprises a CDR-H3 of SEQ ID NO:33, a CDR-H2 of SEQ ID NO:44, a CDR-H1 of SEQ ID NO:59, a CDR-L3 of SEQ ID NO:65, a CDR-L2 of SEQ ID NO:69, and a CDR-L1 of SEQ ID NO:72.

In some embodiments, an ABP provided herein comprises a CDR-H3 of SEQ ID NO:35, a CDR-H2 of SEQ ID NO:45, a CDR-H1 of SEQ ID NO:62, a CDR-L3 of SEQ ID NO:66, a CDR-L2 of SEQ ID NO:69, and a CDR-L1 of SEQ ID NO:72.

In some embodiments, an ABP provided herein comprises a CDR-H3 of SEQ ID NO:35, a CDR-H2 of SEQ ID NO:46, a CDR-H1 of SEQ ID NO:62, a CDR-L3 of SEQ ID NO:66, a CDR-L2 of SEQ ID NO:69, and a CDR-L1 of SEQ ID NO:72.

In some embodiments, an ABP provided herein comprises a CDR-H3 of SEQ ID NO:35, a CDR-H2 of SEQ ID NO:47, a CDR-H1 of SEQ ID NO:62, a CDR-L3 of SEQ ID NO:66, a CDR-L2 of SEQ ID NO:69, and a CDR-L1 of SEQ ID NO:72.

2.2.5. Heavy Chains and Light Chains

In some embodiments, an ABP provided herein comprises a $V_H$ selected from a $V_H$ of SEQ ID NO:4-24 (or a variant described herein) and a constant region selected from SEQ ID NOs: 55-57 or 125. In some embodiments, an ABP provided herein comprises a $V_L$ selected from a $V_L$ of SEQ ID NO:25-28 (or a variant described herein) and a constant region of SEQ ID NO:126.

In some embodiments, an ABP provided herein comprises a heavy chain of SEQ ID NO:79. In some embodiments, an ABP provided herein comprises a heavy chain of SEQ ID NO:80. In some embodiments, an ABP provided herein comprises a light chain of SEQ ID NO:81. In some embodiments, an APB provided herein comprises a heavy chain of SEQ ID NO:79 and a light chain of SEQ ID NO: 81. In some embodiments, an APB provided herein comprises a heavy chain of SEQ ID NO:80 and a light chain of SEQ ID NO: 81.

In some embodiments, an ABP provided herein comprises a heavy chain of SEQ ID NO:82. In some embodiments, an ABP provided herein comprises a heavy chain of SEQ ID NO:83. In some embodiments, an APB provided herein comprises a heavy chain of SEQ ID NO:82 and a light chain of SEQ ID NO: 81. In some embodiments, an APB provided herein comprises a heavy chain of SEQ ID NO:83 and a light chain of SEQ ID NO: 81.

In some embodiments, an ABP provided herein comprises a heavy chain of SEQ ID NO:84. In some embodiments, an ABP provided herein comprises a heavy chain of SEQ ID NO:85. In some embodiments, an APB provided herein comprises a heavy chain of SEQ ID NO:84 and a light chain of SEQ ID NO: 81. In some embodiments, an APB provided herein comprises a heavy chain of SEQ ID NO:85 and a light chain of SEQ ID NO: 81.

In some embodiments, an ABP provided herein comprises a heavy chain of SEQ ID NO:86. In some embodiments, an ABP provided herein comprises a heavy chain of SEQ ID NO:87. In some embodiments, an APB provided herein comprises a heavy chain of SEQ ID NO:86 and a light chain of SEQ ID NO: 81. In some embodiments, an APB provided herein comprises a heavy chain of SEQ ID NO:87 and a light chain of SEQ ID NO: 81.

In some embodiments, an ABP provided herein comprises a heavy chain of SEQ ID NO:88. In some embodiments, an ABP provided herein comprises a heavy chain of SEQ ID NO:89. In some embodiments, an APB provided herein comprises a heavy chain of SEQ ID NO:88 and a light chain of SEQ ID NO: 81. In some embodiments, an APB provided herein comprises a heavy chain of SEQ ID NO:89 and a light chain of SEQ ID NO: 81.

In some embodiments, an ABP provided herein comprises a heavy chain of SEQ ID NO:90. In some embodiments, an ABP provided herein comprises a heavy chain of SEQ ID NO:91. In some embodiments, an ABP provided herein comprises a light chain of SEQ ID NO:92. In some embodiments, an APB provided herein comprises a heavy chain of SEQ ID NO:90 and a light chain of SEQ ID NO:92. In some embodiments, an APB provided herein comprises a heavy chain of SEQ ID NO:91 and a light chain of SEQ ID NO:92.

In some embodiments, an ABP provided herein comprises a heavy chain of SEQ ID NO:93. In some embodiments, an ABP provided herein comprises a heavy chain of SEQ ID NO:94. In some embodiments, an APB provided herein comprises a heavy chain of SEQ ID NO:93 and a light chain of SEQ ID NO:92. In some embodiments, an APB provided herein comprises a heavy chain of SEQ ID NO:94 and a light chain of SEQ ID NO:92.

In some embodiments, an ABP provided herein comprises a heavy chain of SEQ ID NO:95. In some embodiments, an ABP provided herein comprises a heavy chain of SEQ ID NO:96. In some embodiments, an APB provided herein comprises a heavy chain of SEQ ID NO:95 and a light chain of SEQ ID NO:92. In some embodiments, an APB provided herein comprises a heavy chain of SEQ ID NO:96 and a light chain of SEQ ID NO:92.

In some embodiments, an ABP provided herein comprises a heavy chain of SEQ ID NO:97. In some embodiments, an ABP provided herein comprises a heavy chain of SEQ ID NO:98. In some embodiments, an APB provided herein comprises a heavy chain of SEQ ID NO:97 and a light chain of SEQ ID NO:92. In some embodiments, an APB provided herein comprises a heavy chain of SEQ ID NO:98 and a light chain of SEQ ID NO:92.

In some embodiments, an ABP provided herein comprises a heavy chain of SEQ ID NO:99. In some embodiments, an ABP provided herein comprises a heavy chain of SEQ ID NO:100. In some embodiments, an APB provided herein comprises a heavy chain of SEQ ID NO:99 and a light chain of SEQ ID NO:92. In some embodiments, an APB provided herein comprises a heavy chain of SEQ ID NO:100 and a light chain of SEQ ID NO:92.

In some embodiments, an ABP provided herein comprises a heavy chain of SEQ ID NO:101. In some embodiments, an ABP provided herein comprises a heavy chain of SEQ ID NO:102. In some embodiments, an APB provided herein comprises a heavy chain of SEQ ID NO:101 and a light chain of SEQ ID NO:92. In some embodiments, an APB provided herein comprises a heavy chain of SEQ ID NO:102 and a light chain of SEQ ID NO:92.

In some embodiments, an ABP provided herein comprises a heavy chain of SEQ ID NO:103. In some embodiments, an ABP provided herein comprises a heavy chain of SEQ ID NO:104. In some embodiments, an APB provided herein comprises a heavy chain of SEQ ID NO:103 and a light chain of SEQ ID NO:92. In some embodiments, an APB provided herein comprises a heavy chain of SEQ ID NO:104 and a light chain of SEQ ID NO:92.

In some embodiments, an ABP provided herein comprises a heavy chain of SEQ ID NO:105. In some embodiments, an ABP provided herein comprises a heavy chain of SEQ ID NO:106. In some embodiments, an ABP provided herein comprises a light chain of SEQ ID NO:107. In some embodiments, an APB provided herein comprises a heavy chain of SEQ ID NO:105 and a light chain of SEQ ID NO:107. In some embodiments, an APB provided herein comprises a heavy chain of SEQ ID NO:106 and a light chain of SEQ ID NO:107.

In some embodiments, an ABP provided herein comprises a heavy chain of SEQ ID NO:108. In some embodiments, an ABP provided herein comprises a heavy chain of SEQ ID NO:109. In some embodiments, an APB provided herein comprises a heavy chain of SEQ ID NO:108 and a light chain of SEQ ID NO:107. In some embodiments, an APB provided herein comprises a heavy chain of SEQ ID NO:109 and a light chain of SEQ ID NO:107.

In some embodiments, an ABP provided herein comprises a heavy chain of SEQ ID NO:110. In some embodiments, an ABP provided herein comprises a heavy chain of SEQ ID NO:111. In some embodiments, an APB provided herein comprises a heavy chain of SEQ ID NO:110 and a light chain of SEQ ID NO:107. In some embodiments, an APB provided herein comprises a heavy chain of SEQ ID NO:111 and a light chain of SEQ ID NO:107.

In some embodiments, an ABP provided herein comprises a heavy chain of SEQ ID NO:112. In some embodiments, an ABP provided herein comprises a heavy chain of SEQ ID NO:113. In some embodiments, an APB provided herein comprises a heavy chain of SEQ ID NO:112 and a light chain of SEQ ID NO:107. In some embodiments, an APB provided herein comprises a heavy chain of SEQ ID NO:113 and a light chain of SEQ ID NO:107.

In some embodiments, an ABP provided herein comprises a heavy chain of SEQ ID NO:114. In some embodiments, an ABP provided herein comprises a heavy chain of SEQ ID NO:115. In some embodiments, an APB provided herein comprises a heavy chain of SEQ ID NO:114 and a light chain of SEQ ID NO:107. In some embodiments, an APB provided herein comprises a heavy chain of SEQ ID NO:115 and a light chain of SEQ ID NO:107.

In some embodiments, an ABP provided herein comprises a heavy chain of SEQ ID NO:116. In some embodiments, an ABP provided herein comprises a heavy chain of SEQ ID NO:117. In some embodiments, an APB provided herein comprises a heavy chain of SEQ ID NO:116 and a light chain of SEQ ID NO:107. In some embodiments, an APB provided herein comprises a heavy chain of SEQ ID NO:117 and a light chain of SEQ ID NO:107.

In some embodiments, an ABP provided herein comprises a heavy chain of SEQ ID NO:118. In some embodiments, an ABP provided herein comprises a heavy chain of SEQ ID NO:119. In some embodiments, an ABP provided herein comprises a light chain of SEQ ID NO:120. In some embodiments, an APB provided herein comprises a heavy chain of SEQ ID NO:118 and a light chain of SEQ ID NO:120. In some embodiments, an APB provided herein comprises a heavy chain of SEQ ID NO:119 and a light chain of SEQ ID NO:120.

In some embodiments, an ABP provided herein comprises a heavy chain of SEQ ID NO:121. In some embodiments, an ABP provided herein comprises a heavy chain of SEQ ID NO:122. In some embodiments, an APB provided herein comprises a heavy chain of SEQ ID NO:121 and a light chain of SEQ ID NO:120. In some embodiments, an APB provided herein comprises a heavy chain of SEQ ID NO:122 and a light chain of SEQ ID NO:120.

In some embodiments, an ABP provided herein comprises a heavy chain of SEQ ID NO:123. In some embodiments, an ABP provided herein comprises a heavy chain of SEQ ID NO:124. In some embodiments, an APB provided herein comprises a heavy chain of SEQ ID NO:123 and a light chain of SEQ ID NO:120. In some embodiments, an APB provided herein comprises a heavy chain of SEQ ID NO:124 and a light chain of SEQ ID NO:120.

2.2.6. Consensus Sequences

In some embodiments, provided herein is a first family of ABPs, wherein an ABP of such family comprises the following six CDR sequences: (a) a CDR-H3 having the sequence A-R-D-G-V-L-$X_1$-L-N-K-R-S-F-D-I, wherein $X_1$ is A or T (SEQ ID NO: 128); (b) a CDR-H2 having the sequence S-I-Y-Y-S-G-$X_2$-T-Y-Y-N-P-S-L-K-S, wherein $X_2$ is S, Q or G (SEQ ID NO: 129); (c) a CDR-H1 having the sequence G-S-I-$X_3$-S-G-$X_4$-Y-Y-W-G, wherein $X_3$ is E or A, and $X_4$ is L, V or S (SEQ ID NO: 130); (d) a CDR-L3 having the sequence QQHTVRPPLT (SEQ ID NO: 64); (e) a CDR-L2 having the sequence GASSRAT (SEQ ID NO: 68); and (f) a CDR-L1 having the sequence RASQSVSSSYLA (SEQ ID NO: 71). In some embodiments, provided herein is an ABP within such first family.

In some embodiments, provided herein is a second family of ABPs, wherein an ABP of such family comprises the following six CDR sequences: (a) a CDR-H3 having the sequence A-R-D-A-N-Y-Y-G-$X_1$-A-W-A-F-D-P, wherein $X_1$ is S or G (SEQ ID NO: 131); (b) a CDR-H2 having the sequence S-I-Y-Y-S-G-$X_2$-T-F-Y-N-P-S-L-K-$X_3$, wherein $X_2$ is S or A, and $X_3$ is S or G (SEQ ID NO: 132); (c) a CDR-H1 having the sequence G-S-I-$X_4$-S-$X_5$-$X_6$-$X_7$-Y-W-G, wherein $X_4$ is S or T, $X_5$ is S or T, $X_6$ is S or K, and $X_7$ is H or Y (SEQ ID NO: 133); (d) a CDR-L3 having the sequence QQHFNLPT (SEQ ID NO: 63); (e) a CDR-L2 having the sequence DASNRAT (SEQ ID NO: 67); and (f) a CDR-L1 having the sequence RASQSVSSYLA (SEQ ID NO: 70). In some embodiments, provided herein is an ABP within such second family.

In some embodiments, provided herein is a third family of ABPs, wherein an ABP of such family comprises the following six CDR sequences: (a) a CDR-H3 having the sequence A-R-G-G-R-T-T-W-I-G-A-$X_1$-D-I, wherein $X_1$ is F or L (SEQ ID NO: 134); (b) a CDR-H2 having the sequence I-I-N-P-S-$X_2$-G-L-T-S-Y-A-$X_3$-K-F-Q-G, wherein $X_2$ is L or I, and $X_3$ is Q or R (SEQ ID NO: 135); (c) a CDR-H1 having the sequence Y-T-F-$X_4$-$X_5$-Y-Y-$X_6$-H, wherein $X_4$ is G, P or R, $X_5$ is N, A or E, and $X_6$ is M or I (SEQ ID NO: 136); (d) a CDR-L3 having the sequence QQYVVWPPLT (SEQ ID NO:65); (e) a CDR-L2 having the sequence GASTRAT (SEQ ID NO:69); and (f) a CDR-L1 having the sequence RASQSVSSNLA (SEQ ID NO:72). In some embodiments, provided herein is an ABP within such third family.

In some embodiments, provided herein is a fourth family of ABPs, wherein an ABP of such family comprises the following six CDR sequences: (a) a CDR-H3 having the sequence ARLHVSGSYYPAYLDY (SEQ ID NO: 35); (b) a CDR-H2 having the sequence $X_1$-I-N-P-S-M-G-A-T-S-Y-$X_2$-Q-K-F-$X_3$-G, wherein $X_1$ is V or I, $X_2$ is A or T, and $X_3$ is Q or R (SEQ ID NO: 137); (c) a CDR-H1 having the sequence YTFTSHYMG (SEQ ID NO: 62); (d) a CDR-L3 having the sequence QQYIVFPWT (SEQ ID NO: 66); (e) a CDR-L2 having the sequence GASTRAT (SEQ ID NO: 69); and (f) a CDR-L1 having the sequence RASQSVSSNLA, (SEQ ID NO: 72). In some embodiments, provided herein is an ABP within such fourth family.

2.2.7. Functional Properties of ABP Variants

As described above, and elsewhere in this disclosure, provided herein are ABP variants defined based on percent identity to an illustrative ABP sequence provided herein, or substitution of amino acid residues in comparison to an illustrative ABP sequence provided herein.

In some embodiments, a variant of an ABP provided herein has specificity for hTIGIT. In some embodiments, a variant of an ABP provided herein has specificity for cTIGIT. In some embodiments, a variant of an ABP provided herein has specificity for mTIGIT. In some embodiments, a variant of an ABP provided herein has specificity for hTIGIT and cTIGIT. In some embodiments, a variant of an ABP provided herein has specificity for hTIGIT and mTIGIT. In some embodiments, a variant of an ABP provided herein has specificity for cTIGIT and mTIGIT. In some embodiments, a variant of an ABP provided herein has specificity for hTIGIT, cTIGIT and mTIGIT.

In some embodiments, a variant of an ABP that is derived from an illustrative ABP sequence provided herein retains affinity, as measured by $K_D$, for hTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP. In some embodiments, a variant of an ABP that is derived from an illustrative ABP sequence provided herein retains affinity, as measured by $K_D$, for cTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP. In some embodiments, a variant of an ABP that is derived from an illustrative ABP sequence provided herein retains affinity, as measured by $K_D$, for mTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP. In some embodiments, a variant of an ABP that is derived from an illustrative ABP sequence provided herein retains affinity, as measured by $K_D$, for both hTIGIT and cTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP. In some embodiments, a variant of an ABP that is derived from an illustrative ABP sequence provided herein retains affinity, as measured by $K_D$, for both hTIGIT and mTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP. In some embodiments, a variant of an ABP that is derived from an illustrative ABP sequence provided herein retains affinity, as measured by $K_D$, for both cTIGIT and mTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP. In some embodiments, a variant of an ABP that is derived from an illustrative ABP sequence provided herein retains affinity, as measured by $K_D$, for all three of hTIGIT, cTIGIT and mTIGIT that is within about 1.5-fold, about 2-fold, about 3-fold, about 4-fold, about 5-fold, about 6-fold, about 7-fold, about 8-fold, about 9-fold or about 10-fold the affinity of such illustrative ABP.

In some embodiments, a variant of an ABP provided herein retains the ability to antagonize TIGIT, as measured by one or more assays or biological effects described herein. In some embodiments, a variant of an ABP provided herein retains the ability to prevent TIGIT from interacting with one or more of its ligands, as described herein.

In some embodiments, a variant of an ABP provided herein competes for binding to TIGIT with an antibody selected from MAB1, MAB2, MAB3, MAB4, MAB5, MAB6, MAB7, MAB8, MAB9, MAB10, MAB11, MAB12, MAB13, MAB14, MAB15, MAB16, MAB17, MAB18, MAB19, MAB20, or MAB21, each as provided in Table 5 of this disclosure.

In some embodiments, a variant of an ABP provided herein inhibits binding of CD155 to TIGIT. In some embodiments, a variant of an ABP provided herein inhibits binding of CD112 to TIGIT. In some embodiments, a variant of an ABP provided herein inhibits association of CD226 with TIGIT.

In some embodiments, a variant of an ABP provided herein activates an effector T cell or a natural killer (NK) cell. In some embodiments, a variant of an ABP provided herein decreases the number of regulatory T cells in a tissue or in circulation. In some embodiments, a variant of an ABP provided herein inhibits the suppression of an effector T cell by a regulatory T cell.

In some embodiments, a variant of an ABP provided herein does not bind specifically to any of PVRL1, PVRL2, PVRL3, or PVRL4.

In some embodiments, a variant of an ABP provided herein binds murine TIGIT (SEQ ID NO: 3) with an affinity lower (as indicated by higher $K_D$) than the affinity of the ABP for hTIGIT, or does not bind mTIGIT. In some embodiments, a variant of an ABP provided herein binds murine TIGIT (SEQ ID NO: 138) with an affinity lower (as indicated by higher $K_D$) than the affinity of the ABP for hTIGIT, or does not bind mTIGIT.

In some embodiments, a variant of an ABP provided herein binds the same epitope of TIGIT as such ABP.

2.2.8. Other Functional Properties of ABPs

In some embodiments, an ABP provided herein has one or more of the characteristics listed in the following (a)-(j): (a) competes for binding to TIGIT with an antibody selected from MAB1, MAB2, MAB3, MAB4, MAB5, MAB6, MAB7, MAB8, MAB9, MAB10, MAB11, MAB12, MAB13, MAB14, MAB15, MAB16, MAB17, MAB18, MAB19, MAB20, or MAB21, each as provided in Table 5 of this disclosure; (b) inhibits binding of CD155 to TIGIT; (c) inhibits binding of CD112 to TIGIT; (d) inhibits association of CD226 with TIGIT; (e) activates an effector T cell or a natural killer (NK) cell; (f) decreases the number of regulatory T cells in a tissue or in circulation; (g) inhibits the suppression of an effector T cell by a regulatory T cell; (h) does not bind specifically to any of PVRL1, PVRL2, PVRL3, or PVRL4; (i) specifically binds cynomolgus monkey TIGIT (cTIGIT; SEQ ID NO: 2); or (j) binds murine TIGIT (mTIGIT; SEQ ID NO: 3) with an affinity lower (as indicated by higher $K_D$) than the affinity of the ABP for hTIGIT, or does not bind mTIGIT. In some embodiments, an ABP provided herein has two or more of the characteristics listed in the foregoing (a)-(j). In some embodiments, an ABP provided herein has three or more of the characteristics listed in the foregoing (a)-(j). In some embodiments, an ABP provided herein has four or more of the characteristics listed in the foregoing (a)-(j). In some embodiments, an ABP provided herein has five or more of the characteristics listed in the foregoing (a)-(j). In some embodiments, an ABP provided herein has six or more of the characteristics listed in the foregoing (a)-(j). In some embodiments, an ABP provided herein has seven or more of the characteristics listed in the foregoing (a)-(j). In some embodiments, an ABP provided herein has eight or more of the characteristics listed in the foregoing (a)-(j). In some embodiments, an ABP provided herein has nine or more of the characteristics listed in the foregoing (a)-(j). In some embodiments, an ABP provided herein has all ten of the characteristics listed in the foregoing (a)-(j).

In some embodiments, an ABP provided herein exhibits a combination of the characteristics listed in the following (a)-(j): (a) competes for binding to TIGIT with an antibody selected from MAB1, MAB2, MAB3, MAB4, MAB5, MAB6, MAB7, MAB8, MAB9, MAB10, MAB11, MAB12, MAB13, MAB14, MAB15, MAB16, MAB17, MAB18, MAB19, MAB20, or MAB21, each as provided in Table 5 of this disclosure; (b) inhibits binding of CD155 to TIGIT; (c) inhibits binding of CD112 to TIGIT; (d) inhibits association of CD226 with TIGIT; (e) activates an effector T cell or a natural killer (NK) cell; (f) decreases the number of regulatory T cells in a tissue or in circulation; (g) inhibits the suppression of an effector T cell by a regulatory T cell; (h) does not bind specifically to any of PVRL1, PVRL2, PVRL3, or PVRL4; (i) specifically binds cynomolgus monkey TIGIT (cTIGIT; SEQ ID NO: 2); or (j) binds murine TIGIT (mTIGIT; SEQ ID NO: 3) with an affinity lower (as indicated by higher $K_D$) than the affinity of the ABP for hTIGIT, or does not bind mTIGIT. In some embodiments, such ABP exhibits a combination of the characteristics selected from (a and b), (a and c), (a and d), (a and e), (a and f), (a and g), (a and h), (a and i), (a and j), (b and a), (b and c), (b and d), (b and e), (b and f), (b and g), (b and h), (b and i), (b and j), (c and a), (c and b), (c and d), (c and e), (c and f), (c and g), (c and h), (c and i), (c and j), (d and a), (d and b), (d and c), (d and e), (d and f), (d and g), (d and h), (d and i), (d and j), (e and a), (e and b), (e and c), (e and d), (e and f), (e and g), (e and h), (e and i), (e and j), (f and a), (f and b), (f and c), (f and d), (f and e), (f and g), (f and h), (f and i), (f and j), (g and a), (g and b), (g and c), (g and d), (g and e), (g and f), (g and h), (g and i), (g and j), (h and a), (h and b), (h and c), (h and d), (h and e), (h and f), (h and g), (h and i), (h and j), (i and a), (i and b), (i and c), (i and d), (i and e), (i and f), (i and g), (i and h), (i and j), (j and a), (j and b), (j and c), (j and d), (j and e), (j and f), (j and g), (j and h), and (j and i). In some embodiments, such ABP exhibits a combination of the characteristics selected from (a and b and c), (a and b and d), (a and b and e), (a and b and f), (a and b and g), (a and b and h), (a and b and i), (a and b and j), (a and c and b), (a and c and d), (a and c and e), (a and c and f), (a and c and g), (a and c and h), (a and c and i), (a and c and j), (a and d and b), (a and d and c), (a and d and e), (a and d and f), (a and d and g), (a and d and h), (a and d and i), (a and d and j), (a and e and b), (a and e and c), (a and e and d), (a and e and f), (a and e and g), (a and e and h), (a and e and i), (a and e and j), (a and f and b), (a and f and c), (a and f and d), (a and f and e), (a and f and g), (a and f and h), (a and f and i), (a and f and j), (a and g and b), (a and g and c), (a and g and d), (a and g and e), (a and g and f), (a and g and h), (a and g and i), (a and g and j), (a and h and b), (a and h and c), (a and h and d), (a and h and e), (a and h and f), (a and h and g), (a and h and i), (a and h and j), (a and i and b), (a and i and c), (a and i and d), (a and i and e), (a and i and f), (a and i and g), (a and i and h), (a and i and j), (a and j and b), (a and j and c), (a and j and d), (a and j and e), (a and j and f), (a and j and g), (a and j and h), (a and j and i), (b and a and j), (b and a and c), (b and a and d), (b and a and e), (b and a and f), (b and a and g), (b and a and h), (b and a and i), (b and c and j), (b and c and a), (b and c and d), (b and c and e), (b and c and f), (b and c and g), (b and c and h), (b and c and i), (b and d and j), (b and d and a), (b and d and c), (b and d and e), (b and d and f), (b and d and g), (b and d and h), (b and d and i), (b and e and j), (b and e and a), (b and e and c), (b and e and d), (b and e and f), (b and e and g), (b and e and h), (b and e and i), (b and f and j), (b and f and a), (b and f and c), (b and f and d), (b and f and e), (b and f and g), (b and f and h), (b and f and i), (b and g and j), (b and g and a), (b and g and c), (b and g and d), (b and g and e), (b and g and f), (b and g and h), (b and g and i), (b and h and j), (b and h and a), (b and h and c), (b and h and d), (b and h and e), (b and h and f), (b and h and g), (b and h and i), (b and i and j), (b and i and a), (b and i and c), (b and i and d), (b and i and e), (b and i and f), (b and i and g), (b and i and h), (b and j and i), (b and j and a), (b and j and c), (b and j and d), (b and j and e), (b and j and f), (b and j and g), (b and j and h), (c and a and i), (c and a and j), (c and a and b), (c and a and d), (c and a and e), (c and a and f), (c and a and g), (c and a and h), (c and b and i), (c and b and j), (c and b and a), (c and b and d), (c and b and e), (c and b and f), (c and b and g), (c and b and h), (c and d and i), (c and d and j), (c and d and a), (c and d and b), (c and d and e), (c and d and f), (c and d and g), (c and d and h), (c and e and i), (c and e and j), (c and e and a), (c and e and b), (c and e and d), (c and e and f), (c and e and g), (c and e and h), (c and f and i), (c and f and j), (c and f and a), (c and f and b), (c and f and d), (c and f and e), (c and f and g), (c and f and h), (c and g and i), (c and g and j), (c and g and a), (c and g and b), (c and g and d), (c and g and e), (c and g and f), (c and g and h), (c and h and i), (c and h and j), (c and h and a), (c and h and b), (c and h and d), (c and h and e), (c and h and f), (c and h and g), (c and i and h), (c and i and j), (c and i and a), (c and i and b), (c and i and d), (c and i and e), (c and i and f), (c and i and g), (c and j and h), (c and j and i), (c and j and a), (c and j and b), (c and j and d), (c and j and e), (c and j and f), (c and j and g), (d and a and h), (d and a and i), (d and a and j), (d and a and b), (d and a and c), (d and a and e), (d and a and f), (d and a and g), (d and b and h), (d and b and i), (d and b and j), (d and b and a), (d and b and c), (d and b and e), (d and b and f), (d and b and g), (d and c and h), (d and c and i), (d and c and j), (d and c and a), (d and c and b), (d and c and e), (d and c and f), (d and c and g), (d and e and h), (d and e and i), (d and e and j), (d and e and a), (d and e and b), (d and e and c), (d and e and f), (d and e and g), (d and f and h), (d and f and i), (d and f and j), (d and f and a), (d and f and b), (d and f and c), (d and f and e), (d and f and g), (d and g and h), (d and g and i), (d and g and j), (d and g and a), (d and g and b), (d and g and c), (d and g and e), (d and g and f), (d and h and g), (d and h and i), (d and h and j), (d and h and a), (d and h and b), (d and h and c), (d and h and e), (d and h and f), (d and i and g), (d and i and h), (d and i and j), (d and i and a), (d and i and b), (d and i and c), (d and i and e), (d and i and f), (d and j and g), (d and j and h), (d and j and i), (d and j and a), (d and j and b), (d and j and c), (d and j and e), (d and j and f), (e and a and g), (e and a and h), (e and a and i), (e and a and j), (e and a and b), (e and a and c), (e and a and d), (e and a and f), (e and b and g), (e and b and h), (e and b and i), (e and b and j), (e and b and a), (e and b and c), (e and b and d), (e and b and f), (e and c and g), (e and c and h), (e and c and i), (e and c and j), (e and c and a), (e and c and b), (e and c and d), (e and c and f), (e and d and g), (e and d and h), (e and d and i), (e and d and j), (e and d and a), (e and d and b), (e and d and c), (e and d and f), (e and f and g), (e and f and h), (e and f and i), (e and f and j), (e and f and a), (e and f and b), (e and f and c), (e and f and d), (e and g and f), (e and g and h), (e and g and i), (e and g and j), (e and g and a), (e and g and b), (e and g and c), (e and g and d), (e and h and f), (e and h and g), (e and h and i), (e and h and j), (e and h and a), (e and h and b), (e and h and c), (e and h and d), (e and i and f), (e and i and g), (e and i and h), (e and i and j), (e and i and a), (e and i and b), (e and i and c), (e and i and d), (e and j and f), (e and j and g), (e and j and h), (e and j and i), (e and j and a), (e and j and b), (e and j and c), (e and j and d), (f and a and e), (f and a and g), (f and a and h), (f and a and i), (f and a and j), (f and a and b), (f and a and c), (f and a and d), (f and b and e), (f and b and g), (f and b and h), (f and b and i), (f and b and j), (f and b and a), (f and b and c), (f and b and d), (f and c and e), (f and c and g), (f and c and h), (f and c and i), (f and c and j), (f and c and a), (f and c and b), (f and c and d), (f and d and e), (f and d and g), (f and d and h), (f and d and i), (f and d and j), (f and d and a), (f and d and b), (f and d and c), (f and e and d), (f and e and g), (f and e and h), (f and e and i), (f and e and j), (f and e and a), (f and e and b), (f and e and c), (f and g and d), (f and g and e), (f and g and h), (f and g and i), (f and g and j), (f and g and a), (f and g and b), (f and g and c), (f and h and d), (f and h and e), (f and h and g), (f and h and i), (f and h and j), (f and h and a), (f and h and b), (f and h and c), (f and i and d), (f and i and e), (f and i and g), (f and i and h), (f and i and j), (f and i and a), (f and i and b), (f and i and c), (f and j and d), (f and j and e), (f and j and g), (f and j and h), (f and j and i), (f and j and a), (f and j and b), (f and j and c), (g and a and d), (g and a and e), (g and a and f), (g and a and h), (g and a and i), (g and a and j), (g and a and b), (g and a and c), (g and b and d), (g and b and e), (g and b and f), (g and b and h), (g and b and i), (g and b and j), (g and b and a), (g and b and c), (g and c and d), (g and c and e), (g and c and f), (g and c and h), (g and c and i), (g and c and j), (g and c and a), (g and c and b), (g and d and c), (g and d and e), (g and d and f), (g and d and h), (g and d and i), (g and d and j), (g and d and a), (g and d and b), (g and e and c), (g and e and d), (g and e and f), (g and e and h), (g and e and i), (g and e and j), (g and e and a), (g and e and b), (g and f and c), (g and f and e), (g and f and d), (g and f and h), (g and f and i), (g and f and j), (g and f and a), (g and f and b), (g and h and c), (g and h and d), (g and h and e), (g and h and f), (g and h and i), (g and h and j), (g and h and a), (g and h and b), (g and i and c), (g and i and d), (g and i and e), (g and i and f), (g and i and h), (g and i and j), (g and i and a), (g and i and b), (g and j and c), (g and j and d), (g and j and e), (g and j and f), (g and j and h), (g and j and i), (g and j and a), (g and j and b), (h and a and c), (h and a and d), (h and a and e), (h and a and f), (h and a and g), (h and a and i), (h and a and j), (h and a and b), (h and b and c), (h and b and d), (h and b and e), (h and b and f), (h and b and g), (h and b and i), (h and b and j), (h and b and a), (h and c and b), (h and c and d), (h and c and e), (h and c and f), (h and c and g), (h and c and i), (h and c and j), (h and c and a), (h and d and b), (h and d and c), (h and d and e), (h and d and f), (h and d and g), (h and d and i), (h and d and j), (h and d and a), (h and e and b), (h and e and c), (h and e and d), (h and e and f), (h and e and g), (h and e and i), (h and e and j), (h and e and a), (h and f and b), (h and f and c), (h and f and d), (h and f and e), (h and f and g), (h and f and i), (h and f and j), (h and f and a), (h and g and b), (h and g and c), (h and g and d), (h and g and e), (h and g and f), (h and g and i), (h and g and j), (h and g and a), (h and i and b), (h and i and c), (h and i and d), (h and i and e), (h and i and f), (h and i and g), (h and i and j), (h and i and a), (h and j and b), (h and j and c), (h and j and d), (h and j and e), (h and j and f), (h and j and g), (h and j and i), (h and j and a), (i and a and b), (i and a and c), (i and a and d), (i and a and e), (i and a and f), (i and a and g), (i and a and h), (i and a and j), (i and b and a), (i and b and c), (i and b and d), (i and b and e), (i and b and f), (i and b and g), (i and b and h), (i and b and j), (i and c and a), (i and c and b), (i and c and d), (i and c and e), (i and c and f), (i and c and g), (i and c and h), (i and c and j), (i and d and a), (i and d and b), (i and d and c), (i and d and e), (i and d and f), (i and d and g), (i and d and h), (i and d and j), (i and e and a), (i and e and b), (i and e and c), (i and e and d), (i and e and f), (i and e and g), (i and e and h), (i and e and j), (i and f and a), (i and f and b), (i and f and c), (i and f and d), (i and f and e), (i and f and g), (i and f and h), (i and f and j), (i and g and a), (i and g and b), (i and g and c), (i and g and d), (i and g and e), (i and g and f), (i and g and h), (i and g and j), (i and h and a), (i and h and b), (i and h and c), (i and h and d), (i and h and e), (i and h and f), (i and h and g), (i and h and j), (i and j and a), (i and j and b), (i and j and c), (i and j and d), (i and j and e), (i and j and f), (i and j and g), (i and j and h), (j and a and i), (j and a and b), (j and a and c), (j and a and d), (j and a and e), (j and a and f), (j and a and g), (j and a and h), (j and b and i), (j and b and a), (j and b and c), (j and b and d), (j and b and e), (j and b and f), (j and b and g), (j and b and h), (j and c and i), (j and c and a), (j and c and b), (j and c and d), (j and c and e), (j and c and f), (j and c and g), (j and c and h), (j and d and i), (j and d and a), (j and d and b), (j and d and c), (j and d and e), (j and d and f), (j and d and g), (j and d and h), (j and e and i), (j and e and a), (j and e and b), (j and e and c), (j and e and d), (j and e and f), (j and e and g), (j and e and h), (j and f and i), (j and f and a), (j and f and b), (j and f and c), (j and f and d), (j and f and e), (j and f and g), (j and f and h), (j and g and i), (j and g and a), (j and g and b), (j and g and c), (j and g and d), (j and g and e), (j and g and f), (j and g and h), (j and h and i), (j and h and a), (j and h and b), (j and h and c), (j and h and d), (j and h and e), (j and h and f), (j and h and g), (j and i and h), (j and i and a), (j and i and b), (j and i and c), (j and i and d), (j and i and e), (j and i and f), and (j and i and g).

2.3. Germlines

The ABPs provided herein may comprise any suitable $V_H$ and $V_L$ germline sequences.

In some embodiments, the $V_H$ region of an ABP provided herein is from the $V_H4$ germline. In some embodiments, the $V_H$ region of an ABP provided herein is from the $V_H1$ germline.

In some embodiments, the $V_H$ region of an ABP provided herein is from the $V_H4$-39 germline. In some embodiments, the $V_H$ region of an ABP provided herein is from the $V_H4$-31 germline. In some embodiments, the $V_H$ region of an ABP provided herein is from the $V_H1$-46 germline.

In some embodiments, the $V_L$ region of an ABP provided herein is from the VK3 germline.

In some embodiments, the $V_L$ region of an ABP provided herein is from the VK3-11 germline. In some embodiments, the $V_L$ region of an ABP provided herein is from the VK3-20 germline. In some embodiments, the $V_L$ region of an ABP provided herein is from the VK3-15 germline.

TABLE 5

Sequences and germlines (GL) of TIGIT ABPs.

| Ab | VHGL | CDR-H1[1] | CDR-H2[2] | CDR-H3[3] | VH Protein | VLGL | CDR-L1[4] | CDR-L2[5] | CDR-L3[6] | VL Protein |
|---|---|---|---|---|---|---|---|---|---|---|
| MAB1-IgG4 | VH4-39 | GSITSSSYYWG (SEQ ID NO: 48) | SIYYSGATFYNPSLKS (SEQ ID NO: 36) | ARDANYYGSAWAFDP (SEQ ID NO: 29) | QLQLQESGPGLVKPSETLSLTCTVSGGSITSSSYYWGWIRQPPGKGLEWIGSIYYSGATFYNPSLKSRVTISVDTSKNQFSLKLSSVTAADTAVYYCARDANYYGSAWAFDPWGQGTLVTVSS (SEQ ID NO: 4) | VK3-11 | RASQSVSSYLA (SEQ ID NO: 70) | DASNRAT (SEQ ID NO: 67) | QQHFNLPT (SEQ ID NO: 63) | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK (SEQ ID NO: 25) |
| MAB2-IgG4 | VH4-39 | GSISSSKYYWG (SEQ ID NO: 49) | SIYYSGSTFYNPSLKS (SEQ ID NO: 37) | ARDANYYGSAWAFDP (SEQ ID NO: 29) | QLQLQESGPGLVKPSETLSLTCTVSGGSISSSKYYWGWIRQPPGKGLEWIGSIYYSGSTFYNPSLKSRVTISVDTSKNQFSLKLSSVTAADTAVYYCARDANYYGSAWAFDPWGQGTLVTVSS (SEQ ID NO: 5) | VK3-11 | RASQSVSSYLA (SEQ ID NO: 70) | DASNRAT (SEQ ID NO: 67) | QQHFNLPT (SEQ ID NO: 63) | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK (SEQ ID NO: 25) |
| MAB3-IgG4 | VH4-39 | GSISSTSHYWG (SEQ ID NO: 50) | SIYYSGSTFYNPSLKS (SEQ ID NO: 37) | ARDANYYGSAWAFDP (SEQ ID NO: 29) | QLQLQESGPGLVKPSETLSLTCTVSGGSISSTSHYWGWIRQPPGKGLEWIGSIYYSGSTFYNPSLKSRVTISVDTSKNQFSLKLSSVTAADTAVYYCARDANYYGSAWAFDPWGQGTLVTVSS (SEQ ID NO: 6) | VK3-11 | RASQSVSSYLA (SEQ ID NO: 70) | DASNRAT (SEQ ID NO: 67) | QQHFNLPT (SEQ ID NO: 63) | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK (SEQ ID NO: 25) |
| MAB4-IgG4 | VH4-39 | GSISSTSHYWG (SEQ ID NO: 50) | SIYYSGSTFYNPSLKS (SEQ ID NO: 37) | ARDANYYGGAWAFDP (SEQ ID NO: 30) | QLQLQESGPGLVKPSETLSLTCTVSGGSISSTSHYWGWIRQPPGKGLEWIGSIYYSGSTFYNPSLKSRVTISVDTSKNQFSLKLSSVTAADTAVYYCARDANYYGGAWAFDPWGQGTLVTVSS (SEQ ID NO: 7) | VK3-11 | RASQSVSSYLA (SEQ ID NO: 70) | DASNRAT (SEQ ID NO: 67) | QQHFNLPT (SEQ ID NO: 63) | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK (SEQ ID NO: 25) |

TABLE 5-continued

Sequences and germlines (GL) of TIGIT ABPs.

| Ab | VHGL | CDR-H1[1] | CDR-H2[2] | CDR-H3[3] | VH Protein | VLGL | CDR-L1[4] | CDR-L2[5] | CDR-L3[6] | VL Protein |
|---|---|---|---|---|---|---|---|---|---|---|
| MAB5-IgG4 | VH4-39 | GSISSTSHYWG (SEQ ID NO: 50) | SIYYSGSTFYNPSLKG (SEQ ID NO: 38) | ARDANYYGSAWAFDP (SEQ ID NO: 29) | QLQLQESGPGLVKPSETLSLTCTVSGGSISSTSHYWGWIRQPPGKGLEWIGSIYYSGSTFYNPSLKGRVTISVDTSKNQFSLKLSSVTAADTAVYYCARDANYYGSAWAFDPWGQGTLVTVSS (SEQ ID NO: 8) | VK3-11 | RASQSVSSYLA (SEQ ID NO: 70) | DASNRAT (SEQ ID NO: 67) | QQHFNLPT (SEQ ID NO: 63) | EIVLTQSPATLSLSPGERATLSCRASQSVSSYLAWYQQKPGQAPRLLIYDASNRATGIPARFSGSGSGTDFTLTISSLEPEDFAVYYCQQHFNLPTFGGGTKVEIK (SEQ ID NO: 25) |
| MAB6-IgG4 | VH4-39 | GSIESGSYYWG (SEQ ID NO: 51) | SIYYGGTYYNPSLKS (SEQ ID NO: 39) | ARDGVLTLNKRSFDI (SEQ ID NO: 31) | QLQLQESGPGLVKPSETLSLTCTVSGGSIESGSYYWGWIRQPPGKGLEWIGSIYYSGGTYYNPSLKSRVTISVDTSKNQFSLKLSSVTAADTAVYYCARDGVLTLNKRSFDIWGQGTMVTVSS (SEQ ID NO: 9) | VK3-20 | RASQSVSSSYLA (SEQ ID NO: 71) | GASSRAT (SEQ ID NO: 68) | QQHTVRPPLT (SEQ ID NO: 64) | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIK (SEQ ID NO: 26) |
| MAB7-IgG4 | VH4-31 | GSIESGVYYWG (SEQ ID NO: 52) | SIYYGSTYYNPSLKS (SEQ ID NO: 40) | ARDGVLTLNKRSFDI (SEQ ID NO: 31) | QVQLQESGPGLVKPSQTLSLTCTVSGGSIESGVYYWGWIRQPPGKGLEWIGSIYYSGSTYYNPSLKSRVTISVDTSKNQFSLKLSSVTAADTAVYYCARDGVLTLNKRSFDIWGQGTMVTVSS (SEQ ID NO: 10) | VK3-20 | RASQSVSSSYLA (SEQ ID NO: 71) | GASSRAT (SEQ ID NO: 68) | QQHTVRPPLT (SEQ ID NO: 64) | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIK (SEQ ID NO: 26) |
| MAB8-IgG4 | VH4-39 | GSIASGSYYWG (SEQ ID NO: 53) | SIYYGQTYYNPSLKS (SEQ ID NO: 41) | ARDGVLTLNKRSFDI (SEQ ID NO: 31) | QLQLQESGPGLVKPSETLSLTCTVSGGSIASGSYYWGWIRQPPGKGLEWIGSIYYSGQTYYNPSLKSRVTISVDTSKNQFSLKLSSVTAADTAVYYCARDGVLTLNKRSFDIWGQGTMVTVSS (SEQ ID NO: 11) | VK3-20 | RASQSVSSSYLA (SEQ ID NO: 71) | GASSRAT (SEQ ID NO: 68) | QQHTVRPPLT (SEQ ID NO: 64) | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIK (SEQ ID NO: 26) |

TABLE 5-continued

Sequences and germlines (GL) of TIGIT ABPs.

| Ab | VHGL | CDR-H1[1] | CDR-H2[2] | CDR-H3[3] | VH Protein | VLGL | CDR-L1[4] | CDR-L2[5] | CDR-L3[6] | VL Protein |
|---|---|---|---|---|---|---|---|---|---|---|
| MAB9-IgG4 | VH4-31 | GSIESGLYYWG (SEQ ID NO: 54) | SIYYSGSTYYNPSLKS (SEQ ID NO: 40) | ARDGVLTLNKRSFDI (SEQ ID NO: 31) | QVQLQESGPGLVKPSQTLSLTCTVSGGSIESGLYYWGWIRQPPGKGLEWIGSIYYSGSTYYNPSLKSRVTISVDTSKNQFSLKLSSVTAADTAVYYCARDGVLTLNKRSFDIWGQGTMVTVSS (SEQ ID NO: 12) | VK3-20 | RASQSVSSSYLA (SEQ ID NO: 71) | GASSRAT (SEQ ID NO: 68) | QQHTVRPPLT (SEQ ID NO: 64) | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIK (SEQ ID NO: 26) |
| MAB10-IgG4 | VH4-31 | GSIESGLYYWG (SEQ ID NO: 54) | SIYYSGSTYYNPSLKS (SEQ ID NO: 40) | ARDGVLALNKRSFDI (SEQ ID NO: 32) | QVQLQESGPGLVKPSQTLSLTCTVSGGSIESGLYYWGWIRQPPGKGLEWIGSIYYSGSTYYNPSLKSRATISVDTSKNQFSLKLSSVTAADTAVYYCARDGVLALNKRSFDIWGQGTMVTVSS (SEQ ID NO: 13) | VK3-20 | RASQSVSSSYLA (SEQ ID NO: 71) | GASSRAT (SEQ ID NO: 68) | QQHTVRPPLT (SEQ ID NO: 64) | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIK (SEQ ID NO: 26) |
| MAB11-IgG4 | VH4-31 | GSIESGLYYWG (SEQ ID NO: 54) | SWYSGSTYYNPSLKS (SEQ ID NO: 40) | ARDGVLALNKRSFDI (SEQ ID NO: 32) | QVQLQESGPGLVKPSQTLSLTCTVSGGSIESGLYYWGWIRQPPGKGLEWIGSIYYSGSTYYNPSLKSRVTISVDTSKNQFSLKLSSVTAADTAVYYCARDGVLALNKRSFDIWGQGTMVTVSS (SEQ ID NO: 14) | VK3-20 | RASQSVSSSYLA (SEQ ID NO: 71) | GASSRAT (SEQ ID NO: 68) | QQHTVRPPLT (SEQ ID NO: 64) | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIK (SEQ ID NO: 26) |
| MAB12-IgG4 | VH4-31 | GSIESGLYYWG (SEQ ID NO: 54) | SIYYSGSTYYNPSLKS (SEQ ID NO: 40) | ARDGVLALNKRSFDI (SEQ ID NO: 32) | QVQLQESGPGLVKPSQTLSLTCTASGGSIESGLYYWGWIRQPPGKGLEWIGSIYYSGSTYYNPSLKSRVTISVDTSKNQFSLKLSSVTAADTAVYYCARDGVLALNKRSFDIWGQGTMVTVSS (SEQ ID NO: 15) | VK3-20 | RASQSVSSSYLA (SEQ ID NO: 71) | GASSRAT (SEQ ID NO: 68) | QQHTVRPPLT (SEQ ID NO: 64) | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIK (SEQ ID NO: 26) |

TABLE 5-continued

Sequences and germlines (GL) of TIGIT ABPs.

| Ab | VHGL | CDR-H1[1] | CDR-H2[2] | CDR-H3[3] | VH Protein | VLGL | CDR-L1[4] | CDR-L2[5] | CDR-L3[6] | VL Protein |
|---|---|---|---|---|---|---|---|---|---|---|
| MAB13-IgG4 | VH1-46 | YTFGNYYMH (SEQ ID NO: 58) | IINPSLGLTSYAQKFQG (SEQ ID NO: 42) | ARGGRTTWIGAFDI (SEQ ID NO: 33) | QVQLVQSGAEVKKPGASVKVSCKASGYTFGNYYMHWVRQAPGQGLEWMGIINPSLGLTSYAQKFQGRVTMTRDTSTSTVYMELSSLRSEDTAVYYCARGGRTTWIGAFDIWGQGTMVTVSS (SEQ ID NO: 16) | VK3-15 | RASQSVSSNLA (SEQ ID NO: 72) | GASTRAT (SEQ ID NO: 69) | QQYVVWPPLT (SEQ ID NO: 65) | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIK (SEQ ID NO: 27) |
| MAB14-IgG4 | VH1-46 | YTFPAYYMH (SEQ ID NO: 59) | IINPSLGLTSYAQKFQG (SEQ ID NO: 42) | ARGGRTTWIGAFDI (SEQ ID NO: 33) | QVQLVQSGAEVKKPGASVKVSCKASGYTFPAYYMHWVRQAPGQGLEWMGIINPSLGLTSYAQKFQGRVTMTRDTSTSTVYMELSSLRSEDTAVYYCARGGRTTWIGAFDIWGQGTMVTVSS (SEQ ID NO: 17) | VK3-15 | RASQSVSSNLA (SEQ ID NO: 72) | GASTRAT (SEQ ID NO: 69) | QQYVVWPPLT (SEQ ID NO: 65) | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIK (SEQ ID NO: 27) |
| MAB15-IgG4 | VH1-46 | YTFREYYMH (SEQ ID NO: 60) | IINPSIGLTSYARKFQG (SEQ ID NO: 43) | ARGGRTTWIGAFDI (SEQ ID NO: 33) | QVQLVQSGAEVKKPGASVKVSCKASGYTFREYYMHWVRQAPGQGLEWMGIINPSIGLTSYARKFQGRVTMTRDTSTSTVYMELSSLRSEDTAVYYCARGGRTTWIGAFDIWGQGTMVTVSS (SEQ ID NO: 18) | VK3-15 | RASQSVSSNLA (SEQ ID NO: 72) | GASTRAT (SEQ ID NO: 69) | QQYVVWPPLT (SEQ ID NO: 65) | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIK (SEQ ID NO: 27) |
| MAB16-IgG4 | VH1-46 | YTFREYYMH (SEQ ID NO: 60) | IINPSIGLTSYARKFQG (SEQ ID NO: 43) | ARGGRTTWIGALDI (SEQ ID NO: 34) | QVQLVQSGAEVKKPGASVKVSCKASGYTFREYYMHWVRQAPGQGLEWMGIINPSIGLTSYARKFQGRVTMTRDTSTSTVYMELSSLRSEDTAVYYCARGGRTTWIGALDIWGQGTMVTVSS (SEQ ID NO: 19) | VK3-15 | RASQSVSSNLA (SEQ ID NO: 72) | GASTRAT (SEQ ID NO: 69) | QQYVVWPPLT (SEQ ID NO: 65) | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIK (SEQ ID NO: 27) |

TABLE 5-continued

Sequences and germlines (GL) of TIGIT ABPs.

| Ab | VHGL | CDR-H1[1] | CDR-H2[2] | CDR-H3[3] | VH Protein | VLGL | CDR-L1[4] | CDR-L2[5] | CDR-L3[6] | VL Protein |
|---|---|---|---|---|---|---|---|---|---|---|
| MAB17-IgG4 | VH1-46 | YTFPAYYIH (SEQ ID NO: 61) | IINPSLGLTSYARKFQG (SEQ ID NO: 44) | ARGGRTTWIGALDI (SEQ ID NO: 34) | QVQLVQSGAEVKKPGASVKVSCKASGYTFPAYYIHWVRQAPGQGLEWMGIINPSLGLTSYARKFQGRVTMTRDTSTSTVYMELSSLRSEDTAVYYCARGGRTTWIGALDIWGQGTMVTVSS (SEQ ID NO: 20) | VK3-15 | RASQSVSSNLA (SEQ ID NO: 72) | GASTRAT (SEQ ID NO: 69) | QQYVVWPPLT (SEQ ID NO: 65) | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIK (SEQ ID NO: 27) |
| MAB18-IgG4 | VH1-46 | YTFPAYYMH (SEQ ID NO: 59) | IINPSLGLTSYARKFQG (SEQ ID NO: 44) | ARGGRTTWIGAFDI (SEQ ID NO: 33) | QVQLVQSGAEVKKPGASVKVSCKASGYTFPAYYMHWVRQAPGQGLEWMGIINPSLGLTSYARKFQGRVTMTRDTSTSTVYMELSSLRSEDTAVYYCARGGRTTWIGAFDIWGQGTMVTVSS (SEQ ID NO: 21) | VK3-15 | RASQSVSSNLA (SEQ ID NO: 72) | GASTRAT (SEQ ID NO: 69) | QQYVVWPPLT (SEQ ID NO: 65) | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIK (SEQ ID NO: 27) |
| MAB19-IgG4 | VH1-46 | YTFTSHYMG (SEQ ID NO: 62) | VINPSMGATSYAQKFQG (SEQ ID NO: 45) | ARLHVSGSYYPAYLDY (SEQ ID NO: 35) | QVQLVQSGAEVKKPGASVKVSCKASGYTFTSHYMGWVRQAPGQGLEWMGVINPSMGATSYAQKFQGRVTMTRDTSTSTVYMELSSLRSEDTAVYYCARLHVSGSYYPAYLDYWGQGTMVTVSS (SEQ ID NO: 22) | VK3-15 | RASQSVSSNLA (SEQ ID NO: 72) | GASTRAT (SEQ ID NO: 69) | QQYIVFPWT (SEQ ID NO: 66) | EIVMTQSPATLSVSPGERATLSCRASQSVSSNLAWYQQKPGQAPRHLIYGASTRATGIPARFSGSGSGTEFTLTISSLQSEDFAVYYCQQYIVFPWTFGGGTKVEIK (SEQ ID NO: 28) |
| MAB20-IgG4 | VH1-46 | YTFTSHYMG (SEQ ID NO: 62) | IINPSMGATSYAQKFQG (SEQ ID NO: 46) | ARLHVSGSYYPAYLDY (SEQ ID NO: 35) | QVQLVQSGAEVKKPGASVKVSCKASGYTFTSHYMGWVRQAPGQGLEWVGIINPSMGATSYAQKFQGRVTMTRDTSTSTVYMELSSLRSEDTAVYYCARLHVSGSYYPAYLDYWGQGTMVTVSS (SEQ ID NO: 23) | VK3-15 | RASQSVSSNLA (SEQ ID NO: 72) | GASTRAT (SEQ ID NO: 69) | QQYIVFPWT (SEQ ID NO: 66) | EIVMTQSPATLSVSPGERATLSCRASQSVSSNLAWYQQKPGQAPRHLIYGASTRATGIPARFSGSGSGTEFTLTISSLQSEDFAVYYCQQYIVFPWTFGGGTKVEIK (SEQ ID NO: 28) |

TABLE 5-continued

Sequences and germlines (GL) of TIGIT ABPs.

| Ab | VHGL | CDR-H1[1] | CDR-H2[2] | CDR-H3[3] | VH Protein | VLGL | CDR-L1[4] | CDR-L2[5] | CDR-L3[6] | VL Protein |
|---|---|---|---|---|---|---|---|---|---|---|
| MAB21-IgG4 | VH1-46 | YTFTSHYMG (SEQ ID NO: 62) | IINPSMGATSYTQKFRG (SEQ ID NO: 47) | ARLHVSGSYYPAYLDY (SEQ ID NO: 35) | QVQLVQSGAEVKPGASVKVSCKASGYTFTSHYMGWVRQAPGQGLEWMGIINPSMGATSYTQKFRGRVTMTRDTSTSTVYMELSSLRSEDTAVYYCARLHVSGSYYPAYLDYWGQGTMVTVSS (SEQ ID NO: 24) | VK3-15 | RASQSVSSNLA (SEQ ID NO: 72) | GASTRAT (SEQ ID NO: 69) | QQYIVFPWT (SEQ ID NO: 66) | EIVMTQSPATLSVSPGERATLSCRASQSVSSNLAWYQQKPGQAPRHLIYGASTRATGIPARFSGSGSGTEFTLTISSLQSEDFAVYYCQQYIVFPWTFGGGTKVEIK (SEQ ID NO: 28) |

[1] Includes CDR-H1 as defined by both the Chothia and Kabat numbering systems, inclusive of the boundaries of both numbering systems.
[2] According to the Kabat numbering system.
[3] According to the IMGT numbering system.
[4] According to the Kabat and Chothia numbering systems.
[5] According to the Kabat and Chothia numbering systems.
[6] According to the Kabat, Chothia, and IMGT numbering systems.

2.4. TIGIT Antagonism

In some embodiments, the ABPs provided herein antagonize TIGIT upon binding.

In some embodiments, antagonism of TIGIT by an ABP provided herein results in dimerization and/or activation of CD226 (also known as DNAM-1), a co-stimulatory receptor whose dimerization and function is impaired by direct interaction with TIGIT. See Grogan et al., *J. Immunol.*, 2014, 192 (1 Supplement) 2013.15, incorporated by reference in its entirety.

In some embodiments, antagonism of TIGIT by an ABP provided herein increases the amount of CD226 and CD155 that interact in comparison to the amount that interact in the absence of the ABP.

In some embodiments, antagonism of TIGIT by an ABP provided herein results in activation of an effector T cell. In some aspects, the effector T cell is a CD8+ T cell. In some aspects, the effector T cell is a CD4+ T cell.

In some embodiments, antagonism of TIGIT by an ABP provided herein results in activation of an NK cell. In some embodiments, antagonism of TIGIT by an ABP provided herein results in activation of an NKT cell.

In some embodiments, antagonism of TIGIT by an ABP provided herein results in a reduction of the inhibitory activity of a regulatory T cell toward an effector T cell.

In some embodiments, antagonism of TIGIT by an ABP provided herein results in increased secretion of IL-2, IL-6, GM-CSF, TNF, LT-α, and/or IFN-γ by a target cell.

In some embodiments, antagonism of TIGIT by an ABP provided herein increases the proliferation, survival, and/or function of an effector T cell. In some aspects the effector T cell is a CD4+ effector T cell. In some aspects, the effector T cell is a CD8+ effector T cell.

In some embodiments, antagonism of TIGIT by an ABP provided herein abrogates suppression of an effector T cell by a regulatory T cell. In some aspects, the regulatory T cell is a CD4+CD25+Foxp3+ regulator T cell. In some aspects, the regulatory T cell is a CD8+CD25+ regulatory T cell.

In some embodiments, antagonism of TIGIT by an ABP provided herein results in an enhancement of an immune response.

In some embodiments, antagonism of TIGIT by an ABP provided herein results in the prevention of a tumor. In some embodiments, antagonism of TIGIT by an ABP provided herein results in the delay of onset of a tumor. In some embodiments, antagonism of TIGIT by an ABP provided herein results in a reduction of the size of a tumor. In some embodiments, antagonism of TIGIT by an ABP provided herein results in elimination of a tumor. In some embodiments, antagonism of TIGIT by an ABP provided herein results in a reduction in the number of metastases.

In some embodiments, antagonism of TIGIT by an ABP provided herein results in the prevention of a viral disease. In some embodiments, antagonism of TIGIT by an ABP provided herein results in the delay of onset of a viral disease. In some embodiments, antagonism of TIGIT by an ABP provided herein results in a reduction of the viral load in a subject. In some embodiments, antagonism of TIGIT by an ABP provided herein results in the elimination of a viral infection.

2.5. Affinity and Kinetics of Antigen-Binding Proteins for TIGIT; Potency

In some embodiments, the affinity of an ABP provided herein for TIGIT is measured by the methods disclosed in the Examples section of International Publication No. WO/2017/059095 and U.S. Pat. No. 9,713,641, both of which are herein incorporated by reference in their entirety. In some embodiments, the affinity of an ABP provided herein for TIGIT, as indicated by $K_D$, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the ABP is between about $10^{-7}$ M and $10^{-12}$ M. In some embodiments, the affinity of the ABP is between about $10^{-7}$ M and $10^{-11}$ M. In some embodiments, the affinity of the ABP is between about $10^{-7}$ M and $10^{-10}$ M. In some embodiments, the affinity of the ABP is between about $10^{-7}$ M and $10^{-9}$ M. In some embodiments, the affinity of the ABP is between about $10^{-7}$ M and $10^{-8}$ M. In some embodiments, the affinity of the ABP is between about $10^{-8}$ M and $10^{-12}$ M. In some embodiments, the affinity of the ABP is between about $10^{-8}$ M and $10^{-11}$ M. In some embodiments, the affinity of the ABP is between about $10^{-9}$ M and $10^{-11}$ M. In some embodiments, the affinity of the ABP is between about $10^{-10}$ M and $10^{-11}$ M.

In some embodiments, the affinity of an ABP provided herein for hTIGIT, as indicated by $K_D$ measured by ForteBio, is selected from about $5.24\times10^{-10}$ M, about $4.57\times10^{-10}$ M, about $3.32\times10^{-10}$ M, about $2.46\times10^{-10}$ M, about $1.96\times10^{-10}$ M, about $3.11\times10^{-9}$ M, about $2.54\times10^{-9}$ M, about $3.13\times10^{-9}$ M, about $2.83\times10^{-9}$ M, about $1.71\times10^{-9}$ M, about $2.47\times10^{-9}$ M, about $2.35\times10^{-9}$ M, about $1.44\times10^{-9}$ M, about $1.23\times10^{-9}$ M, about $5.26\times10^{-10}$ M, about $3.78\times10^{-10}$ M, about $4.29\times10^{-10}$ M, or about $4.48\times10^{-10}$ M. In some embodiments, such affinity ranges from about $3.13\times10^{-9}$ M to about $1.96\times10^{-10}$ M. In some embodiments, such $K_D$ is about $3.13\times10^{-9}$ M or less.

In some embodiments, the affinity of an ABP provided herein for cTIGIT, as indicated by $K_D$ measured by ForteBio, is selected from about $2.64\times10^{-9}$ M, about $6.55\times10^{-9}$ M, about $8.14\times10^{-9}$ M, about $6.57\times10^{-9}$ M, about $7.94\times10^{-8}$ M, about $7.04\times10^{-8}$ M, about $1.10\times10^{-7}$ M, about $7.20\times10^{-8}$ M, about $1.57\times10^{-9}$ M, about $8.02\times10^{-10}$ M, about $3.67\times10^{-10}$ M, about $8.98\times10^{-10}$ M, about $1.75\times10^{-8}$ M, or about $2.58\times10^{-8}$ M, about $9.35\times10^{-9}$ M. In some embodiments, such affinity ranges from about $1.10\times10^{-7}$ M to about $3.69\times10^{-10}$ M. In some embodiments, such $K_D$ is about $1.10\times10^{-7}$ M or less.

In some embodiments, the affinity of an ABP provided herein for hTIGIT, as indicated by $K_D$ measured by solution equilibrium methods (MSD-SET), is selected from about $5.40\times10^{-11}$ M, about $1.10\times10^{-10}$ M, about $1.50\times10^{-10}$ M, about $5.60\times10^{-11}$ M, about $4.00\times10^{-10}$ M, about $3.80\times10^{-10}$ M, about $2.10\times10^{-10}$ M, about $7.00\times10^{-11}$ M, about $4.10\times10^{-11}$ M, about $2.50\times10^{-11}$ M, about $3.00\times10^{-11}$ M, about $8.00\times10^{-11}$ M, about $8.10\times10^{-12}$ M, about $5.00\times10^{-12}$ M, or about $4.90\times10^{-12}$ M. In some embodiments, such affinity ranges from about $4.00\times10^{-10}$ M to about $4.90\times10^{-12}$ M. In some embodiments, such $K_D$ is about $4.00\times10^{-10}$ M or less.

In some embodiments, the affinity of an ABP provided herein for cTIGIT as indicated by $K_D$ measured by MSD-SET, is selected from about $3.20\times10^{-10}$ M, about $2.30\times10^{-10}$ M, about $3.50\times10^{-11}$ M, about $1.50\times10^{-11}$ M, or about $4.60\times10^{-11}$ M. In some embodiments, such affinity ranges from about $3.20\times10^{-10}$ M to about $1.50\times10^{-11}$ M. In some embodiments, such $K_D$ is about $3.20\times10^{-10}$ M or less.

In some embodiments, the affinity of an ABP provided herein for hTIGIT, as indicated by $K_D$ measured by ForteBio, is selected from about $7.1\times10^{-10}$ M, about $8.1\times10^{-11}$ M, about $1.9\times10^{-10}$ M, about $5.6\times10^{-10}$ M, about $2.4\times10^{-10}$ M, about $2.8\times10^{-1}$ M, about $1.6\times10^{-10}$ M, about $5.8\times10^{-10}$ M, about $1.1\times10^{-9}$ M, about $8.1\times10^{-10}$ M, about $4.6\times10^{-10}$ M, or about $3.6\times10^{-10}$ M. In some embodiments, such affinity ranges from about $1.1\times10^{-9}$ M to about $8.1\times10^{-11}$ M. In some embodiments, such $K_D$ is about $1.1\times10^{-9}$ M or less.

In some embodiments, the affinity of an ABP provided herein for hTIGIT as indicated by $K_D$ measured by ForteBio, is about $2.4\times10^{-10}$ M. In some embodiments, the affinity of an ABP provided herein for cTIGIT, as indicated by $K_D$ measured by ForteBio, is about $6.2\times10^{-9}$ M. In some embodiments, such $K_D$ is about $6.2\times10^{-9}$ M or less.

In some embodiments, the affinity of an ABP provided herein for hTIGIT expressed on the surface of a Jurkat cell, as indicated by $K_D$, is about $5.1\times10^{-10}$ M. In some embodiments, such $K_D$ is about $5.1\times10^{-10}$ M or less.

In some embodiments, the affinity of an ABP provided herein for cTIGIT expressed on the surface of a Jurkat cell, as indicated by $K_D$, is about $4.0\times10^{-10}$ M. In some embodiments, such $K_D$ is about $4.0\times10^{-10}$ M or less.

In some embodiments, the affinity of an ABP provided herein for mTIGIT (SEQ ID NO: 3) expressed on the surface of a Jurkat cell, as indicated by $K_D$, is about $9.8\times10^{-9}$ M. In some embodiments, such $K_D$ is about $9.8\times10^{-9}$ M or less. In some embodiments, such $K_D$ is about $9.8\times10^{-9}$ M or greater.

In some embodiments, the affinity of an ABP provided herein for hTIGIT expressed on the surface of a human CD8+ T cell, as indicated by $K_D$, is about $1.3\times10^{-9}$ M. In some embodiments, such $K_D$ is about $1.3\times10^{-9}$ M or less.

In some embodiments, the affinity of an ABP provided herein for cTIGIT expressed on the surface of a cynomolgus monkey CD8+ T cell, as indicated by $K_D$, is about $2.8\times10^{-9}$ M. In some embodiments, such $K_D$ is about $2.8\times10^{-9}$ M or less.

In some embodiments, the affinity of an ABP provided herein for mTIGIT expressed on the surface of a murine T regulatory cell (i.e., mTIGIT as it naturally occurs on such cells, whether or not such mTIGIT is of SEQ ID NOs: 3 or 138, but inclusive of such SEQ ID NOs), as indicated by $K_D$, is about $2.5\times10^{-8}$ M. In some embodiments, such $K_D$ is about $2.5\times10^{-8}$ M or less.

In some embodiments, the ABPs provided herein specifically bind to hTIGIT (SEQ ID NO:1) with a $K_D$ of X and to cTIGIT (SEQ ID NO:2) or mTIGIT (SEQ ID NO:3 or 138) with a $K_D$ of $\leq 10X$. In some embodiments, the ABPs provided herein specifically bind to hTIGIT (SEQ ID NO:1) with a $K_D$ of X and to cTIGIT (SEQ ID NO:2) or mTIGIT (SEQ ID NO:3 or 138) with a $K_D$ of $<5X$. In some embodiments, the ABPs provided herein specifically bind to hTIGIT (SEQ ID NO:1) with a $K_D$ of X and to cTIGIT (SEQ ID NO:2) or mTIGIT (SEQ ID NO:3 or 138) with a $K_D$ of $\leq 2X$. In some aspects, X is any $K_D$ described in this disclosure. In some aspects, X is 0.01 nM, 0.1 nM, 1 nM, 10 nM, 20 nM, 50 nM, or 100 nM.

In some embodiments, the ratio of $K_{D(hTIGIT)}:K_{D(cTIGIT)}$ for an ABP provided herein, as measured by ForteBio, is selected from about $1.98\times10^{-1}$, about $2.61\times10^{-1}$, about $3.03\times10^{-1}$, about $3.58\times10^{-1}$, about $6.62\times10^{-3}$, about $1.98\times10^{-1}$, about $5.37\times10^{-3}$, about $3.90\times10^{-3}$, about $6.22\times10^{-3}$, about $2.91\times10^{-1}$, about $4.14\times10^{-1}$, about $6.67\times10^{-1}$, about $2.18\times10^{-1}$, about $1.78\times10^{-1}$, about $1.21\times10^{-1}$, or about $3.03\times10^{-1}$. In some embodiments, such ratio ranges from about $3.90\times10^{-3}$ to about $6.67\times10^{-1}$.

In some embodiments, the ratio of $K_{D(hTIGIT)}:K_{D(cTIGIT)}$ for an ABP provided herein, as measured by ForteBio, is about $3.87\times10^{-2}$.

In some embodiments, the ratio of $K_{D(hTIGIT)}:K_{D(cTIGIT)}$ for an ABP provided herein, as measured by MSD-SET, is selected from about $3.33\times10^{-1}$, about $2.31\times10^{-1}$, about $1.09\times10^{-1}$, about $1.07\times10^{-1}$, or about $1.69\times10^{-1}$. In some embodiments, such ratio ranges from about $1.07\times10^{-1}$ M to about $3.33\times10^{-1}$ M.

In some embodiments an ABP provided herein has a $k_a$ of at least about $10^4$ $M^{-1}\times sec^{-1}$. In some embodiments the ABP has a $k_a$ of at least about $10^5$ $M^{-1}\times sec^{-1}$. In some embodiments the ABP has a $k_a$ of at least about $10^6$ $M^{-1}\times sec^{-1}$. In some embodiments the ABP has a $k_a$ of between about $10^4$ $M^{-1}\times sec^{-1}$ and about $10^5$ $M^{-1}\times sec^{-1}$. In some embodiments the ABP has a $k_a$ of between about $10^5$ $M^{-1}\times sec^{-1}$ and about $10^6$ $M^{-1}\times sec^{-1}$. In some embodiments, such $k_a$ is at least about $10^5$ $M^{-1}\times sec^{-1}$.

In some embodiments, an ABP provided herein has a $k_a$ for hTIGIT, as measured by ForteBio, selected from about $3.2\times10^5$ $M^{-1}\times sec^{-1}$, about $7.0\times10^5$ $M^{-1}\times sec^{-1}$, about $7.7\times10^5$ $M^{-1}\times sec^{-1}$, about $1.6\times10^6$ $M^{-1}\times sec^{-1}$, about $2.0\times10^6$ $M^{-1} \times sec^{-1}$, about $1.3 \times 10^6$ $M^{-1} \times sec^{-1}$, about $1.5 \times 10^6$ $M^{-1} \times sec^{-1}$, about $1.1 \times 10^6$ $M^{-1} \times sec^{-1}$, about $4.5 \times 10^5$ $M^{-1} \times sec^{-1}$, about $7.5 \times 10^5$ $M^{-1} \times sec^{-1}$, about $8.9 \times 10^5$ $M^{-1} \times sec^{-1}$, or about $1.4 \times 10^6$ $M^{-1} \times sec^{-1}$. In some embodiments, such $k_a$ ranges from about $3.2 \times 10^5$ $M^{-1} \times sec^{-1}$ to about $2.0 \times 10^6$ $M^{-1} \times sec^{-1}$. In some embodiments, such $k_a$ is about $2.0 \times 10^6$ M or less.

In some embodiments, an ABP provided herein has a $k_a$ for hTIGIT, as measured by ForteBio as, of about $2.0 \times 10^6$ $M^{-1} \times sec^{-1}$. In some embodiments, such $k_a$ is at least about $2.0 \times 10^6$ $M^{-1} \times sec^{-1}$.

In some embodiments, an ABP provided herein has a $k_a$ for cTIGIT, as measured by ForteBio, of about $7.9 \times 10^5$ $M^{-1} \times sec^{-1}$. In some embodiments, such $k_a$ is at least about $7.9 \times 10^5$ $M^{-1} \times sec^{-1}$.

In some embodiments an ABP provided herein has a $k_a$ of about $10^{-5}$ $sec^{-1}$ or less. In some embodiments the ABP has a $k_a$ of about $10^{-4}$ $sec^{-1}$ or less. In some embodiments the ABP has a $k_a$ of about $10^{-3}$ $sec^{-1}$ or less. In some embodiments the ABP has a $k_d$ of between about $10^{-2}$ $sec^{-1}$ and about $10^{-5}$ $sec^{-1}$. In some embodiments the ABP has a $k_d$ of between about $10^{-2}$ $sec^{-1}$ and about $10^{-4}$ $sec^{-1}$. In some embodiments the ABP has a $k_d$ of between about $10^{-3}$ $sec^{-1}$ and $10^{-5}$ $sec^{-1}$.

In some embodiments, an ABP provided herein has a $k_d$ for hTIGIT, as measured by ForteBio, selected from about $2.3 \times 10^{-4}$ $sec^{-1}$, about $6.3 \times 10^{-5}$ $sec^{-1}$, about $1.4 \times 10^{-4}$ $sec^{-1}$, about $8.5 \times 10^{-4}$ $sec^{-1}$, about $3.8 \times 10^{-4}$ $sec^{-1}$, about $3.5 \times 10^{-4}$ $sec^{-1}$, about $2.4 \times 10^{-4}$ $sec^{-1}$, about $6.6 \times 10^{-4}$ $sec^{-1}$, about $5.9 \times 10^4$ $sec^{-1}$, or about $5.0 \times 10^{-4}$ $sec^{-1}$. In some embodiments, such $k_d$ ranges from about $6.3 \times 10^{-5}$ $sec^{-1}$ to about $8.5 \times 10^{-4}$ $sec^{-1}$. In some embodiments, such $k_d$ is less than about $8.5 \times 10^{-4}$ $sec^{-1}$.

In some embodiments, an ABP provided herein has a $k_d$ for hTIGIT, as measured by ForteBio, of about $3.8 \times 10^{-4}$ $sec^{-1}$. In some embodiments, such $k_d$ is less than about $3.8 \times 10^{-4}$ $sec^{-1}$.

In some embodiments, an ABP provided herein has a $k_d$ for cTIGIT, as measured by ForteBio, of about $4.6 \times 10^{-3}$ $sec^{-1}$. In some embodiments, such $k_d$ is less than about $4.6 \times 10^{-3}$ $sec^{-1}$.

In some embodiments, an ABP provided herein has a $k_a$ for hTIGIT of about $3.2 \times 10^5$ $M^{-1} \times sec^{-1}$, a $k_d$ for hTIGIT of about $2.3 \times 10^{-4}$ $sec^{-1}$, and a $K_D$ for hTIGIT of about $7.1 \times 10^{-10}$ M. In some embodiments, an ABP provided herein has a $k_a$ for hTIGIT of about $7.0 \times 10^5$ $M^{-1} \times sec^{-1}$, a $k_d$ for hTIGIT of about $6.3 \times 10^{-5}$ $sec^{-1}$, and a $K_D$ for hTIGIT of about $8.1 \times 10^{-11}$ M. In some embodiments, an ABP provided herein has a $k_a$ for hTIGIT of about $7.7 \times 10^5$ $M^{-1} \times sec^{-1}$, a $k_d$ for hTIGIT of about $1.4 \times 10^{-4}$ $sec^{-1}$, and a $K_D$ for hTIGIT of about $1.9 \times 10^{-10}$ M. In some embodiments, an ABP provided herein has a $k_a$ for hTIGIT of about $1.6 \times 10^6$ $M^{-1} \times sec^{-1}$, a $k_d$ for hTIGIT of about $8.5 \times 10^{-4}$ $sec^{-1}$, and a $K_D$ for hTIGIT of about $5.6 \times 10^{-10}$ M. In some embodiments, an ABP provided herein has a $k_a$ for hTIGIT of about $2.0 \times 10^6$ $M^{-1} \times sec^{-1}$, a $k_d$ for hTIGIT of about $3.8 \times 10^{-4}$ $sec^{-1}$, and a $K_D$ for hTIGIT of about $2.4 \times 10^{-10}$ M. In some embodiments, an ABP provided herein has a $k_a$ for hTIGIT of about $1.3 \times 10^6$ $M^{-1} \times sec^{-1}$, a $k_d$ for hTIGIT of about $3.5 \times 10^{-4}$ $sec^{-1}$, and a $K_D$ for hTIGIT of about $2.8 \times 10^{-10}$ M. In some embodiments, an ABP provided herein has a $k_a$ for hTIGIT of about $1.5 \times 10^6$ $M^{-1} \times sec^{-1}$, a $k_d$ for hTIGIT of about $2.4 \times 10^{-4}$ $sec^{-1}$, and a $K_D$ for hTIGIT of about $1.6 \times 10^{-10}$ M. In some embodiments, an ABP provided herein has a $k_a$ for hTIGIT of about $1.1 \times 10^6$ $M^{-1} \times sec^{-1}$, a $k_d$ for hTIGIT of about $6.6 \times 10^{-4}$ $sec^{-1}$, and a $K_D$ for hTIGIT of about $5.8 \times 10^{-10}$ M. In some embodiments, an ABP provided herein has a $k_a$ for hTIGIT of about $4.5 \times 10^5$ $M^{-1} \times sec^{-1}$, a $k_d$ for hTIGIT of about $3.5 \times 10^{-4}$ $sec^{-1}$, and a $K_D$ for hTIGIT of about $1.1 \times 10^{-9}$ M. In some embodiments, an ABP provided herein has a $k_a$ for hTIGIT of about $7.5 \times 10^5$ $M^{-1} \times sec^{-1}$, a $k_d$ for hTIGIT of about $5.9 \times 10^{-4}$ $sec^{-1}$, and a $K_D$ for hTIGIT of about $8.1 \times 10^{-10}$ M. In some embodiments, an ABP provided herein has a $k_a$ for hTIGIT of about $8.9 \times 10^5$ $M^{-1} \times sec^{-1}$, a $k_d$ for hTIGIT of about $3.8 \times 10^{-4}$ $sec^{-1}$, and a $K_D$ for hTIGIT of about $4.6 \times 10^{-10}$ M. In some embodiments, an ABP provided herein has a $k_a$ for hTIGIT of about $1.4 \times 10^6$ $M^{-1} \times sec^{-1}$, a $k_d$ for hTIGIT of about $5.0 \times 10^{-4}$ $sec^{-1}$, and a $K_D$ for hTIGIT of about $3.6 \times 10^{-10}$ M. In some embodiments, such $k_a$, $k_d$ and $K_D$ are determined according to the methods described, e.g., in Example 6 of U.S. Pat. No. 9,713,641.

In some embodiments, an ABP provided herein has a $k_a$ for hTIGIT of about $2.0 \times 10^6$ $M^{-1} \times sec^{-1}$, a $k_d$ for hTIGIT of about $3.8 \times 10^{-4}$ $sec^{-1}$, a $K_D$ for hTIGIT of about $2.4 \times 10^{-10}$ M, a $k_a$ for cTIGIT of about $7.9 \times 10^5$ $M^{-1} \times sec^{-1}$, a $k_a$ for cTIGIT of about $4.6 \times 10^{-3}$ $sec^{-1}$, a $K_D$ for cTIGIT of about $6.2 \times 10^{-9}$ M, and a $K_D$ for mTIGIT (SEQ ID NO: 3) of greater than about $7.0 \times 10^{-7}$ M. In some embodiments, such $k_a$, $k_a$ and $K_D$ are determined according to the methods described, e.g., in Example 6 of U.S. Pat. No. 9,713,641.

In some embodiments, $K_D$, $k_a$, and $k_a$ are determined using surface plasmon resonance (SPR). In some aspects, the SPR analysis utilizes a BIACORE® instrument. In some aspects, the antigen is immobilized on a carboxymethylated dextran biosensor chip (CM4 or CM5) and contacted with an ABP provided herein. Association and dissociation rate constants may be calculated using the BIAevaluation® software and a one-to-one Langmuir binding model. In some aspects, the assay is performed at 25° C. In some aspects, the assay is performed at 37° C.

In some embodiments, $K_D$, $k_a$, and $k_a$ are determined using biolayer interferometry (BLI). Any suitable BLI method may be used. In some aspects, the BLI analysis utilizes a FORTEBIO® instrument. In some aspects, an anti-human IgG Fc capture (AHC) biosensor is used to capture ABPs onto the surface of a sensor. Subsequently, association of the ABP and antigen is monitored by contacting the immobilized ABP with different concentrations of TIGIT. Dissociation of the antigen and ABP is then measured in a buffer without TIGIT. Association and dissociation rate constants are calculated using the kinetic modules of the FORTEBIO® Analysis Software. In some aspects, the assay is performed at 30° C.

In other embodiments, $K_D$ may be determined by a radiolabeled antigen-binding assay, as described in Chen et al. *J. Mol. Biol.*, 1999, 293:865-881, incorporated by reference in its entirety.

In other embodiments, $K_D$ may be determined by using MSD-SET, as described, e.g., in Example 4 of U.S. Pat. No. 9,713,641.

In some embodiments, an ABP provided herein has a n $EC_{50}$, as measured by IL-2 production in a human TIGIT Jurkat co-culture assay as described, e.g., in Example 7 of U.S. Pat. No. 9,713,641, of about 0.22 nM, about 0.31 nM, about 0.33 nM, about 0.34 nM, about 0.25 nM, about 0.24 nM, about 0.11 nM, about 0.06 nM, about 0.14 nM, about 0.16 nM, about 1.40 nM, about 0.71 nM, about 0.21 nM, about 1.11 nM, about 0.13 nM, about 0.20 nM, about 0.68 nM, or about 0.61 nM. In some embodiments, such $EC_{50}$ ranges from about 0.06 nM to about 1.40 nM. In some embodiments, such $EC_{50}$ is about 1.40 nM or less.

In some embodiments, an ABP provided herein has an $EC_{50}$, as measured by IL-2 production in a cynomolgus monkey TIGIT Jurkat co-culture assay of about 2.87 nM. In some embodiments, such $EC_{50}$ is about 2.87 nM or less. In some embodiments, the ratio of $EC_{50(cTIGIT)}:EC_{50(hTIGIT)}$ in such assay ranges from about 2.05 to about 47.8.

In some embodiments, an ABP provided herein has an $EC_{10}$, as measured by TNF production in PBMCs isolated from a human donor and treated as described, e.g., in Example 9 of U.S. Pat. No. 9,713,641, in a range of about 5.02 nM to about 18.86 nM. In some embodiments, such $EC_{10}$ is about 18.86 nM or less.

In some embodiments, an ABP provided herein has an $EC_{50}$, as measured by TNF production in PBMCs isolated from a human donor, in a range of about 12.60 nM to about 20.60 nM. In some embodiments, such $EC_{50}$ is about 20.60 nM or less.

In some embodiments, an ABP provided herein has an $EC_{90}$, as measured by TNF production in PBMCs isolated from a human donor, in a range of about 22.49 nM to about 31.59 nM. In some embodiments, such $EC_{90}$ is about 31.59 nM or less.

In some embodiments, an ABP provided herein has an $EC_{10}$ in a range of about 5.02 nM to about 18.86 nM, an $EC_{50}$ in a range of about 12.60 nM to about 20.60 nM, and $EC_{90}$ in a range of about 22.49 nM to about 31.59 nM, in each case as measured by TNF production in PBMCs isolated from a human donor.

In some embodiments, an ABP provided herein has an $EC_{10}$ of about 11.94 nM or less, an $EC_{50}$ of about 16.60 nM or less, and $EC_{90}$ of about 27.04 nM or less, in each case as measured by TNF production in PBMCs isolated from a human donor.

In some embodiments, an ABP provided herein has an $EC_{10}$ of about 18.86 nM or less, an $EC_{50}$ of about 20.06 nM or less, and $EC_{90}$ of about 31.59 nM or less, in each case as measured by TNF production in PBMCs isolated from a human donor.

In some embodiments, an ABP provided herein has an $EC_{10}$ of about 5.02 nM or less, an $EC_{50}$ of about 12.60 nM or less, and $EC_{90}$ of about 22.49 nM or less, in each case as measured by TNF production in PBMCs isolated from a human donor.

In some embodiments, an ABP provided herein has an $EC_{10}$, as measured by IFN-γ production in CD4+ T cells isolated from a human donor, in a range of about 0.37 nM to about 1.05 nM. In some embodiments, such $EC_{10}$ is about 1.05 nM or less.

In some embodiments, an ABP provided herein has an $EC_{50}$, as measured by IFN-γ production in CD4+ T cells isolated from a human donor, in a range of about 0.94 nM to about 1.12 nM. In some embodiments, such $EC_{50}$ is about 1.12 nM or less.

In some embodiments, an ABP provided herein has an $EC_{90}$, as measured by IFN-γ production in CD4+ T cells isolated from a human donor and treated as described in Example 9, in a range of about 1.04 nM to about 2.72 nM. In some embodiments, such $EC_{90}$ is about 2.72 nM or less.

In some embodiments, an ABP provided herein has an $EC_{10}$ in a range of about 0.37 nM to about 1.05 nM, an $EC_{50}$ in a range of about 0.94 nM to about 1.12 nM, and $EC_{90}$ in a range of about 1.04 nM to about 2.72 nM, in each case as measured by IFN-γ production in PBMCs isolated from a human donor.

In some embodiments, an ABP provided herein has an $EC_{10}$ of about 0.37 nM or less, an $EC_{50}$ of about 1.00 nM or less, and $EC_{90}$ of about 2.72 nM or less, in each case as measured by IFN-γ production in PBMCs isolated from a human donor.

In some embodiments, an ABP provided herein has an $EC_{50}$ of about 0.85 nM or less, an $EC_{50}$ of about 0.94 nM or less, and $EC_{90}$ of about 1.04 nM or less, in each case as measured by IFN-γ production in PBMCs isolated from a human donor.

In some embodiments, an ABP provided herein has an $EC_{10}$ of about 1.05 nM or less, an $EC_{50}$ of about 1.12 nM or less, and $EC_{90}$ of about 1.19 nM or less, in each case as measured by IFN-γ production in PBMCs isolated from a human donor.

In some embodiments, an ABP provided herein has an $EC_{50}$ of about 0.75 nM or less, an $EC_{50}$ of about 1.02 nM or less, and $EC_{90}$ of about 1.65 nM or less, in each case as measured by IFN-γ production in PBMCs isolated from a human donor.

In some embodiments, an ABP provided herein binds hTIGIT with a $K_D$ of about $5.24 \times 10^{-10}$ M (as determined by ForteBio), cTIGIT with a $K_D$ of about $2.64 \times 10^{-9}$ M (as determined by ForteBio), hTIGIT with a $K_D$ of about $5.40 \times 10^{-11}$ M (as determined by MSD-SET), and cTIGIT with a $K_D$ of about $3.20 \times 10^{-10}$ M (as determined by MSD-SET.

In some embodiments, an ABP provided herein binds hTIGIT with a $K_D$ of about $4.57 \times 10^{-10}$ M (as determined by ForteBio), cTIGIT with a $K_D$ of about $1.57 \times 10^{-9}$ M (as determined by ForteBio), hTIGIT with a $K_D$ of about $2.50 \times 10^{-11}$ M (as determined by MSD-SET), and cTIGIT with a $K_D$ of about $2.30 \times 10^{-10}$ M (as determined by MSD-SET).

In some embodiments, an ABP provided herein binds hTIGIT with a $K_D$ of about $3.32 \times 10^{-10}$ M (as determined by ForteBio), cTIGIT with a $K_D$ of about $8.02 \times 10^{-10}$ M (as determined by ForteBio), hTIGIT with a $K_D$ of about $8.10 \times 10^{-12}$ M (as determined by MSD-SET), and cTIGIT with a $K_D$ of about $3.50 \times 10^{-1}$ M (as determined by MSD-SET).

In some embodiments, an ABP provided herein binds hTIGIT with a $K_D$ of about $2.46 \times 10^{-10}$ M (as determined by ForteBio), cTIGIT with a $K_D$ of about $3.69 \times 10^{-10}$ M (as determined by ForteBio), hTIGIT with a $K_D$ of about $5.00 \times 10^{-12}$ M (as determined by MSD-SET), and cTIGIT with a $K_D$ of about $1.50 \times 10^{-11}$ M (as determined by MSD-SET).

In some embodiments, an ABP provided herein binds hTIGIT with a $K_D$ of about $1.96 \times 10^{-10}$ M (as determined by ForteBio), cTIGIT with a $K_D$ of about $8.98 \times 10^{-10}$ M (as determined by ForteBio), hTIGIT with a $K_D$ of about $4.90 \times 10^{-12}$ M (as determined by MSD-SET), and cTIGIT with a $K_D$ of about $4.60 \times 10^{-11}$ M (as determined by MSD-SET).

In some embodiments, an ABP provided herein binds hTIGIT with a $K_D$ of about $3.11 \times 10^{-9}$ M (as determined by ForteBio) and cTIGIT with a $K_D$ of about $1.75 \times 10^{-8}$ M (as determined by ForteBio.

In some embodiments, an ABP provided herein binds hTIGIT with a $K_D$ of about $2.54 \times 10^{-9}$ M, as determined by ForteBio.

In some embodiments, an ABP provided herein binds hTIGIT with a $K_D$ of about $3.13 \times 10^{-9}$ M (as determined by ForteBio) and cTIGIT with a $K_D$ of about $2.58 \times 10^{-8}$ M (as determined by ForteBio).

In some embodiments, an ABP provided herein binds hTIGIT with a $K_D$ of about $2.83 \times 10^{-9}$ M (as determined by ForteBio) and cTIGIT with a $K_D$ of about $9.35 \times 10^{-9}$ M (as determined by ForteBio).

In some embodiments, an ABP provided herein binds hTIGIT with a $K_D$ of about $1.71 \times 10^{-9}$ M (as determined by ForteBio), cTIGIT with a $K_D$ of about $6.55 \times 10^{-9}$ M (as determined by ForteBio), and hTIGIT with a $K_D$ of about $1.10 \times 10^{-10}$ M (as determined by MSD-SET.

In some embodiments, an ABP provided herein binds hTIGIT with a $K_D$ of about $2.47 \times 10^{-9}$ M (as determined by ForteBio), cTIGIT with a $K_D$ of about $8.14 \times 10^{-9}$ M (as determined by ForteBio), and hTIGIT with a $K_D$ of about $1.50\times10^{-10}$ M (as determined by MSD-SET).

In some embodiments, an ABP provided herein binds hTIGIT with a $K_D$ of about $2.35\times10^{-9}$ M (as determined by ForteBio), cTIGIT with a $K_D$ of about $6.57\times10^{-9}$ M (as determined by ForteBio), and hTIGIT with a $K_D$ of about $5.60\times10^{-11}$ M (as determined by MSD-SET).

In some embodiments, an ABP provided herein binds hTIGIT with a $K_D$ of about $1.44\times10^{-9}$ M (as determined by ForteBio) and hTIGIT with a $K_D$ of about $4.00\times10^{-10}$ M (as determined by MSD-SET).

In some embodiments, an ABP provided herein binds hTIGIT with a $K_D$ of about $1.23\times10^{-9}$ M (as determined by ForteBio) and hTIGIT with a $K_D$ of about $3.80\times10^{-10}$ M (as determined by MSD-SET).

In some embodiments, an ABP provided herein binds hTIGIT with a $K_D$ of about $5.26\times10^{-10}$ M (as determined by ForteBio), cTIGIT with a $K_D$ of about $7.94\times10^{-8}$ M (as determined by ForteBio), and hTIGIT with a $K_D$ of about $2.10\times10^{-10}$ M (as determined by MSD-SET).

In some embodiments, an ABP provided herein binds hTIGIT with a $K_D$ of about $3.78\times10^{-10}$ M (as determined by ForteBio), cTIGIT with a $K_D$ of about $7.04\times10^{-8}$ M (as determined by ForteBio), and hTIGIT with a $K_D$ of about $7.00\times10^{-11}$ M (as determined by MSD-SET).

In some embodiments, an ABP provided herein binds hTIGIT with a $K_D$ of about $4.29\times10^{-10}$ M (as determined by ForteBio), cTIGIT with a $K_D$ of about $1.10\times10^{-7}$ M (as determined by ForteBio), and hTIGIT with a $K_D$ of about $4.10\times10^{-11}$ M (as determined by MSD-SET)

In some embodiments, an ABP provided herein binds hTIGIT with a $K_D$ of about $4.48\times10^{-10}$ M (as determined by ForteBio) and cTIGIT with a $K_D$ of about $7.20\times10^{-8}$ M (as determined by ForteBio).

In some embodiments, an ABP provided herein binds hTIGIT with a $K_D$ of about $3.00\times10^{-11}$ M.

In some embodiments, an ABP provided herein binds hTIGIT with a $K_D$ of about $8.00\times10^{11}$ M In some embodiments, an ABP provided herein inhibits binding of PVR to TIGIT with an $IC_{50}$ of about 2.2 nM, about 2.3 nM, about 1.6 nM, about 1.9 nM, about 1.7 nM, about 3.2 nM, about 2.6 nM, about 2.9 nM, about 3.3 nM, about 2 nM, about 2.2 nM, about 2.1 nM, about 1.8 nM, about 6.4 nM, or about 1 nM. In some embodiments, such $IC_{50}$ ranges from about 1 nM to about 6.4 nM. In some embodiments, such $IC_{50}$ is about 6.4 nM or less. In some embodiments, such $IC_{50}$ is determined as described in Example 5 of U.S. Pat. No. 9,713,641.

In some embodiments, an ABP provided herein inhibits binding of PVRL2 to TIGIT with an $IC_{50}$ of about 1.4 nM, about 1.3 nM, about 1.2 nM, about 1.6 nM, about 2 nM, about 1.2 nM, about 1.1 nM, about 1 nM, about 1.8 nM, about 1.9 nM, about 2 nM, or about 0.8 nM. In some embodiments, such $IC_{50}$ ranges from about 0.8 nM to about 2 nM. In some embodiments, such $IC_{50}$ is about 2 nM or less.

In some embodiments, an ABP provided herein inhibits binding of PVR to TIGIT with an $IC_{50}$ of about 2.2 nM and inhibits binding of PVRL2 to TIGIT with an $IC_{50}$ of about 1.4 nM. In some embodiments, an ABP provided herein inhibits binding of PVR to TIGIT with an $IC_{50}$ of about 2.3 nM and inhibits binding of PVRL2 to TIGIT with an $IC_{50}$ of about 1.3 nM. In some embodiments, an ABP provided herein inhibits binding of PVR to TIGIT with an $IC_{50}$ of about 1.6 nM and inhibits binding of PVRL2 to TIGIT with an $IC_{50}$ of about 1.2 nM. In some embodiments, an ABP provided herein inhibits binding of PVR to TIGIT with an $IC_{50}$ of about 1.9 nM and inhibits binding of PVRL2 to TIGIT with an $IC_{50}$ of about 1.6 nM. In some embodiments, an ABP provided herein inhibits binding of PVR to TIGIT with an $IC_{50}$ of about 1.7 nM and inhibits binding of PVRL2 to TIGIT with an $IC_{50}$ of about 1.4 nM. In some embodiments, an ABP provided herein inhibits binding of PVR to TIGIT with an $IC_{50}$ of about 3.2 nM and inhibits binding of PVRL2 to TIGIT with an $IC_{50}$ of about 1.4 nM. In some embodiments, an ABP provided herein inhibits binding of PVR to TIGIT with an $IC_{50}$ of about 2.6 nM and inhibits binding of PVRL2 to TIGIT with an $IC_{50}$ of about 2 nM. In some embodiments, an ABP provided herein inhibits binding of PVR to TIGIT with an $IC_{50}$ of about 2.9 nM and inhibits binding of PVRL2 to TIGIT with an $IC_{50}$ of about 1.2 nM. In some embodiments, an ABP provided herein inhibits binding of PVR to TIGIT with an $IC_{50}$ of about 1.9 nM and inhibits binding of PVRL2 to TIGIT with an $IC_{50}$ of about 1.1 nM. In some embodiments, an ABP provided herein inhibits binding of PVR to TIGIT with an $IC_{50}$ of about 3.3 nM and inhibits binding of PVRL2 to TIGIT with an $IC_{50}$ of about 1 nM. In some embodiments, an ABP provided herein inhibits binding of PVR to TIGIT with an $IC_{50}$ of about 2 nM and inhibits binding of PVRL2 to TIGIT with an $IC_{50}$ of about 1.2 nM. In some embodiments, an ABP provided herein inhibits binding of PVR to TIGIT with an $IC_{50}$ of about 1.7 nM and inhibits binding of PVRL2 to TIGIT with an $IC_{50}$ of about 1.2 nM. In some embodiments, an ABP provided herein inhibits binding of PVR to TIGIT with an $IC_{50}$ of about 2.1 nM and inhibits binding of PVRL2 to TIGIT with an $IC_{50}$ of about 1.8 nM. In some embodiments, an ABP provided herein inhibits binding of PVR to TIGIT with an $IC_{50}$ of about 2.6 nM and inhibits binding of PVRL2 to TIGIT with an $IC_{50}$ of about 1.6 nM. In some embodiments, an ABP provided herein inhibits binding of PVR to TIGIT with an $IC_{50}$ of about 2.2 nM and inhibits binding of PVRL2 to TIGIT with an $IC_{50}$ of about 1.1 nM. In some embodiments, an ABP provided herein inhibits binding of PVR to TIGIT with an $IC_{50}$ of about 2.1 nM and inhibits binding of PVRL2 to TIGIT with an $IC_{50}$ of about 1.3 nM. In some embodiments, an ABP provided herein inhibits binding of PVR to TIGIT with an $IC_{50}$ of about 2.6 nM and inhibits binding of PVRL2 to TIGIT with an $IC_{50}$ of about 1.9 nM. In some embodiments, an ABP provided herein inhibits binding of PVR to TIGIT with an $IC_{50}$ of about 1.8 nM and inhibits binding of PVRL2 to TIGIT with an $IC_{50}$ of about 1.9 nM. In some embodiments, an ABP provided herein inhibits binding of PVR to TIGIT with an $IC_{50}$ of about 6.4 nM and inhibits binding of PVRL2 to TIGIT with an $IC_{50}$ of about 2 nM. In some embodiments, an ABP provided herein inhibits binding of PVR to TIGIT with an $IC_{50}$ of about 2.3 nM and inhibits binding of PVRL2 to TIGIT with an $IC_{50}$ of about 1.9 nM. In some embodiments, an ABP provided herein inhibits binding of PVR to TIGIT with an $IC_{50}$ of about 1 nM and inhibits binding of PVRL2 to TIGIT with an $IC_{50}$ of about 0.8 nM. In some embodiments, such $IC_{50}$ is about 2 nM or less.

2.5.1. Glycosylation Variants

In certain embodiments, an ABP provided herein may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to or from an ABP provided herein may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an ABP.

In some embodiments, an ABP provided herein comprises a glycosylation motif that is different from a naturally occurring ABP. Any suitable naturally occurring glycosylation motif can be modified in the ABPs provided herein. The structural and glycosylation properties of immunoglobulins, for example, are known in the art and summarized, for example, in Schroeder and Cavacini, *J. Allergy Clin. Immunol.*, 2010, 125:S41-52, incorporated by reference in its entirety.

In some embodiments, an ABP provided herein comprises an IgG1 Fc region with modification to the oligosaccharide attached to asparagine 297 (Asn 297). Naturally occurring IgG1 antibodies produced by mammalian cells typically comprise a branched, biantennary oligosaccharide that is generally attached by an N-linkage to Asn 297 of the $C_{H2}$ domain of the Fc region. See Wright et al., *TIBTECH*, 1997, 15:26-32, incorporated by reference in its entirety. The oligosaccharide attached to Asn 297 may include various carbohydrates such as mannose, N-acetyl glucosamine (GlcNAc), galactose, and sialic acid, as well as a fucose attached to a GlcNAc in the "stem" of the biantennary oligosaccharide structure.

In some embodiments, the oligosaccharide attached to Asn 297 is modified to create ABPs having altered ADCC. In some embodiments, the oligosaccharide is altered to improve ADCC. In some embodiments, the oligosaccharide is altered to reduce ADCC.

In some aspects, an ABP provided herein comprises an IgG1 domain with reduced fucose content at position Asn 297 compared to a naturally occurring IgG1 domain. Such Fc domains are known to have improved ADCC. See Shields et al., *J. Biol. Chem.*, 2002, 277:26733-26740, incorporated by reference in its entirety. In some aspects, such ABPs do not comprise any fucose at position Asn 297. The amount of fucose may be determined using any suitable method, for example as described in WO 2008/077546, incorporated by reference in its entirety.

In some embodiments, an ABP provided herein comprises a bisected oligosaccharide, such as a biantennary oligosaccharide attached to the Fc region of the ABP that is bisected by GlcNAc. Such ABP variants may have reduced fucosylation and/or improved ADCC function. Examples of such ABP variants are described, for example, in WO 2003/011878; U.S. Pat. No. 6,602,684; and U.S. Pat. Pub. No. 2005/0123546; each of which is incorporated by reference in its entirety.

Other illustrative glycosylation variants which may be incorporated into the ABPs provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., *J. Mol. Biol.*, 2004, 336:1239-1249; and Yamane-Ohnuki et al., *Biotech. Bioeng.*, 2004, 87: 614-622; each of which is incorporated by reference in its entirety.

In some embodiments, an ABP provided herein comprises an Fc region with at least one galactose residue in the oligosaccharide attached to the Fc region. Such ABP variants may have improved CDC function. Examples of such ABP variants are described, for example, in WO 1997/30087; WO 1998/58964; and WO 1999/22764; each of which his incorporated by reference in its entirety.

Examples of cell lines capable of producing defucosylated ABPs include Lec13 CHO cells, which are deficient in protein fucosylation (see Ripka et al., *Arch. Biochem. Biophys.*, 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., *Biotech. Bioeng.*, 2004, 87: 614-622; Kanda et al., *Biotechnol. Bioeng.*, 2006, 94:680-688; and WO 2003/085107; each of which is incorporated by reference in its entirety).

In some embodiments, an ABP provided herein is an aglycosylated ABP. An aglycosylated ABP can be produced using any method known in the art or described herein. In some aspects, an aglycosylated ABP is produced by modifying the ABP to remove all glycosylation sites. In some aspects, the glycosylation sites are removed only from the Fc region of the ABP. In some aspects, an aglycosylated ABP is produced by expressing the ABP in an organism that is not capable of glycosylation, such as *E. coli*, or by expressing the ABP in a cell-free reaction mixture.

In some embodiments, an ABP provided herein has a constant region with reduced effector function compared to a native IgG1 antibody. In some embodiments, the affinity of a constant region of an Fc region of an ABP provided herein for Fc receptor is less than the affinity of a native IgG1 constant region for such Fc receptor.

2.6. Fc Region Amino Acid Sequence Variants

In certain embodiments, an ABP provided herein comprises an Fc region with one or more amino acid substitutions, insertions, or deletions in comparison to a naturally occurring Fc region. In some aspects, such substitutions, insertions, or deletions yield ABPs with altered stability, glycosylation, or other characteristics. In some aspects, such substitutions, insertions, or deletions yield aglycosylated ABPs.

In some aspects, the Fc region of an ABP provided herein is modified to yield an ABP with altered affinity for an Fc receptor, or an ABP that is more immunologically inert. In some embodiments, the ABP variants provided herein possess some, but not all, effector functions. Such ABPs may be useful, for example, when the half-life of the ABP is important in vivo, but when certain effector functions (e.g., complement activation and ADCC) are unnecessary or deleterious.

In some embodiments, the Fc region of an ABP provided herein is a human IgG4 Fc region comprising one or more of the hinge stabilizing mutations S228P and L235E. See Aalberse et al., *Immunology*, 2002, 105:9-19, incorporated by reference in its entirety. In some embodiments, the IgG4 Fc region comprises one or more of the following mutations: E233P, F234V, and L235A. See Armour et al., *Mol. Immunol.*, 2003, 40:585-593, incorporated by reference in its entirety. In some embodiments, the IgG4 Fc region comprises a deletion at position G236.

In some embodiments, the Fc region of an ABP provided herein is a human IgG1 Fc region comprising one or more mutations to reduce Fc receptor binding. In some aspects, the one or more mutations are in residues selected from S228 (e.g., S228A), L234 (e.g., L234A), L235 (e.g., L235A), D265 (e.g., D265A), and N297 (e.g., N297A). In some aspects, the ABP comprises a PVA236 mutation. PVA236 means that the amino acid sequence ELLG, from amino acid position 233 to 236 of IgG1 or EFLG of IgG4, is replaced by PVA. See U.S. Pat. No. 9,150,641, incorporated by reference in its entirety.

In some embodiments, the Fc region of an ABP provided herein is modified as described in Armour et al., *Eur. J. Immunol.*, 1999, 29:2613-2624; WO 1999/058572; and/or U.K. Pat. App. No. 98099518; each of which is incorporated by reference in its entirety.

In some embodiments, the Fc region of an ABP provided herein is a human IgG2 Fc region comprising one or more of mutations A330S and P331S.

In some embodiments, the Fc region of an ABP provided herein has an amino acid substitution at one or more positions selected from 238, 265, 269, 270, 297, 327 and 329. See U.S. Pat. No. 6,737,056, incorporated by reference in its entirety. Such Fc mutants include Fc mutants with substitutions at two or more of amino acid positions 265, 269, 270, 297 and 327, including the so-called "DANA" Fc mutant with substitution of residues 265 and 297 with alanine. See U.S. Pat. No. 7,332,581, incorporated by reference in its entirety. In some embodiments, the ABP comprises an alanine at amino acid position 265. In some embodiments, the ABP comprises an alanine at amino acid position 297.

In certain embodiments, an ABP provided herein comprises an Fc region with one or more amino acid substitutions which improve ADCC, such as a substitution at one or more of positions 298, 333, and 334 of the Fc region. In some embodiments, an ABP provided herein comprises an Fc region with one or more amino acid substitutions at positions 239, 332, and 330, as described in Lazar et al., *Proc. Natl. Acad. Sci. USA*, 2006, 103:4005-4010, incorporated by reference in its entirety.

In some embodiments, an ABP provided herein comprises one or more alterations that improves or diminishes C1q binding and/or CDC. See U.S. Pat. No. 6,194,551; WO 99/51642; and Idusogie et al., *J. Immunol.*, 2000, 164:4178-4184; each of which is incorporated by reference in its entirety.

In some embodiments, an ABP provided herein comprises one or more alterations to increase half-life. ABPs with increased half-lives and improved binding to the neonatal Fc receptor (FcRn) are described, for example, in Hinton et al., *J. Immunol.*, 2006, 176:346-356; and U.S. Pat. Pub. No. 2005/0014934; each of which is incorporated by reference in its entirety. Such Fc variants include those with substitutions at one or more of Fc region residues: 238, 250, 256, 265, 272, 286, 303, 305, 307, 311, 312, 314, 317, 340, 356, 360, 362, 376, 378, 380, 382, 413, 424, 428, and 434 of an IgG.

In some embodiments, an ABP provided herein comprises one or more Fc region variants as described in U.S. Pat. Nos. 7,371,826 5,648,260, and 5,624,821; Duncan and Winter, *Nature*, 1988, 322:738-740; and WO 94/29351; each of which is incorporated by reference in its entirety.

2.7. Pyroglutamate

As is known in the art, both glutamate (E) and glutamine (Q) at the N-termini of recombinant proteins can cyclize spontaneously to form pyroglutamate (pE) in vitro and in vivo. See Liu et al., *J. Biol. Chem.*, 2011, 286:11211-11217, incorporated by reference in its entirety.

In some embodiments, provided herein are ABPs comprising a polypeptide sequence having a pE residue at the N-terminal position. In some embodiments, provided herein are ABPs comprising a polypeptide sequence in which the N-terminal residue has been converted from Q to pE. In some embodiments, provided herein are ABPs comprising a polypeptide sequence in which the N-terminal residue has been converted from E to pE.

In some embodiments, provided herein are ABPs comprising $V_H$ sequences having a pE residue at the N-terminal position. In some embodiments, provided herein are ABPs comprising a $V_H$ sequence in which the N-terminal residue has been converted from Q to pE. In some embodiments, provided herein is an ABP comprising a $V_H$ sequence selected from SEQ ID NOs: 4-24, wherein the N-terminal Q residue has been converted to pE. In some embodiments, provided herein is a composition comprising an ABP, wherein the ABP comprises a $V_H$ selected from SEQ ID NOs: 4-24, in which at least about 20%, at least about 40%, at least about 60%, at least about 80%, at least about 90%, at least about 95%, or at least about 99% of the N-terminal residues of such $V_H$ in such composition have been converted from Q to pE.

In some embodiments, provided herein are ABPs comprising $V_L$ sequences having a pE residue at the N-terminal position. In some embodiments, provided herein are ABPs comprising a $V_L$ sequence in which the N-terminal residue has been converted from E to pE. In some embodiments, provided herein is an ABP comprising a $V_L$ sequence selected from SEQ ID NOs: 25-28, wherein the N-terminal E residue has been converted to pE. In some embodiments, provided herein is a composition comprising an ABP, wherein the ABP comprises a $V_L$ selected from SEQ ID NOs: 25-28, in which at least about 20%, at least about 40%, at least about 60%, at least about 80%, at least about 90%, at least about 95%, or at least about 99% of the N-terminal residues of such $V_L$ in such composition have been converted from E to pE.

In some embodiments, provided herein are ABPs comprising heavy chain sequences having a pE residue at the N-terminal position. In some embodiments, provided herein are ABPs comprising a heavy chain sequence in which the N-terminal residue has been converted from Q to pE. In some embodiments, provided herein is an ABP comprising a heavy chain sequence selected from SEQ ID NOs: 79, 80, 82, 83, 84, 85, 86, 87, 88, 89, 90, 91, 93, 94, 95, 96, 97, 98, 99, 100, 101, 102, 103, 104, 105, 106, 108, 109, 110, 111, 112, 113, 114, 115, 116, 117, 118, 119, 121, 122, 123 or 124, wherein the N-terminal Q residue has been converted to pE. In some embodiments, provided herein is a composition comprising an ABP, wherein the ABP comprises a heavy chain selected from SEQ ID NOs: 79, 80, 82, 83, 84, 85, 86, 87, 88, 89, 90, 91, 93, 94, 95, 96, 97, 98, 99, 100, 101, 102, 103, 104, 105, 106, 108, 109, 110, 111, 112, 113, 114, 115, 116, 117, 118, 119, 121, 122, 123 or 124, in which at least about 20%, at least about 40%, at least about 60%, at least about 80%, at least about 90%, at least about 95%, or at least about 99% of the N-terminal residues of such heavy chain in such composition have been converted from Q to pE.

In some embodiments, provided herein are ABPs comprising light chain sequences having a pE residue at the N-terminal position. In some embodiments, provided herein are ABPs comprising a light chain sequence in which the N-terminal residue has been converted from E to pE. In some embodiments, provided herein is an ABP comprising a light chain sequence selected from SEQ ID NOs: 81, 92, 107 or 120, wherein the N-terminal E residue has been converted to pE. In some embodiments, provided herein is a composition comprising an ABP, wherein the ABP comprises a light chain selected from SEQ ID NOs: 81, 92, 107 or 120, in which at least about 20%, at least about 40%, at least about 60%, at least about 80%, at least about 90%, at least about 95%, or at least about 99% of the N-terminal residues of such light chain in such composition have been converted from E to pE.

2.8. Cysteine Engineered Antigen-Binding Protein Variants

In certain embodiments, provided herein are cysteine engineered ABPs, also known as "thioMAbs," in which one or more residues of the ABP are substituted with cysteine residues. In particular embodiments, the substituted residues occur at solvent accessible sites of the ABP. By substituting such residues with cysteine, reactive thiol groups are introduced at solvent accessible sites of the ABP and may be used to conjugate the ABP to other moieties, such as drug moieties or linker-drug moieties, for example, to create an immunoconjugate.

In certain embodiments, any one or more of the following residues may be substituted with cysteine: V205 of the light chain; A118 of the heavy chain Fc region; and S400 of the heavy chain Fc region. Cysteine engineered ABPs may be generated as described, for example, in U.S. Pat. No. 7,521,541, which is incorporated by reference in its entirety.

2.8.1. Immunoconjugates 2.8.1.1. Antigen-Binding Protein-Polymer Conjugates

In some embodiments, an ABP provided herein is derivatized by conjugation with a polymer. Any suitable polymer may be conjugated to the ABP.

In some embodiments, the polymer is a water-soluble polymer. Illustrative examples of water soluble polymers include polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)-co-polyethylene glycol, propropylene glycol homopolymers, polypropylene oxide/ethylene oxide co-polymers, polyoxyethylated polyols (e.g., glycerol), polyvinyl alcohol, and mixtures thereof. In some aspects, polyethylene glycol propionaldehyde may be useful for manufacturing purposes due to its stability in water.

The polymer may be of any molecular weight and may be branched or unbranched. The number of polymers attached to each ABP may vary, and if more than one polymer is attached, they may be the same polymer or different polymers. In general, the number and/or type of polymers used for derivatization can be determined based on considerations including the particular properties or functions of the ABP to be improved and the intended use of the ABP.

2.8.1.2. Antigen-Binding Protein-Drug Conjugates

In some embodiments, the ABPs provided herein are conjugated to one or more therapeutic agents. Any suitable therapeutic agent may be conjugated to the ABP. Exemplary therapeutic agents include cytokines, chemokines, and other agents that induce a desired T cell activity, such as OX40L, 4-1BBL, TNF-alpha (as used herein, "TNF"), IL-2, IL-15 fusion, CXCL9, CXCL10, IL-10 trap, IL-27 trap, and IL-35 trap. Cytokine traps and their use are known in the art and described, for example, in Economides et al., *Nature Medicine*, 2003, 9:47-52, incorporated by reference in its entirety.

3. Methods of Making TIGIT Antigen-Binding Proteins 3.1. TIGIT Antigen Preparation The TIGIT antigen used for isolation of the ABPs provided herein may be intact TIGIT or a fragment of TIGIT. The TIGIT antigen may be, for example, in the form of an isolated protein or a protein expressed on the surface of a cell.

In some embodiments, the TIGIT antigen is a non-naturally occurring variant of TIGIT, such as a TIGIT protein having an amino acid sequence or post-translational modification that does not occur in nature.

In some embodiments, the TIGIT antigen is truncated by removal of, for example, intracellular or membrane-spanning sequences, or signal sequences. In some embodiments, the TIGIT antigen is fused at its C-terminus to a human IgG1 Fc domain or a polyhistidine tag.

3.2. Methods of Making Monoclonal Antibodies

Monoclonal antibodies may be obtained, for example, using the hybridoma method first described by Kohler et al., *Nature*, 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage display or yeast-based presentation libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* 3$^{rd}$ ed. (1986) Academic Press, San Diego, Calif., incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.*, 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

3.3. Methods of Making Chimeric Antibodies

Illustrative methods of making chimeric antibodies are described, for example, in U.S. Pat. No. 4,816,567; and Morrison et al., *Proc. Natl. Acad. Sci. USA*, 1984, 81:6851-6855; each of which is incorporated by reference in its entirety. In some embodiments, a chimeric antibody is made by using recombinant techniques to combine a non-human variable region (e.g., a variable region derived from a mouse, rat, hamster, rabbit, or non-human primate, such as a monkey) with a human constant region.

3.4. Methods of Making Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. USA.*, 1998, 95:8910-8915; Steinberger et al., *J. Biol. Chem.*, 2000, 275:36073-36078; Queen et al., *Proc. Natl. Acad. Sci. USA.*, 1989, 86:10029-10033; and U.S. Pat. Nos. 5,585,089, 5,693,761, 5,693,762, and 6,180,370; each of which is incorporated by reference in its entirety.

3.5. Methods of Making Human Antibodies

Human antibodies can be generated by a variety of techniques known in the art, for example by using transgenic animals (e.g., humanized mice). See, e.g., Jakobovits et al., *Proc. Natl. Acad. Sci. USA.*, 1993, 90:2551; Jakobovits et al., *Nature*, 1993, 362:255-258; Bruggermann et al., *Year in Immuno.*, 1993, 7:33; and U.S. Pat. Nos. 5,591,669, 5,589,369 and 5,545,807; each of which is incorporated by reference in its entirety. Human antibodies can also be derived from phage-display libraries (see e.g., Hoogenboom et al., *J. Mol. Biol.*, 1991, 227:381-388; Marks et al., *J. Mol. Biol.*, 1991, 222:581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based presentation libraries (see e.g., U.S. Pat. No. 8,691,730, incorporated by reference in its entirety).

3.6. Methods of Making Antibody Fragments

The antibody fragments provided herein may be made by any suitable method, including the illustrative methods described herein or those known in the art. Suitable methods include recombinant techniques and proteolytic digestion of whole antibodies. Illustrative methods of making antibody fragments are described, for example, in Hudson et al., *Nat. Med.*, 2003, 9:129-134, incorporated by reference in its entirety. Methods of making scFv antibodies are described, for example, in Plückthun, in *The Pharmacology of Monoclonal Antibodies*, vol. 113, Rosenburg and Moore eds., Springer-Verlag, New York, pp. 269-315 (1994); WO 93/16185; and U.S. Pat. Nos. 5,571,894 and 5,587,458; each of which is incorporated by reference in its entirety.

3.7. Methods of Making Alternative Scaffolds

The alternative scaffolds provided herein may be made by any suitable method, including the illustrative methods described herein or those known in the art. For example, methods of preparing Adnectins™ are described in Emanuel et al., *mAbs*, 2011, 3:38-48, incorporated by reference in its entirety. Methods of preparing iMabs are described in U.S. Pat. Pub. No. 2003/0215914, incorporated by reference in its entirety. Methods of preparing Anticalins® are described in Vogt and Skerra, *Chem. Biochem.*, 2004, 5:191-199, incorporated by reference in its entirety. Methods of preparing Kunitz domains are described in Wagner et al., *Biochem. & Biophys. Res. Comm.*, 1992, 186:118-1145, incorporated by reference in its entirety. Methods of preparing thioredoxin peptide aptamers are provided in Geyer and Brent, *Meth. Enzymol.*, 2000, 328:171-208, incorporated by reference in its entirety. Methods of preparing Affibodies are provided in Fernandez, *Curr. Opinion in Biotech.*, 2004, 15:364-373, incorporated by reference in its entirety. Methods of preparing DARPins are provided in Zahnd et al., *J. Mol. Biol.*, 2007, 369:1015-1028, incorporated by reference in its entirety. Methods of preparing Affilins are provided in Ebersbach et al., *J. Mol. Biol.*, 2007, 372:172-185, incorporated by reference in its entirety. Methods of preparing Tetranectins are provided in Graversen et al., *J. Biol. Chem.*, 2000, 275:37390-37396, incorporated by reference in its entirety. Methods of preparing Avimers are provided in Silverman et al., *Nature Biotech.*, 2005, 23:1556-1561, incorporated by reference in its entirety. Methods of preparing Fynomers are provided in Silacci et al., *J. Biol. Chem.*, 2014, 289:14392-14398, incorporated by reference in its entirety.

Further information on alternative scaffolds is provided in Binz et al., *Nat. Biotechnol.*, 2005 23:1257-1268; and Skerra, *Current Opin. in Biotech.*, 2007 18:295-304, each of which is incorporated by reference in its entirety.

3.8. Methods of Making Variants

In some embodiments, an ABP provided herein is an affinity matured variant of a parent ABP, which may be generated, for example, using phage display-based affinity maturation techniques. Briefly, one or more CDR residues may be mutated and the variant ABPs, or portions thereof, displayed on phage and screened for affinity. Such alterations may be made in CDR "hotspots," or residues encoded by codons that undergo mutation at high frequency during the somatic maturation process (see Chowdhury, *Methods Mol. Biol.*, 2008, 207:179-196, incorporated by reference in its entirety), and/or residues that contact the antigen. Alternatively, affinity matured variants of a parent ABP may be generated or otherwise selected for using a yeast-based presentation platform (see, e.g., WO2009/036379, WO 2010/105256, WO 2012/009568, and Xu et al., *Protein Eng Des Sel.*, Vol. 26(10), pp. 663-670 (2013)).

Any suitable method can be used to introduce variability into a polynucleotide sequence(s) encoding an ABP, including error-prone PCR, chain shuffling, and oligonucleotide-directed mutagenesis such as trinucleotide-directed mutagenesis (TRIM). In some aspects, several CDR residues (e.g., 4-6 residues at a time) are randomized. CDR residues involved in antigen binding may be specifically identified, for example, using alanine scanning mutagenesis or modeling. CDR-H3 and CDR-L3 in particular are often targeted for mutation.

The introduction of diversity into the variable regions and/or CDRs can be used to produce a secondary library. The secondary library is then screened to identify ABP variants with improved affinity. Affinity maturation by constructing and reselecting from secondary libraries has been described, for example, in Hoogenboom et al., *Methods in Molecular Biology*, 2001, 178:1-37, incorporated by reference in its entirety.

3.9. Vectors, Host Cells, and Recombinant Methods

Also provided are isolated nucleic acids encoding TIGIT ABPs, vectors comprising the nucleic acids, and host cells comprising the vectors and nucleic acids, as well as recombinant techniques for the production of the ABPs.

For recombinant production of an ABP, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting, and any suitable host cell may be used to produce the ABPs provided herein.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella, Bacilli* (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are also suitable.

In addition to prokaryotes, eukaryotic microbes such as filamentous fungi or yeast are also suitable cloning or expression hosts for TIGIT ABP-encoding vectors. *Saccharomyces cerevisiae*, or common baker's yeast, is a commonly used lower eukaryotic host microorganism. However, a number of other genera, species, and strains are available and useful, such as *Schizosaccharomyces pombe, Kluyveromyces* (*K. lactis, K. fragilis, K. bulgaricus K. wickeramii, K. waltii, K. drosophilarum, K. thermotolerans*, and *K. marxianus*), *Yarrowia, Pichia pastoris, Candida* (*C. albicans*), *Trichoderma reesia, Neurospora crassa, Schwanniomyces* (*S. occidentalis*), and filamentous fungi such as, for example *Penicillium, Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the TIGIT ABP of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44; Barnes et al., *Anal. Biochem.*, 1980, 102:255; and U.S. Pat. Nos. 4,767,704, 4,657,866, 4,927,762, 4,560,655, and 5,122,469; or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the ABP can be produced intracellularly, in the periplasmic space, or directly secreted into the medium. If the ABP is produced intracellularly, as a first step, the particulate debris, either host cells or lysed fragments, is removed, for example, by centrifugation or ultrafiltration. For example, Carter et al. (*Bio/Technology*, 1992, 10:163-167, incorporated by reference in its entirety) describes a procedure for isolating ABPs which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the ABP is produced in a cell-free system. In some aspects, the cell-free system is an in vitro transcription and translation system as described in Yin et al., *mAbs*, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the ABP may be useful, for example, where the ABP accumulates in a cell as an insoluble aggregate, or where yields from periplasmic expression are low.

Where the ABP is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The ABP composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the ABP. Protein A can be used to purify ABPs that comprise human γ1, γ2, or γ4 heavy chains (Lindmark et al., *J. Immunol. Meth.*, 1983, 62:1-13, incorporated by reference in its entirety). Protein G is useful for all mouse isotypes and for human γ3 (Guss et al., *EMBO J.*, 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the ABP comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the ABP of interest and contaminants may be subjected to low pH hydrophobic interaction chromatography using an elution buffer at a pH between about 2.5 to about 4.5, generally performed at low salt concentrations (e.g., from about 0 to about 0.25 M salt).

4. Assays

A variety of assays known in the art may be used to identify and characterize the TIGIT ABPs provided herein.

4.1. Binding, Competition, and Epitope Mapping Assays

Specific antigen-binding activity of the ABPs provided herein may be evaluated by any suitable method, including using SPR, BLI, RIA and MSD-SET, as described elsewhere in this disclosure. Additionally, antigen-binding activity may be evaluated by ELISA assays and western blot assays.

Assays for measuring competition between two ABPs, or an ABP and another molecule (e.g., one or more ligands of TIGIT) are described elsewhere in this disclosure and, for example, in Harlow and Lane, *Antibodies: A Laboratory Manual* ch. 14, 1988, Cold Spring Harbor Laboratory, Cold Spring Harbor, N.Y., incorporated by reference in its entirety.

Assays for mapping the epitopes to which the ABPs provided herein bind are described, for example, in Morris "Epitope Mapping Protocols," in *Methods in Molecular Biology* vol. 66, 1996, Humana Press, Totowa, N.J., incorporated by reference in its entirety. In some embodiments, the epitope is determined by peptide competition. In some embodiments, the epitope is determined by mass spectrometry. In some embodiments, the epitope is determined by crystallography.

In some embodiments, "alanine scanning" or "alanine mapping" is used to map epitopes of a target protein and/or paratopes of an antibody. Alanine scanning is used to determine the contribution of a specific residue to the stability or function of a given protein. See, e.g., Weiss et al., *Proc Natl Acad Sci* 2000 Aug. 1; 97(16): 8950-8954.

4.2. TIGIT Antagonism Assays

In some embodiments, the ABPs provided herein are screened to identify or characterize ABPs with antagonistic activity against TIGIT. Any suitable assay may be used to identify or characterize such ABPs. In some aspects, the assay measures the amount of a cytokine secreted by an effector T cell after contacting the effector T cell with an ABP provided herein. In some aspects, the cytokine is selected from IL-2, IL-6, LT-α, TNF, GM-CSF, IFNγ, and combinations thereof. In some aspects, the cytokine is selected from sCD40L, VEGF, TGF-α, RANTES, PDGF-AB/BB, PDGF-AA, MIP-1β, MIP-1α, MDC (CCL22), MCP-3, MCP-1, IP-10, IL-17A, IL-2Rα, IL-15, IL-13, IL-12 (p70), IL-12 (p40), IL-10, IL-9, IL-8, IL-7, IL-5, IL-4, IL-3, IL-2, IL-2Rα, IL-1RA, IL-1β, IL-1α, IFNγ, IFNα2, GRO, GM-CSF, G-CSF, fractalkine, Flt-3 ligand, FGF-2, eotaxin, EGF, and combinations thereof.

In some embodiments, the effector cells are co-stimulated with an agonist of CD3, to promote the secretion of cytokines by the effector cell. In some aspects, the CD3 agonist is provided at a submaximal level.

In some aspects, such assays may measure the proliferation of an effector T cell after contacting the effector T cell with an ABP provided herein. In some aspects, proliferation of the effector T cell is measured by dilution of a dye (e.g., carboxyfluorescein diacetate succinimidyl ester; CFSE), by tritiated thymidine uptake, by luminescent cell viability assays, or by other assays known in the art.

In some aspects, such assays may measure the differentiation, cytokine production, viability (e.g., survival), proliferation, or suppressive activity of a regulatory T cell after contacting the regulatory T cell with an ABP provided herein.

In some aspects, such assays may measure the cytotoxic activity of an NK cell after contacting the NK cell with an ABP provided herein. In some aspects, the cytotoxic activity of the NK cell is measured using a cytotoxicity assay that quantifies NK-mediated killing of target cells (e.g., a K562 cell line). See Jang et al., *Ann. Clin. Lab. Sci.*, 2012, 42:42-49, incorporated by reference in its entirety.

In some aspects, such assays may measure the amount of granzyme B. In some aspects, such assays may measure the amount of perforin.

4.3. Assays for Effector Functions

Effector function following treatment with the ABPs provided herein may be evaluated using a variety of in vitro and in vivo assays known in the art, including those described in Ravetch and Kinet, *Annu. Rev. Immunol.*, 1991, 9:457-492; U.S. Pat. Nos. 5,500,362, 5,821,337; Hellstrom et al., *Proc. Nat'l Acad. Sci. USA*, 1986, 83:7059-7063; Hellstrom et al., *Proc. Nat'l Acad. Sci. USA*, 1985, 82:1499-1502; Bruggemann et al., *J. Exp. Med.*, 1987, 166:1351-1361; Clynes et al., *Proc. Nat'l Acad. Sci. USA*, 1998, 95:652-656; WO 2006/029879; WO 2005/100402; Gazzano-Santoro et al., *J. Immunol. Methods*, 1996, 202:163-171; Cragg et al., *Blood*, 2003, 101:1045-1052; Cragg et al. *Blood*, 2004, 103:2738-2743; and Petkova et al., *Int'l. Immunol.*, 2006, 18:1759-1769; each of which is incorporated by reference in its entirety.

5. Pharmaceutical Compositions

The ABPs provided herein can be formulated in any appropriate pharmaceutical composition and administered by any suitable route of administration. Suitable routes of administration include, but are not limited to, the intraarterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, propylene glycol, and combinations thereof.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, monosodium glutamate, and combinations thereof.

In some embodiments, the pharmaceutical composition comprises a carrier or filler. Illustrative examples of carriers or fillers include lactose, maltodextrin, mannitol, sorbitol, chitosan, stearic acid, xanthan gum, guar gum, and combinations thereof.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, vitamin E polyethylene(glycol) succinate, and combinations thereof.

In some embodiments, the pharmaceutical composition comprises an anti-caking agent. Illustrative examples of anti-caking agents include calcium phosphate (tribasic), hydroxymethyl cellulose, hydroxypropyl cellulose, magnesium oxide, and combinations thereof.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, sugars, and combinations thereof. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an ABP, since water can facilitate the degradation of some ABPs.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

5.1. Parenteral Dosage Forms

In certain embodiments, the ABPs provided herein are formulated as parenteral dosage forms. Parenteral dosage forms can be administered to subjects by various routes including, but not limited to, subcutaneous, intravenous (including infusions and bolus injections), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry (e.g., lyophilized) products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the ABPs disclosed herein can also be incorporated into the parenteral dosage forms.

In some embodiments, the parenteral dosage form is lyophilized. Exemplary lyophilized formulations are described, for example, in U.S. Pat. Nos. 6,267,958 and 6,171,586; and WO 2006/044908; each of which is incorporated by reference in its entirety.

6. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic ABPs.

The amount of the ABP or composition which will be effective in the prevention or treatment of a disorder or one or more symptoms thereof will vary with the nature and severity of the disease or condition, and the route by which the ABP is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the ABP per kilogram of subject or sample weight (e.g., about 10 micrograms per kilogram to about 50 milligrams per kilogram, about 100 micrograms per kilogram to about 25 milligrams per kilogram, or about 100 micrograms per kilogram to about 10 milligrams per kilogram). In certain embodiment, the dosage of the ABP provided herein, based on weight of the ABP, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. It may be necessary to use dosages of the ABP outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the ABPs provided herein are also encompassed by the dosage amounts and dose frequency schedules provided herein. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an ABP or composition provided herein followed by one or more maintenance doses.

In certain embodiments, a dose of an ABP or composition provided herein can be administered to achieve a steady-state concentration of the ABP in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months.

As discussed in more detail elsewhere in this disclosure, an ABP provided herein may optionally be administered with one or more additional agents useful to prevent or treat a disease or disorder. The effective amount of such additional agents may depend on the amount of ABP present in the formulation, the type of disorder or treatment, and the other factors known in the art or described herein.

7. Therapeutic Applications

For therapeutic applications, the ABPs of the invention are administered to a mammal, generally a human, in a pharmaceutically acceptable dosage form such as those known in the art and those discussed above. For example, the ABPs of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The ABPs also are suitably administered by peritumoral, intralesional, or perilesional routes, to exert local as well as systemic therapeutic effects. The intraperitoneal route may be particularly useful, for example, in the treatment of ovarian tumors.

The ABPs provided herein may be useful for the treatment of any disease or condition involving TIGIT. In some embodiments, the disease or condition is a disease or condition that can benefit from treatment with an anti-TIGIT ABP. In some embodiments, the disease or condition is a tumor. In some embodiments, the disease or condition is a cell proliferative disorder. In some embodiments, the disease or condition is a cancer. In some embodiments, the disease or condition is a viral infection.

In some embodiments, the ABPs provided herein are provided for use as a medicament. In some embodiments, the ABPs provided herein are provided for use in the manufacture or preparation of a medicament. In some embodiments, the medicament is for the treatment of a disease or condition that can benefit from an anti-TIGIT ABP. In some embodiments, the disease or condition is a tumor. In some embodiments, the disease or condition is a cell proliferative disorder. In some embodiments, the disease or condition is a cancer. In some embodiments, the disease or condition is a viral infection.

In some embodiments, provided herein is a method of treating a disease or condition in a subject in need thereof by administering an effective amount of an ABP provided herein to the subject. In some aspects, the disease or condition is a cancer. In some aspects, the disease or condition is a viral infection.

Any suitable cancer may be treated with the ABPs provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

Any suitable virus may be treated with the ABPs provided herein. Illustrative suitable viruses include, for example, adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, cowpox virus, Coxsackievirus, Crimean-Congo hemorrhagic fever virus, Dengue virus, Dhori virus, Dugbe virus, Duvenhage virus, eastern equine encephalitis virus, ebolavirus, echovirus, encephalomyocarditis virus, Epstein-Barr virus, European bat lyssavirus, GB virus C/Hepatitis G virus, Hantaan virus, Hendra virus, hepatitis A virus, hepatitis B virus, hepatitis C virus, hepatitis E virus, hepatitis delta virus, horsepox virus, human adenovirus, human astrovirus, human coronavirus, human cytomegalovirus, human enterovirus, human herpesvirus 1, human herpesvirus 2, human herpesvirus 6, human herpesvirus 7, human herpesvirus 8, human immunodeficiency virus, human papillomavirus 1, human papillomavirus 2, human papillomavirus, human parainfluenza, human parvovirus B19, human respiratory syncytial virus, human rhinovirus, human SARS coronavirus, human spumaretrovirus, human T-lymphotropic virus, human torovirus, influenza A virus, influenza B virus, influenza C virus, Isfahan virus, JC polyomavirus, Japanese encephalitis virus, Junin arenavirus, KI polyomavirus, Kunjin virus, Lagos bat virus, Lake Victoria marburgvirus, Langat virus, Lassa virus, Lordsdale virus, Louping ill virus, lymphocytic choriomeningitis virus, Machupo virus, Mayaro virus, MERS coronavirus, measles virus, Mengo encephalomyocarditis virus, Merkel cell polyomavirus, Mokola virus, molluscum contagiosum virus, monkeypox virus, mumps virus, Murray valley encephalitis virus, New York virus, Nipah virus, Norwalk virus, O'nyong-nyong virus, Orf virus, Oropouche virus, Pichinde virus, poliovirus, Punta toro phlebovirus, Puumala virus, rabies virus, Rift Valley fever virus, Rosavirus A, Ross River virus, rotavirus A, rotavirus B, rotavirus C, rubella virus, Sagiyama virus, salivirus A, sandfly fever Sicilian virus, Sapporo virus, Semliki Forest virus, Seoul virus, simian foamy virus, simian virus 5, Sindbis virus, Southampton virus, St. Louis encephalitis virus, tick-borne powassan virus, torque teno virus, Toscana virus, Uukuniemi virus, vaccinia virus, varicella-zoster virus, variola virus, Venezuelan equine encephalitis virus, vesicular stomatitis virus, western equine encephalitis virus, WU polyomavirus, West Nile virus, Yaba monkey tumor virus, Yaba-like disease virus, yellow fever virus, and Zika virus.

In some embodiments, provided herein is a method of antagonizing TIGIT in a target cell of a subject in need thereof by administering an effective amount of an ABP provided herein to the subject. In some aspects, antagonism of TIGIT by an ABP provided herein results in increased secretion of IL-2, LT-α, IL-6, TNF, GM-CSF, IFNγ or combinations thereof by a target cell.

In some embodiments, provided herein is a method of increasing the proliferation, survival, and/or function of an effector T cell in a subject in need thereof by administering an effective amount of an ABP provided herein to the subject. In some aspects the effector T cell is a CD4+ effector T cell. In some aspects, the effector T cell is a CD8+ effector T cell.

In some embodiments, provided herein is a method of abrogating suppression of an effector T cell by a regulatory T cell in a subject in need thereof by administering an effective amount of an ABP provided herein to the subject. In some aspects, the regulatory T cell is a CD4+CD25+ Foxp3+ regulator T cell. In some aspects, the regulatory T cell is a CD8+CD25+ regulatory T cell.

In some embodiments, provided herein is a method of increasing the activity of a natural killer (NK) or natural killer T (NKT) cell in a subject in need thereof by administering an effective amount of an ABP provided herein to the subject.

In some embodiments, provided herein is a method of enhancing an immune response in a subject in need thereof by administering an effective amount of an ABP provided herein to the subject.

In some embodiments, provided herein is a method delaying the onset of a tumor in a subject in need thereof by administering an effective amount of an ABP provided herein to the subject.

In some embodiments, provided herein is a method preventing the onset of a tumor in a subject in need thereof by administering an effective amount of an ABP provided herein to the subject.

In some embodiments, provided herein is a method of delaying the onset of a cancer in a subject in need thereof by administering an effective amount of an ABP provided herein to the subject.

In some embodiments, provided herein is a method of preventing the onset of a cancer in a subject in need thereof by administering an effective amount of an ABP provided herein to the subject.

In some embodiments, provided herein is a method of reducing the size of a tumor in a subject in need thereof by administering an effective amount of an ABP provided herein to the subject.

In some embodiments, provided herein is a method of reducing the number of metastases in a subject in need thereof by administering an effective amount of an ABP provided herein to the subject.

In some embodiments, provided herein is a method of delaying the onset of a viral infection in a subject in need thereof by administering an effective amount of an ABP provided herein to the subject.

In some embodiments, provided herein is a method of preventing the onset of a viral infection in a subject in need thereof by administering an effective amount of an ABP provided herein to the subject.

In some embodiments, provided herein is a method of reducing viral titer a subject in need thereof by administering an effective amount of an ABP provided herein to the subject.

In some embodiments, provided herein is a method of eliminating a virus from subject in need thereof by administering an effective amount of an ABP provided herein to the subject.

In some embodiments, provided herein is a method for extending the period of overall survival, median survival time, or progression-free survival in a subject in need thereof by administering an effective amount of an ABP provided herein to the subject.

In some embodiments, provided herein is a method for treating a subject who has become resistant to a standard of care therapeutic by administering an effective amount of an ABP provided herein to the subject. In some embodiments, the standard-of-care therapeutic to which the subject has become resistant is a PD-1 inhibitor. In other embodiments, the standard-of-care therapeutic to which the subject has become resistant is a PD-L1 inhibitor. In other embodiments, the standard-of-care therapeutic to which the subject has become resistant is a CTLA-4 inhibitor.

8. Combination Therapies

In some embodiments, an ABP provided herein is administered with at least one additional therapeutic agent. Any suitable additional therapeutic agent may be administered with an ABP provided herein. In some aspects, the additional therapeutic agent is selected from radiation, a cytotoxic agent, a chemotherapeutic agent, a cytostatic agent, an anti-hormonal agent, an EGFR inhibitor, an immunostimulatory agent, an anti-angiogenic agent, and combinations thereof.

In some embodiments, an ABP provided herein is administered after surgical resection of a tumor.

In some embodiments, the additional therapeutic agent comprises an epigenetic modifier. Exemplary epigenetic modifiers include DNA methyltransferase (DNMT) inhibitors such as 5-aza-2'-deoxycytidine or 5-azacytidine, which have been approved in myelodysplastic syndrome (MDS) and acute myelogenous leukemia (AML), and histone deacetylase inhibitors (HDIs) including vorinostat, romidepsin, panobinostat, belinostat, and entinostat, which have been shown to be active in cutaneous and peripheral T-cell lymphoma. In some embodiments the at least one additional therapeutic agent is an epigenetic modifier combined with an inhibitor of PD-1 or PD-L1.

In some embodiments, the additional therapeutic agent comprises an immunostimulatory agent.

In some embodiments, the immunostimulatory agent is an agent that blocks signaling of an inhibitory receptor of an immune cell, or a ligand thereof. In some aspects, the inhibitory receptor or ligand is selected from cytotoxic T-lymphocyte-associated protein 4 (CTLA-4, also known as CD152), programmed cell death protein 1 (also PD-1 or CD279), programmed death ligand 1 (also PD-L1 or CD274), transforming growth factor beta (TGFβ), lymphocyte-activation gene 3 (LAG-3, also CD223), Tim-3 (hepatitis A virus cellular receptor 2 or HAVCR2 or CD366), neuritin, B- and T-lymphocyte attenuator (also BTLA or CD272), killer cell immunoglobulin-like receptors (KIRs), and combinations thereof. In some aspects, the agent is selected from an anti-PD-1 antibody (e.g., pembrolizumab or nivolumab), and anti-PD-L1 antibody (e.g., atezolizumab), an anti-CTLA-4 antibody (e.g., ipilimumab), an anti-TIM3 antibody, carcinoembryonic antigen-related cell adhesion molecule 1 (CECAM-1, also CD66a) and 5 (CEACAM-5, also CD66e), vset immunoregulatory receptor (also VISR or VISTA), leukocyte-associated immunoglobulin-like receptor 1 (also LAIR1 or CD305), CD160, natural killer cell receptor 2B4 (also CD244 or SLAMF4), and combinations thereof. In some aspects, the agent is pembrolizumab. In some aspects, the agent is nivolumab. In some aspects, the agent is atezolizumab.

In some embodiments, the additional therapeutic agent is an agent that inhibits the interaction between PD-1 and PD-L1. In some aspects, the additional therapeutic agent that inhibits the interaction between PD-1 and PD-L1 is selected from an antibody, a peptidomimetic and a small molecule. In some aspects, the additional therapeutic agent that inhibits the interaction between PD-1 and PD-L1 is selected from pembrolizumab (KEYTRUDA), nivolumab (OPDIVO), atezolizumab, avelumab, pidilizumab, durvalumab, BMS-936559, sulfamonomethoxine 1, and sulfamethizole 2. In some embodiments, the additional therapeutic agent that inhibits the interaction between PD-1 and PD-L1 is any therapeutic known in the art to have such activity, for example as described in Weinmann et al., *Chem Med Chem*, 2016, 14:1576 (DOI: 10.1002/cmdc.201500566), incorporated by reference in its entirety. In some embodiments, the agent that inhibits the interaction between PD-1 and PD-L1 is formulated in the same pharmaceutical composition an ABP provided herein. In some embodiments, the agent that inhibits the interaction between PD-1 and PD-L1 is formulated in a different pharmaceutical composition from an ABP provided herein. In some embodiments, the agent that inhibits the interaction between PD-1 and PD-L1 is administered prior to administration of an ABP provided herein. In some embodiments, the agent that inhibits the interaction between PD-1 and PD-L1 is administered after administration of an ABP provided herein. In some embodiments, the agent that inhibits the interaction between PD-1 and PD-L1 is administered contemporaneously with an ABP provided herein, but the agent and ABP are administered in separate pharmaceutical compositions.

In some embodiments, the immunostimulatory agent is an agonist of a co-stimulatory receptor of an immune cell. In some aspects, the co-stimulatory receptor is selected from GITR, OX40, ICOS, LAG-2, CD27, CD28, 4-1BB, CD40, STING, a toll-like receptor, RIG-1, and a NOD-like receptor. In some embodiments, the agonist is an antibody.

In some embodiments, the immunostimulatory agent modulates the activity of arginase, indoleamine-2 3-dioxygenase, or the adenosine A2A receptor.

In some embodiments, the immunostimulatory agent is a cytokine. In some aspects, the cytokine is selected from IL-2, IL-5, IL-7, IL-12, IL-15, IL-21, and combinations thereof.

In some embodiments, the immunostimulatory agent is an oncolytic virus. In some aspects, the oncolytic virus is selected from a herpes simplex virus, a vesicular stomatitis virus, an adenovirus, a Newcastle disease virus, a vaccinia virus, and a maraba virus.

In some embodiments, the immunostimulatory agent is a T cell with a chimeric antigen receptor (CAR-T cell). In some embodiments, the immunostimulatory agent is a bi- or multi-specific T cell directed antibody. In some embodiments, the immunostimulatory agent is an anti-TGF-B antibody. In some embodiments, the immunostimulatory agent is a TGF-B trap.

In some embodiments, the additional therapeutic agent is a vaccine to a tumor antigen. Any suitable antigen may be targeted by the vaccine, provided that it is present in a tumor treated by the methods provided herein. In some aspects, the tumor antigen is a tumor antigen that is overexpressed in comparison its expression levels in normal tissue. In some aspects, the tumor antigen is selected from cancer testis antigen, differentiation antigen, NY-ESO-1, MAGE-A1, MART, and combinations thereof.

Further examples of additional therapeutic agents include a taxane (e.g., paclitaxel or docetaxel); a platinum agent (e.g., carboplatin, oxaliplatin, and/or cisplatin); a topoisomerase inhibitor (e.g., irinotecan, topotecan, etoposide, and/or mitoxantrone); folinic acid (e.g., leucovorin); or a nucleoside metabolic inhibitor (e.g., fluorouracil, capecitabine, and/or gemcitabine). In some embodiments, the additional therapeutic agent is folinic acid, 5-fluorouracil, and/or oxaliplatin. In some embodiments, the additional therapeutic agent is 5-fluorouracil and irinotecan. In some embodiments, the additional therapeutic agent is a taxane and a platinum agent. In some embodiments, the additional therapeutic agent is paclitaxel and carboplatin. In some embodiments, the additional therapeutic agent is pemetrexate. In some embodiments, the additional therapeutic agent is a targeted therapeutic such as an EGFR, RAF or MEK-targeted agent.

The additional therapeutic agent may be administered by any suitable means. In some embodiments, an ABP provided herein and the additional therapeutic agent are included in the same pharmaceutical composition. In some embodiments, an ABP provided herein and the additional therapeutic agent are included in different pharmaceutical compositions.

In embodiments where an ABP provided herein and the additional therapeutic agent are included in different pharmaceutical compositions, administration of the ABP can occur prior to, simultaneously, and/or following, administration of the additional therapeutic agent. In some aspects, administration of an ABP provided herein and the additional therapeutic agent occur within about one month of each other. In some aspects, administration of an ABP provided herein and the additional therapeutic agent occur within about one week of each other. In some aspects, administration of an ABP provided herein and the additional therapeutic agent occur within about one day of each other. In some aspects, administration of an ABP provided herein and the additional therapeutic agent occur within about twelve hours of each other. In some aspects, administration of an ABP provided herein and the additional therapeutic agent occur within about one hour of each other.

In one aspect, the present invention provides a pharmaceutical composition comprising an effective amount of an anti-hTIGIT antibody for treating or preventing cancer in a subject, wherein the composition is administered in combination with an antibody against Tim-3, 4-1BB, GITR, PD-1 or PD-L1 or OX40L, wherein the anti-hTIGIT antibody comprises a CDR-H3 of SEQ ID NO:32, a CDR-H2 of SEQ ID NO:40, a CDR-H1 of SEQ ID NO:54, a CDR-L3 of SEQ ID NO:64, a CDR-L2 of SEQ ID NO:68, and a CDR-L1 of SEQ ID NO:71. In one aspect, the present invention provides a pharmaceutical composition comprising an effective amount of an anti-hTIGIT antibody for treating or preventing cancer in a subject, wherein the composition is administered in combination with an antibody against Tim-3, 41BB, GITR, PD-1 or PD-L1 or OX40L, wherein the anti-hTIGIT antibody comprises a $V_H$ sequence of SEQ ID NO:13 and a $V_L$ sequence of SEQ ID NO:26. In one aspect, the present invention provides a pharmaceutical composition comprising an effective amount of an anti-hTIGIT antibody for treating or preventing cancer in a subject, wherein the composition is administered in combination with an antibody against Tim-3, 41BB, GITR, PD-1 or PD-L1 or OX40L, wherein the anti-hTIGIT antibody comprises a heavy chain of SEQ ID NO:99 and a light chain of SEQ ID NO:92.

In one aspect, the present invention provides an anti-hTIGIT antibody for use in treating or preventing cancer in a subject, wherein the anti-hTIGIT antibody is administered in combination with an antibody against Tim-3, 41BB, GITR, PD-1 or PD-L1 or OX40L, wherein the anti-hTIGIT antibody comprises a CDR-H3 of SEQ ID NO:32, a CDR-H2 of SEQ ID NO:40, a CDR-H1 of SEQ ID NO:54, a CDR-L3 of SEQ ID NO:64, a CDR-L2 of SEQ ID NO:68, and a CDR-L1 of SEQ ID NO:71. In one aspect, the present invention provides an anti-hTIGIT antibody for use in treating or preventing cancer in a subject, wherein the anti-hTIGIT antibody is administered in combination with an antibody against Tim-3, 41BB, GITR, PD-1 or PD-L1 or OX40L, wherein the anti-hTIGIT antibody comprises a $V_H$ sequence of SEQ ID NO:13 and a $V_L$ sequence of SEQ ID NO:26. In one aspect, the present invention provides an anti-hTIGIT antibody for use in treating or preventing cancer in a subject, wherein the anti-hTIGIT antibody is administered in combination with an antibody against Tim-3, 41BB, GITR, PD-1 or PD-L1 or OX40L, wherein the anti-hTIGIT antibody comprises a heavy chain of SEQ ID NO:99 and a light chain of SEQ ID NO:92.

9. Diagnostic Methods

Also provided are methods for detecting the presence of TIGIT on cells from a subject. Such methods may be used, for example, to predict and evaluate responsiveness to treatment with an ABP provided herein.

In some embodiments, a blood sample is obtained from a subject and the fraction of cells expressing TIGIT is determined. In some aspects, the relative amount of TIGIT expressed by such cells is determined. The fraction of cells expressing TIGIT and the relative amount of TIGIT expressed by such cells can be determined by any suitable method. In some embodiments, flow cytometry is used to make such measurements. In some embodiments, fluorescence assisted cell sorting (FACS) is used to make such measurement. See Li et al., *J. Autoimmunity*, 2003, 21:83-92 for methods of evaluating expression of TIGIT in peripheral blood.

10. Kits

Also provided are kits comprising the ABPs provided herein. The kits may be used for the treatment, prevention, and/or diagnosis of a disease or disorder, as described herein.

In some embodiments, the kit comprises a container and a label or package insert on or associated with the container. Suitable containers include, for example, bottles, vials, syringes, and IV solution bags. The containers may be formed from a variety of materials, such as glass or plastic. The container holds a composition that is by itself, or when combined with another composition, effective for treating, preventing and/or diagnosing a disease or disorder. The container may have a sterile access port. For example, if the container is an intravenous solution bag or a vial, it may have a port that can be pierced by a needle. At least one active agent in the composition is an ABP provided herein. The label or package insert indicates that the composition is used for treating the selected condition.

In some embodiments, the kit comprises (a) a first container with a first composition contained therein, wherein the first composition comprises an ABP provided herein; and (b) a second container with a second composition contained therein, wherein the second composition comprises a further therapeutic agent. The kit in this embodiment of the invention may further comprise a package insert indicating that the compositions can be used to treat a particular condition.

Alternatively, or additionally, the kit may further comprise a second (or third) container comprising a pharmaceutically-acceptable excipient. In some aspects, the excipient is a buffer. The kit may further include other materials desirable from a commercial and user standpoint, including filters, needles, and syringes.

EXAMPLES

The following are examples of methods and compositions of the invention. It is understood that various other embodiments may be practiced, given the general description provided herein.

Example 1: Mutational Analysis for Epitope Determination

Alanine Scanning

To identify the epitope for MAB10 binding to human TIGIT, 18 alanine single point mutations were made. Proteins were expressed in HEK-293 cells, secreted as soluble protein, purified on Ni-NTA resin, and characterized by SDS-PAGE. Binding was assessed by Bio-Layer Interferometry (BLI) using the Octet platform. MAB10 was captured on anti-human Fc sensors, washed, and exposed to either monomeric wild type human TIGIT or to one of a selection of point mutants. Residues considered part of the binding epitope demonstrated reduced binding (e.g., a $K_D$ more than 5-fold poorer than that of binding to wild type human TIGIT). Alanine substitution at residues Q56, N58, L65, I68, N70, L73, H76, I77 and P79 resulted in reduced binding Alanine substitution at residues M23, T24, T55, Q62, S78, S80, K82, Y113, and P114 did not result in reduced binding.

To identify the epitope for MAB2, MAB15, and MAB21 binding to human TIGIT, binding to 7 alanine single point mutations was assessed using BLI as described in the preceding paragraph.

For MAB2, alanine substitution at residues Q56 and I77 resulted in reduced binding, and alanine substitution at residues I68, L73, H76, S78, and P79 did not result in reduced binding.

For MAB15, alanine substitution at residues Q56, I68, L73, H76, and I77 resulted in reduced binding, and alanine substitution at residues S78 and P79 did not result in reduced binding.

For MAB21, alanine substitution at residues Q56, I68, L73, and I77 resulted in reduced binding, and alanine substitution at residues H76, S78, and P79 did not result in reduced binding.

Mass Spectrometry

To identify the epitope for MAB10 binding human TIGIT, purified MAB10 and human TIGIT HIS samples were submitted to CovalX (Saugus, Mass. USA) for mass spectrometry analysis using a cross-linking approach which allows for the detection of non-covalent interactions. MAB10 and human TIGIT HIS were incubated with deuterated cross-linkers and subjected to multi-enzymatic cleavage. After enrichment of the cross-linked peptides, the samples were analyzed by high resolution mass spectrometry. Proteolysis with both trypsin and elastase did not produce any cross-linked peptides, while proteolysis with chymotrypsin, ASP-N and thermolysin did detect at least one cross-linked peptide, for a total of 11 cross-linked peptides. The results indicate that the binding epitope includes residues that were cross-linked. These include residues in two regions, one inclusive of residues S78 and R84, and another inclusive of residues T117, S129 and S130.

Crystallographic Approach for Epitope Determination

The binding epitope of MAB10 was also identified through crystallographic studies. MAB10 Fab was complexed with human TIGIT, purified by size exclusion chromatography, and concentrated to 10 mg/ml. Crystals were grown out of 14% PEG4000, 0.1M MES pH 6, 10 mM β-nicotinamide adenine dinucleotide hydrate, 0.5% n-dodecyl-β-D-maltoside. X-ray data were collected at Argonne National Laboratories (GM/CA CAT 23ID-D) and processed using CCP4 (Collaborative Computational Project No. 4, Software for Macromolecular X-Ray Crystallography) and Phenix (Python-based Hierarchical ENvironment for Integrated Xtallography). TIGIT residues within a contact distance of 3.8 Å from the heavy and light chain were considered part of the binding epitope and include T55, Q56, L65, D72, L73, H76, I77, S78, P79 and H111.

Example 2: Combination Therapies Comprising Anti-TIGIT ABPs and Immunotherapeutics A lymphoproliferation assay was used to test for T cell responses in cytomegalovirus specific (CMV+) T cells. PBMCs from individual donors that have been screened for CMV antigen reactivity were purchased from Astarte Biologics (Bothell, Wash.). Cell lysates from CMV-infected cells were also purchased from Astarte Biologics. The PBMCs were plated at $5 \times 10^5$ cells/well and the antigen-specific stimulation was performed by the addition of cell lysate, which stimulates the CMV+ T cells in the sample, at 1 mg/ml, 0.1 mg/ml, or 0.01 mg/ml. Controls used were unstimulated cells, stimulated cells with no immunotherapy treatment, and stimulated cells with both control antibodies for the combination treatment group. Experimental groups were treated with MAB10 (20 μg/ml) along with the control antibody for the additional immunotherapeutic agent, an additional immunotherapeutic agent with IgG4 control antibody (as control for MAB10) (see Table 6), or a combination of MAB10 and the additional therapeutic agent. Each treatment was performed on cells stimulated with all three lysate concentrations. Dosing of the immunotherapeutics was determined based on a mixture of reported functional doses, ED50 values, and empirical data. Cells were cultured for four days, and the supernatants were collected and analyzed for the production of the effector cytokine TNF as quantification of activation.

TABLE 6

| Immunotherapeutic | Dose | Source | CAT# | Clone | Function |
|---|---|---|---|---|---|
| αTIM-3 | 25 μg/mL | eBioscience ® | 16-3109-85 | F38-2E2 | Antagonist |
| αTGFβ | 10 μg/mL | R&D Systems ® | MAB1835 | 1D11 | Antagonist |
| OX40L | 500 ng/mL | R&D Systems ® | 1054-OX-010 | N/A | Agonist |
| α41BB | 30 μg/mL | R&D Systems ® | AF838 | Polyclonal | Agonist |

TABLE 6-continued

| Immuno-therapeutic | Dose | Source | CAT# | Clone | Function |
|---|---|---|---|---|---|
| αLAG-3 | 20 µg/mL | Novus Biologicals ® | NBP1-97657 | 17B4 | Antagonist |
| PD-1 | 10 µg/mL | Potenza Therapeutics ™ | N/A | pembrolizumab | Antagonist |
| αCTLA-4 | 20 µg/mL | BioLegend ® | 349902 | L3D10 | Antagonist |

Results

Figure 1J:
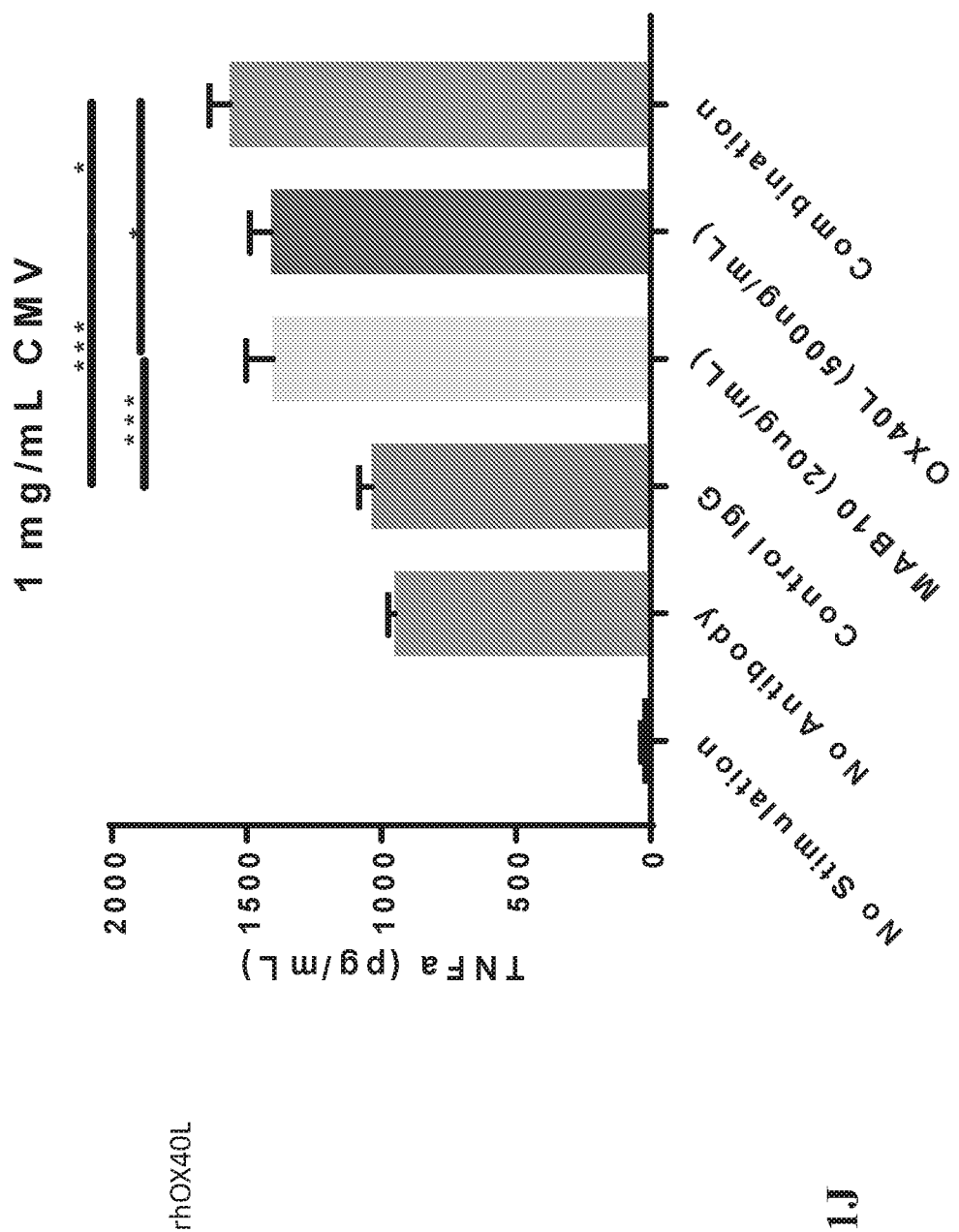
Figure 1K:
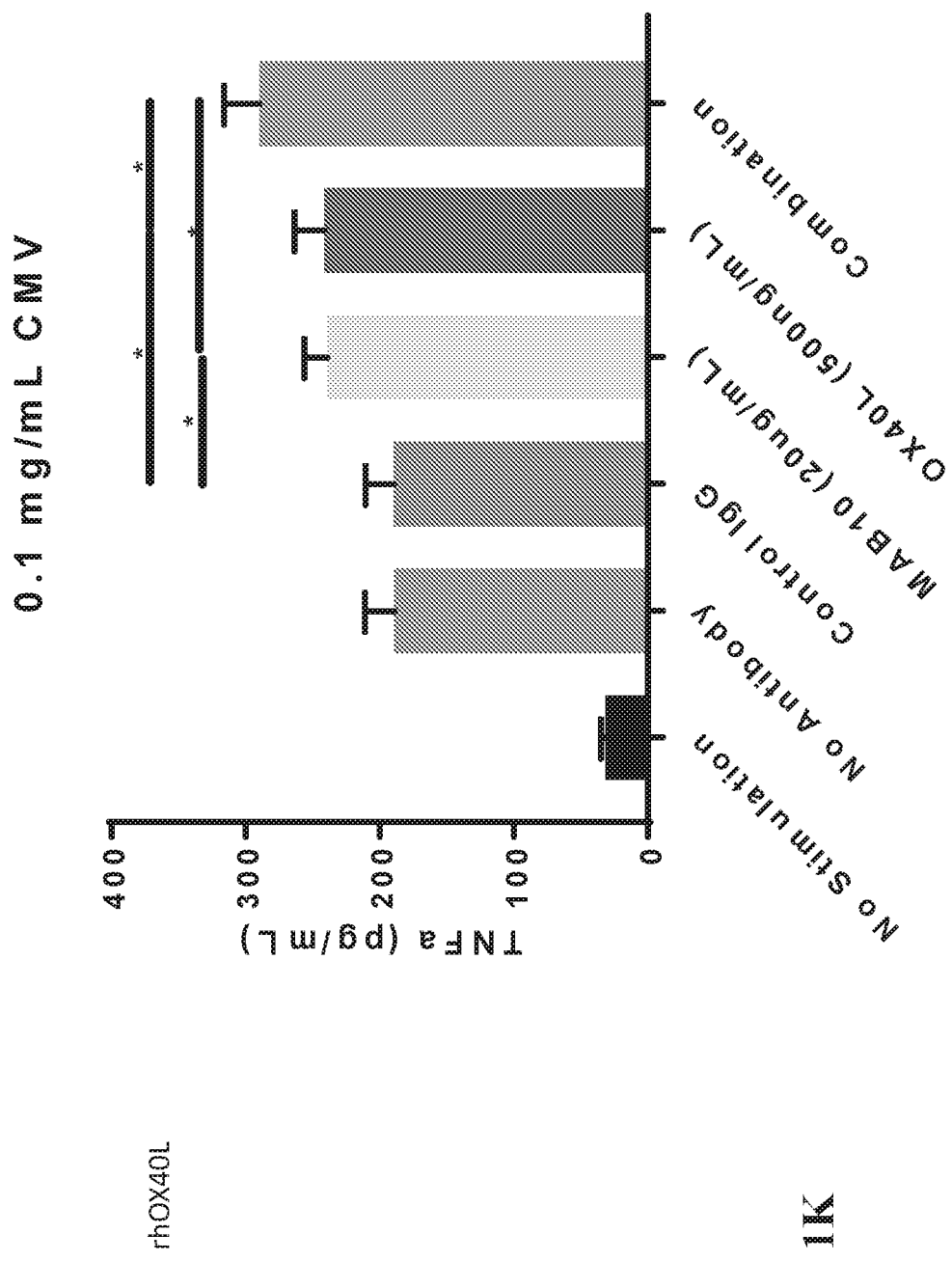
Figure 1L:
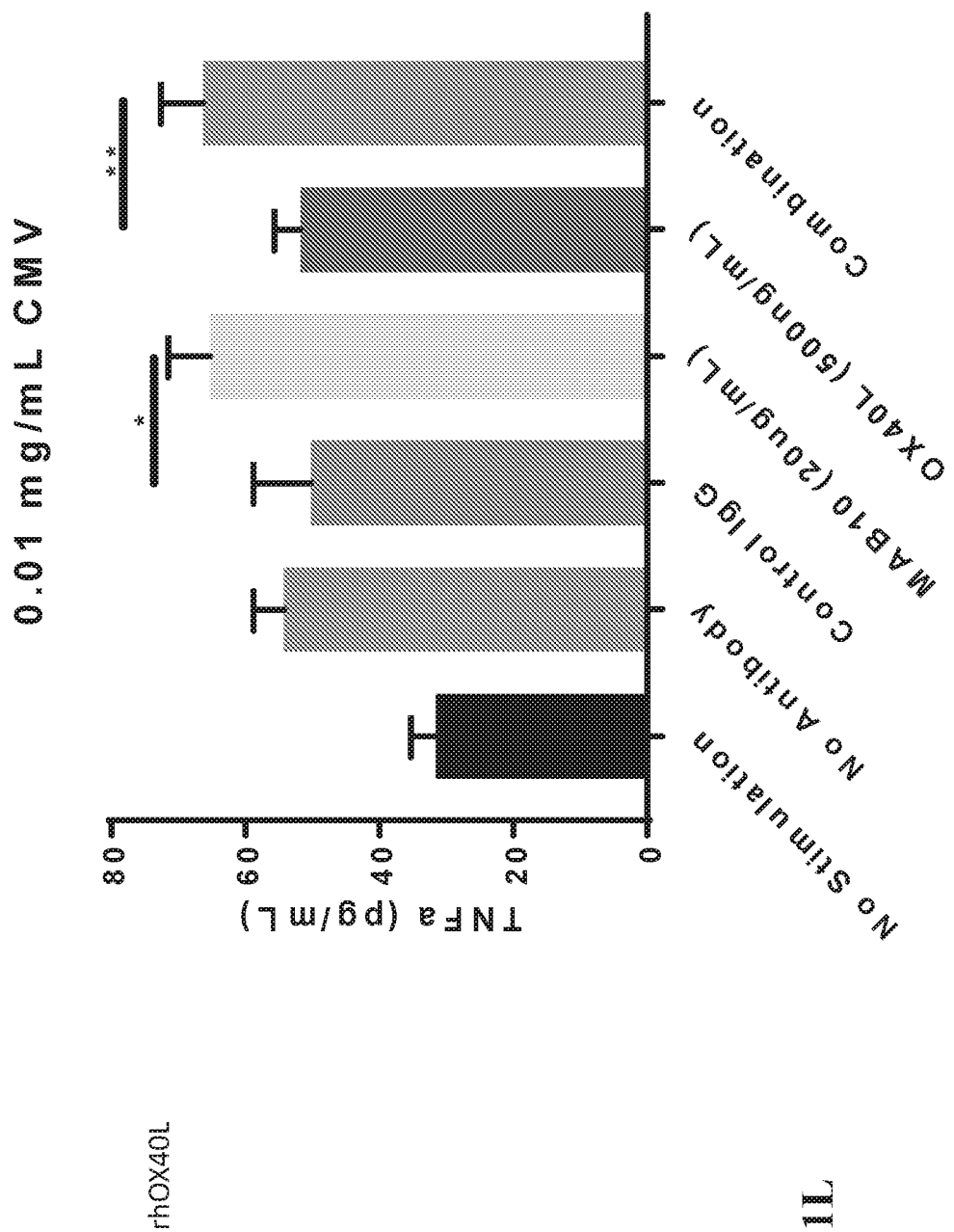

Results are shown in FIG. 1 as follows: cells were stimulated with 1 µg/ml, 0.1 µg/ml, or 0.01 µg/ml CMV lysate and treated with MAB10 and pembrolizumab each individually or in combination (FIGS. 1A-1C, respectively); cells stimulated with 1 µg/ml, 0.1 µg/ml, or 0.01 µg/ml CMV lysate and treated with MAB10 and anti-TIM-3 antibody each individually or in combination (FIGS. 1D-1F); cells stimulated with 1 µg/ml, 0.1 µg/ml, or 0.01 µg/ml CMV lysate and treated with MAB10 and anti-41BB antibody each individually or in combination (FIGS. 1G-1I); and cells stimulated with 1 µg/ml, 0.1 µg/ml, or 0.01 µg/ml CMV lysate and treated with MAB10 and rhOX40L each individually or in combination (FIGS. 1J-1L). Each combination treatment comprising pembrolizumab, anti-TIM-3 antibody, anti-41BB antibody, or OX40 ligand showed an additive effect on immune activation (as measured by TNFα production) compared to the individual treatments alone.

In the case of treatment with anti-LAG-3 and anti-TGFβ, the individual treatments dominated the results and it was not possible to determine whether there were additive or synergistic effects in this assay. Treatment with anti-CTLA-4 alone did not result in an increased immune response, and thus a different assay should be used to determine any potential combinatorial effects.

Further determination of the ability of MAB10 combinations to activate cells was performed using dissociated tumor cells (DTCs, Conversant Bio) from treatment-naïve cancer patients. DTCs are a single cell suspension containing all cells from a tumor specimen including immune cells, tumor cells and support cells.

DTCs from a 50-year-old male with stage IV melanoma were set in culture and stimulated with a control OVA peptide (3 µg/ml, Miltenyi Biotec, Cat #130-099-771) or a melanoma peptide mix consistent of 1 µg/mL NY-ESO-1+1 µg/mL MelanA/MART-1+1 µg/mL gp100 (Miltenyi Biotec, Cat #s 130-095-381, 130-094-477, and 130-094-450, respectively). An anti-GITR antibody MAB22 (see, e.g., copending International Patent Application No. PCT/US2017/062443), pembrolizumab, and MAB10 were added to the peptide-stimulated samples, either alone or in pairwise combinations. As a control, equal amounts of isotype control antibodies were used. For single antibody stimulation, the total amount of antibody was kept constant by supplementing with the isotype control antibody. MAB10 and pembrolizumab were used at a final concentration of 10 µg/ml, and MAB22 was used at a final concentration of 1 µg/ml. To assess activation, cells were in culture for 7 days, the supernatants were collected, and the level of IFNγ produced was quantified using AlphaLISA® (PerkinElmer). Statistical significance was calculated using One-Way ANOVA with multiple comparisons.

Results

Figure 2A:
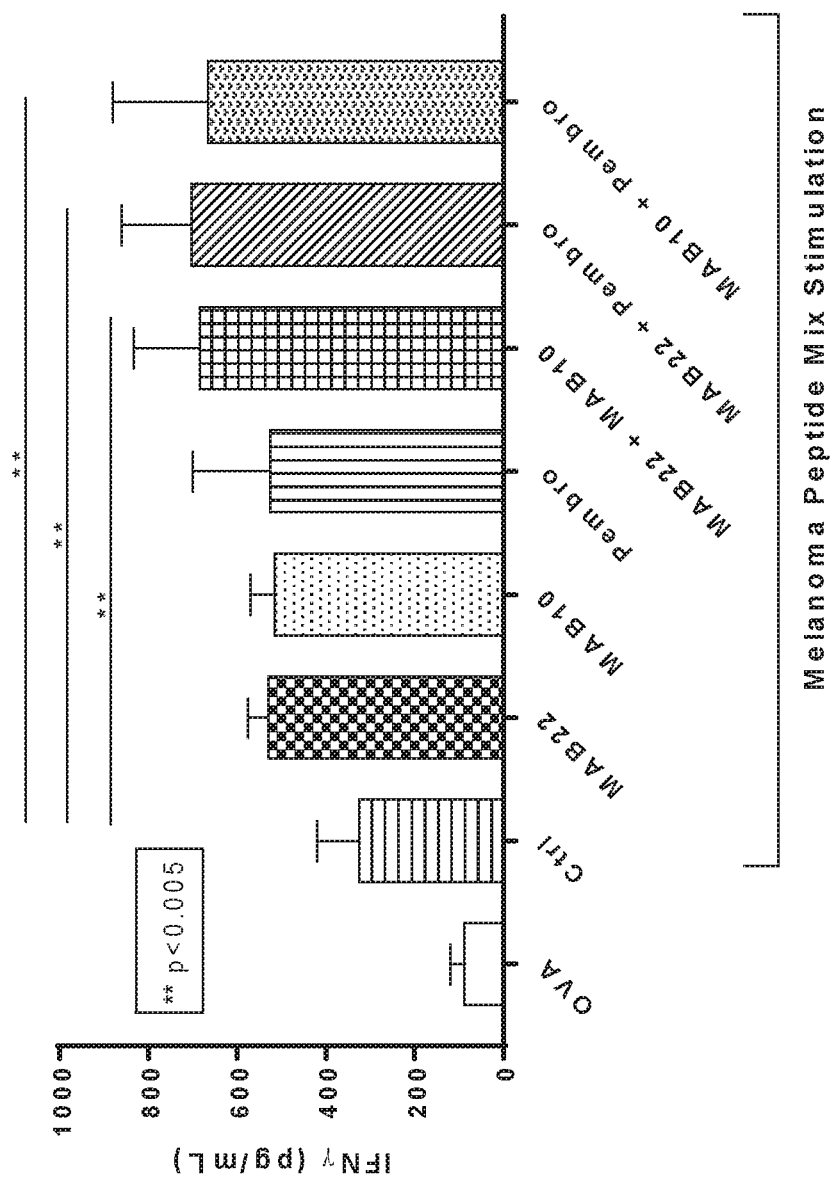
FIGS. 2A-2B are graphs showing a dissociated tumor cell (DTC) assay to test for T cell responses in DTCs from treatment-naïve cancer patients.

As can be seen in FIG. 2A, each combination therapy treatment resulted in greater stimulation of IFNγ production than treatment with single agents alone, suggesting an additive effect.

Next, DTCs from an 80-year-old female with stage IIa non-small cell lung cancer) NSCLC were set in culture and left unstimulated or were stimulated with soluble anti-CD3+ anti-CD28 antibodies (Becton Dickenson Cat #s 555336 and 555726, respectively) for two days. As a control, an equal amount of an isotype control antibody (IgG4) was used. For single antibody stimulation, the total amount of antibody was kept constant by supplementing the samples with the isotype control antibody. MAB10 and pembrolizumab were used at a final concentration of 10 mg/ml. To assess activation, Brefeldin A (EBioscience, Cat #00-4506-51) was added to the cells during the last 5 hours of culture and FACS analysis and quantification of IFNγ-producing CD4+ and CD8+ T cells was performed using intracellular cytokine staining. Statistical significance was calculated using One-Way ANOVA with multiple comparisons.

Results

Figure 2B:
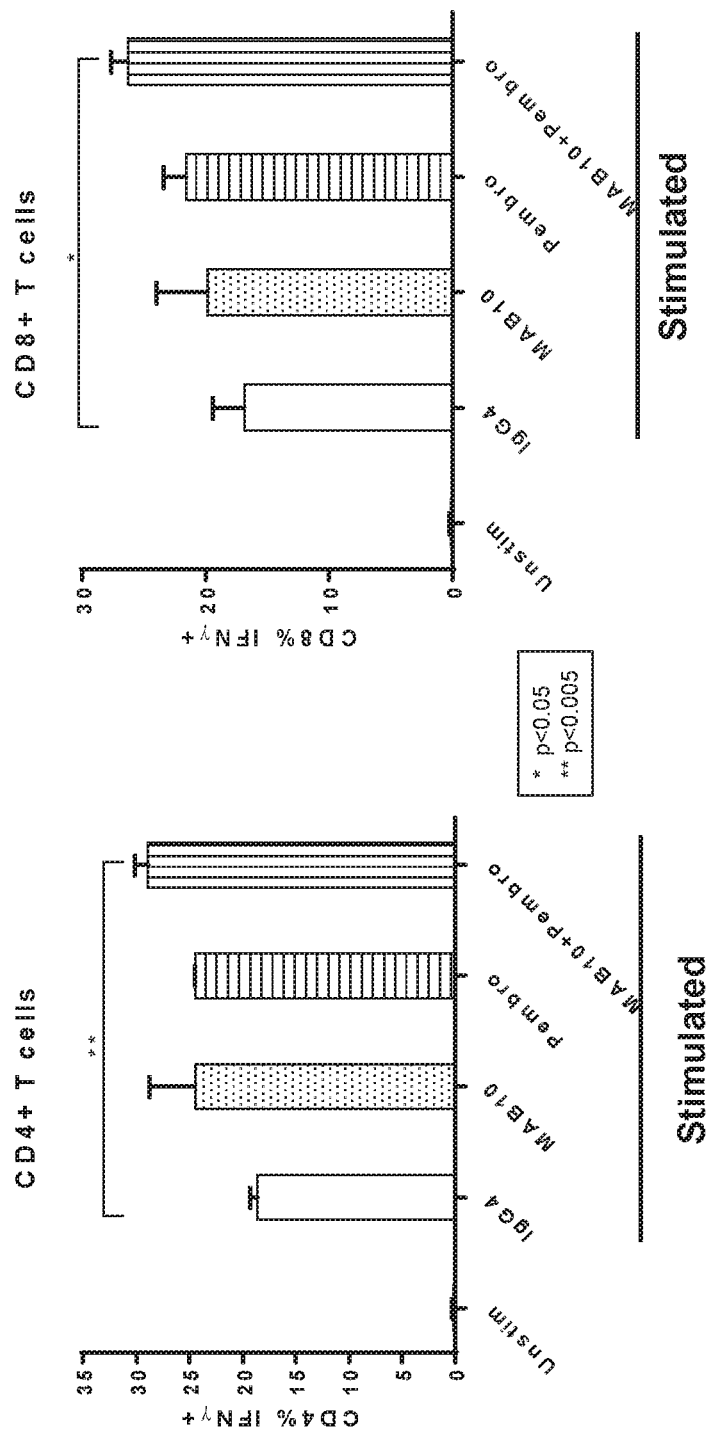

As can be seen in FIG. 2B, the treatment of cells with the combination of MAB10 and pembrolizumab resulted in an additive effect over treatment with either single agent alone, as measured by IFNγ production in both CD4+ and CD8+ T cells.

Example 3: Combination Therapies Comprising Anti-TIGIT ABPs and Immunotherapeutics In Vivo In order to determine whether a combination of an anti-TIGIT antibody and an anti-neuropilin-1 antibody provides improved anti-tumor activity over the single agents alone in vivo, the combination was tested in in the EMT6 breast cancer mouse model (Charles River Labs).

Anti-NRP-1 antibodies are described, e.g., in co-pending international Patent Application No. PCT/US2017/067782, filed Dec. 21, 2017, which also discloses a panel of murine versions of the anti-NRP-1 antibodies, which were tested as chimeric mouse IgG2a antibodies containing the N297A mutation which abolishes ADCC and CDC effector function.

In order to test the combination of anti-NRP and anti-TIGIT antibodies in mice, the murine version of the anti-human-NRP-1 antibody MAB23 (murine version "mMAB23," SEQ ID NOS:143-144, Appendix A) was used in combination with the antibody against murine TIGIT, 1B4 (mouse IgG1, Cell Essentials). A control antibody used was mouse IgG2b MPC-11 (BioXCell, Cat #BE0086).

EMT6 Tumor Model

Female Balb/c mice were inoculated with 1×10⁵ EMT6 cells. The mice were randomized based on tumor volume into 12 groups once the tumors reached an average size of 80-120 mm³. Treatment started on the same day as randomization (therapeutic treatment). Antibodies were administered by intraperitoneal (i.p.) injections. Tumors and body weights were measured three times per week. The study endpoint was defined as Day 40 or mean tumor volume of 2,000 mm³ dependent on the treatment group.

Results

Figure 3A:
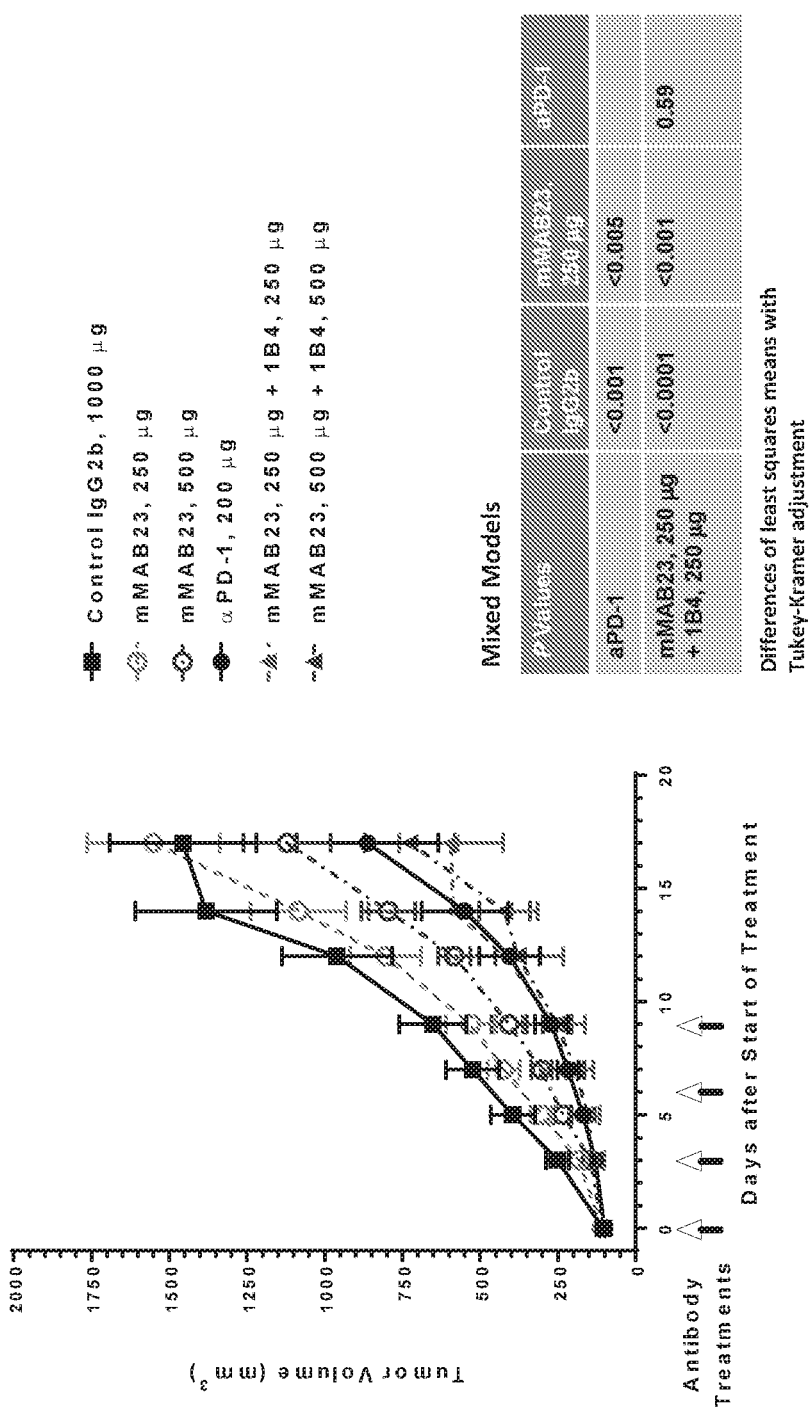
FIGS. 3A-3D are graphs showing the results as measured by tumor volume of a combination of an anti-TIGIT and an anti-NRP-1 antibody in the EMT6 breast cancer mouse model. mMAB23 with 1B4 combinations compared to mMAB23 monotherapy and aPD-1 monotherapy are shown in FIGS. 3A (average tumor volume) and 3C (individual tumor volume for each mouse), and mMAB23 with 1B4 combinations compared to 1B4 monotherapy and aPD-1 monotherapy are shown in FIGS. 3B (average tumor volume) and 3D (individual tumor volume).
Figure 3B:
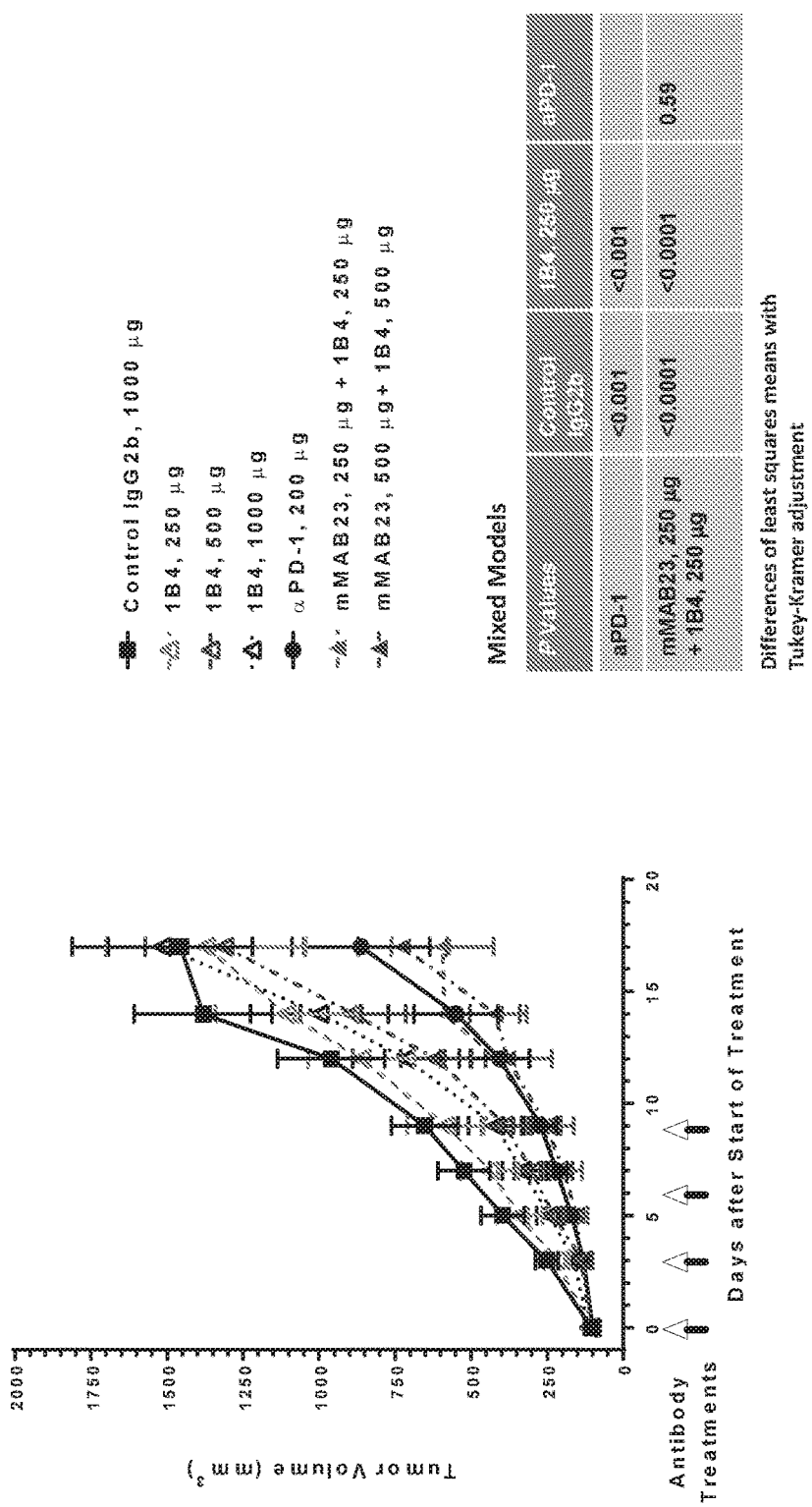

In the mouse EMT6 tumor study, the combination treatment of mMAB23 and 1B4 inhibited tumor growth to a greater degree than their single agent controls (FIG. 3A-3B).

Combination treatment comprising 250 μg murine mMAB23+250 μg 1B4 produced 57.4% TGI (tumor growth inhibition), and combination treatment comprising 500 μg mMAB23+500 μg 1B4 produced 69.4% TGI compared with control antibody treatment. The combination treatment of mMAB23+1B4 at both concentrations was statistically significant after 14 days of treatment (p<0.05). Treatment with anti-PD-1 produced 60.2% TGI at day 14. Evaluation of the control, rat anti-mouse αPD-1 (clone RMP1-14), single agent (250 μg), and combination (250 μg each) curves over time using a mixed models analysis (similar to RM ANOVA) showed that both the αPD-1 and mMAB239+1B4 combination treatments were significantly different from the control group and both single agents (p<0.03).

Figure 3C:
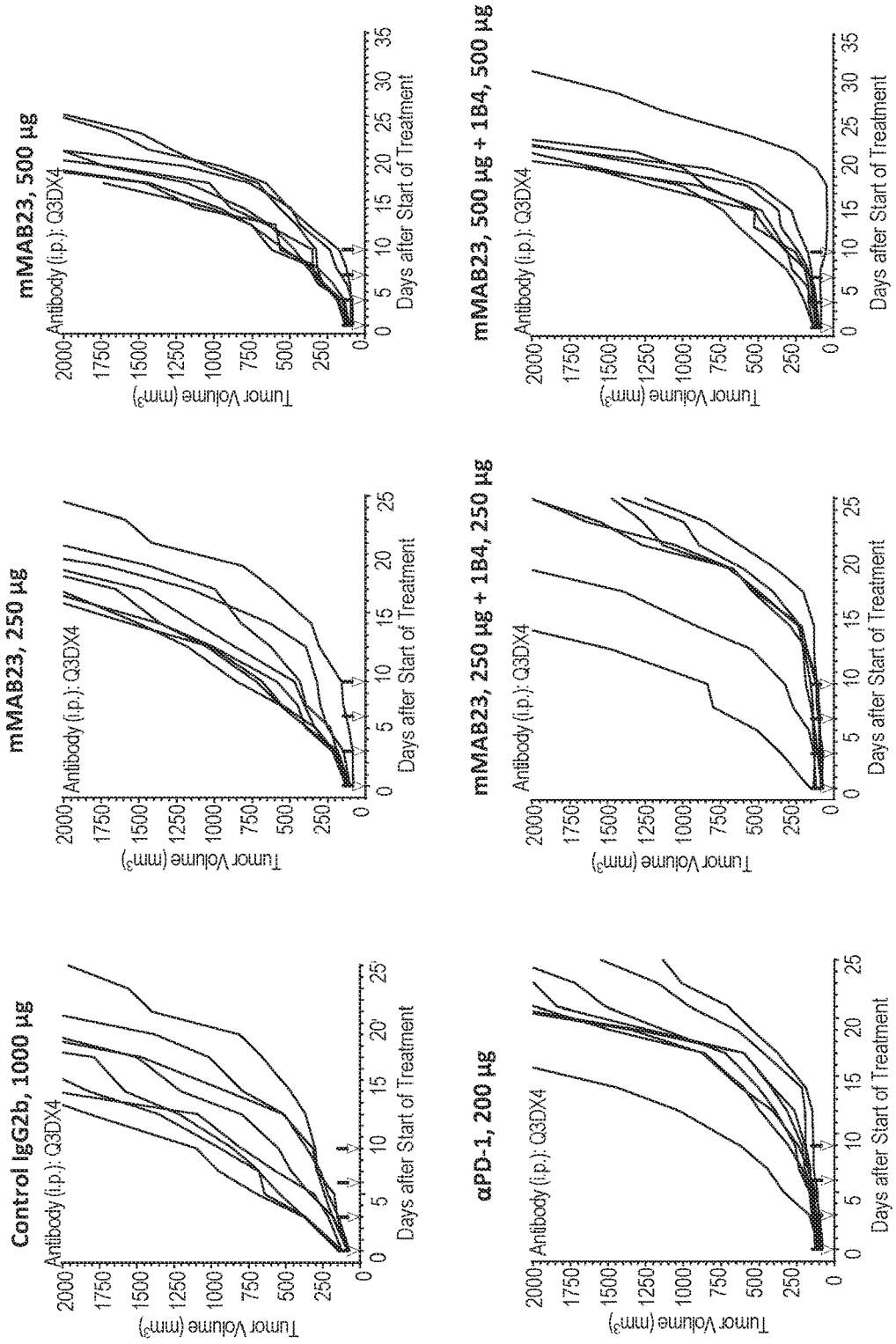
Figure 3D:
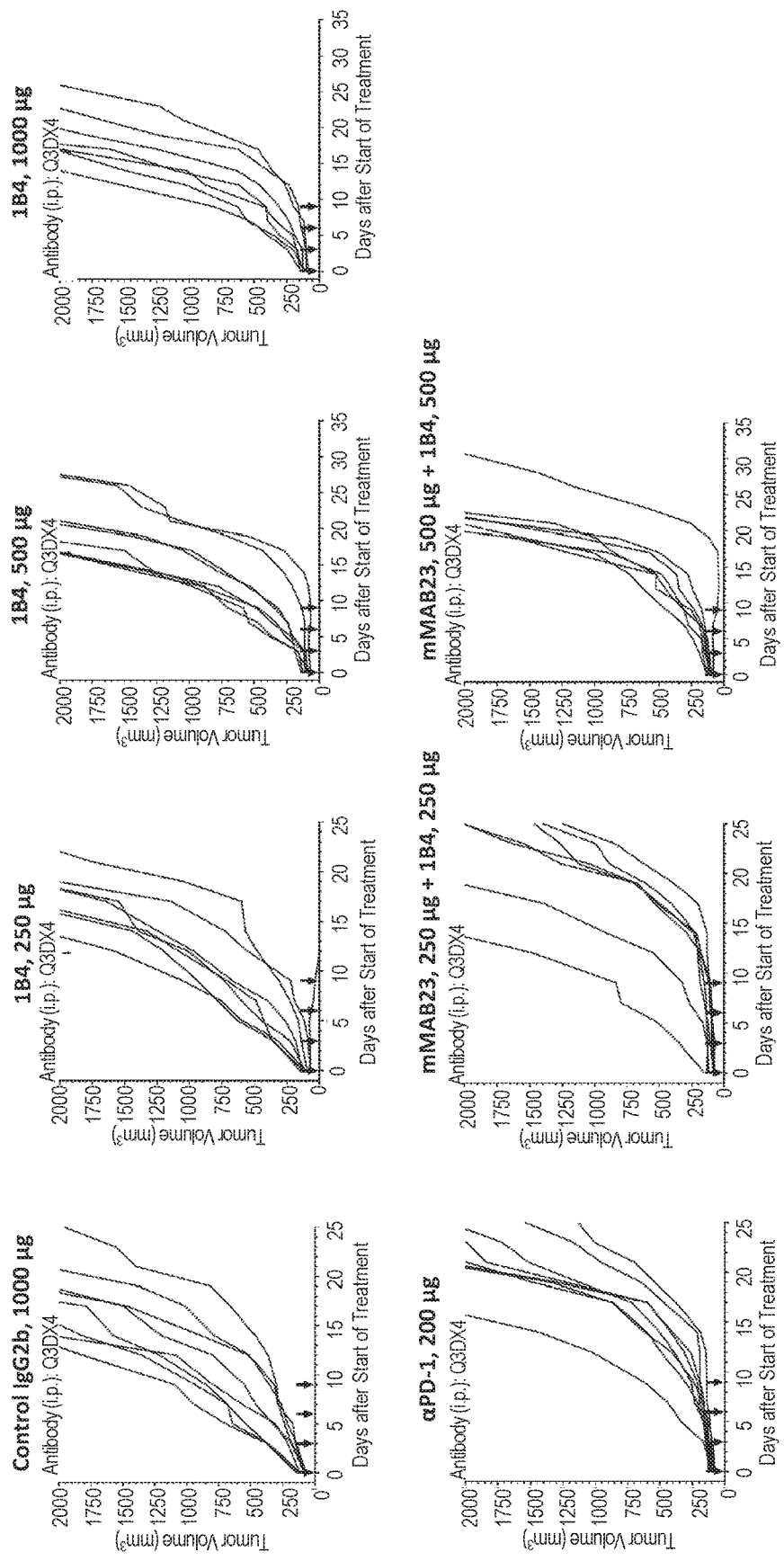

A spider plot analysis of the growth curves of individual tumors from all treated mice showed a marked delay of tumor growth in mice treated with the combination of mMAB23 and 1B4 (FIG. 3C-3D). The individual EMT6 tumor volumes for each of the 8 mice per group are shown for all treatment groups (indicated at the top of each graph). The EMT6 mouse tumor cells were injected into female BALB/c mice and randomized at an average size of 80-120 mm$^3$. Treatment began at randomization and the indicated antibodies were administered intraperitoneally at 1000 μg/animal (control IgG2b and 1B4), 500 μg/animal (mMAB23 and 1B4), 250 μg/animal (mMAB23 and 1B4), or 200 μg/animal (αPD-1). The black arrows indicate treatment days. The study endpoint was defined as Day 40 or mean tumor volume of 2,000 mm$^3$ dependent on the treatment group.

These data demonstrate that the combination of mMAB23 and 1B4 provide improved anti-tumor growth inhibition over the single agents. Mice treated with this combination displayed a marked inhibition of tumor growth (57.4% TGI and 69.4% TGI for 250 μg and 500 μg of each antibody, respectively) that was similar to anti-PD-1 treatment (60.2% TGI).

INCORPORATION BY REFERENCE

The entire disclosures of all patent and non-patent publications cited herein are each incorporated by reference in their entireties for all purposes.

Other Embodiments

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

APPENDIX A

SEQUENCE REFERENCE TABLE

| SEQ ID NO | Molecule | Region | Sequence |
| --- | --- | --- | --- |
| 1 | hTIGIT | | MRWCLLLIWAQGLRQAPLASGMMTGTIETTGNISA EKGGSIILQCHLSSTTAQVTQVNWEQQDQLLAICN ADLGWHISPSFKDRVAPGPGLGLTLQSLTVNDTGE YFCIYHTYPDGTYTGRIFLEVLESSVAEHGARFQIPL LGAMAATLVVICTAVIVVVALTRKKKALRIHSVEG DLRRKSAGQEEWSPSAPSPPGSCVQAEAAPAGLCG EQRGEDCAELHDYFNVLSYRSLGNCSFFTETG |
| 2 | cTIGIT | | MRWCLFLIWAQGLRQAPLASGMMTGTIETTGNISA KKGGSVILQCHLSSTMAQVTQVNWEQHDHSLLAIR NAELGWHIYPAFKDRVAPGPGLGLTLQSLTMNDTG EYFCTYHTYPDGTYRGRIFLEVLESSVAEHSARFQI PLLGAMAMMLVVICIAVIVVVVLARKKKSLRIHSV ESGLQRKSTGQEEQIPSAPSPPGSCVQAEAAPAGLC GEQQGDDCAELHDYFNVLSYRSLGSCSFFTETG |
| 3 | mTIGIT | | MHGWLLLVWVQGLIQAAFLATGATAGTIDTKRNIS AEEGGSVILQCHFSSDTAEVTQVDWKQQDQLLAIY SVDLGWHVASVFSDRVVPGPSLGLTFQSLTMNDTG EYFCTYHTYPGGIYKGRIFLKVQESSVAQFQTAPLG GTMAAVLGLICLMVTGVTVLARKKSIRMHSIESGL GRTEAEPQEWNLRSLSSPGSPVQTQTAPAGPCGEQ AEDDYADPQEYFNVLSYRSLESFIAVSKTG |
| 4 | MAB1-IgG4 | VH | QLQLQESGPGLVKPSETLSLTCTVSGGSITSSSYYW GWIRQPPGKGLEWIGSIYYSGATFYNPSLKSRVTIS VDTSKNQFSLKLSSVTAADTAVYYCARDANYYGS AWAFDPWGQGTLVTVSS |

APPENDIX A-continued

SEQUENCE REFERENCE TABLE

| SEQ ID NO | Molecule | Region | Sequence |
|---|---|---|---|
| 5 | MAB2-IgG4 | VH | QLQLQESGPGLVKPSETLSLTCTVSGGSISSSKYYW GWIRQPPGKGLEWIGSIYYSGSTFYNPSLKSRVTISV DTSKNQFSLKLSSVTAADTAVYYCARDANYYGSA WAFDPWGQGTLVTVSS |
| 6 | MAB3-IgG4 | VH | QLQLQESGPGLVKPSETLSLTCTVSGGSISSTSHYW GWIRQPPGKGLEWIGSIYYSGSTFYNPSLKSRVTISV DTSKNQFSLKLSSVTAADTAVYYCARDANYYGSA WAFDPWGQGTLVTVSS |
| 7 | MAB4-IgG4 | VH | QLQLQESGPGLVKPSETLSLTCTVSGGSISSTSHYW GWIRQPPGKGLEWIGSIYYSGSTFYNPSLKSRVTISV DTSKNQFSLKLSSVTAADTAVYYCARDANYYGGA WAFDPWGQGTLVTVSS |
| 8 | MAB5-IgG4 | VH | QLQLQESGPGLVKPSETLSLTCTVSGGSISSTSHYW GWIRQPPGKGLEWIGSIYYSGSTFYNPSLKGRVTIS VDTSKNQFSLKLSSVTAADTAVYYCARDANYYGS AWAFDPWGQGTLVTVSS |
| 9 | MAB6-IgG4 | VH | QLQLQESGPGLVKPSETLSLTCTVSGGSIESGSYYW GWIRQPPGKGLEWIGSIYYSGGTYYNPSLKSRVTIS VDTSKNQFSLKLSSVTAADTAVYYCARDGVLTLN KRSFDIWGQGTMVTVSS |
| 10 | MAB7-IgG4 | VH | QVQLQESGPGLVKPSQTLSLTCTVSGGSIESGVYY WGWIRQPPGKGLEWIGSIYYSGSTYYNPSLKSRVTI SVDTSKNQFSLKLSSVTAADTAVYYCARDGVLTLN KRSFDIWGQGTMVTVSS |
| 11 | MAB8-IgG4 | VH | QLQLQESGPGLVKPSETLSLTCTVSGGSIASGSYYW GWIRQPPGKGLEWIGSIYYSGQTYYNPSLKSRVTIS VDTSKNQFSLKLSSVTAADTAVYYCARDGVLTLN KRSFDIWGQGTMVTVSS |
| 12 | MAB9-IgG4 | VH | QVQLQESGPGLVKPSQTLSLTCTVSGGSIESGLYYW GWIRQPPGKGLEWIGSIYYSGSTYYNPSLKSRVTIS VDTSKNQFSLKLSSVTAADTAVYYCARDGVLTLN KRSFDIWGQGTMVTVSS |
| 13 | MAB10-IgG4 | VH | QVQLQESGPGLVKPSQTLSLTCTVSGGSIESGLYYW GWIRQPPGKGLEWIGSIYYSGSTYYNPSLKSRATIS VDTSKNQFSLKLSSVTAADTAVYYCARDGVLALN KRSFDIWGQGTMVTVSS |
| 14 | MAB11-IgG4 | VH | QVQLQESGPGLVKPSQTLSLTCTVSGGSIESGLYYW GWIRQPPGKGLEWIGSIYYSGSTYYNPSLKSRVTIS VDTSKNQFSLKLSSVTAADTAVYYCARDGVLALN KRSFDIWGQGTMVTVSS |
| 15 | MAB12-IgG4 | VH | QVQLQESGPGLVKPSQTLSLTCTASGGSIESGLYYW GWIRQPPGKGLEWIGSIYYSGSTYYNPSLKSRVTIS VDTSKNQFSLKLSSVTAADTAVYYCARDGVLALN KRSFDIWGQGTMVTVSS |
| 16 | MAB13-IgG4 | VH | QVQLVQSGAEVKKPGASVKVSCKASGYTFGNYYM HWVRQAPGQGLEWMGIINPSLGLTSYAQKFQGRV TMTRDTSTSTVYMELSSLRSEDTAVYYCARGGRTT WIGAFDIWGQGTMVTVSS |
| 17 | MAB14-IgG4 | VH | QVQLVQSGAEVKKPGASVKVSCKASGYTFPAYYM HWVRQAPGQGLEWMGIINPSLGLTSYAQKFQGRV TMTRDTSTSTVYMELSSLRSEDTAVYYCARGGRTT WIGAFDIWGQGTMVTVSS |
| 18 | MAB15-IgG4 | VH | QVQLVQSGAEVKKPGASVKVSCKASGYTFREYYM HWVRQAPGQGLEWMGIINPSIGLTSYARKFQGRVT MTRDTSTSTVYMELSSLRSEDTAVYYCARGGRTT WIGAFDIWGQGTMVTVSS |

APPENDIX A-continued

SEQUENCE REFERENCE TABLE

| SEQ ID NO | Molecule | Region | Sequence |
|---|---|---|---|
| 19 | MAB16-IgG4 | VH | QVQLVQSGAEVKKPGASVKVSCKASGYTFREYYM HWVRQAPGQGLEWMGIINPSIGLTSYARKFQGRVT MTRDTSTSTVYMELSSLRSEDTAVYYCARGGRTT WIGALDIWGQGTMVTVSS |
| 20 | MAB17-IgG4 | VH | QVQLVQSGAEVKKPGASVKVSCKASGYTFPAYYIH WVRQAPGQGLEWMGIINPSLGLTSYARKFQGRVT MTRDTSTSTVYMELSSLRSEDTAVYYCARGGRTT WIGALDIWGQGTMVTVSS |
| 21 | MAB18-IgG4 | VH | QVQLVQSGAEVKKPGASVKVSCKASGYTFPAYYM HWVRQAPGQGLEWMGIINPSLGLTSYARKFQGRV TMTRDTSTSTVYMELSSLRSEDTAVYYCARGGRTT WIGAFDIWGQGTMVTVSS |
| 22 | MAB19-IgG4 | VH | QVQLVQSGAEVKKPGASVKVSCKASGYTFTSHYM GWVRQAPGQGLEWMGVINPSMGATSYAQKFQGR VTMTRDTSTSTVYMELSSLRSEDTAVYYCARLHVS GSYYPAYLDYWGQGTMVTVSS |
| 23 | MAB20-IgG4 | VH | QVQLVQSGAEVKKPGASVKVSCKASGYTFTSHYM GWVRQAPGQGLEWVGIINPSMGATSYAQKFQGRV TMTRDTSTSTVYMELSSLRSEDTAVYYCARLHVSG SYYPAYLDYWGQGTMVTVSS |
| 24 | MAB21-IgG4 | VH | QVQLVQSGAEVKKPGASVKVSCKASGYTFTSHYM GWVRQAPGQGLEWMGIINPSMGATSYTQKFRGRV TMTRDTSTSTVYMELSSLRSEDTAVYYCARLHVSG SYYPAYLDYWGQGTMVTVSS |
| 25 | MAB1-IgG4 | VL | EIVLTQSPATLSLSPGERATLSCRASQSVSSYLAWY QQKPGQAPRLLIYDASNRATGIPARFSGSGSGTDFT LTISSLEPEDFAVYYCQQHFNLPTFGGGTKVEIK |
| 25 | MAB2-IgG4 | VL | EIVLTQSPATLSLSPGERATLSCRASQSVSSYLAWY QQKPGQAPRLLIYDASNRATGIPARFSGSGSGTDFT LTISSLEPEDFAVYYCQQHFNLPTFGGGTKVEIK |
| 25 | MAB3-IgG4 | VL | EIVLTQSPATLSLSPGERATLSCRASQSVSSYLAWY QQKPGQAPRLLIYDASNRATGIPARFSGSGSGTDFT LTISSLEPEDFAVYYCQQHFNLPTFGGGTKVEIK |
| 25 | MAB4-IgG4 | VL | EIVLTQSPATLSLSPGERATLSCRASQSVSSYLAWY QQKPGQAPRLLIYDASNRATGIPARFSGSGSGTDFT LTISSLEPEDFAVYYCQQHFNLPTFGGGTKVEIK |
| 25 | MAB5-IgG4 | VL | EIVLTQSPATLSLSPGERATLSCRASQSVSSYLAWY QQKPGQAPRLLIYDASNRATGIPARFSGSGSGTDFT LTISSLEPEDFAVYYCQQHFNLPTFGGGTKVEIK |
| 26 | MAB6-IgG4 | VL | EIVLTQSPGTLSLSPGERATLSCRASQSVSSSYLAW YQQKPGQAPRLLIYGASSRATGIPDRFSGSGSGTDF TLTISRLEPEDFAVYYCQQHTVRPPLTFGGGTKVEI K |
| 26 | MAB7-IgG4 | VL | EIVLTQSPGTLSLSPGERATLSCRASQSVSSSYLAW YQQKPGQAPRLLIYGASSRATGIPDRFSGSGSGTDF TLTISRLEPEDFAVYYCQQHTVRPPLTFGGGTKVEI K |
| 26 | MAB8-IgG4 | VL | EIVLTQSPGTLSLSPGERATLSCRASQSVSSSYLAW YQQKPGQAPRLLIYGASSRATGIPDRFSGSGSGTDF TLTISRLEPEDFAVYYCQQHTVRPPLTFGGGTKVEI K |
| 26 | MAB9-IgG4 | VL | EIVLTQSPGTLSLSPGERATLSCRASQSVSSSYLAW YQQKPGQAPRLLIYGASSRATGIPDRFSGSGSGTDF TLTISRLEPEDFAVYYCQQHTVRPPLTFGGGTKVEI K |

APPENDIX A-continued

SEQUENCE REFERENCE TABLE

| SEQ ID NO | Molecule | Region | Sequence |
|---|---|---|---|
| 26 | MAB10-IgG4 | VL | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIK |
| 26 | MAB11-IgG4 | VL | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIK |
| 26 | MAB12-IgG4 | VL | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIK |
| 27 | MAB13-IgG4 | VL | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIK |
| 27 | MAB14-IgG4 | VL | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIK |
| 27 | MAB15-IgG4 | VL | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIK |
| 27 | MAB16-IgG4 | VL | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIK |
| 27 | MAB17-IgG4 | VL | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIK |
| 27 | MAB18-IgG4 | VL | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIK |
| 28 | MAB19-IgG4 | VL | EIVMTQSPATLSVSPGERATLSCRASQSVSSNLAWYQQKPGQAPRHLIYGASTRATGIPARFSGSGSGTEFTLTISSLQSEDFAVYYCQQYIVFPWTFGGGTKVEIK |
| 28 | MAB20-IgG4 | VL | EIVMTQSPATLSVSPGERATLSCRASQSVSSNLAWYQQKPGQAPRHLIYGASTRATGIPARFSGSGSGTEFTLTISSLQSEDFAVYYCQQYIVFPWTFGGGTKVEIK |
| 28 | MAB21-IgG4 | VL | EIVMTQSPATLSVSPGERATLSCRASQSVSSNLAWYQQKPGQAPRHLIYGASTRATGIPARFSGSGSGTEFTLTISSLQSEDFAVYYCQQYIVFPWTFGGGTKVEIK |
| 29 | MAB1-IgG4 | H3-IMGT | ARDANYYGSAWAFDP |
| 29 | MAB2-IgG4 | H3-IMGT | ARDANYYGSAWAFDP |
| 29 | MAB3-IgG4 | H3-IMGT | ARDANYYGSAWAFDP |
| 30 | MAB4-IgG4 | H3-IMGT | ARDANYYGAWAFDP |
| 29 | MAB5-IgG4 | H3-IMGT | ARDANYYGSAWAFDP |
| 31 | MAB6-IgG4 | H3-IMGT | ARDGVLTLNKRSFDI |
| 31 | MAB7-IgG4 | H3-IMGT | ARDGVLTLNKRSFDI |

APPENDIX A-continued

SEQUENCE REFERENCE TABLE

| SEQ ID NO | Molecule | Region | Sequence |
|---|---|---|---|
| 31 | MAB8-IgG4 | H3-IMGT | ARDGVLTLNKRSFDI |
| 31 | MAB9-IgG4 | H3-IMGT | ARDGVLTLNKRSFDI |
| 32 | MAB10-IgG4 | H3-IMGT | ARDGVLALNKRSFDI |
| 32 | MAB11-IgG4 | H3-IMGT | ARDGVLALNKRSFDI |
| 32 | MAB12-IgG4 | H3-IMGT | ARDGVLALNKRSFDI |
| 33 | MAB13-IgG4 | H3-IMGT | ARGGRTTWIGAFDI |
| 33 | MAB14-IgG4 | H3-IMGT | ARGGRTTWIGAFDI |
| 33 | MAB15-IgG4 | H3-IMGT | ARGGRTTWIGAFDI |
| 34 | MAB16-IgG4 | H3-IMGT | ARGGRTTWIGALDI |
| 34 | MAB17-IgG4 | H3-IMGT | ARGGRTTWIGALDI |
| 33 | MAB18-IgG4 | H3-IMGT | ARGGRTTWIGAFDI |
| 35 | MAB19-IgG4 | H3-IMGT | ARLHVSGSYYPAYLDY |
| 35 | MAB20-IgG4 | H3-IMGT | ARLHVSGSYYPAYLDY |
| 35 | MAB21-IgG4 | H3-IMGT | ARLHVSGSYYPAYLDY |
| 36 | MAB1-IgG4 | H2-Kabat | SIYYSGATFYNPSLKS |
| 37 | MAB2-IgG4 | H2-Kabat | SIYYSGSTFYNPSLKS |
| 37 | MAB3-IgG4 | H2-Kabat | SIYYSGSTFYNPSLKS |
| 37 | MAB4-IgG4 | H2-Kabat | SIYYSGSTFYNPSLKS |
| 38 | MAB5-IgG4 | H2-Kabat | SIYYSGSTFYNPSLKG |
| 39 | MAB6-IgG4 | H2-Kabat | SIYYSGGTYYNPSLKS |
| 40 | MAB7-IgG4 | H2-Kabat | SIYYSGSTYYNPSLKS |
| 41 | MAB8-IgG4 | H2-Kabat | SIYYSGQTYYNPSLKS |
| 40 | MAB9-IgG4 | H2-Kabat | SIYYSGSTYYNPSLKS |
| 40 | MAB10-IgG4 | H2-Kabat | SIYYSGSTYYNPSLKS |

APPENDIX A-continued

SEQUENCE REFERENCE TABLE

| SEQ ID NO | Molecule | Region | Sequence |
|---|---|---|---|
| 40 | MAB11-IgG4 | H2-Kabat | SIYYSGSTYYNPSLKS |
| 40 | MAB12-IgG4 | H2-Kabat | SIYYSGSTYYNPSLKS |
| 42 | MAB13-IgG4 | H2-Kabat | IINPSLGLTSYAQKFQG |
| 42 | MAB14-IgG4 | H2-Kabat | IINPSLGLTSYAQKFQG |
| 43 | MAB15-IgG4 | H2-Kabat | IINPSIGLTSYARKFQG |
| 43 | MAB16-IgG4 | H2-Kabat | IINPSIGLTSYARKFQG |
| 44 | MAB17-IgG4 | H2-Kabat | IINPSLGLTSYARKFQG |
| 44 | MAB18-IgG4 | H2-Kabat | IINPSLGLTSYARKFQG |
| 45 | MAB19-IgG4 | H2-Kabat | VINPSMGATSYAQKFQG |
| 46 | MAB20-IgG4 | H2-Kabat | IINPSMGATSYAQKFQG |
| 47 | MAB21-IgG4 | H2-Kabat | IINPSMGATSYTQKFRG |
| 48 | MAB1-IgG4 | H1-Chothia + Kabat | GSITSSSYYWG |
| 49 | MAB2-IgG4 | H1-Chothia + Kabat | GSISSSKYYWG |
| 50 | MAB3-IgG4 | H1-Chothia + Kabat | GSISSTSHYWG |
| 50 | MAB4-IgG4 | H1-Chothia + Kabat | GSISSTSHYWG |
| 50 | MAB5-IgG4 | H1-Chothia + Kabat | GSISSTSHYWG |
| 51 | MAB6-IgG4 | H1-Chothia + Kabat | GSIESGSYYWG |
| 52 | MAB7-IgG4 | H1-Chothia + Kabat | GSIESGVYYWG |
| 53 | MAB8-IgG4 | H1-Chothia + Kabat | GSIASGSYYWG |
| 54 | MAB9-IgG4 | H1-Chothia + Kabat | GSIESGLYYWG |
| 54 | MAB10-IgG4 | H1-Chothia + Kabat | GSIESGLYYWG |
| 54 | MAB11-IgG4 | H1-Chothia + Kabat | GSIESGLYYWG |
| 54 | MAB12-IgG4 | H1-Chothia + Kabat | GSIESGLYYWG |
| 55 | IgG4 | Constant, S228P hinge stabilizing | ASTKGPSVFPLAPCSRSTSESTAALGCLVKDYFPEP VTVSWNSGALTSGVHTFPAVLQSSGLYSLSSVVTV PSSSLGTKTYTCNVDHKPSNTKVDKRVESKYGPPC PPCPAPEFLGGPSVFLFPPKPKDTLMISRTPEVTCVV |

APPENDIX A-continued

SEQUENCE REFERENCE TABLE

| SEQ ID NO | Molecule | Region | Sequence |
|---|---|---|---|
| | | | VDVSQEDPEVQFNWYVDGVEVHNAKTKPREEQFN STYRVVSVLTVLHQDWLNGKEYKCKVSNKGLPSSI EKTISKAKGQPREPQVYTLPPSQEEMTKNQVSLTCL VKGFYPSDIAVEWESNGQPENNYKTTPPVLDSDGS FFLYSRLTVDKSRWQEGNVFSCSVMHEALHNHYT QKSLSLSLGK |
| 56 | IgG4 | Constant S228P, N297A, C terminal Lys deleted | ASTKGPSVFPLAPCSRSTSESTAALGCLVKDYFPEP VTVSWNSGALTSGVHTFPAVLQSSGLYSLSSVVTV PSSSLGTKTYTCNVDHKPSNTKVDKRVESKYGPPC PPCPAPEFLGGPSVFLFPPKPKDTLMISRTPEVTCVV VDVSQEDPEVQFNWYVDGVEVHNAKTKPREEQFA STYRVVSVLTVLHQDWLNGKEYKCKVSNKGLPSSI EKTISKAKGQPREPQVYTLPPSQEEMTKNQVSLTCL VKGFYPSDIAVEWESNGQPENNYKTTPPVLDSDGS FFLYSRLTVDKSRWQEGNVFSCSVMHEALHNHYT QKSLSLSLG |
| 57 | IgG1 | Constant (G1m(3) allotype) | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKRVEPKSCDKT HTCPPCPAPELLGGPSVFLFPPKPKDTLMISRTPEVT CVVVDVSHEDPEVKFNWYVDGVEVHNAKTKPREE QYNSTYRVVSVLTVLHQDWLNGKEYKCKVSNKAL PAPIEKTISKAKGQPREPQVYTLPPSREEMTKNQVS LTCLVKGFYPSDIAVEWESNGQPENNYKTTPPVLD SDGSFFLYSKLTVDKSRWQQGNVFSCSVMHEALH NHYTQKSLSLSPGK |
| 58 | MAB13-IgG4 | H1-Chothia + Kabat | YTFGNYYMH |
| 59 | MAB14-IgG4 | H1-Chothia + Kabat | YTFPAYYMH |
| 60 | MAB15-IgG4 | H1-Chothia + Kabat | YTFREYYMH |
| 60 | MAB16-IgG4 | H1-Chothia + Kabat | YTFREYYMH |
| 61 | MAB17-IgG4 | H1-Chothia + Kabat | YTFPAYYIH |
| 59 | MAB18-IgG4 | H1-Chothia + Kabat | YTFPAYYMH |
| 62 | MAB19-IgG4 | H1-Chothia + Kabat | YTFTSHYMG |
| 62 | MAB20-IgG4 | H1-Chothia + Kabat | YTFTSHYMG |
| 62 | MAB21-IgG4 | H1-Chothia + Kabat | YTFTSHYMG |
| 63 | MAB1-IgG4 | L3-Chothia/Kabat/IMGT | QQHFNLPT |
| 63 | MAB2-IgG4 | L3-Chothia/Kabat/IMGT | QQHFNLPT |
| 63 | MAB3-IgG4 | L3-Chothia/Kabat/IMGT | QQHFNLPT |
| 63 | MAB4-IgG4 | L3-Chothia/Kabat/IMGT | QQHFNLPT |

APPENDIX A-continued

SEQUENCE REFERENCE TABLE

| SEQ ID NO | Molecule | Region | Sequence |
|---|---|---|---|
| 63 | MAB5-IgG4 | L3-Chothia/Kabat/IMGT | QQHFNLPT |
| 64 | MAB6-IgG4 | L3-Chothia/Kabat/IMGT | QQHTVRPPLT |
| 64 | MAB7-IgG4 | L3-Chothia/Kabat/IMGT | QQHTVRPPLT |
| 64 | MAB8-IgG4 | L3-Chothia/Kabat/IMGT | QQHTVRPPLT |
| 64 | MAB9-IgG4 | L3-Chothia/Kabat/IMGT | QQHTVRPPLT |
| 64 | MAB10-IgG4 | L3-Chothia/Kabat/IMGT | QQHTVRPPLT |
| 64 | MAB11-IgG4 | L3-Chothia/Kabat/IMGT | QQHTVRPPLT |
| 64 | MAB12-IgG4 | L3-Chothia/Kabat/IMGT | QQHTVRPPLT |
| 65 | MAB13-IgG4 | L3-Chothia/Kabat/IMGT | QQYVVWPPLT |
| 65 | MAB14-IgG4 | L3-Chothia/Kabat/IMGT | QQYVVWPPLT |
| 65 | MAB15-IgG4 | L3-Chothia/Kabat/IMGT | QQYVVWPPLT |
| 65 | MAB16-IgG4 | L3-Chothia/Kabat/IMGT | QQYVVWPPLT |
| 65 | MAB17-IgG4 | L3-Chothia/Kabat/IMGT | QQYVVWPPLT |
| 65 | MAB18-IgG4 | L3-Chothia/Kabat/IMGT | QQYVVWPPLT |
| 66 | MAB19-IgG4 | L3-Chothia/Kabat/IMGT | QQYIVFPWT |
| 66 | MAB20-IgG4 | L3-Chothia/Kabat/IMGT | QQYIVFPWT |
| 66 | MAB21-IgG4 | L3-Chothia/Kabat/IMGT | QQYIVFPWT |
| 67 | MAB1-IgG4 | L2-Chothia/Kabat | DASNRAT |
| 67 | MAB2-IgG4 | L2-Chothia/Kabat | DASNRAT |

APPENDIX A-continued

SEQUENCE REFERENCE TABLE

| SEQ ID NO | Molecule | Region | Sequence |
|---|---|---|---|
| 67 | MAB3-IgG4 | L2-Chothia/Kabat | DASNRAT |
| 67 | MAB4-IgG4 | L2-Chothia/Kabat | DASNRAT |
| 67 | MAB5-IgG4 | L2-Chothia/Kabat | DASNRAT |
| 68 | MAB6-IgG4 | L2-Chothia/Kabat | GASSRAT |
| 68 | MAB7-IgG4 | L2-Chothia/Kabat | GASSRAT |
| 68 | MAB8-IgG4 | L2-Chothia/Kabat | GASSRAT |
| 68 | MAB9-IgG4 | L2-Chothia/Kabat | GASSRAT |
| 68 | MAB10-IgG4 | L2-Chothia/Kabat | GASSRAT |
| 68 | MAB11-IgG4 | L2-Chothia/Kabat | GASSRAT |
| 68 | MAB12-IgG4 | L2-Chothia/Kabat | GASSRAT |
| 69 | MAB13-IgG4 | L2-Chothia/Kabat | GASTRAT |
| 69 | MAB14-IgG4 | L2-Chothia/Kabat | GASTRAT |
| 69 | MAB15-IgG4 | L2-Chothia/Kabat | GASTRAT |
| 69 | MAB16-IgG4 | L2-Chothia/Kabat | GASTRAT |
| 69 | MAB17-IgG4 | L2-Chothia/Kabat | GASTRAT |
| 69 | MAB18-IgG4 | L2-Chothia/Kabat | GASTRAT |
| 69 | MAB19-IgG4 | L2-Chothia/Kabat | GASTRAT |
| 69 | MAB20-IgG4 | L2-Chothia/Kabat | GASTRAT |
| 69 | MAB21-IgG4 | L2-Chothia/Kabat | GASTRAT |
| 70 | MAB1-IgG4 | L1-Chothia/Kabat | RASQSVSSYLA |
| 70 | MAB2-IgG4 | L1-Chothia/Kabat | RASQSVSSYLA |
| 70 | MAB3-IgG4 | L1-Chothia/Kabat | RASQSVSSYLA |
| 70 | MAB4-IgG4 | L1-Chothia/Kabat | RASQSVSSYLA |
| 70 | MAB5-IgG4 | L1-Chothia/Kabat | RASQSVSSYLA |

APPENDIX A-continued

SEQUENCE REFERENCE TABLE

| SEQ ID NO | Molecule | Region | Sequence |
|---|---|---|---|
| 71 | MAB6-IgG4 | L1-Chothia/Kabat | RASQSVSSSYLA |
| 71 | MAB7-IgG4 | L1-Chothia/Kabat | RASQSVSSSYLA |
| 71 | MAB8-IgG4 | L1-Chothia/Kabat | RASQSVSSSYLA |
| 71 | MAB9-IgG4 | L1-Chothia/Kabat | RASQSVSSSYLA |
| 71 | MAB10-IgG4 | L1-Chothia/Kabat | RASQSVSSSYLA |
| 71 | MAB11-IgG4 | L1-Chothia/Kabat | RASQSVSSSYLA |
| 71 | MAB12-IgG4 | L1-Chothia/Kabat | RASQSVSSSYLA |
| 72 | MAB13-IgG4 | L1-Chothia/Kabat | RASQSVSSNLA |
| 72 | MAB14-IgG4 | L1-Chothia/Kabat | RASQSVSSNLA |
| 72 | MAB15-IgG4 | L1-Chothia/Kabat | RASQSVSSNLA |
| 72 | MAB16-IgG4 | L1-Chothia/Kabat | RASQSVSSNLA |
| 72 | MAB17-IgG4 | L1-Chothia/Kabat | RASQSVSSNLA |
| 72 | MAB18-IgG4 | L1-Chothia/Kabat | RASQSVSSNLA |
| 72 | MAB19-IgG4 | L1-Chothia/Kabat | RASQSVSSNLA |
| 72 | MAB20-IgG4 | L1-Chothia/Kabat | RASQSVSSNLA |
| 72 | MAB21-IgG4 | L1-Chothia/Kabat | RASQSVSSNLA |
| 73 | SEC1 | Human IgG4 S228P Heavy Chain | EVQLVESGGGLTQPGKSLKLSCEASGFTFSSFTMH WVRQSPGKGLEWVAFIRSGSGIVFYADAVRGRFTI SRDNAKNLLFLQMNDLKSEDTAMYYCARRPLGHN TFDSWGQGTLVTVSSATKGPSVFPLAPCSRSTSES TAALGCLVKDYFPEPVTVSWNSGALTSGVHTFPAV LQSSGLYSLSSVVTVPSSSLGTKTYTCNVDHKPSNT KVDKRVESKYGPPCPPCPAPEFLGGPSVFLFPPKPK DTLMISRTPEVTCVVVDVSQEDPEVQFNWYVDGV EVHNAKTKPREEQFNSTYRVVSVLTVLHQDWLNG KEYKCKVSNKGLPSSIEKTISKAKGQPREPQVYTLP PSQEEMTKNQVSLTCLVKGFYPSDIAVEWESNGQP ENNYKTTPPVLDSDGSFFLYSRLTVDKSRWQEGNV FSCSVMHEALHNHYTQKSLSLSLGK |
| 74 | SEC1 | Heavy Chain Variable Region | EVQLVESGGGLTQPGKSLKLSCEASGFTFSSFTMH WVRQSPGKGLEWVAFIRSGSGIVFYADAVRGRFTI SRDNAKNLLFLQMNDLKSEDTAMYYCARRPLGHN TFDSWGQGTLVTVSS |

APPENDIX A-continued

SEQUENCE REFERENCE TABLE

| SEQ ID NO | Molecule | Region | Sequence |
|---|---|---|---|
| 75 | SEC1 | SEC1 Human Kappa Chain | DIVMTQSPSSLAVSPGEKVTMTCKSSQSLYYSGVK ENLLAWYQQKPGQSPKLLIYYASIRFTGVPDRFTGS GSGTDYTLTITSVQAEDMGQYFCQQGINNPLTFGD GTKLEIKRTVAAPSVFIFPPSDEQLKSGTASVVCLLN NFYPREAKVQWKVDNALQSGNSQESVTEQDSKDS TYSLSSTLTLSKADYEKHKVYACEVTHQGLSSPVT KSFNRGEC |
| 76 | SEC1 | Light Chain Variable Region | DIVMTQSPSSLAVSPGEKVTMTCKSSQSLYYSGVK ENLLAWYQQKPGQSPKLLIYYASIRFTGVPDRFTGS GSGTDYTLTITSVQAEDMGQYFCQQGINNPLTFGD GTKLEIK |
| 77 | SEC1 | Mouse IgG2a N297A Heavy Chain | EVQLVESGGGLTQPGKSLKLSCEASGFTFSSFTMH WVRQSPGKGLEWVAFIRSGSGIVFYADAVRGRFTI SRDNAKNLLFLQMNDLKSEDTAMYYCARRPLGHN TFDSWGQGTLVTVSSAKTTAPSVYPLAPVCGDTTG SSVTLGCLVKGYFPEPVTLTWNSGSLSSGVHTFPAV LQSDLYTLSSSVTVTSSTWPSQSITCNVAHPASSTK VDKKIEPRGPTIKPCPPCKCPAPNLLGGPSVFIFPPKI KDVLMISLSPIVTCVVVDVSEDDPDVQISWFVNNV EVHTAQTQTHREDYASTLRVVSALPIQHQDWMSG KEFKCKVNNKDLPAPIERTISKPKGSVRAPQVYVLP PPEEEMTKKQVTLTCMVTDFMPEDIYVEWTNNGK TELNYKNTEPVLDSDGSYFMYSKLRVEKKNWVER NSYSCSVVHEGLHNHHTTKSFSRTPGK |
| 74 | SEC1 | Heavy Chain Variable region | EVQLVESGGGLTQPGKSLKLSCEASGFTFSSFTMH WVRQSPGKGLEWVAFIRSGSGIVFYADAVRGRFTI SRDNAKNLLFLQMNDLKSEDTAMYYCARRPLGHN TFDSWGQGTLVTVSS |
| 78 | SEC1 | Mouse Kappa Chain | DIVMTQSPSSLAVSPGEKVTMTCKSSQSLYYSGVK ENLLAWYQQKPGQSPKLLIYYASIRFTGVPDRFTGS GSGTDYTLTITSVQAEDMGQYFCQQGINNPLTFGD GTKLEIKRADAAPTVSIFPPSSEQLTSGGASVVCFLN NFYPKDINVKWKIDGSERQNGVLNSWTDQDSKDS TYSMSSTLTLTKDEYERHNSYTCEATHKTSTSPIVK SFNRNEC |
| 76 | SEC1 | Light Chain Variable Region | DIVMTQSPSSLAVSPGEKVTMTCKSSQSLYYSGVK ENLLAWYQQKPGQSPKLLIYYASIRFTGVPDRFTGS GSGTDYTLTITSVQAEDMGQYFCQQGINNPLTFGD GTKLEIK |
| 79 | MAB1 | Full length IgG4 S228P | QLQLQESGPGLVKPSETLSLTCTVSGGSITSSSYYW GWIRQPPGKGLEWIGSIYYSGATFYNPSLKSRVTIS VDTSKNQFSLKLSSVTAADTAVYYCARDANYYGS AWAFDPWGQGTLVTVSSASTKGPSVFPLAPCSRST SESTAALGCLVKDYFPEPVTVSWNSGALTSGVHTF PAVLQSSGLYSLSSVVTVPSSSLGTKTYTCNVDHKP SNTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWL NGKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLGK |
| 80 | MAB1 | Full length IgG1 | QLQLQESGPGLVKPSETLSLTCTVSGGSITSSSYYW GWIRQPPGKGLEWIGSIYYSGATFYNPSLKSRVTIS VDTSKNQFSLKLSSVTAADTAVYYCARDANYYGS AWAFDPWGQGTLVTVSSASTKGPSVFPLAPSSKST SGGTAALGCLVKDYFPEPVTVSWNSGALTSGVHTF PAVLQSSGLYSLSSVVTVPSSSLGTQTYICNVNHKP SNTKVDKRVEPKSCDKTHTCPPCPAPELLGGPSVFL FPPKPKDTLMISRTPEVTCVVVDVSHEDPEVKFNW YVDGVEVHNAKTKPREEQYNSTYRVVSVLTVLHQ DWLNGKEYKCKVSNKALPAPIEKTISKAKGQPREP QVYTLPPSREEMTKNQVSLTCLVKGFYPSDIAVEW ESNGQPENNYKTTPPVLDSDGSFFLYSKLTVDKSR WQQGNVFSCSVMHEALHNHYTQKSLSLSPGK |

APPENDIX A-continued

SEQUENCE REFERENCE TABLE

| SEQ ID NO | Molecule | Region | Sequence |
|---|---|---|---|
| 81 | MAB1 | Full length Kappa | EIVLTQSPATLSLSPGERATLSCRASQSVSSYLAWY QQKPGQAPRLLIYDASNRATGIPARFSGSGSGTDFT LTISSLEPEDFAVYYCQQHFNLPTFGGGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| 82 | MAB2 | Full length IgG4 S228P | QLQLQESGPGLVKPSETLSLTCTVSGGSISSSKYYW GWIRQPPGKGLEWIGSIYYSGSTFYNPSLKSRVTISV DTSKNQFSLKLSSVTAADTAVYYCARDANYYGSA WAFDPWGQGTLVTVSSASTKGPSVFPLAPCSRSTS ESTAALGCLVKDYFPEPVTVSWNSGALTSGVHTFP AVLQSSGLYSLSSVVTVPSSSLGTKTYTCNVDHKPS NTKVDKRVESKYGPPCPPCPAPEFLGGPSVFLFPPK PKDTLMISRTPEVTCVVVDVSQEDPEVQFNWYVDG VEVHNAKTKPREEQFNSTYRVVSVLTVLHQDWLN GKEYKCKVSNKGLPSSIEKTISKAKGQPREPQVYTL PPSQEEMTKNQVSLTCLVKGFYPSDIAVEWESNGQ PENNYKTTPPVLDSDGSFFLYSRLTVDKSRWQEGN VFSCSVMHEALHNHYTQKSLSLSLGK |
| 83 | MAB2 | Full length IgG1 | QLQLQESGPGLVKPSETLSLTCTVSGGSISSSKYYW GWIRQPPGKGLEWIGSIYYSGSTFYNPSLKSRVTISV DTSKNQFSLKLSSVTAADTAVYYCARDANYYGSA WAFDPWGQGTLVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKRVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK |
| 81 | MAB2 | Full length Kappa | EIVLTQSPATLSLSPGERATLSCRASQSVSSYLAWY QQKPGQAPRLLIYDASNRATGIPARFSGSGSGTDFT LTISSLEPEDFAVYYCQQHFNLPTFGGGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| 84 | MAB3 | Full length IgG4 S228P | QLQLQESGPGLVKPSETLSLTCTVSGGSISSTSHYW GWIRQPPGKGLEWIGSIYYSGSTFYNPSLKSRVTISV DTSKNQFSLKLSSVTAADTAVYYCARDANYYGSA WAFDPWGQGTLVTVSSASTKGPSVFPLAPCSRSTS ESTAALGCLVKDYFPEPVTVSWNSGALTSGVHTFP AVLQSSGLYSLSSVVTVPSSSLGTKTYTCNVDHKPS NTKVDKRVESKYGPPCPPCPAPEFLGGPSVFLFPPK PKDTLMISRTPEVTCVVVDVSQEDPEVQFNWYVDG VEVHNAKTKPREEQFNSTYRVVSVLTVLHQDWLN GKEYKCKVSNKGLPSSIEKTISKAKGQPREPQVYTL PPSQEEMTKNQVSLTCLVKGFYPSDIAVEWESNGQ PENNYKTTPPVLDSDGSFFLYSRLTVDKSRWQEGN VFSCSVMHEALHNHYTQKSLSLSLGK |
| 85 | MAB3 | Full length IgG1 | QLQLQESGPGLVKPSETLSLTCTVSGGSISSTSHYW GWIRQPPGKGLEWIGSIYYSGSTFYNPSLKSRVTISV DTSKNQFSLKLSSVTAADTAVYYCARDANYYGSA WAFDPWGQGTLVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKRVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK |
| 81 | MAB3 | Full length Kappa | EIVLTQSPATLSLSPGERATLSCRASQSVSSYLAWY QQKPGQAPRLLIYDASNRATGIPARFSGSGSGTDFT LTISSLEPEDFAVYYCQQHFNLPTFGGGTKVEIKRT |

APPENDIX A-continued

SEQUENCE REFERENCE TABLE

| SEQ ID NO | Molecule | Region | Sequence |
|---|---|---|---|
|  |  |  | VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| 86 | MAB4 | Full length IgG4 S228P | QLQLQESGPGLVKPSETLSLTCTVSGGSISSTSHYW GWIRQPPGKGLEWIGSIYYSGSTFYNPSLKSRVTISV DTSKNQFSLKLSSVTAADTAVYYCARDANYYGGA WAFDPWGQGTLVTVSSASTKGPSVFPLAPCSRSTS ESTAALGCLVKDYFPEPVTVSWNSGALTSGVHTFP AVLQSSGLYSLSSVVTVPSSSLGTKTYTCNVDHKPS NTKVDKRVESKYGPPCPPCPAPEFLGGPSVFLFPPK PKDTLMISRTPEVTCVVVDVSQEDPEVQFNWYVDG VEVHNAKTKPREEQFNSTYRVVSVLTVLHQDWLN GKEYKCKVSNKGLPSSIEKTISKAKGQPREPQVYTL PPSQEEMTKNQVSLTCLVKGFYPSDIAVEWESNGQ PENNYKTTPPVLDSDGSFFLYSRLTVDKSRWQEGN VFSCSVMHEALHNHYTQKSLSLSLGK |
| 87 | MAB4 | Full length IgG1 | QLQLQESGPGLVKPSETLSLTCTVSGGSISSTSHYW GWIRQPPGKGLEWIGSIYYSGSTFYNPSLKSRVTISV DTSKNQFSLKLSSVTAADTAVYYCARDANYYGGA WAFDPWGQGTLVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKRVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK |
| 81 | MAB4 | Full length Kappa | EIVLTQSPATLSLSPGERATLSCRASQSVSSYLAWY QQKPGQAPRLLIYDASNRATGIPARFSGSGSGTDFT LTISSLEPEDFAVYYCQQHFNLPTFGGGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| 88 | MAB5 | Full length IgG4 S228P | QLQLQESGPGLVKPSETLSLTCTVSGGSISSTSHYW GWIRQPPGKGLEWIGSIYYSGSTFYNPSLKGRVTIS VDTSKNQFSLKLSSVTAADTAVYYCARDANYYGS AWAFDPWGQGTLVTVSSASTKGPSVFPLAPCSRST SESTAALGCLVKDYFPEPVTVSWNSGALTSGVHTF PAVLQSSGLYSLSSVVTVPSSSLGTKTYTCNVDHKP SNTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWL NGKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLGK |
| 89 | MAB5 | Full length IgG1 | QLQLQESGPGLVKPSETLSLTCTVSGGSISSTSHYW GWIRQPPGKGLEWIGSIYYSGSTFYNPSLKGRVTIS VDTSKNQFSLKLSSVTAADTAVYYCARDANYYGS AWAFDPWGQGTLVTVSSASTKGPSVFPLAPSSKST SGGTAALGCLVKDYFPEPVTVSWNSGALTSGVHTF PAVLQSSGLYSLSSVVTVPSSSLGTQTYICNVNHKP SNTKVDKRVEPKSCDKTHTCPPCPAPELLGGPSVFL FPPKPKDTLMISRTPEVTCVVVDVSHEDPEVKFNW YVDGVEVHNAKTKPREEQYNSTYRVVSVLTVLHQ DWLNGKEYKCKVSNKALPAPIEKTISKAKGQPREP QVYTLPPSREEMTKNQVSLTCLVKGFYPSDIAVEW ESNGQPENNYKTTPPVLDSDGSFFLYSKLTVDKSR WQQGNVFSCSVMHEALHNHYTQKSLSLSPGK |
| 81 | MAB5 | Full length Kappa | EIVLTQSPATLSLSPGERATLSCRASQSVSSYLAWY QQKPGQAPRLLIYDASNRATGIPARFSGSGSGTDFT LTISSLEPEDFAVYYCQQHFNLPTFGGGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |

APPENDIX A-continued

SEQUENCE REFERENCE TABLE

| SEQ ID NO | Molecule | Region | Sequence |
|---|---|---|---|
| 90 | MAB6 | Full length IgG4 S228P | QLQLQESGPGLVKPSETLSLTCTVSGGSIESGSYYW GWIRQPPGKGLEWIGSIYYSGGTYYNPSLKSRVTIS VDTSKNQFSLKLSSVTAADTAVYYCARDGVLTLN KRSFDIWGQGTMVTVSSASTKGPSVFPLAPCSRSTS ESTAALGCLVKDYFPEPVTVSWNSGALTSGVHTFP AVLQSSGLYSLSSVVTVPSSSLGTKTYTCNVDHKPS NTKVDKRVESKYGPPCPPCPAPEFLGGPSVFLFPPK PKDTLMISRTPEVTCVVVDVSQEDPEVQFNWYVDG VEVHNAKTKPREEQFNSTYRVVSVLTVLHQDWLN GKEYKCKVSNKGLPSSIEKTISKAKGQPREPQVYTL PPSQEEMTKNQVSLTCLVKGFYPSDIAVEWESNGQ PENNYKTTPPVLDSDGSFFLYSRLTVDKSRWQEGN VFSCSVMHEALHNHYTQKSLSLSLGK |
| 91 | MAB6 | Full length IgG1 | QLQLQESGPGLVKPSETLSLTCTVSGGSIESGSYYW GWIRQPPGKGLEWIGSIYYSGGTYYNPSLKSRVTIS VDTSKNQFSLKLSSVTAADTAVYYCARDGVLTLN KRSFDIWGQGTMVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKRVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK |
| 92 | MAB6 | Full length Kappa | EIVLTQSPGTLSLSPGERATLSCRASQSVSSSYLAW YQQKPGQAPRLLIYGASSRATGIPDRFSGSGSGTDF TLTISRLEPEDFAVYYCQQHTVRPPLTFGGGTKVEI KRTVAAPSVFIFPPSDEQLKSGTASVVCLLNNFYPR EAKVQWKVDNALQSGNSQESVTEQDSKDSTYSLSS TLTLSKADYEKHKVYACEVTHQGLSSPVTKSFNRG EC |
| 93 | MAB7 | Full length IgG4 S228P | QVQLQESGPGLVKPSQTLSLTCTVSGGSIESGVYY WGWIRQPPGKGLEWIGSIYYSGSTYYNPSLKSRVTI SVDTSKNQFSLKLSSVTAADTAVYYCARDGVLTLN KRSFDIWGQGTMVTVSSASTKGPSVFPLAPCSRSTS ESTAALGCLVKDYFPEPVTVSWNSGALTSGVHTFP AVLQSSGLYSLSSVVTVPSSSLGTKTYTCNVDHKPS NTKVDKRVESKYGPPCPPCPAPEFLGGPSVFLFPPK PKDTLMISRTPEVTCVVVDVSQEDPEVQFNWYVDG VEVHNAKTKPREEQFNSTYRVVSVLTVLHQDWLN GKEYKCKVSNKGLPSSIEKTISKAKGQPREPQVYTL PPSQEEMTKNQVSLTCLVKGFYPSDIAVEWESNGQ PENNYKTTPPVLDSDGSFFLYSRLTVDKSRWQEGN VFSCSVMHEALHNHYTQKSLSLSLGK |
| 94 | MAB7 | Full length IgG1 | QVQLQESGPGLVKPSQTLSLTCTVSGGSIESGVYY WGWIRQPPGKGLEWIGSIYYSGSTYYNPSLKSRVTI SVDTSKNQFSLKLSSVTAADTAVYYCARDGVLTLN KRSFDIWGQGTMVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKRVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK |
| 92 | MAB7 | Full length Kappa | EIVLTQSPGTLSLSPGERATLSCRASQSVSSSYLAW YQQKPGQAPRLLIYGASSRATGIPDRFSGSGSGTDF TLTISRLEPEDFAVYYCQQHTVRPPLTFGGGTKVEI KRTVAAPSVFIFPPSDEQLKSGTASVVCLLNNFYPR EAKVQWKVDNALQSGNSQESVTEQDSKDSTYSLSS TLTLSKADYEKHKVYACEVTHQGLSSPVTKSFNRG EC |

APPENDIX A-continued

SEQUENCE REFERENCE TABLE

| SEQ ID NO | Molecule | Region | Sequence |
|---|---|---|---|
| 95 | MAB8 | Full length IgG4 S228P | QLQLQESGPGLVKPSETLSLTCTVSGGSIASGSYYW GWIRQPPGKGLEWIGSIYYSGQTYYNPSLKSRVTIS VDTSKNQFSLKLSSVTAADTAVYYCARDGVLTLN KRSFDIWGQGTMVTVSSASTKGPSVFPLAPCSRSTS ESTAALGCLVKDYFPEPVTVSWNSGALTSGVHTFP AVLQSSGLYSLSSVVTVPSSSLGTKTYTCNVDHKPS NTKVDKRVESKYGPPCPPCPAPEFLGGPSVFLFPPK PKDTLMISRTPEVTCVVVDVSQEDPEVQFNWYVDG VEVHNAKTKPREEQFNSTYRVVSVLTVLHQDWLN GKEYKCKVSNKGLPSSIEKTISKAKGQPREPQVYTL PPSQEEMTKNQVSLTCLVKGFYPSDIAVEWESNGQ PENNYKTTPPVLDSDGSFFLYSRLTVDKSRWQEGN VFSCSVMHEALHNHYTQKSLSLSLGK |
| 96 | MAB8 | Full length IgG1 | QLQLQESGPGLVKPSETLSLTCTVSGGSIASGSYYW GWIRQPPGKGLEWIGSIYYSGQTYYNPSLKSRVTIS VDTSKNQFSLKLSSVTAADTAVYYCARDGVLTLN KRSFDIWGQGTMVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKRVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK |
| 92 | MAB8 | Full length Kappa | EIVLTQSPGTLSLSPGERATLSCRASQSVSSSYLAW YQQKPGQAPRLLIYGASSRATGIPDRFSGSGSGTDF TLTISRLEPEDFAVYYCQQHTVRPPLTFGGGTKVEI KRTVAAPSVFIFPPSDEQLKSGTASVVCLLNNFYPR EAKVQWKVDNALQSGNSQESVTEQDSKDSTYSLSS TLTLSKADYEKHKVYACEVTHQGLSSPVTKSFNRG EC |
| 97 | MAB9 | Full length IgG4 S228P | QVQLQESGPGLVKPSQTLSLTCTVSGGSIESGLYYW GWIRQPPGKGLEWIGSIYYSGSTYYNPSLKSRVTIS VDTSKNQFSLKLSSVTAADTAVYYCARDGVLTLN KRSFDIWGQGTMVTVSSASTKGPSVFPLAPCSRSTS ESTAALGCLVKDYFPEPVTVSWNSGALTSGVHTFP AVLQSSGLYSLSSVVTVPSSSLGTKTYTCNVDHKPS NTKVDKRVESKYGPPCPPCPAPEFLGGPSVFLFPPK PKDTLMISRTPEVTCVVVDVSQEDPEVQFNWYVDG VEVHNAKTKPREEQFNSTYRVVSVLTVLHQDWLN GKEYKCKVSNKGLPSSIEKTISKAKGQPREPQVYTL PPSQEEMTKNQVSLTCLVKGFYPSDIAVEWESNGQ PENNYKTTPPVLDSDGSFFLYSRLTVDKSRWQEGN VFSCSVMHEALHNHYTQKSLSLSLGK |
| 98 | MAB9 | Full length IgG1 | QVQLQESGPGLVKPSQTLSLTCTVSGGSIESGLYYW GWIRQPPGKGLEWIGSIYYSGSTYYNPSLKSRVTIS VDTSKNQFSLKLSSVTAADTAVYYCARDGVLTLN KRSFDIWGQGTMVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKRVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK |
| 92 | MAB9 | Full length Kappa | EIVLTQSPGTLSLSPGERATLSCRASQSVSSSYLAW YQQKPGQAPRLLIYGASSRATGIPDRFSGSGSGTDF TLTISRLEPEDFAVYYCQQHTVRPPLTFGGGTKVEI KRTVAAPSVFIFPPSDEQLKSGTASVVCLLNNFYPR EAKVQWKVDNALQSGNSQESVTEQDSKDSTYSLSS TLTLSKADYEKHKVYACEVTHQGLSSPVTKSFNRG EC |

APPENDIX A-continued

SEQUENCE REFERENCE TABLE

| SEQ ID NO | Molecule | Region | Sequence |
|---|---|---|---|
| 99 | MAB10 | Full length IgG4 S228P | QVQLQESGPGLVKPSQTLSLTCTVSGGSIESGLYYW GWIRQPPGKGLEWIGSIYYSGSTYYNPSLKSRATIS VDTSKNQFSLKLSSVTAADTAVYYCARDGVLALN KRSFDIWGQGTMVTVSSASTKGPSVFPLAPCSRSTS ESTAALGCLVKDYFPEPVTVSWNSGALTSGVHTFP AVLQSSGLYSLSSVVTVPSSSLGTKTYTCNVDHKPS NTKVDKRVESKYGPPCPPCPAPEFLGGPSVFLFPPK PKDTLMISRTPEVTCVVVDVSQEDPEVQFNWYVDG VEVHNAKTKPREEQFNSTYRVVSVLTVLHQDWLN GKEYKCKVSNKGLPSSIEKTISKAKGQPREPQVYTL PPSQEEMTKNQVSLTCLVKGFYPSDIAVEWESNGQ PENNYKTTPPVLDSDGSFFLYSRLTVDKSRWQEGN VFSCSVMHEALHNHYTQKSLSLSLGK |
| 100 | MAB10 | Full length IgG1 | QVQLQESGPGLVKPSQTLSLTCTVSGGSIESGLYYW GWIRQPPGKGLEWIGSIYYSGSTYYNPSLKSRATIS VDTSKNQFSLKLSSVTAADTAVYYCARDGVLALN KRSFDIWGQGTMVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKRVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK |
| 92 | MAB10 | Full length Kappa | EIVLTQSPGTLSLSPGERATLSCRASQSVSSSYLAW YQQKPGQAPRLLIYGASSRATGIPDRFSGSGSGTDF TLTISRLEPEDFAVYYCQQHTVRPPLTFGGGTKVEI KRTVAAPSVFIFPPSDEQLKSGTASVVCLLNNFYPR EAKVQWKVDNALQSGNSQESVTEQDSKDSTYSLSS TLTLSKADYEKHKVYACEVTHQGLSSPVTKSFNRG EC |
| 101 | MAB11 | Full length IgG4 S228P | QVQLQESGPGLVKPSQTLSLTCTVSGGSIESGLYYW GWIRQPPGKGLEWIGSIYYSGSTYYNPSLKSRVTIS VDTSKNQFSLKLSSVTAADTAVYYCARDGVLALN KRSFDIWGQGTMVTVSSASTKGPSVFPLAPCSRSTS ESTAALGCLVKDYFPEPVTVSWNSGALTSGVHTFP AVLQSSGLYSLSSVVTVPSSSLGTKTYTCNVDHKPS NTKVDKRVESKYGPPCPPCPAPEFLGGPSVFLFPPK PKDTLMISRTPEVTCVVVDVSQEDPEVQFNWYVDG VEVHNAKTKPREEQFNSTYRVVSVLTVLHQDWLN GKEYKCKVSNKGLPSSIEKTISKAKGQPREPQVYTL PPSQEEMTKNQVSLTCLVKGFYPSDIAVEWESNGQ PENNYKTTPPVLDSDGSFFLYSRLTVDKSRWQEGN VFSCSVMHEALHNHYTQKSLSLSLGK |
| 102 | MAB11 | Full length IgG1 | QVQLQESGPGLVKPSQTLSLTCTVSGGSIESGLYYW GWIRQPPGKGLEWIGSIYYSGSTYYNPSLKSRVTIS VDTSKNQFSLKLSSVTAADTAVYYCARDGVLALN KRSFDIWGQGTMVTVSSASTKGPSVFPLAPSSKSTS GGTAALGCLVKDYFPEPVTVSWNSGALTSGVHTFP AVLQSSGLYSLSSVVTVPSSSLGTQTYICNVNHKPS NTKVDKRVEPKSCDKTHTCPPCPAPELLGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWE SNGQPENNYKTTPPVLDSDGSFFLYSKLTVDKSRW QQGNVFSCSVMHEALHNHYTQKSLSLSPGK |
| 92 | MAB11 | Full length Kappa | EIVLTQSPGTLSLSPGERATLSCRASQSVSSSYLAW YQQKPGQAPRLLIYGASSRATGIPDRFSGSGSGTDF TLTISRLEPEDFAVYYCQQHTVRPPLTFGGGTKVEI KRTVAAPSVFIFPPSDEQLKSGTASVVCLLNNFYPR EAKVQWKVDNALQSGNSQESVTEQDSKDSTYSLSS TLTLSKADYEKHKVYACEVTHQGLSSPVTKSFNRG EC |

APPENDIX A-continued

SEQUENCE REFERENCE TABLE

| SEQ ID NO | Molecule | Region | Sequence |
|---|---|---|---|
| 103 | MAB12 | Full length IgG4 S228P | QVQLQESGPGLVKPSQTLSLTCTASGGSIESGLYYWGWIRQPPGKGLEWIGSIYYSGSTYYNPSLKSRVTISVDTSKNQFSLKLSSVTAADTAVYYCARDGVLALNKRSFDIWGQGTMVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 104 | MAB12 | Full length IgG1 | QVQLQESGPGLVKPSQTLSLTCTASGGSIESGLYYWGWIRQPPGKGLEWIGSIYYSGSTYYNPSLKSRVTISVDTSKNQFSLKLSSVTAADTAVYYCARDGVLALNKRSFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 92 | MAB12 | Full length Kappa | EIVLTQSPGTLSLSPGERATLSCRASQSVSSSYLAWYQQKPGQAPRLLIYGASSRATGIPDRFSGSGSGTDFTLTISRLEPEDFAVYYCQQHTVRPPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 105 | MAB13 | Full length IgG4 S228P | QVQLVQSGAEVKKPGASVKVSCKASGYTFGNYYMHWVRQAPGQGLEWMGIINPSLGLTSYAQKFQGRVTMTRDTSTSTVYMELSSLRSEDTAVYYCARGGRTTWIGAFDIWGQGTMVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 106 | MAB13 | Full length IgG1 | QVQLVQSGAEVKKPGASVKVSCKASGYTFGNYYMHWVRQAPGQGLEWMGIINPSLGLTSYAQKFQGRVTMTRDTSTSTVYMELSSLRSEDTAVYYCARGGRTTWIGAFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 107 | MAB13 | Full length Kappa | EIVMTQSPATLSVSPGERATLSCRASQSVSSNLAWYQQKPGQAPRLLIYGASTRATGIPARFSGSGSGTEFTLTISSLQSEDFAVYYCQQYVVWPPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

APPENDIX A-continued

SEQUENCE REFERENCE TABLE

| SEQ ID NO | Molecule | Region | Sequence |
|---|---|---|---|
| 108 | MAB14 | Full length IgG4 S228P | QVQLVQSGAEVKKPGASVKVSCKASGYTFPAYYM HWVRQAPGQGLEWMGIINPSLGLTSYAQKFQGRV TMTRDTSTSTVYMELSSLRSEDTAVYYCARGGRTT WIGAFDIWGQGTMVTVSSASTKGPSVFPLAPCSRST SESTAALGCLVKDYFPEPVTVSWNSGALTSGVHTF PAVLQSSGLYSLSSVVTVPSSSLGTKTYTCNVDHKP SNTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWL NGKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLGK |
| 109 | MAB14 | Full length IgG1 | QVQLVQSGAEVKKPGASVKVSCKASGYTFPAYYM HWVRQAPGQGLEWMGIINPSLGLTSYAQKFQGRV TMTRDTSTSTVYMELSSLRSEDTAVYYCARGGRTT WIGAFDIWGQGTMVTVSSASTKGPSVFPLAPSSKST SGGTAALGCLVKDYFPEPVTVSWNSGALTSGVHTF PAVLQSSGLYSLSSVVTVPSSSLGTQTYICNVNHKP SNTKVDKRVEPKSCDKTHTCPPCPAPELLGGPSVFL FPPKPKDTLMISRTPEVTCVVVDVSHEDPEVKFNW YVDGVEVHNAKTKPREEQYNSTYRVVSVLTVLHQ DWLNGKEYKCKVSNKALPAPIEKTISKAKGQPREP QVYTLPPSREEMTKNQVSLTCLVKGFYPSDIAVEW ESNGQPENNYKTTPPVLDSDGSFFLYSKLTVDKSR WQQGNVFSCSVMHEALHNHYTQKSLSLSPGK |
| 107 | MAB14 | Full length Kappa | EIVMTQSPATLSVSPGERATLSCRASQSVSSNLAWY QQKPGQAPRLLIYGASTRATGIPARFSGSGSGTEFT LTISSLQSEDFAVYYCQQYVVWPPLTFGGGTKVEIK RTVAAPSVFIFPPSDEQLKSGTASVVCLLNNFYPRE AKVQWKVDNALQSGNSQESVTEQDSKDSTYSLSST LTLSKADYEKHKVYACEVTHQGLSSPVTKSFNRGE C |
| 110 | MAB15 | Full length IgG4 S228P | QVQLVQSGAEVKKPGASVKVSCKASGYTFREYYM HWVRQAPGQGLEWMGIINPSIGLTSYARKFQGRVT MTRDTSTSTVYMELSSLRSEDTAVYYCARGGRTT WIGAFDIWGQGTMVTVSSASTKGPSVFPLAPCSRST SESTAALGCLVKDYFPEPVTVSWNSGALTSGVHTF PAVLQSSGLYSLSSVVTVPSSSLGTKTYTCNVDHKP SNTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWL NGKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLGK |
| 111 | MAB15 | Full length IgG1 | QVQLVQSGAEVKKPGASVKVSCKASGYTFREYYM HWVRQAPGQGLEWMGIINPSIGLTSYARKFQGRVT MTRDTSTSTVYMELSSLRSEDTAVYYCARGGRTT WIGAFDIWGQGTMVTVSSASTKGPSVFPLAPSSKST SGGTAALGCLVKDYFPEPVTVSWNSGALTSGVHTF PAVLQSSGLYSLSSVVTVPSSSLGTQTYICNVNHKP SNTKVDKRVEPKSCDKTHTCPPCPAPELLGGPSVFL FPPKPKDTLMISRTPEVTCVVVDVSHEDPEVKFNW YVDGVEVHNAKTKPREEQYNSTYRVVSVLTVLHQ DWLNGKEYKCKVSNKALPAPIEKTISKAKGQPREP QVYTLPPSREEMTKNQVSLTCLVKGFYPSDIAVEW ESNGQPENNYKTTPPVLDSDGSFFLYSKLTVDKSR WQQGNVFSCSVMHEALHNHYTQKSLSLSPGK |
| 107 | MAB15 | Full length Kappa | EIVMTQSPATLSVSPGERATLSCRASQSVSSNLAWY QQKPGQAPRLLIYGASTRATGIPARFSGSGSGTEFT LTISSLQSEDFAVYYCQQYVVWPPLTFGGGTKVEIK RTVAAPSVFIFPPSDEQLKSGTASVVCLLNNFYPRE AKVQWKVDNALQSGNSQESVTEQDSKDSTYSLSST LTLSKADYEKHKVYACEVTHQGLSSPVTKSFNRGE C |

APPENDIX A-continued

SEQUENCE REFERENCE TABLE

| SEQ ID NO | Molecule | Region | Sequence |
|---|---|---|---|
| 112 | MAB16 | Full length IgG4 S228P | QVQLVQSGAEVKKPGASVKVSCKASGYTFREYYM HWVRQAPGQGLEWMGIINPSIGLTSYARKFQGRVT MTRDTSTSTVYMELSSLRSEDTAVYYCARGGRTT WIGALDIWGQGTMVTVSSASTKGPSVFPLAPCSRS TSESTAALGCLVKDYFPEPVTVSWNSGALTSGVHT FPAVLQSSGLYSLSSVVTVPSSSLGTKTYTCNVDHK PSNTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWL NGKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLGK |
| 113 | MAB16 | Full length IgG1 | QVQLVQSGAEVKKPGASVKVSCKASGYTFREYYM HWVRQAPGQGLEWMGIINPSIGLTSYARKFQGRVT MTRDTSTSTVYMELSSLRSEDTAVYYCARGGRTT WIGALDIWGQGTMVTVSSASTKGPSVFPLAPSSKST SGGTAALGCLVKDYFPEPVTVSWNSGALTSGVHTF PAVLQSSGLYSLSSVVTVPSSSLGTQTYICNVNHKP SNTKVDKRVEPKSCDKTHTCPPCPAPELLGGPSVFL FPPKPKDTLMISRTPEVTCVVVDVSHEDPEVKFNW YVDGVEVHNAKTKPREEQYNSTYRVVSVLTVLHQ DWLNGKEYKCKVSNKALPAPIEKTISKAKGQPREP QVYTLPPSREEMTKNQVSLTCLVKGFYPSDIAVEW ESNGQPENNYKTTPPVLDSDGSFFLYSKLTVDKSR WQQGNVFSCSVMHEALHNHYTQKSLSLSPGK |
| 107 | MAB16 | Full length Kappa | EIVMTQSPATLSVSPGERATLSCRASQSVSSNLAWY QQKPGQAPRLLIYGASTRATGIPARFSGSGSGTEFT LTISSLQSEDFAVYYCQQYVVWPPLTFGGGTKVEIK RTVAAPSVFIFPPSDEQLKSGTASVVCLLNNFYPRE AKVQWKVDNALQSGNSQESVTEQDSKDSTYSLSST LTLSKADYEKHKVYACEVTHQGLSSPVTKSFNRGE C |
| 114 | MAB17 | Full length IgG4 S228P | QVQLVQSGAEVKKPGASVKVSCKASGYTFPAYYIH WVRQAPGQGLEWMGIINPSLGLTSYARKFQGRVT MTRDTSTSTVYMELSSLRSEDTAVYYCARGGRTT WIGALDIWGQGTMVTVSSASTKGPSVFPLAPCSRS TSESTAALGCLVKDYFPEPVTVSWNSGALTSGVHT FPAVLQSSGLYSLSSVVTVPSSSLGTKTYTCNVDHK PSNTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWL NGKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLGK |
| 115 | MAB17 | Full length IgG1 | QVQLVQSGAEVKKPGASVKVSCKASGYTFPAYYIH WVRQAPGQGLEWMGIINPSLGLTSYARKFQGRVT MTRDTSTSTVYMELSSLRSEDTAVYYCARGGRTT WIGALDIWGQGTMVTVSSASTKGPSVFPLAPSSKST SGGTAALGCLVKDYFPEPVTVSWNSGALTSGVHTF PAVLQSSGLYSLSSVVTVPSSSLGTQTYICNVNHKP SNTKVDKRVEPKSCDKTHTCPPCPAPELLGGPSVFL FPPKPKDTLMISRTPEVTCVVVDVSHEDPEVKFNW YVDGVEVHNAKTKPREEQYNSTYRVVSVLTVLHQ DWLNGKEYKCKVSNKALPAPIEKTISKAKGQPREP QVYTLPPSREEMTKNQVSLTCLVKGFYPSDIAVEW ESNGQPENNYKTTPPVLDSDGSFFLYSKLTVDKSR WQQGNVFSCSVMHEALHNHYTQKSLSLSPGK |
| 107 | MAB17 | Full length Kappa | EIVMTQSPATLSVSPGERATLSCRASQSVSSNLAWY QQKPGQAPRLLIYGASTRATGIPARFSGSGSGTEFT LTISSLQSEDFAVYYCQQYVVWPPLTFGGGTKVEIK RTVAAPSVFIFPPSDEQLKSGTASVVCLLNNFYPRE AKVQWKVDNALQSGNSQESVTEQDSKDSTYSLSST LTLSKADYEKHKVYACEVTHQGLSSPVTKSFNRGE C |

APPENDIX A-continued

SEQUENCE REFERENCE TABLE

| SEQ ID NO | Molecule | Region | Sequence |
|---|---|---|---|
| 116 | MAB18 | Full length IgG4 S228P | QVQLVQSGAEVKKPGASVKVSCKASGYTFPAYYM HWVRQAPGQGLEWMGIINPSLGLTSYARKFQGRV TMTRDTSTSTVYMELSSLRSEDTAVYYCARGGRTT WIGAFDIWGQGTMVTVSSASTKGPSVFPLAPCSRST SESTAALGCLVKDYFPEPVTVSWNSGALTSGVHTF PAVLQSSGLYSLSSVVTVPSSSLGTKTYTCNVDHKP SNTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLTVLHQDWL NGKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLGK |
| 117 | MAB18 | Full length IgG1 | QVQLVQSGAEVKKPGASVKVSCKASGYTFPAYYM HWVRQAPGQGLEWMGIINPSLGLTSYARKFQGRV TMTRDTSTSTVYMELSSLRSEDTAVYYCARGGRTT WIGAFDIWGQGTMVTVSSASTKGPSVFPLAPSSKST SGGTAALGCLVKDYFPEPVTVSWNSGALTSGVHTF PAVLQSSGLYSLSSVVTVPSSSLGTQTYICNVNHKP SNTKVDKRVEPKSCDKTHTCPPCPAPELLGGPSVFL FPPKPKDTLMISRTPEVTCVVVDVSHEDPEVKFNW YVDGVEVHNAKTKPREEQYNSTYRVVSVLTVLHQ DWLNGKEYKCKVSNKALPAPIEKTISKAKGQPREP QVYTLPPSREEMTKNQVSLTCLVKGFYPSDIAVEW ESNGQPENNYKTTPPVLDSDGSFFLYSKLTVDKSR WQQGNVFSCSVMHEALHNHYTQKSLSLSPGK |
| 107 | MAB18 | Full length Kappa | EIVMTQSPATLSVSPGERATLSCRASQSVSSNLAWY QQKPGQAPRLLIYGASTRATGIPARFSGSGSGTEFT LTISSLQSEDFAVYYCQQYVVWPPLTFGGGTKVEIK RTVAAPSVFIFPPSDEQLKSGTASVVCLLNNFYPRE AKVQWKVDNALQSGNSQESVTEQDSKDSTYSLSST LTLSKADYEKHKVYACEVTHQGLSSPVTKSFNRGE C |
| 118 | MAB19 | Full length IgG4 S228P | QVQLVQSGAEVKKPGASVKVSCKASGYTFTSHYM GWVRQAPGQGLEWMGVINPSMGATSYAQKFQGR VTMTRDTSTSTVYMELSSLRSEDTAVYYCARLHVS GSYYPAYLDYWGQGTMVTVSSASTKGPSVFPLAP CSRSTSESTAALGCLVKDYFPEPVTVSWNSGALTS GVHTFPAVLQSSGLYSLSSVVTVPSSSLGTKTYTCN VDHKPSNTKVDKRVESKYGPPCPPCPAPEFLGGPS VFLFPPKPKDTLMISRTPEVTCVVVDVSQEDPEVQF NWYVDGVEVHNAKTKPREEQFNSTYRVVSVLTVL HQDWLNGKEYKCKVSNKGLPSSIEKTISKAKGQPR EPQVYTLPPSQEEMTKNQVSLTCLVKGFYPSDIAVE WESNGQPENNYKTTPPVLDSDGSFFLYSRLTVDKS RWQEGNVFSCSVMHEALHNHYTQKSLSLSLGK |
| 119 | MAB19 | Full length IgG1 | QVQLVQSGAEVKKPGASVKVSCKASGYTFTSHYM GWVRQAPGQGLEWMGVINPSMGATSYAQKFQGR VTMTRDTSTSTVYMELSSLRSEDTAVYYCARLHVS GSYYPAYLDYWGQGTMVTVSSASTKGPSVFPLAPS SKSTSGGTAALGCLVKDYFPEPVTVSWNSGALTSG VHTFPAVLQSSGLYSLSSVVTVPSSSLGTQTYICNV NHKPSNTKVDKRVEPKSCDKTHTCPPCPAPELLGG PSVFLFPPKPKDTLMISRTPEVTCVVVDVSHEDPEV KFNWYVDGVEVHNAKTKPREEQYNSTYRVVSVLT VLHQDWLNGKEYKCKVSNKALPAPIEKTISKAKGQ PREPQVYTLPPSREEMTKNQVSLTCLVKGFYPSDIA VEWESNGQPENNYKTTPPVLDSDGSFFLYSKLTVD KSRWQQGNVFSCSVMHEALHNHYTQKSLSLSPGK |
| 120 | MAB19 | Full length Kappa | EIVMTQSPATLSVSPGERATLSCRASQSVSSNLAWY QQKPGQAPRHLIYGASTRATGIPARFSGSGSGTEFT LTISSLQSEDFAVYYCQQYIVFPWTFGGGTKVEIKR TVAAPSVFIFPPSDEQLKSGTASVVCLLNNFYPREA KVQWKVDNALQSGNSQESVTEQDSKDSTYSLSSTL TLSKADYEKHKVYACEVTHQGLSSPVTKSFNRGEC |

APPENDIX A-continued

SEQUENCE REFERENCE TABLE

| SEQ ID NO | Molecule | Region | Sequence |
|---|---|---|---|
| 121 | MAB20 | Full length IgG4 S228P | QVQLVQSGAEVKKPGASVKVSCKASGYTFTSHYM GWVRQAPGQGLEWVGIINPSMGATSYAQKFQGRV TMTRDTSTSTVYMELSSLRSEDTAVYYCARLHVSG SYYPAYLDYWGQGTMVTVSSASTKGPSVFPLAPCS RSTSESTAALGCLVKDYFPEPVTVSWNSGALTSGV HTFPAVLQSSGLYSLSSVVTVPSSSLGTKTYTCNVD HKPSNTKVDKRVESKYGPPCPPCPAPEFLGGPSVFL FPPKPKDTLMISRTPEVTCVVVDVSQEDPEVQFNW YVDGVEVHNAKTKPREEQFNSTYRVVSVLTVLHQ DWLNGKEYKCKVSNKGLPSSIEKTISKAKGQPREP QVYTLPPSQEEMTKNQVSLTCLVKGFYPSDIAVEW ESNGQPENNYKTTPPVLDSDGSFFLYSRLTVDKSR WQEGNVFSCSVMHEALHNHYTQKSLSLSLGK |
| 122 | MAB20 | Full length IgG1 | QVQLVQSGAEVKKPGASVKVSCKASGYTFTSHYM GWVRQAPGQGLEWVGIINPSMGATSYAQKFQGRV TMTRDTSTSTVYMELSSLRSEDTAVYYCARLHVSG SYYPAYLDYWGQGTMVTVSSASTKGPSVFPLAPSS KSTSGGTAALGCLVKDYFPEPVTVSWNSGALTSGV HTFPAVLQSSGLYSLSSVVTVPSSSLGTQTYICNVN HKPSNTKVDKRVEPKSCDKTHTCPPCPAPELLGGPS VFLFPPKPKDTLMISRTPEVTCVVVDVSHEDPEVKF NWYVDGVEVHNAKTKPREEQYNSTYRVVSVLTVL HQDWLNGKEYKCKVSNKALPAPIEKTISKAKGQPR EPQVYTLPPSREEMTKNQVSLTCLVKGFYPSDIAVE WESNGQPENNYKTTPPVLDSDGSFFLYSKLTVDKS RWQQGNVFSCSVMHEALHNHYTQKSLSLSPGK |
| 120 | MAB20 | Full length Kappa | EIVMTQSPATLSVSPGERATLSCRASQSVSSNLAWY QQKPGQAPRHLIYGASTRATGIPARFSGSGSGTEFT LTISSLQSEDFAVYYCQQYIVFPWTFGGGTKVEIKR TVAAPSVFIFPPSDEQLKSGTASVVCLLNNFYPREA KVQWKVDNALQSGNSQESVTEQDSKDSTYSLSSTL TLSKADYEKHKVYACEVTHQGLSSPVTKSFNRGEC |
| 123 | MAB21 | Full length IgG4 S228P | QVQLVQSGAEVKKPGASVKVSCKASGYTFTSHYM GWVRQAPGQGLEWMGIINPSMGATSYTQKFRGRV TMTRDTSTSTVYMELSSLRSEDTAVYYCARLHVSG SYYPAYLDYWGQGTMVTVSSASTKGPSVFPLAPCS RSTSESTAALGCLVKDYFPEPVTVSWNSGALTSGV HTFPAVLQSSGLYSLSSVVTVPSSSLGTKTYTCNVD HKPSNTKVDKRVESKYGPPCPPCPAPEFLGGPSVFL FPPKPKDTLMISRTPEVTCVVVDVSQEDPEVQFNW YVDGVEVHNAKTKPREEQFNSTYRVVSVLTVLHQ DWLNGKEYKCKVSNKGLPSSIEKTISKAKGQPREP QVYTLPPSQEEMTKNQVSLTCLVKGFYPSDIAVEW ESNGQPENNYKTTPPVLDSDGSFFLYSRLTVDKSR WQEGNVFSCSVMHEALHNHYTQKSLSLSLGK |
| 124 | MAB21 | Full length IgG1 | QVQLVQSGAEVKKPGASVKVSCKASGYTFTSHYM GWVRQAPGQGLEWMGIINPSMGATSYTQKFRGRV TMTRDTSTSTVYMELSSLRSEDTAVYYCARLHVSG SYYPAYLDYWGQGTMVTVSSASTKGPSVFPLAPSS KSTSGGTAALGCLVKDYFPEPVTVSWNSGALTSGV HTFPAVLQSSGLYSLSSVVTVPSSSLGTQTYICNVN HKPSNTKVDKRVEPKSCDKTHTCPPCPAPELLGGPS VFLFPPKPKDTLMISRTPEVTCVVVDVSHEDPEVKF NWYVDGVEVHNAKTKPREEQYNSTYRVVSVLTVL HQDWLNGKEYKCKVSNKALPAPIEKTISKAKGQPR EPQVYTLPPSREEMTKNQVSLTCLVKGFYPSDIAVE WESNGQPENNYKTTPPVLDSDGSFFLYSKLTVDKS RWQQGNVFSCSVMHEALHNHYTQKSLSLSPGK |
| 120 | MAB21 | Full length Kappa | EIVMTQSPATLSVSPGERATLSCRASQSVSSNLAWY QQKPGQAPRHLIYGASTRATGIPARFSGSGSGTEFT LTISSLQSEDFAVYYCQQYIVFPWTFGGGTKVEIKR TVAAPSVFIFPPSDEQLKSGTASVVCLLNNFYPREA KVQWKVDNALQSGNSQESVTEQDSKDSTYSLSSTL TLSKADYEKHKVYACEVTHQGLSSPVTKSFNRGEC |

APPENDIX A-continued

SEQUENCE REFERENCE TABLE

| SEQ ID NO | Molecule | Region | Sequence |
|---|---|---|---|
| 125 | IgG1 | Constant (G1m(17,1) allotype, N297A | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEVT CVVVDVSHEDPEVKFNWYVDGVEVHNAKTKPREE QYASTYRVVSVLTVLHQDWLNGKEYKCKVSNKAL PAPIEKTISKAKGQPREPQVYTLPPSRDELTKNQVSL TCLVKGFYPSDIAVEWESNGQPENNYKTTPPVLDS DGSFFLYSKLTVDKSRWQQGNVFSCSVMHEALHN HYTQKSLSLSPGK |
| 126 | Kappa | Constant | RTVAAPSVFIFPPSDEQLKSGTASVVCLLNNFYPRE AKVQWKVDNALQSGNSQESVTEQDSKDSTYSLSST LTLSKADYEKHKVYACEVTHQGLSSPVTKSFNRGE C |
| 127 | Linker |  | GGGGS |

128...137-See other portions of this disclosure and the electronic version of the Sequence Listing submitted herewith.

| | | | |
|---|---|---|---|
| 138 | mTIGIT2 |  | MHGWLLLVWVQGLIQAAFLATAIGATAGTIDTKR NISAEEGGSVILQCHFSSDTAEVTQVDWKQQDQLL AIYSVDLGWHVASVFSDRVVPGPSLGLTFQSLTMN DTGEYFCTYHTYPGGIYKGRIFLKVQESSDDRNGL AQFQTAPLGGTMAAVLGLICLMVTGVTVLARKDK SIRMHSIESGLGRTEAEPQEWNLRSLSSPGSPVQTQ TAPAGPCGEQAEDDYADPQEYFNVLSYRSLESFIA VSKTG |
| 139 | MAB22 | Full Heavy | QVQLQESGPGLVKPSETLSLTCAVSGYSISSGLGWG WIRQPPGKGLEWIGGIYESGSTYYNPSLKSRVTISV DTSKNQFSLKLSSVTAADTAVYYCAHERVRGYGD YGGHHAFDIWGQGTMVTVSSASTKGPSVFPLAPSS KSTSGGTAALGCLVKDYFPEPVTVSWNSGALTSGV HTFPAVLQSSGLYSLSSVVTVPSSSLGTQTYICNVN HKPSNTKVDKRVEPKSCGGGGSQVQLQESGPGLV KPSETLSLTCAVSGYSISSGLGWGWIRQPPGKGLEW IGGIYESGSTYYNPSLKSRVTISVDTSKNQFSLKLSS VTAADTAVYYCAHERVRGYGDYGGHHAFDIWGQ GTMVTVSSASTKGPSVFPLAPCSRSTSESTAALGCL VKDYFPEPVTVSWNSGALTSGVHTFPAVLQSSGLY SLSSVVTVPSSSLGTKTYTCNVDHKPSNTKVDKRV ESKYGPPCPPCPAPEFLGGPSVFLFPPKPKDTLMISR TPEVTCVVVDVSQEDPEVQFNWYVDGVEVHNAKT KPREEQFNSTYRVVSVLTVLHQDWLNGKEYKCKV SNKGLPSSIEKTISKAKGQPREPQVYTLPPSQEEMT KNQVSLTCLVKGFYPSDIAVEWESNGQPENNYKTT PPVLDSDGSFFLYSRLTVDKSRWQEGNVFSCSVMH EALHNHYTQKSLSLSLGK |
| 140 | MAB22 | Full Light | DIQMTQSPSSLSASVGDRVTITCRASQSISSYLNWY QQKPGKAPKLLIYAASSLQSGVPSRFSGSGSGTDFT LTISSLQPEDFATYYCQQEYATPPTFGGGTKVEIKR TVAAPSVFIFPPSDEQLKSGTASVVCLLNNFYPREA KVQWKVDNALQSGNSQESVTEQDSKDSTYSLSSTL TLSKADYEKHKVYACEVTHQGLSSPVTKSFNRGEC |
| 141 | MAB23 | Full Heavy, IgG4 S228P | EVQLLESGGGLVQPGGSLRLSCAASGFTFSSVAMV WVRQAPGKGLEWVSAISGSGGATYYADSVEGRFTI SRDNSKNTLYLQMNSLRAEDTAVYYCAKDPGYDS SRYYYSNYGMDVWGQGTTVTVSSASTKGPSVFPL APCSRSTSESTAALGCLVKDYFPEPVTVSWNSGAL TSGVHTFPAVLQSSGLYSLSSVVTVPSSSLGTKTYT CNVDHKPSNTKVDKRVESKYGPPCPPCPAPEFLGG PSVFLFPPKPKDTLMISRTPEVTCVVVDVSQEDPEV QFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDIA VEWESNGQPENNYKTTPPVLDSDGSFFLYSRLTVD KSRWQEGNVFSCSVMHEALHNHYTQKSLSLSLGK |

APPENDIX A-continued

SEQUENCE REFERENCE TABLE

| SEQ ID NO | Molecule | Region | Sequence |
|---|---|---|---|
| 142 | MAB23 | Full Light, human kappa constant | DIQMTQSPSSLSASVGDRVTITCRASQSISSYLNWY QQKPGKAPKLLIYGASSLQSGVPSRFSGSGSGTDFT LTISSLQPEDFATYYCQQTYSLYTFGGGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| 143 | mMAB23 (MAB23 with mouse IgG2a N297A and mouse kappa constant regions) | Heavy Chain, | EVQLLESGGGLVQPGGSLRLSCAASGFTFSSVAMV WVRQAPGKGLEWVSAISGSGGATYYADSVEGRFTI SRDNSKNTLYLQMNSLRAEDTAVYYCAKDPGYDS SRYYYSNYGMDVWGQGTTVTVSSAKTTAPSVYPL APVCGDTTGSSVTLGCLVKGYFPEPVTLTWNSGSL SSGVHTFPAVLQSDLYTLSSSVTVTSSTWPSQSITCN VAHPASSTKVDKKIEPRGPTIKPCPPCKCPAPNLLG GPSVFIFPPKIKDVLMISLSPIVTCVVVDVSEDDPDV QISWFVNNVEVHTAQTQTHREDYASTLRVVSALPI QHQDWMSGKEFKCKVNNKDLPAPIERTISKPKGSV RAPQVYVLPPPEEEMTKKQVTLTCMVTDFMPEDIY VEWTNNGKTELNYKNTEPVLDSDGSYFMYSKLRV EKKNWVERNSYSCSVVHEGLHNHEITTKSFSRTPGK |
| 144 | mMAB23 (MAB23 with mouse IgG2a N297A and mouse kappa constant regions) | Light Chain, | DIQMTQSPSSLSASVGDRVTITCRASQSISSYLNWY QQKPGKAPKLLIYGASSLQSGVPSRFSGSGSGTDFT LTISSLQPEDFATYYCQQTYSLYTFGGGTKVEIKRA DAAPTVSIFPPSSEQLTSGGASVVCFLNNFYPKDINV KWKIDGSERQNGVLNSWTDQDSKDSTYSMSSTLTL TKDEYERHNSYTCEATHKTSTSPIVKSFNRNEC |

What is claimed is:

1. A method of treating cancer in a subject in need thereof, comprising administering to the subject an effective amount of:
   (i) an antibody or antigen binding fragment thereof comprising
   a) a $V_H$ sequence of SEQ ID NO: 4 and a $V_L$ sequence of SEQ ID NO: 25;
   b) a $V_H$ sequence of SEQ ID NO: 5 and a $V_L$ sequence of SEQ ID NO: 25;
   c) a $V_H$ sequence of SEQ ID NO: 6 and a $V_L$ sequence of SEQ ID NO: 25;
   d) a $V_H$ sequence of SEQ ID NO: 7 and a $V_L$ sequence of SEQ ID NO: 25;
   e) a $V_H$ sequence of SEQ ID NO: 8 and a $V_L$ sequence of SEQ ID NO: 25;
   f) a $V_H$ sequence of SEQ ID NO: 9 and a $V_L$ sequence of SEQ ID NO: 26;
   g) a $V_H$ sequence of SEQ ID NO: 10 and a $V_L$ sequence of SEQ ID NO: 26;
   h) a $V_H$ sequence of SEQ ID NO: 11 and a $V_L$ sequence of SEQ ID NO: 26;
   i) a $V_H$ sequence of SEQ ID NO: 12 and a $V_L$ sequence of SEQ ID NO: 26;
   j) a $V_H$ sequence of SEQ ID NO: 13 and a $V_L$ sequence of SEQ ID NO: 26;
   k) a $V_H$ sequence of SEQ ID NO: 14 and a $V_L$ sequence of SEQ ID NO: 26;
   l) a $V_H$ sequence of SEQ ID NO: 15 and a $V_L$ sequence of SEQ ID NO: 26;
   m) a $V_H$ sequence of SEQ ID NO: 16 and a $V_L$ sequence of SEQ ID NO: 27;
   n) a $V_H$ sequence of SEQ ID NO: 17 and a $V_L$ sequence of SEQ ID NO: 27;
   o) a $V_H$ sequence of SEQ ID NO: 18 and a $V_L$ sequence of SEQ ID NO: 27;
   p) a $V_H$ sequence of SEQ ID NO: 19 and a $V_L$ sequence of SEQ ID NO: 27;
   q) a $V_H$ sequence of SEQ ID NO: 20 and a $V_L$ sequence of SEQ ID NO: 27;
   r) a $V_H$ sequence of SEQ ID NO: 21 and a $V_L$ sequence of SEQ ID NO: 27;
   s) a $V_H$ sequence of SEQ ID NO: 22 and a $V_L$ sequence of SEQ ID NO: 28;
   t) a $V_H$ sequence of SEQ ID NO: 23 and a $V_L$ sequence of SEQ ID NO: 28; or
   u) a $V_H$ sequence of SEQ ID NO: 24 and a $V_L$ sequence of SEQ ID NO: 28; and
   (ii) one or more additional immunotherapeutic agents selected from the group consisting of:
   a) an immunotherapeutic agent that blocks signaling of an inhibitory receptor of an immune cell or a ligand thereof; and
   b) an immunotherapeutic agent that modulates signaling of a co-stimulatory receptor.

2. The method of claim 1, wherein the inhibitory receptor or ligand thereof is selected from the group consisting of CTLA-4, PD-1, PD-L1, PD-L2, Tim-3, neuritin, BTLA, CECAM-1, CECAM-5, VISTA, LAIR1, CD160, 2B4, KIR, and combinations thereof.

3. The method of claim 1, wherein the co-stimulatory receptor is CD3, GITR, OX40, ICOS, LAG-3, CD27, CD28, CD40, or 4-1BB.

4. The method of claim 1, wherein the cancer is selected from a solid tumor and a hematological tumor.

5. The method of claim 4, wherein the cancer is a solid tumor.

6. The method of claim 1, wherein the additional immunotherapeutic agent is an antibody against Tim-3, 41BB, GITR, PD-1 or PD-L1, or is OX40L.

7. The method of claim 1, wherein the additional immunotherapeutic is an anti-GITR antibody.

8. The method of claim 1, wherein the additional immunotherapeutic is an anti-NRP-1 antibody.

9. The method of claim 7 or 8, wherein the antibody or antigen binding fragment thereof comprises a $V_H$ sequence of SEQ ID NO: 13 and a $V_L$ sequence of SEQ ID NO: 26.

10. The method of claim 7 or 8, wherein the antibody or antigen binding fragment thereof comprises a $V_H$ sequence of SEQ ID NO: 5 and a $V_L$ sequence of SEQ ID NO: 25.

11. The method of claim 7 or 8, wherein the antibody or antigen binding fragment thereof comprises a $V_H$ sequence of SEQ ID NO: 18 and a $V_L$ sequence of SEQ ID NO: 27.

12. The method of claim 7 or 8, wherein the antibody or antigen binding fragment thereof comprises a $V_H$ sequence of SEQ ID NO: 24 and a $V_L$ sequence of SEQ ID NO: 28.

13. The method of claim 1, wherein the combination therapy has an additive effect on immune activation.

14. The method of claim 1, wherein the combination therapy has a synergistic effect on immune activation.

15. The method of claim 13 or claim 14, wherein determination of an additive or synergistic effect on immune activation is determined using a CMV recall assay.

16. The method of claim 13 or claim 14, wherein determination of an additive or synergistic effect on immune activation is determined using a dissociated tumor cell assay.

17. The method of claim 1, wherein the additional therapeutic agent is formulated in the same pharmaceutical composition as the antibody or antigen binding fragment thereof.

18. The method of claim 1, wherein the additional therapeutic agent is formulated in a different pharmaceutical composition from the antibody or antigen binding fragment thereof.

19. The method of claim 1, wherein the additional therapeutic agent is administered prior to administering the antibody or antigen binding fragment thereof.

20. The method of claim 1, wherein the additional therapeutic agent is administered after administering the antibody or antigen binding fragment thereof.

21. The method of claim 1, wherein the additional therapeutic agent is administered contemporaneously with the antibody or antigen binding fragment thereof.

* * * * *